US007262339B2

(12) United States Patent
Norris et al.

(10) Patent No.: US 7,262,339 B2
(45) Date of Patent: Aug. 28, 2007

(54) TOCOPHEROL METHYLTRANSFERASE TMT2 AND USES THEREOF

(75) Inventors: Susan R. Norris, University City, MO (US); Kim Lincoln, University City, MO (US); Joshua C. Stein, Acton, MA (US); Henry E. Valentin, Chesterfield, MO (US); Alison Van Eenennaam, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 503 days.

(21) Appl. No.: 10/279,029

(22) Filed: Oct. 24, 2002

(65) Prior Publication Data

US 2003/0150015 A1   Aug. 7, 2003

Related U.S. Application Data

(60) Provisional application No. 60/330,563, filed on Oct. 25, 2001.

(51) Int. Cl.
C12N 15/82 (2006.01)
C12N 15/29 (2006.01)
A01H 5/00 (2006.01)
A01H 5/10 (2006.01)

(52) U.S. Cl. .................. 800/298; 536/23.6; 435/320.1; 800/306; 800/312; 800/313; 800/314; 800/315; 800/316; 800/317.1; 800/317.2; 800/317.4; 800/319; 800/320; 800/320.1; 800/320.2; 800/320.3; 800/322

(58) Field of Classification Search ............... 536/23.6; 435/320.1, 419; 800/298
See application file for complete search history.

(56) References Cited

U.S. PATENT DOCUMENTS

| 4,727,219 | A | 2/1988 | Brar et al. |
|---|---|---|---|
| 5,304,478 | A | 4/1994 | Bird et al. |
| 5,429,939 | A | 7/1995 | Misawa et al. |
| 5,432,069 | A | 7/1995 | Gruninger et al. |
| 5,545,816 | A | 8/1996 | Ausich et al. |
| 5,618,988 | A | 4/1997 | Hauptmann et al. |
| 5,684,238 | A | 11/1997 | Ausich et al. |
| 5,693,507 | A | 12/1997 | Daniell et al. |
| 5,750,865 | A | 5/1998 | Bird et al. |
| 5,792,903 | A | 8/1998 | Hirschberg et al. |
| 5,876,964 | A | 3/1999 | Croteau et al. |
| 5,908,940 | A | 6/1999 | Lane et al. |
| 6,281,017 | B1 | 8/2001 | Croteau et al. |
| 6,303,365 | B1 | 10/2001 | Martin et al. |
| 6,541,259 | B1 | 4/2003 | Lassner et al. |
| 2002/0069426 | A1 | 6/2002 | Boronat et al. |
| 2002/0108148 | A1 | 8/2002 | Boronat et al. |
| 2003/0148300 | A1 | 8/2003 | Valantin et al. |
| 2003/0150015 | A1 | 8/2003 | Norris et al. |
| 2003/0154513 | A1 | 8/2003 | van Eenennam et al. |
| 2003/0166205 | A1 | 9/2003 | van Eenennaam et al. |
| 2003/0170833 | A1 | 9/2003 | Lassner et al. |
| 2003/0176675 | A1 | 9/2003 | Valentin et al. |
| 2003/0213017 | A1 | 11/2003 | Valentin et al. |
| 2004/0018602 | A1 | 1/2004 | Lassner et al. |
| 2004/0045051 | A1 | 3/2004 | Norris et al. |

FOREIGN PATENT DOCUMENTS

| CA | 2339519 | 2/2000 |
|---|---|---|
| CA | 2343919 | 3/2000 |
| CA | 2372332 | 11/2000 |
| DE | 198 35 219 A1 | 8/1998 |
| EP | 0 531 639 A2 | 3/1993 |
| EP | 0 531 639 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO91/02059 | 2/1991 |
| WO | WO91/09128 | 6/1991 |
| WO | WO91/13078 | 9/1991 |
| WO | WO96/02650 | 1/1993 |
| WO | WO93/18158 | 9/1993 |
| WO | WO96/36717 A2 | 11/1993 |
| WO | WO94/11516 | 5/1994 |
| WO | WO94/12014 | 6/1994 |
| WO | WO94/18337 | 8/1994 |
| WO | WO95/08914 | 4/1995 |
| WO | WO95/18220 | 7/1995 |
| WO | WO95/23863 | 8/1995 |
| WO | WO95/34668 | 12/1995 |
| WO | WO96/06172 | 2/1996 |
| WO | WO96/13149 | 5/1996 |
| WO | WO96/13159 | 5/1996 |
| WO | WO96/36717 A3 | 11/1996 |
| WO | WO96/38567 | 12/1996 |

(Continued)

OTHER PUBLICATIONS

Rieger M. et al. I GenBank ACCESSION AL163818, *Arabidopsis thaliana* DNA chromosome 3, P1 clone MAA21 (ESSA project), Apr. 13, 2000.*

(Continued)

*Primary Examiner*—Cynthia Collins
(74) *Attorney, Agent, or Firm*—Fulbright & Jaworski L.L.P.

(57) ABSTRACT

The present invention relates to genes associated with the tocopherol biosynthesis pathway. More particularly, the present invention provides and includes nucleic acid molecules, proteins, and antibodies associated with genes that encode polypeptides that have tocopherol methyltransferase (tMT2) activity. The present invention also provides methods for utilizing such agents, for example in gene isolation, gene analysis and the production of transgenic plants. Moreover, the present invention includes transgenic plants modified to express the aforementioned polypeptides. in addition, the present invention includes methods for the production of products from the tocopherol biosynthesis pathway.

7 Claims, 34 Drawing Sheets

FOREIGN PATENT DOCUMENTS

| WO | WO97/17447 | 5/1997 |
|---|---|---|
| WO | WO97/27285 | 7/1997 |
| WO | WO97/49816 | 12/1997 |
| WO | WO98/04685 | 2/1998 |
| WO | WO98/06862 | 2/1998 |
| WO | WO98/18910 | 5/1998 |
| WO | WO99/04021 | 1/1999 |
| WO | WO99/04622 | 2/1999 |
| WO | WO99/06580 | 2/1999 |
| WO | WO99/07867 | 2/1999 |
| WO | WO99/11757 | 3/1999 |
| WO | WO99/19460 | 4/1999 |
| WO | WO99/55889 | 11/1999 |
| WO | WO99/58649 | 11/1999 |
| WO | WO 00/01650 | 1/2000 |
| WO | WO 00/08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WP 00/17233 | 3/2000 |
| WO | WO 00/22150 A3 | 4/2000 |
| WO | WO 00/28005 | 5/2000 |
| WO | WO 00/32757 A2 | 6/2000 |
| WO | WO 00/32757 A3 | 6/2000 |
| WO | WO 00/34448 | 6/2000 |
| WO | WO 00/42205 A2 | 7/2000 |
| WO | WO 00/42205 A3 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 A2 | 11/2000 |
| WO | WO 00/65036 A3 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 | 11/2001 |
| WO | WO 01/88169 A3 | 11/2001 |
| WO | WO 02/00901 A1 | 1/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Rieger M. et al. II GenBank ACCESSION T49182 probable chloroplast inner envelope protein—*Arabidopsis thaliana*, Jun. 2, 2000.*

Cahoon E.B. et al. Metabolic redesign of vitamin E biosynthesis in plants for tocotrienol production and increased antioxidant content. Nat Biotechnol. Sep. 2003;21(9): 1082-7. Epub Aug. 3, 2003.*

Collakova E. et al. Homogentisate phytyltransferase activity is limiting for tocopherol biosynthesis in Arabidopsis. Plant Physiol. Feb. 2003;131(2):632-42.*

Rieger M. et al. I GenBank ACCESSION AL163818, *Arabidopsis thaliana* DNA chromosomes 3, P1 clone MAA21 (ESSA project), Apr. 13, 2000.*

Rieger M. et al. II GenBank ACCESSION T49182 probable chloroplast inner envelope protein—*Arabidopsis thaliana*, Jun. 2, 2000.*

Neill J.D. et al. Expression of a wheat alpha-gliadin gene in *Saccharomyces cerevisiae*. Gene. 1987;55(2-3):303-17.*

Addlesee et al., "Cloning, sequencing and functional assignment of the chlorophyll biosyntheses gene, *chlP*, of *Synechocystis* sp. PCC 6803", FEBS Letters 389 (1996) 126-130.

Arango et al., "Tocopherol synthesis from homogentisate in *Capsicum anuum* L. (yellow pepper) chromoplast membranes: evidence for tocopherol cyclase", Biochem J., 336:531-533 (1998).

Arigoni et al., "Terpenoid biosynthesis from 1-deoxy-D-xylulose in higher plants by intramolecular skeletal rearrngement", Proc. Natl. Acad. Sci. USA, 94:10600-10605 (1997).

Baker et al., "Sequence and characterization of the *gcpE* gene of *Escherichia coli*", FEMS Microbiology Letters, 94:175-180 (1992).

Bayley et al., "Engineering 2,4-D resistance into cotton," Theor Appl Genet, 83:645-649 (1992).

Bentley, R., "The Shikimate Pathwat—Metabolic Tree with Many Branches," Critical Reviews™ in Biochemistry and Molecular Biology; vol. 25, Issue 5, 307-384 (1990).

Bevan, M., "Binary *Agrobacterium* vectors for plant transformation", Nucleic Acids Research, 12:8711-8721 (1984).

Beyer et al., "Phytoene-forming activities in wild-type and transformed rice endosperm," IRRN 21:2-3, p. 44-45 (Aug.-Dec. 1996).

Bork et al., "Go hunting in sequence database but watch out for the traps", TIG 12, 10:425-427 (Oct. 1996).

Bouvier et al., "Dedicated Roles of Plastid Transketolases during the Early Onset of Isoprenoid Biogenesis in Pepper Fruits", Plant Physiol., 117:1423-1431 (1998).

Bramley et al., "Biochemical characterization of transgenic tomato plants in which carotenoid synthesis has been through the expression of antisense RNA to pTOM5," The Plant Journal, 2(3), 343-349 (1992).

Breitenbach et al., "Expression in *Escherichia coli* and properties of the carotene ketolase from *Haematococcus pluvialis*," FEMS Microbiology Letters 140, 241-246 (1996).

Broun et al., "Catalytic Plasticity of Fatty Acid Modification Enzymes Underlying Chemical Diversity of Plant Lipids," Science, 282:1315-1317 (1998).

Buckner et al., "The y1 Gene of Maize Codes for Phytoene Synthase," Genetics 143:479-488 (May 1996).

Burkhardt et al., "Genetic engineering of provitamin A biosynthesis in rice endosperm," Experientia, 818-821.

Burkhardt et al., "Transgenic rice (*Oryza sativa*) endosperm expressing daffodil (*Narcissus pseudonarcissus*) phytoene synthase accumulates phytoene, a key intermdiate of provitamin A biosynthesis" The Plant Journal, 11(5), 1071-1078 (1997).

Cahoon et al., "Production of Fatty Acid Components of Meadowfoam Oil in Somatic Soybeam Embryos," Plant Physiology, 124:243-251 (2000).

Chaudhuri et al., "The purification of shikimate dehydrogenase from *Escherichia coli*," Biochem. J., 226:217-223 (1985).

Cheng et al., "Highly Divergent Methyltransferase Catalyze a Conserved Reaction in Tocopherol and Plastoquinone Synthesis in Cyanobacteria and Photosynthetic Eukaryotes", The Plant Cell, 15:2343-2356 (2003).

Collakova et al., "Isolation and Functional Analysis of Homogentisate Phytyltransferase from *Synechocystis* sp. PCC 6803 and *Arabidopsis*", Plant Physiology, 127:1113-1124 (2001).

Collakova et al., "Homogentisate Phytyltranslerase Activity is Limiting for Tocopherol Biosynthesis in Arabidopsis", Plant Physiology, 131:632-642 (Feb. 2003).

Collakova et al., "Isolation and Characterization of Tocopherol Prenyl Transferase From Synechocystis and *Arabidopsis*", Poster Abstract see REN-01-026.

Cook et al., "Nuclear Mutations affecting plastoquinone accumulation in maize", Photosynthesis Research, 31:99-111 (1992).

Cunillera et al., "Characterization of dehydrodolichyl diphosphate synthase of *Arabidopsis thaliana*, a key enzyme in dolichol biosynthesis", FEBS Letters, 477:170-174 (2000).

d'Amato et al., "Subcellular localization of chorismate-mutase isoenzymes in protoplasts from mesophyll and suspension-cultured cells of *Nicotiana silvestris*," Planta, 162:104-108 (1984).

Doerks et al., "Protein annotation: detective work for function prediction", TIG, 14:248-250 (1998).

d'Harlingue et al., "Plastid Enzymes of Terpenoid Biosynthesis, Purification and Characterization of γ Tocopherol Methyltransferase from *Capsicum* Chromoplasts," The Journal of Biological Chemistry, vol. 260, No. 28, pp. 15200-15203, Dec. 5, 1985.

De Luca, Vincenzo, "Molecular characterization of secondary metabolic pathways", AgBiotech News and Information, 5(6):225N-229N (1993).

Duncan et al., "The overexpression and complete amino acid sequence of *Escherichia coli* 3-dehydroquinase", Biochem. J., 238:475-483 (1986).

Duvold et al., "Incorporation of 2-C-Methyl-D-erythritol, a Putative Isoprenoid Precursor in the Mevalonate-Independent Pathway, into Ubiquinone and Menaquinone of *Escherichia coli*", Tetrahedron Letters, 38(35):6181-6184 (1997).

Elliott, Thomas, "A Method for Constructing Single-Copy *lac* Fusions in *Salmonella typhimurium* and Its Application to the *hemA-prfA* Operon", Journal of Bacteriology, 174:245-253 (1992).

Eisenreich et al., "The deoxyxylulose phosphate pathway of terpenoid biosynthesis in plants and microorganisms", Chemistry & Biology, 5(9):R221-R233 (1998).

Ericson et al., "Analysis of the promoter region of napin genes from *Brassica napus* demonstrates binding of nuclear protein *in vitro* to a conversed sequenced motif", Eur. J. Biochem., 197:741-746 (1991).

Estévez et al., "1-Deoxy-D-xylulose-5-phosphate Synthase, a Limiting Enzyme for Plastidic Isoprenoid Biosynthesis in Plants", The Journal of Biological Chemistry, 276(25):22901-22909 (2001).

Fellermeier et al., "Cell-free conversion of 1-deoxy-D-xylulose 5-phosphate and 2-C-methyl-D-erythritol 4-phosphate into β-carotene in higher plants and its inhibition by fosmidomycin", Tetrahedron Letters, 40:2743-2746 (1999).

Fiedler et al., "The formation of homogentisate in the biosynthesis of tocopherol and plastoquinone in spinach chloroplasts", Planta, 155:511-515 (1982).

Fourgoux-Nicol et al., "Isolation of rapeseed genes expressed early and specifically during development of the male gametophyte", Plant Molecular Biology, 40:857-872 (1999).

Fraser et al., "Enzymic confirmation of reactions involved in routes to astaxanthin formation, elucidated using a direct substrate *in vitro* assay", Eur. J. Biochem., 252:229-236 (1998).

Fraser et al., "*In Vitro* Characterization of Astaxanthin Biosynthetic Enzymes", The Journal of Biological Chemistry, 272(10) 6128-6135 (1997).

Fray et al., "Constitutive expression of a fruit phytoene synthase gene in trangenic tomatoes causes dwarfism by redirecting metabolites from the gibberellin pathway", The Plant Journal, 8(5):693-701 (1995).

Fray et al., "Identification and genetic analysis of normal and mutant phytoene synthase genes of tomato by sequencing, complementation and co-suppression", Plant Molecular Biology, 22:589-602 (1993).

Fuqua et al., "Characterization of *melA*: a gene encoding melanin biosynthesis from the marine bacterium *Shewanella colwelliana*", Gene, 109:131-136 (1991).

Furuya et al., "Production of Tocopherols by Cell Culture of Safflower", Phytochemistry, 26(10):2741-2747 (1987).

Garcia et al., "Subcellular localization and purification of a p-hydroxyphenylpyruvate dioxygenase from cultured carrot cells and characterization of the corresponding cDNA", Biochem. J., 325:761-769 (1997).

Gaubier et al., "A chlorophyll synthetase gene from *Arabidopsis thaliana*", Mol. Gen. Genet., 249:58-64 (1995).

Goers et al., "Separation and characterization of two chorismate-mutase isoenzymes from *Nicotiana silvestris*", Planta, 162:109-116 (1984).

Grabse et al., "Loss of αtocopherol in tobacco plants with decreased geranylgeranyl reductase activity does not modify photosynthesis in optimal growth conditions but increases sensitivity to high-light stress", Planta, 213:620-628 (2001).

Harker et al., "Biosynthesis of ketocarotenoids in transgenic cyanobacteria expressing the algal gene for β-C-4-oxygenase, crtO", FEBS Letters, 404:129-134 (1997).

Harker et al., "Expression of prokaryotic 1-deoxy-D-xylulose-5-phosphatases in *Escherichia coli* increases carotenoid and ubiquinone biosynthesis", FEBS Letters, 448:115-119 (1999).

Hecht et al., "Studies of the nonmevalonate pathway to terpenes: The role of the GcpE (IspG) protein", PNAS, 98(26):14837-14842 (2001).

Herrmann, K.M., "The Shikimate Pathway as an Entry to Aromatic Secondary Metabolism", Plan Physiol., 107:7-12 (1995).

Herz et al., "Biosynthesis of terpenoids: YgbB protein converts 4-diphosphocytidyl-2C-methyl-o-erythritol 2-phosphate to 2C-methyl-D-erythritol 2,4-cyclodiphosphate", Proc. Natl. Acad. Sci. USA, 97(6):2486-2490 (2000).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343-352 (1995).

Kaneko et al., "Complete Genomic Sequence of the Filamentous Nitrogen-fixing Cyanobacterium *Anabaena* sp. Strain PCC 7120", DNA Research, 8(5):205-213 (2001).

Keegstra, K., "Transport and Routing of Proteins into Chloroplasts", Cell, 56(2):247-253 (1989).

Keller et al., "Metabolic compartmentation of plastid prenyllipid biosynthesis Evidence for the involvement of a multifunctional geranylgeranyl reductase", Eur. J. Biochem., 251:413-417 (1998).

Kishore et al., "Amino Acid Biosynthesis Inhibitors as Herbicides", Ann. Rev. Biochem., 57:627-663 (1988).

Koziel et al., "Optimizing expression of transgenes with an emphasis on post-transcriptional events", Plant Molecular Biology, 32:393-405 (1996).

Kumagai et al., "Cytoplasmic inhibition of carotenoid biosynthesis with virus-derived RNA", Proc. Natl. Acad. Sci. USA, 95:1679-1683 (1995).

Kuntz et al., "Identification of a cDNA for the plastid-located geranylgeranyl pyrophosphate synthase from *Capsicum annunm*: correlative increase in enzyme activity and transcript level during fruit ripening", The Plant Journal, 2(1):25-34 (1992).

Lange et al., "A Family of transketolases that directs isoprenoid biosynthesis via a mevalonate-independent pathway", Proc. Natl. Acad. Sci. USA, 95:2100-2104 (1998).

Lange et al., "Isoprenoid Biosynthesis via a Mevalonate-Independent Pathway in Plants: Cloning and Heterologous Expression of 1-Deoxy-D-xylulose-5-phosphate Reductoisomerase from Peppermint", Archives of Biochemistry and Biophysics, 365(1):170-174 (1999).

Li et al., "Identification of a maize endosperm-specific cDNA encoding farnesyl pyrophosphate synthetase", Gene, 171:193-196 (1996).

Linthorst et al., "Constitutive Expression of Pathogenesis-Related Proteins PR-1,GRP, and PR-S in Tobacco Has No Effect on Virus Infection", The Plant Cell, 1:285-291 (1989).

Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis", Proc. Natl. Acad. Sci. USA, 95(5):2105-2110 (1998).

Lopez et al., "Sequence of the *bchG* Gene from *Chloroflexus aurantiacus*: Relationship between Chlorophyll Synthase and other Polyprenyltransferases", Journal of Bacteriology, 178(11)3369-3373 (1996).

Lotan et al., "Cloning and expression in *Escherichia coli* of the gene encoding β-C-4-oxygenase, that converts β-carotene to the ketocarotenoid canthaxanthin in *Haematococcus pluvialis*", FEBS Letters, 364:125-128 (1995).

Mahmoud et al., "Metabolic engineering of essential oil yield and composition in mint by altering expression of deoxyxylulose phosphate reductoisomerase and menthofuran synthase", PNAS, 98(15):8915-8920 (2001).

Mandel et al., "*CLA1*, a novel gene required for chloroplast development, is highly conserved in evolution", The Plant Journal, 9(5):649-658 (1996).

Marshall et al., "Biosynthesis of Tocopherols: A Re-Examination of the Biosynthesis and Metabolism of 2-Methyl-6-Phytyl-1,4-Benzoquinol", Phytochemistry, 24(8):1705-1711 (1985).

Misawa et al., "Expression of a *Erwinia* phytoene desaturase gene not only confers multiple resistance to herbicides interfering with carotenoid biosynthesis but also alters xanthophyll metabolism in transgenic plants", The Plant Journal, 6(4):481-489 (1994).

Misawa et al., "Elucidation of the *Erwinia uredovora* Carotenoid Biosynthetic Pathway by Functional Analysis of Gene Products Expressed in *Escherichia coli*", Journal of Bacteriology, 172(12):6704-6712 (1990).

Misawa et al., "Functional expression of the *Erwinia uredovora* carotenoid biosynthesis gene crtI in transgenic plants showing an increase of β-carotene biosynthesis activity and resistance to the bleaching herbicide norfluraxon", The Plant Journal, 4(5):833-840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575-6584 (1995).

Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401-414 (1997).

Nawrath et al., "Targeting of the polyhydroxybutyrate biosynthetic pathway to the plastids of *Arabidopsis thaliana* results in high levels of polymer accumulation", Proc. Natl. Sci. USA, 91:12760-12764 (1994).

Norris et al., "Genetic Dissection of Carotenoid Synthetic in Arabidopsis Defines Plastoquinone as an Essential Component of Phytoene Desaturation", The Plant Cell, 7:2139-2149 (1995).

Norris et al., "Complementation of the Arabidopsis *pds1* Mutation with the Gene Encoding *p*-Hydroxyphenylpyruvate Dioxygenase", Plant Physiol., 117:1317-1323 (1998).

Oh et al., "Molecular Clonging, Expression, and Functional Analysis of a *cis*-Prenyltransferase from *Arabidopsis thaliana*", The Journal of Biological Chemistry, 275(24):18482-18488 (2000).

Okada et al., "Five Geranylgeranyl Diphosphate Synthases Expressed in Different Organs Are Localized into Three Subcellular Compartments in Arabidopsis", Plant Physiology, 122:1045-1056 (2000).

Oommen et al., "The Elicitor-Inducible Alfalfa Isoflavone Reductase Promoter Confers Different Patterns of Development Expression in Homologous and Heterologous Transgenic Plants", The Plant Cell, 6:1789-1803 (1994).

Oster et al., "The G4 Gene of *Arabidopsis thaliana* Encodes a Chlorophyll Synthase of Etiolated Plants", Bot. Acta, 110:420-423 (1997).

Peisker et al., "Phytol and the Breakdown of Chlorophyll in Senescent Leaves", J. Plant Physiol., 135:428-432 (1989).

Pompliano et al., "Probing Lethal Metabolic Perturbations in Plants with Chemical Inhibition of Dehydroquinate Synthase", J. Am. Chem. Soc., 111:1866-1871 (1989).

Porfirova et al., "Isolation of an *Arabidopsis* mutant lacking vitamin E and identification of a cyclase essential for all tocopherol biosynthesis", PNAS, 99(19):12495-12500 (2002).

Querol et al., "Functional analysis of the *Arabidopsis thaliana* GCPE protein involved in plastid isoprenoid biosynthesis", FEBS Letters, 514:343-346 (2002).

Rippert et al., "Molecular and biochemical characterization of an *Arabidopsis thaliana* arogenate dehydrogenase with two highly similar and active protein domains", Plant Mol. Biol., 48:361-368 (2002).

Rippert et al., "Engineering Plant Shikimate Pathway for Production of Tocotrienol and Improving Herbicide Resistance", Plant Physiology, 134:92-100 (2004).

Rodriguez-Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079-1089 (2002).

Rodriguez-Concepción et al., "1-Deoxy-D-xylulose 5-phosphate reductoisomerase and plastid isoprenoid biosynthesis during tomato fruit ripening", The Plant Journal, 27(3):213-222 (2001).

Rohdich et al., "Cytidine 5'-triphosphate-dependent biosynthesis of isoprenoids: YgbP protein of *Escherichia coli* catalyzes the formation of 4-diphosphocytidyl-2-C-methylerythritol", Proc. Natl. Acad. Sci. USA, 96(21):11758-11763 (1999).

Rohmer et al., "Glyceraldehyde 3-Phosphate and Pyruvate as Precursors of Isoprenic Units in an Alternative Non-mevalonate Pathway for Terpenoid Biosynthesis", J. Am. Chem. Soc., 118:2564-2566 (1996).

Rohmer et al., "Isoprenoid biosynthesis in bacteria: a novel pathway for the early steps leading to isopentenyl diphosphate", Biochem. J., 295:517-524 (1993).

Rohmer, M., "A Mevalonate-independent Route to Isopentenyl Diphosphate", Comprenhensive Natural Products Chemistry, 2:45-67 (1999).

Rohmer, M., "Isoprenoid biosynthesis via the mevalonate-independent route, a novel target for antibacterial drugs?", Progress in Drug Research, 50:136-154 (1998).

Röer et al., "Expression of the Genes Encoding the Early Carotenoid Biosynthesis Enzymes in *Capsicum Annuum*", Biochemical and Biophysical Research Communications, 196(3):1414-1421 (1993).

Ruzafa et al., "The protein encoded by the *Shewanella colwelliana melA* gene is a *p*-hydroxyphenylpyruvate dioxygenase", FEMS Microbiology Letters, 124:179-184 (1994).

Saint-Guily et al., "Complementary DNA Sequence of an Adenylate Translocator from *Arabidopsis thaliana*", Plant Physiol., 100(2):1069-1071 (1992).

Sandmann et al., "New functional assignment of the carotenogenic genes crtB and crtE with constructs of the these genes from *Erwinia* species", FEMS Microbiology Letters, 90:253-258 (1992).

Sato et al., "Structural Analysis of *Arabidopsis thaliana* Chromosomes 5. X. Sequence Features of the Regions of 3,076,755 bp Covered by Sixty P1 and TAC Clones", DNA Research, 7(1):31-63 (2000).

Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41-54 (1998).

Savidge et al., "Isolation and Characterization of Homogentisate Phytyltransferase Genes from *Synechocystis* sp. PCC 6803 and Arabidopsis", Plant Physiology, 129:321-332 (2002).

Schwender et al., "Cloning and heterologous expression of cDNA encoding 1-deoxy-D-xylulose-5-phosphate reductoisomerase of *Arabidopsis thaliana*", FEBS Letters, 455:140-144 (1999).

Scolnik et al., "Nucleotide Sequence of an *Arabidopsis* cDNA for Geranylgeranyl Pyrophosphate Synthase", Plant Physiol., 104(4):1469-1470 (1994).

Shewmaker et al., "Seed-specific overexpression of phytoene synthases: increase in carotenoids and other metabolic effects", The Plant Journal, 20(4):401-412 (1999).

Shigeoka et al., "Isolation and properties of γ-tocopherol methyltransferase in *Euglena gracilis*", Biochimica et Biophysica Acta, 1128:220-226 (1992).

Shintani et al., "Elevating the Vitamin E Content of Plants Through Metabolic Engineering", SCIENCE, 282:2098-2100 (1998).

Singh et al., "Chorismate Mutase Isoenzymes from *Sorghum bicolor*. Purification and Properties", Archives of Biochemistry and Biophysics, 243(2):374-384 (1985).

Smith, F.W. et al., "The cloning of two *Arabidopsis* genes belonging to a phosphate transporter family", Plant Journal, 11(1):83-92 (1997).

Smith, C.J.S. et al., "Artisense RNA inhibition of polygalacturonase gene expression in transgenic tomatoes", Nature, 334:724-726 (1998).

Smith, T.F. et al., The challenges of genome sequence annotation of "the devil in the details", Nature Biotechnology, 15:1222-1223 (1997).

Soll et al., "Hydrogenation of Geranylgeranoniol", Plant Physiol., 71:849-854 (1983).

Soll et al., "Tocopherol and Plastoquinone Synthesis in Spinach Chloroplasts Subfractions", Archives of Biochemistry and Biophysics, 204(2):544-550 (1980).

Soll et al., "2-Methyl-6-Phytylquinol and 2,3-Dimethyl-5-Phytylquinol as Precursors of Tocopherol Synthesis in Spinach Chloroplasts", Phytochemistry, 19:215-218 (1980).

Sprenger et al., "Identification of a thiamin-dependent synthase in *Escherichia coli* required for the formation of the 1-deoxy-D-xylulose 5-phosphate precursor to isoprenoids, thiamin, and pyridoxol", Proc. Natl. Acad. Sci. USA, 94:12857-12862 (1997).

Spurgeon et al., "Biosynthesis of Isoprenoid Compounds", 1:1-45 (1981).

Stam et al.., "The Silence of Genes in Transgenic Plants", Annals of Botany, 79:3-12 (1997).

Stocker et al., "Identification of the Tocopherol-Cyclase in the Blue-Green Algae *Anabaena variabilis* Kützing (Cyanobacteria)", Helvetica Chimica Acta, 76:1729-1738 (1993).

Stocker et al., "The Substrate Specificity of Tocopherol Cyclase", Bioorganic & Medicinal Chemistry, 4(7):1129-1134 (1996).

Sun et al., "Cloning and Functional Analysis of the β-Carotene Hydroxylase of *Arabidopsis thaliana*", The Journal of Biological Chemistry, 271(40):24349-24352 (1996).

Suzich et al., "3-Deoxy-D-arabino-Heptulosonate 7-Phosphate Synthase from Carrot Root (*Daucus carota*) is a Hysteretic Enzyme", Plant Physiol., 79:765-770 (1985).

Svab et al., "High-frequency plastid transformation in tobacco by selection for a chimeric *aadA* gene", Proc. Natl. Acad. Sci. USA, 90:913-917 (1993).

Svab et al., "Stable transformation of plastids in higher plants", Proc. Natl. Sci. USA, 87:8526-8530 (1990).

Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis", Proc. Natl. Acad. Sci. USA, 95:9879-9884 (1998).

Takatsuji, "Zinc-finger transcription factors in plants", CMLS Cell. Mol. Life Sci., Birkhauser Verlag Basel CH, 54(6):582-596 (1998).

Tjaden et al., "Altered plastidic ATP/ADP-transporter activity influences potato (*Solanum tubersomum* L.) tuber morphology, yield and composition of tuber starch", The Plant Journal, 16(5):531-540 (1998).

Town et al., "Whole genome shotgun sequencing of *Brassica oleracea*, BOGKS71TR BOGK *Brassica oleracea* genomic clone BOGKS71, DNA sequence", Database EMBL Accession No. BH534089 (Dec. 2001).

Town et al, "Whole genome shotgun sequencing of *Brassica oleracea*, BOGAU46TR BOGA *Brassica oleracea* genomic clone BOGAU46, DNA sequence", Database EMBL Accession No. BH248880 (Nov. 2001).

Verwoert et al., "Development specific expression and organelle targeting of the *Escherichia coli* fabD gene, encoding malonyl coenzyme A-acyl carrier protein transacylase in transgenic rape and tobacco seeds", Plant Molecular Biology, 26:189-202 (1994).

Xia et al., "A monofunctional prephenate dehydrogenase created by cleavage of the 5' 109 bp of the *tyrA* gene from *Erwinia herbicola*", Journal of General Microbiology, 138(7):1309-1316 (1992).

Xia et al., "The *pheA/ tyrA/ aroF* Region from *Erwinia herbicola*: An Emerging Comparative Basis for Analysis of Gene Organization and Regulation in *Enteric* Bacteria", Database GENBANK on STN, GenBank Acc. No. (GBN): M74133, J. Mol. Evol., 36(2)107-120 (Abstract) (1993).

Yamamoto, E., "Purification and Metal Requirements of 3-Dehydroquinate Synthase from *Phaseolus mungo* Seedlings", Phytochemistry, 19:779-781 (1980).

Zaka et al., "Changes in Carotenoids and Tocopherols During Maturation of *Cassia* Seeds", Pakistan J. Sci. Ind. Res., 30(11): 812-814 (1987).

Zeidler et al., "Inhibition of the Non-Mevalonate 1-Deoxy-D-xylulose-5-phosphate Pathway of Plant Isoprenoid Biosynthesis by Fosmidomycin", A Journal of Biosciences, Zeitshrift fuer Naturforschung, Section C, 53(11/12):980-986 (Nov./Dec. 1998).

Zhu et al., "Geranylgeranyl pyrophosphate synthase encoded by the newly isolated gene *GGPS6* from *Arabidopsis thaliana* is localized in mitochondria", Plant Molecular Biology, 35:331-341 (1997).

Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357-361 (1997).

Kaneko et al., NCBI General Identifier No. 1653572, Accession No. BAA18485 (Jul. 2001).

Kaneko et al., NCBI General Identifier No. 1001725, Accession No. BAA10562 (Feb. 2003).

Alcala et al., Genbank Accession No. AI 897027 (Jul. 1999).

Bevan et al., Database EMBL, Accession No. AL035394 (Feb. 1999).

Bevan et al., TREMBL Database Accession No. O65524 (Aug. 1998).

Campos et al., NCBI General Identifier BAA 18485, Database EMBL, Accession No.: AF148852, (2000).

Chen et al., EMBL Sequence Database Accession No. AI995392 (Sep. 1999).

Desprez et al., Database EMBL, Accession No. Z34566 (Jun. 1994).

Fedenko et al., Abstract: RU 2005353, Derwent Accession No. 1994-253787.

Gaubier et al., Database EMBL, Accession No. Q38833 (Nov. 1996).

Kaneko et al., Database EMBL, Accession No. P73726 (Feb. 1997).

Kaneko et al., Database EMBO, Accession No. P73962 (Jul. 1998).

Kaneko et al., EMBL Sequence Database Accession No. D90909 (Oct. 1996).

Kaneko et al., TREMBL Database Accession No. P73727 (Feb. 1997).

Lange et al., "Mentha x Piperita 1-deoxy-D-xylulose-5-phosphate Reductoisomerase (DXR) mRNA", complete cds, Entrez Report, Accession No. AF116825 (Apr. 1999).

Lin et al., Database EMBL, Accession No. AC003672 (Dec. 1997).

Lin et al., Database EMBL, Accession No. AC003673 (Dec. 1997).

Lin et al., Database EMBL, Accession No. AC004077 (Feb. 1998).

Malakhov et al., Database TREMBL, Accession No. Q55207 (Nov. 1996).

Murata et al., EMBL Sequence Database Accession No. D13960 (Mar. 1996).

Nakamura et al., Database EMBL, Accession No.: AB009053, Abstract (Dec. 1997) (1998)(2000).

Nakamura et al., Database EMBL, Accession No.: AB005246 (Jul. 1997).

Newman et al., Database EMBL, Accession No.: AA586087, Abstract (Sep. 1997).

Newman et al., Database EMBL, Accession No. R30625 (Aug. 1995).

Newman et al., Database EMBL, Accession No. T44803 (Feb. 1995).

Newman et al., Debest ID:1262303, Entrez Report, Accession No.: AA586087 (Sep. 1997).

Oster et al., Database Biosis, Accession No. PREV199800047824 (Oct. 1997).

Ouyang et al., Database EMBL, Accession No. AF381248 (Jan. 2003).

Rounsley et al., Database EMBL, Accession No. B24116 (Oct. 1997).

Rounsley et al., Database EMBL, Accession No. B29398 (Oct. 1997).

Rounsley et al., Database TREMBL, Accession No. O64684 (Aug. 1998).

Schwender et al., *Arabidopsis thaliana* mRNA for Partial 1-deoxy-d-xylulose-5-phosphate Reductoisomerase (dxr gene), Entrez Report, Accession No.: AJ242588 (Aug. 1999).

Scolnik et al., Database EMBL, Accession No. L40577 (Apr. 1995).

Shintani et al., Database NCBI, Accession No. AF104220 (Jan. 1999).

Shoemaker et al., Database EMBL, Accession No. AI748688 (Jun. 1999).

Shoemaker et al., Database EMBL, Accession No. AI938569 (Aug. 1999).

Shoemaker et al., Database EMBL, Accession No. AI988542 (Sep. 1999).
Shoemaker et al., Database EMBL, Accession No. AW306617 (Jan. 2000).
Tabata et al., Database EMBL, Accession No. D64001 (Sep. 1995).
Tabata et al., Database EMBL, Accession No. D64006 (Sep. 1995).
Tabata et al., Database EMBL, Accession No. D90909 (Oct. 1996).
Tabata et al., Database EMBL, Accession No. D90911 (Oct. 1996).
Tabata et al., Database EMBL, Accession No. Q55145 (Nov. 1996).
Tabata et al., Database EMBL, Accession No. Q55500 (Nov. 1996).
Walbot, V., Database EMBL, Accession No. AI795655 (Jul. 1999).
Wing et al., Database EMBL, Accession No. AQ690643 (Jul. 1999).
XIA et al., Database EMBL, Accession No. M74133 (Jun. 1993).
Bevan et al., Accession T4 8445.
International Search Report, PCT/US00/10367, pp. 1-5 (Sep. 15, 2000).
International Search Report, PCT/US00/10368, pp. 1-14 (Jun. 15, 2001).
Written Opinion, PCT/US00/10368, pp. 1-6 (May 9, 2002).
Iper, PCT/US00/10368, pp. 1-5 (Aug. 16, 2002).
Examination Report, New Zealand Patent Application No. 514600, based on PCT/US/00/10368, pp. 1-2 (Apr. 24, 2003).
Communication pursuant to Article 96(2) EPC, EP Application 00922287.8, based on PCT/US00/10368, pp. 1-6 (Oct. 17, 2003).
Examiner's Report No. 2, Australia Patent Application No. 42492/00, based on PCT/US00/10368, pp. 1-4 (Nov. 12, 2003).
International Search Report, PCT/US01/12334, pp. 1-5 (Apr. 5, 2002).
International Search Report, PCT/US01/24335, pp. 1-8 (Mar. 6, 2003).
International Search Report, PCT/US01/42673, pp. 1-4.
International Search Report, PCT/US02/03294, pp. 1-4 (Mar. 19, 2003).
International Search Report, PCT/US02/13898, pp. 1-3 (Sep. 13, 2002).
IPER, PCT/US02/13898, pp. 1-4 (Apr. 24, 2003).
International Search Report, PCT/US02/14445, pp. 1-6 (Oct. 30, 2003).
International Search Report, PCT/US02/26047, pp. 1-5 (Dec. 5, 2003).
International Search Report, PCT/US02/34079, pp. 1-5 (Jul. 28, 2003).
Written Opinion, PCT/US02/34079, pp. 1-4 (Oct. 23, 2003).
Response to Written Opinion, PCT/US02/34079, pp. 1-6 (Dec. 22, 2003).
Sir 1736 cyanobase www.kazusa.com.
Database EMBL, Oct. 1, 2000, Q9LY74, abstract.
Database EMBL, Jul. 17, 2001, AB054257, abstract.
Soll et al., "Localization and synthesis of prenylquinones in isolated outer and inner envelope membranes from spinach chloroplasts," *Archives of Biochemistry and Biophysics*, NY, 238:290-299, 1985.
Bowie et al., "Deciphering the Message in Protein Sequences: Tolerance to Amino Acid Substitutions", Science, 247:1306-1310 (1990).
McConnell et al., "Role of *Phabulosa* and *Phavoluta* in determining radial patterning in shoots", 411(6838): 709-713 (2001).
Baker et al., NCBI Accession No. X64451 (Dec. 1993).
Karumanandaa et al., "Metabolically enhanced oilseed crops with enhanced seed tocopherol," *Metabol. Eng.*, 4:384-400, 2005.
Savidge et al., "Isolation and characterization of homogentisate phytyltransferase genes from synechocystis sp. PCC 6803 and arabidopsis," *Plant Physio.*, 129:321-332, 2002.
Valentin et al., "The *Arabidopsis* vitamin E pathway gene5-1 mutant reveals a critical role for phytol kinase in seed tocopherol biosynthesis," *Plant Cell*, 18:212, 224, 2005.
Van Eenennaam et al., "Elevation of seed α-tocopherol levels using plant-based transcription factors targeted to an endogenous locus," *Metabol. Eng.*, 6:101-108, 2004.
Van Eenennaam et al., "Engineering vitamin E content: from arabidopsis mutant soy oil," *The Plant Cell*, 15:3007-3019, 2003.

* cited by examiner

```
Query= Arabidopsis TMT2
        (338 letters)

Score      E
Sequences producing significant alignments:             (bits)   Value Brassica1 - LIB4153-013-R1-K1-B7                         668      0.0
Brassica2 - LIB80-011-Q1-E1-E9                           668      0.0
Glycine max TMT2 - LIB3049-032-Q1-E1-G8                  569     e-166
Gossypium hirsutum TMT2 -LIB3272-054-P1-K1-C11           564     e-164
Allium Porrum - Lib4521-015-Q1-K1-D6                     520     e-151
Zea mays TMT2- LIB3587-273-Q1-K6-C5/LIB3600-046-Q1-K6-G1 508     e-148
Oryza sativa TMT2 - LIB4371-041-R1-K1-F7                 506     e-147

>Brassica1 - LIB4153-013-R1-K1-B7 Length = 337
 Score =  668 bits (1706), Expect = 0.0
 Identities = 322/339 (94%), Positives = 328/339 (95%), Gaps = 3/339 (0%)

>Brassica2 - LIB80-011-Q1-E1-E9 Length = 337
 Score =  668 bits (1706), Expect = 0.0
 Identities = 322/339 (94%), Positives = 328/339 (95%), Gaps = 3/339 (0%)

>Glycine max TMT2 - LIB3049-032-Q1-E1-G8 Length = 342
 Score =  569 bits (1450), Expect = e-166
 Identities = 276/346 (79%), Positives = 298/346 (85%), Gaps = 12/346 (3%)

>Gossypium hirsutum TMT2 -LIB3272-054-P1-K1-C11 Length = 341
 Score =  564 bits (1437), Expect = e-164
 Identities = 274/345 (79%), Positives = 297/345 (85%), Gaps = 11/345 (3%)

>Allium Porrum - Lib4521-015-Q1-K1-D6 Length = 344
 Score =  520 bits (1325), Expect = e-151
 Identities = 261/352 (74%), Positives = 289/352 (81%), Gaps = 22/352 (6%)

>Zea mays TMT2- LIB3587-273-Q1-K6-C5/LIB3600-046-Q1-K6-G1 Length = 352
 Score =  508 bits (1293), Expect = e-148
 Identities = 243/329 (73%), Positives = 276/329 (83%), Gaps = 5/329 (1%)

>Oryza sativa TMT2 - LIB4371-041-R1-K1-F7 Length = 348
 Score =  506 bits (1288), Expect = e-147
 Identities = 247/333 (74%), Positives = 279/333 (83%), Gaps = 7/333 (2%)
```

*Fig. 2*

```
                                                                      50
SEQ ID NO.  22         corn  MAMAST.YAP  GGGARA.LAQ  GRCRVRGPAG  LGFLGPS.KA  AGLPRPLALA
SEQ ID NO.  26         rice  MAMASSAYAP  AGGVGTHSAP  G..RIRPPRG  LGF...S.TT  TTKSRPLVLT
SEQ ID NO.  27    Brassical  ~~MASLML..  .NGAITF...  .......PKG  LGFPASNLHA  R..PSPPLSL
SEQ ID NO.  28  ArabidopsisT ~~MASLML..  .NGAITF...  .......PKG  LGSPGSNLHA  RSIPRPTLLS
SEQ ID NO.  23       Cotton  ~~MASSML..  .NGAETFT..  .LIRGVTPKS  IGFLGSGLHG  KQFS..SAGL
SEQ ID NO.  25          soy  ~~MGSVML..  .SGTEKLT..  .L.RTLTGNG  LGFTGSDLHG  KNFPRVSFAA
SEQ ID NO.  24         Leek  ~~MASSML..  .SGAESLS..  .MLRIHHQPK  LTFSSPSLHS  KPTNLKMDLI
SEQ ID NO. 108    Consensus  --M-S-----  --G-------  ----------  ----------  ----------

51                                                     100
SEQ ID NO.  22         corn  LARRMSSPVA  VGARLRCAAS  SSPAAARPAT  APRFIQHKKE  AFWFYRFLSI
SEQ ID NO.  26         rice  RRGGGGGNIS  V.ARLRCAAS  SSSAAARPMS  QPRFIQHKKE  AFWFYRFLSI
SEQ ID NO.  27    Brassical  VSNTATRRL.  .SVATRCSSS  SSVSASRPSA  QPRFIQHKKE  AYWFYRFLSI
SEQ ID NO.  28  ArabidopsisT VTRTSTPRL.  .SVATRC.SS  SSVSSSRPSA  QPRFIQHKKE  AYWFYRFLSI
SEQ ID NO.  23       Cotton  IYSPKMSRVG  TTIAPRC...  .SLSASRPAS  QPRFIQHKKE  AFWFYRFLSI
SEQ ID NO.  25          soy  TTSAKVPNFR  SIVVPKC...  .SVSASRPSS  QPRFIQHKKE  AFWFYRFLSI
SEQ ID NO.  24         Leek  PFATKHQKTK  KASIFTCSAS  SS...SRPAS  QPRFIQHKQE  AFWFYRFLSI
SEQ ID NO. 108    Consensus  ----------  ------C---  -S----RP--  -PRFIQHK-E  A-WFYRFLSI 101                                                    150
SEQ ID NO.  22         corn  VYDHVINPGH  WTEDMRDDAL  EPADLFSRHL  TVVDVGGGTG  FTTLGIVKHV
SEQ ID NO.  26         rice  VYDHVINPGH  WTEDMRDDAL  EPADLYSRKL  RVVDVGGGTG  FTTLGIVKRV
SEQ ID NO.  27    Brassical  VYDHIINPGH  WTEDMRDDAL  EPADLSHPDM  RVVDVGGGTG  FTTLGIVKTV
SEQ ID NO.  28  ArabidopsisT VYDHVINPGH  WTEDMRDDAL  EPADLSHPDM  RVVDVGGGTG  FTTLGIVKTV
SEQ ID NO.  23       Cotton  VYDHVINPGH  WTEDMRDDAL  EPADLNDRDM  VVVDVGGGTG  FTTLGIVQHV
SEQ ID NO.  25          soy  VYDHVINPGH  WTEDMRDDAL  EPADLNDRNM  IVVDVGGGTG  FTTLGIVKHV
SEQ ID NO.  24         Leek  VYDHVINPGH  WTEDMRDDAL  EPAELYDSRM  KVVDVGGGTG  FTTLGIIKHI
SEQ ID NO. 108    Consensus  VYDH-INPGH  WTEDMRDDAL  EPA-L-----  -VVDVGGGTG  FTTLGI----

151                                                    200
SEQ ID NO.  22         corn  NPENVTLLDQ  SPHQLDKARQ  KEALKGVTIM  EGDAEDLPFP  TDSFDRYISA
SEQ ID NO.  26         rice  DPENVTLLDQ  SPHQLEKARE  KEALKGVTIM  EGDAEDLPFP  TDTFDRYVSA
SEQ ID NO.  27    Brassical  KAKNVTILDQ  SPHQLAKAKQ  KEPLKECKIV  EGDAEDLPFP  TDYADRYVSA
SEQ ID NO.  28  ArabidopsisT KAKNVTILDQ  SPHQLAKAKQ  KEPLKECKIV  EGDAEDLPFP  TDYADRYVSA
SEQ ID NO.  23       Cotton  DAKNVTILDQ  SPHQLAKAKQ  KEPLKECNII  EGDAEDLPFP  TDYADRYVSA
SEQ ID NO.  25          soy  DAKNVTILDQ  SPHQLAKAKQ  KEPLKECKII  EGDAEDLPFR  TDYADRYVSA
SEQ ID NO.  24         Leek  DPKNVTILDQ  SPHQLEKARQ  KEALKECTIV  EGDAEDLPFP  TDTFDRYVSA
SEQ ID NO. 108    Consensus  ---NVT-LDQ  SPHQL-KA--  KE-LK---I-  EGDAEDLPF-  TD--DRY-SA
```

*Fig. 3a*

```
                           201                                                              250
SEQ ID NO.  22       corn  GSIEYWPDPQ RGIKEAYRVL RFGGLACVIG PVYPTFWLSR FFADMWMLFP
SEQ ID NO.  26       rice  GSIEYWPDPQ RGIKEAYRVL RLGGVACMIG PVHPTFWLSR FFADMWMLFP
SEQ ID NO.  27   Brassica1 GSIEYWPDPQ RGIREAYRVL KIGGKACLIG PVIIPTFWLSR FFADVWMLFP
SEQ ID NO.  28 ArabidopsisT GSIEYWPDPQ RGIREAYRVL KIGGKACLIG PVYPTFWLSR FFSDVWMLFP
SEQ ID NO.  23     Cotton  GSIEYWPDPQ RGIKEAYRVL KQGGKACLIG PVYPTFWLSR FFADVWMLFP
SEQ ID NO.  25        soy  GSIEYWPDPQ RGIKEAYRVL KLGGKACLIG PVYPTFWLSR FFADVWMLFP
SEQ ID NO.  24       Leek  GSIEYWPDPQ RGIKEAYRVL KLGGVACLIG PVHPTFWLSR FFADMWMLFP
SEQ ID NO. 108  Consensus  GSIEYWPDPQ RGI-EAYRVL --GG-AC-IG PV-PTFWLSR FF-D-WMLFP 251                                                              300
SEQ ID NO.  22       corn  KEEEYIEWFK KAGFRDVKLK RIGPKWYRGV RRHGLIMGCS VTGVKRERGD
SEQ ID NO.  26       rice  KEEEYIEWFK KAGFKDVKLK RIGPKWYRGV RRHGLIMGCS VTGVKREHGD
SEQ ID NO.  27   Brassica1 KEEEYIEWFK NAGFKDVQLK RIGPKWYRGV RRHGLIMGCS VTGVKPASGD
SEQ ID NO.  28 ArabidopsisT KEEEYIEWFK NAGFKDVQLK RIGPKWYRGV RRHGLIMGCS VTGVKPASGD
SEQ ID NO.  23     Cotton  KEEEYIEWFE KAGFKDVQLK RIGPKWYRGV RRHGLIMGCS VTGVKPASGD
SEQ ID NO.  25        soy  KEEEYIEWFQ KAGFKDVQLK RIGPKWYRGV RRHGLIMGCS VTGVKPASGD
SEQ ID NO.  24       Leek  TEEEYIEWFK KAGFKDVKLK RIGPKWYRGV RRHGLIMGCS VTGVKRLSGD
SEQ ID NO. 108  Consensus  -EEEYIEWF- -AGF-DV-LK RIGPKWYRGV RRHGLIMGCS VTGVK---GD 301                                                              350
SEQ ID NO.  22       corn  SPLELGPKAE DVSKPV.NPI TFLFRFLVGT ICAAYYVLVP IYMWIKDQIV
SEQ ID NO.  26       rice  SPLQLGPKVE DVSKPV.NPI TFLFRFLMGT ICAAYYVLVP IYMWIKDQIV
SEQ ID NO.  27   Brassica1 SPLQLGPKEE DVEKPVNNPF SFLGRFLLGT LAAAWFVLIP IYMWIKDQIV
SEQ ID NO.  28 ArabidopsisT SPLQLGPKEE DVEKPVNNPF SFLGRFLLGT LAAAWFVLIP IYMWLKDQIV
SEQ ID NO.  23     Cotton  SPLQLGPKAE DVSKPV.NPF VFLLRFMLGA TAAAYYVLVP IYMWIKDQIV
SEQ ID NO.  25        soy  SPLQLGPKEE DVEKPV.NPF VFALRFVLGA LAATWFVLVP IYMWLKDQVV
SEQ ID NO.  24       Leek  SPLQLGPKAE DVKKPI.NPF SFLLRFILGT IAATYYVLVP IYMWIKDQIV
SEQ ID NO. 108  Consensus  SPL-LGPK-E DV-KP--NP- -F--RF--G- --A---VL-P IYMW-KDQ-V 351
SEQ ID NO.  22       corn  PKGMPI
SEQ ID NO.  26       rice  PKGMPI
SEQ ID NO.  27   Brassica1 PKDQPI
SEQ ID NO.  28 ArabidopsisT PKDQPI
SEQ ID NO.  23     Cotton  PEGQPI
SEQ ID NO.  25        soy  PKGQPI
SEQ ID NO.  24       Leek  PKGQPI
SEQ ID NO. 108  Consensus  P---PI
```

*Fig. 3b*

TOCOPHEROL METHYLTRANSFERASE TMT2 AND USES THEREOF

This application claims the benefit of and priority to U.S. Provisional Application No. 60/330,563, filed Oct. 25, 2001, which is herein incorporated by reference in its entirety.

The present invention is in the field of plant genetics and biochemistry. More specifically, the invention relates to genes associated with the tocopherol biosynthesis pathway, namely those encoding methyltransferase activity, and uses of such genes.

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.* 16:321–347 (1996)). Tocopherol functions, in part, by stabilizing the lipid bilayer of biological membranes (Skrypin and Kagan, *Biochim. Biophys. Acta* 815:209 (1995); Kagan, N. Y. *Acad. Sci.* p 121, (1989); Gomez-Fernandez et al., *Ann. N.Y. Acad. Sci.* p 109 (1989)), reducing polyunsaturated fatty acid (PUFA) free radicals generated by lipid oxidation (Fukuzawa et al., *Lipids* 17:511–513 (1982)), and scavenging oxygen free radicals, lipid peroxy radicals and singlet oxygen species (Diplock et al. *Ann. N Y Acad. Sci.* 570:72 (1989); Fryer, *Plant Cell Environ.* 15(4): 381–392 (1992)).

The compound α-tocopherol, which is often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E", vitamin E is more appropriately defined chemically as α-tocopherol. Vitamin E, or α-tocopherol, is significant for human health, in part because it is readily absorbed and retained by the body, and therefore has a higher degree of bioactivity than other tocopherol species (Traber and Sies, *Annu. Rev. Nutr.* 16:321–347 (1996)). However, other tocopherols such as β, γ, and δ-tocopherols also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10–50 μg of total tocopherols per gram fresh weight, but most of the world's major staple crops (e.g., rice, corn, wheat, potato) produce low to extremely low levels of total tocopherols, of which only a small percentage is α-tocopherol (Hess, Vitamin E, α-tocopherol, *Antioxidants in Higher Plants*, R. Alscher and J. Hess, Eds., CRC Press, Boca Raton. pp. 111–134 (1993)). Oil seed crops generally contain much higher levels of total tocopherols, but α-tocopherol is present only as a minor component in most oilseeds (Taylor and Barnes, *Chemy Ind.*, Oct:722–726 (1981)).

The recommended daily dietary intake of 15–30 mg of vitamin E is quite difficult to achieve from the average American diet. For example, it would take over 750 grams of spinach leaves, in which α-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased α-tocopherol levels in crops have been associated with enhanced stability and extended shelf life of plant products (Peterson, *Cereal-Chem.* 72(1):21–24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.* 65(4):503–507 (1994); Buckley et al., *J. of Animal Science* 73:3122–3130 (1995)).

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methylphytylplastoquinol (Fiedler et al., *Planta* 155:511–515 (1982); Soll et al., *Arch. Biochem. Biophys.* 204:544–550 (1980); Marshall et al., *Phytochem.* 24:1705–1711 (1985)). This plant tocopherol pathway can be divided into four parts: 1) synthesis of homogentisic acid (HGA), which contributes to the aromatic ring of tocopherol; 2) synthesis of phytylpyrophosphate, which contributes to the side chain of tocopherol; 3) joining of HGA and phytylpyrophosphate via a prenyltransferase followed by a subsequent cyclization; 4) and S-adenosyl methionine dependent methylation of an aromatic ring, which affects the relative abundance of each of the tocopherol species. See FIG. 1.

Various genes and their encoded proteins that are involved in tocopherol biosynthesis are listed in the table below.

| Gene ID or Enzyme Abbreviation | Enzyme name |
|---|---|
| tyrA | Bifunctional Prephenate dehydrogenase |
| HPT | Homogentisate phytyl transferase |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| IDI | Isopentenyl diphosphate isomerase |
| MT1 | Methyl transferase 1 |
| tMT2 | Tocopherol methyl transferase 2 |
| GGH | Geranylgeranyl diphosphate reductase |
| slr1737 | Tocopherol cyclase |
| GMT | Gamma Methyl Transferase |

As used herein, homogentisate phytyl transferase (HPT), phytylprenyl transferase (PPT), slr1736, and ATPT2, each refer to proteins or genes encoding proteins that have the same enzymatic activity.

Synthesis of Homogentisic Acid

Homogentisic acid is the common precursor to both tocopherols and plastoquinones. In at least some bacteria the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and *Escherichia coli*. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediate arogenate. Since pathways involved in homogentisic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221–R233 (1998); Rohmer, *Prog. Drug. Res.*, 50:135–154 (1998); Rohmer, *Comprehensive Natural Products Chemistry*, Vol. 2, pp. 45–68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J*, 295:517–524 (1993); Schwarz, Ph.D. thesis, Eidgenössiche Technische Hochschule, Zurich, Switzerland (1994)). Recent studies showed the formation of 1-deoxyxylulose 5-phosphate (Broers, Ph.D. thesis (Eidgenössiche Technische Hochschule, Zurich, Switzerland) (1994)) from one molecule each of glyceraldehyde 3-phosphate (Rohmer, *Comprehensive Natural Products Chemistry*, Vol. 2, pp. 45–68, Barton and Nakanishi, eds., Pergamon Press, Oxford, England (1999)) and pyruvate (Eisenreich et al., *Chem. Biol.*, 5:R223–R233 (1998); Schwarz supra; Rohmer et al., *J. Am. Chem. Soc.*, 118:2564–2566 (1996); and Sprenger et al., *Proc. Natl. Acad. Sci. USA*, 94:12857–12862 (1997)) by an enzyme encoded by the dxs gene (Lois et al., *Proc. Natl. Acad. Sci. USA*, 95:2105–2110 (1997); and Lange et al., *Proc. Natl. Acad. Sci. USA*, 95:2100–2104 (1998)). 1-Deoxyxylulose 5-phosphate can be further converted into 2-C-methylerythritol 4-phosphate (Arigoni et al., *Proc. Natl. Acad. Sci. USA*, 94:10600–10605 (1997)) by a reductoisomerase encoded by the dxr gene (Bouvier et al., *Plant Physiol*, 117:1421–1431 (1998); and Rohdich et al., *Proc. Natl. Acad. Sci. USA*, 96:11758–11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phosphocytidyl-2C-methyl-D-erythritol into 2C-methyl-D-erythritol, 3,4-cyclophosphate. These genes are tightly linked on the *E. coli* genome (Herz et al., *Proc. Natl. Acad. Sci. U.S.A.*, 97(6):2485–2490 (2000)).

Once IPP is formed by the MEP pathway, it is converted to GGDP by GGDP synthase, and then to phytylpyrophosphate, which is the central constituent of the tocopherol side chain.

Combination and Cyclization

Homogentisic acid is combined with either phytyl-pyrophosphate or solanyl-pyrophosphate by phytyl/prenyl transferase forming 2-methylphytyl plastoquinol or 2-methylsolanyl plastoquinol, respectively. 2-methylsolanyl plastoquinol is a precursor to the biosynthesis of plastoquinones, while 2-methylphytyl plastoquinol is ultimately converted to tocopherol.

Methylation of the Aromatic Ring

The major structural difference between each of the tocopherol subtypes is the position of the methyl groups around the phenyl ring. Both 2-methylphytyl plastoquinol and 2-methylsolanyl plastoquinol serve as substrates for the plant enzyme 2-methylphytylplatoquinol/2-methylsolanylplastoquinol methyltransferase (Tocopherol Methyl Transferase 2; Methyl Transferase 2; MT2; tMT2), which is capable of methylating a tocopherol precursor. Subsequent methylation at the 5 position of γ-tocopherol by γ-tocopherol methyl-transferase (GMT) generates the biologically active α-tocopherol.

A possible alternate pathway for the generation of α-tocopherol involves the generation of δ-tocopherol via the cyclization of 2-methylphytylplastoquinol by tocopherol cyclase. δ-tocopherol is then converted to β-tocopherol via the methylation of the 5 position by GMT. δ-tocopherol can be converted to α-tocopherol via methylation of the 3 position by tMT2, followed by methylation of the 5 position by GMT. In a possible alternative pathway, β-tocopherol is directly converted to α-tocopherol by tMT2 via the methylation of the 3 position (see, for example, *Biochemical Society Transactions*, 11:504–510 (1983); *Introduction to Plant Biochemistry*, $2^{nd}$ edition, chapter 11 (1983); *Vitamin Hormone*, 29:153–200 (1971); *Biochemical Journal*, 109: 577 (1968); and, *Biochemical and Biophysical Research Communication*, 28(3):295 (1967)). Since all potential mechanisms for the generation of α-tocopherol involve catalysis by tMT2, plants that are deficient in this activity accumulate δ-tocopherol and β-tocopherol. Plants which have increased tMT2 activity tend to accumulate γ-tocopherol and α-tocopherol. Since there is no GMT activity in the seeds of many plants, these plants tend to accumulate γ-tocopherol.

There is a need in the art for nucleic acid molecules encoding enzymes involved in tocopherol biosynthesis, as well as related enzymes and antibodies for the enhancement or alteration of tocopherol production in plants. There is a further need for transgenic organisms expressing those nucleic acid molecules involved in tocopherol biosynthesis, which are capable of nutritionally enhancing food and feed sources.

BRIEF SUMMARY OF THE INVENTION

The present invention includes and provides a substantially purified nucleic acid molecule encoding a tMT2 enzyme.

The present invention includes and provides a substantially purified nucleic acid molecule comprising a nucleotide sequence selected from the group consisting of SEQ ID NOs: 1 and 2.

The present invention includes and provides a substantially purified nucleic acid molecule comprising a nucleotide sequence selected from the group consisting of SEQ ID NOs: 3 through 7.

The present invention includes and provides a substantially purified nucleic acid molecule comprising a nucleotide sequence selected from the group consisting of SEQ ID NOs: 8 through 14.

The present invention includes and provides a substantially purified nucleic acid molecule encoding a plant polypeptide molecule having 2-Methylphytylplastoquinol methyltransferase activity.

The present invention includes and provides a substantially purified plant polypeptide molecule having 2-Methylphytylplastoquinol methyltransferase activity.

The present invention includes and provides a substantially purified mutant polypeptide molecule having an altered 2-Methylphytylplastoquinol methyltransferase activity relative to a non-mutant polypeptide.

The present invention includes and provides a substantially purified polypeptide molecule comprising an amino acid sequence selected from the group consisting of SEQ ID NOs: 16 and 28.

The present invention includes and provides a substantially purified polypeptide molecule comprising an amino acid sequence selected from the group consisting of SEQ ID NOs: 17 through 21 and 29 through 32.

The present invention includes and provides a substantially purified polypeptide molecule comprising an amino acid sequence selected from the group consisting of SEQ ID NO: 22 through 27 and 33 through 38.

The present invention includes and provides an antibody capable of specifically binding a polypeptide comprising an amino acid sequence selected from the group consisting of SEQ ID NOs: 16 through 38.

The present invention includes and provides a transformed plant comprising an introduced nucleic acid molecule comprising a nucleic acid sequence selected from the group consisting of SEQ ID NOs: 1, 2, 8 through 15, and complements thereof.

The present invention includes and provides a transformed plant comprising an introduced nucleic acid molecule that encodes a polypeptide molecule comprising an amino acid sequence selected from the group consisting of SEQ ID NOs: 16, 22 through 28, and 33 through 38.

The present invention includes and provides a transformed plant comprising a nucleic acid molecule that encodes a polypeptide molecule comprising an amino acid sequence selected from the group consisting of SEQ ID NOs: 17 through 21, and 29 through 32.

The present invention includes and provides a transformed plant comprising an introduced first nucleic acid molecule comprising a sequence selected from the group consisting of SEQ ID NOs: 1, 2, 8 through 15, and complements thereof, and an introduced second nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase.

The present invention includes and provides a transformed plant comprising an introduced first nucleic acid molecule that encodes a polypeptide molecule comprising an amino acid sequence selected from the group consisting of SEQ ID NOs: 16, 22 through 28, 33 through 38, and an introduced second nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase.

The present invention includes and provides a transformed plant comprising an introduced first nucleic acid molecule comprising a nucleic acid sequence selected from the group consisting of SEQ ID NOs: 1, 2, 8 through 15, and complements thereof and an introduced second nucleic acid molecule comprising a sequence selected from the group consisting of SEQ ID NOs: 39 through 54, and complements thereof.

The present invention includes and provides a transformed plant comprising an introduced first nucleic acid molecule that encodes a polypeptide molecule comprising an amino acid sequence selected from the group consisting of SEQ ID NOs: 16, 22 through 28, 33 through 38, and an introduced second nucleic acid molecule having a sequence selected from the group consisting of SEQ ID NOs: 39 through 54, and complements thereof.

The present invention includes and provides a method for reducing expression of the tMT2 gene in a plant comprising: (A) transforming a plant with a nucleic acid molecule, said nucleic acid molecule having an introduced promoter region which functions in plant cells to cause the production of a mRNA molecule, wherein said introduced promoter region is linked to a transcribed nucleic acid molecule having a transcribed strand and a non-transcribed strand, wherein said transcribed strand is complementary to a nucleic acid molecule comprising a nucleic acid sequence selected from the group consisting of SEQ ID NOs: 1 through 15, and wherein said transcribed nucleic acid molecule is linked to a 3' non-translated sequence that functions in the plant cells to cause termination of transcription and addition of polyadenylated ribonucleotides to a 3' end of the mRNA sequence; and (B) growing said transformed plant.

The present invention includes and provides a transformed plant comprising a nucleic acid molecule comprising an introduced promoter region which functions in plant cells to cause the production of an mRNA molecule, wherein said introduced promoter region is linked to a transcribed nucleic acid molecule having a transcribed strand and a non-transcribed strand, wherein said transcribed strand is complementary to a nucleic acid molecule comprising a nucleic acid sequence selected from the group consisting of SEQ ID NOs: 1 through 15, and wherein said transcribed nucleic acid molecule is linked to a 3' non-translated sequence that functions in the plant cells to cause termination of transcription and addition of polyadenylated ribonucleotides to a 3' end of the mRNA sequence.

The present invention includes and provides a method of producing a plant having a seed with an increased γ-tocopherol level comprising: (A) transforming said plant with an introduced nucleic acid molecule, wherein said nucleic acid molecule comprises a sequence encoding a polypeptide molecule comprising an amino acid sequence selected from the group consisting of SEQ ID NOs: 16, 22 through 28, and 33 through 38; and (B) growing said transformed plant.

The present invention includes and provides a method of producing a plant having a seed with an increased γ-tocopherol level comprising: (A) transforming said plant with an introduced first nucleic acid molecule, wherein said first nucleic acid molecule comprises a nucleic acid sequence selected from the group consisting of SEQ ID NOs: 1, 2, 8 through 15, and an introduced second nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase; and (B) growing said transformed plant.

The present invention includes and provides a method of producing a plant having a seed with an increased γ-tocopherol level comprising: (A) transforming said plant with an introduced first nucleic acid molecule, wherein said first nucleic acid molecule comprises a sequence encoding a polypeptide molecule comprising an amino acid sequence selected from the group consisting of SEQ ID NOs: 16, 22 through 28, 33 through 38, and an introduced second nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase; and (B) growing said transformed plant.

The present invention includes and provides a method of producing a plant having a seed with an increased α-tocopherol level comprising: (A) transforming said plant with an introduced first nucleic acid molecule, wherein said first nucleic acid molecule comprises a nucleic acid sequence selected from the group consisting of SEQ ID NOs: 1, 2, 8 through 15, and an introduced second nucleic acid molecule comprising a sequence selected from the group consisting of SEQ ID NOs: 39 through 54, and complements thereof; and (B) growing said transformed plant.

The present invention includes and provides a method of producing a plant having a seed with an increased α-tocopherol level comprising: (A) transforming said plant with an introduced first nucleic acid molecule, wherein said first nucleic acid molecule comprises a sequence encoding a polypeptide molecule comprising an amino acid sequence selected from the group consisting of SEQ ID NOs: 16, 22 through 28, 33 through 38, and an introduced second nucleic acid molecule comprising a sequence selected from the group consisting of SEQ ID NOs: 39 through 54, and complements thereof; and (B) growing said transformed plant.

The present invention includes and provides a seed derived from a transformed plant comprising an introduced nucleic acid molecule comprising a nucleic acid sequence selected from the group consisting of SEQ ID NOs: 1, 2, and 8 through 15.

The present invention includes and provides a seed derived from a transformed plant comprising an introduced nucleic acid molecule comprising an introduced first nucleic acid sequence selected from the group consisting of SEQ ID NOs: 1, 2, 8 through 15, and an introduced second nucleic acid encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase.

The present invention includes and provides a seed derived from a transformed plant comprising an introduced first nucleic acid molecule comprising a nucleic acid sequence selected from the group consisting of SEQ ID NOs: 1, 2, 8 through 15, and an introduced second nucleic acid molecule comprising a sequence selected from the group consisting of SEQ ID NOs: 39 through 54.

The present invention includes and provides a transformed plant comprising an introduced first nucleic acid molecule comprising a sequence selected from the group consisting of SEQ ID NOs: 1, 2, 8 through 15, and complements thereof, and an introduced second nucleic acid molecule comprising a sequence selected from the group consisting of SEQ ID NOs: 39 through 54, and complements thereof, and an introduced third nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof, a plant ortholog thereof, and an antisense construct for homogentisic acid dioxygenase.

The present invention includes and provides a transformed plant comprising an introduced first nucleic acid molecule that encodes a polypeptide molecule comprising an amino acid sequence selected from the group consisting of SEQ ID NOs: 16, 22 through 28, 33 through 38, an introduced second nucleic acid molecule having a sequence selected from the group consisting of SEQ ID NOs: 39 through 54, and complements thereof, and an introduced third nucleic acid molecule encoding an enzyme selected from the group consisting of tyrA, slr1736, HPT, GMT, tocopherol cyclase, dxs, dxr, GGPPS, HPPD, AANT1, slr1737, IDI, GGH, and complements thereof.

The present invention includes and provides a transformed plant comprising an introduced first nucleic acid molecule encoding a tMT2 enzyme, and a second nucleic acid molecule encoding a GMT enzyme.

The present invention includes and provides a method of producing a plant having seed with an increased α-tocopherol level comprising: (A) transforming said plant with a nucleic acid molecule encoding a tMT2 enzyme and a nucleic acid molecule encoding a GMT enzyme; and (B) growing said plant.

BRIEF DESCRIPTION OF THE NUCLEIC AND AMINO ACID SEQUENCES

SEQ ID NO: 1 sets forth a nucleic acid sequence of a DNA molecule that encodes a wild type *Arabidopsis thaliana*, Columbia ecotype, tMT2 enzyme.

SEQ ID NO: 2 sets forth a nucleic acid sequence of a DNA molecule that encodes a wild type *Arabidopsis thaliana*, Landsberg ecotype, tMT2 enzyme.

SEQ ID NO: 3 sets forth a nucleic acid sequence of a DNA molecule that encodes an hdt2 mutant of the *Arabidopsis thaliana*, Landsberg ecotype, tMT2 enzyme.

SEQ ID NO: 4 sets forth a nucleic acid sequence of a DNA molecule that encodes an hdt6 mutant of the *Arabidopsis thaliana*, Columbia ecotype, tMT2 enzyme.

SEQ ID NO: 5 sets forth a nucleic acid sequence of a DNA molecule that encodes an hdt9 mutant of the *Arabidopsis thaliana*, Columbia ecotype, tMT2 enzyme.

SEQ ID NO: 6 sets forth a nucleic acid sequence of a DNA molecule that encodes an hdt10 mutant of the *Arabidopsis thaliana*, Landsberg ecotype, tMT2 enzyme.

SEQ ID NO: 7 sets forth a nucleic acid sequence of a DNA molecule that encodes an hdt16 mutant of the *Arabidopsis thaliana*, Columbia ecotype, tMT2 enzyme.

SEQ ID NO: 8 sets forth a nucleic acid sequence of a DNA molecule that encodes a *Zea mays* tMT2 enzyme.

SEQ ID NO: 9 sets forth a nucleic acid sequence of a DNA molecule that encodes a *Gossypium hirsutum* tMT2 enzyme.

SEQ ID NO: 10 sets forth a nucleic acid sequence of a DNA molecule that encodes an *Allium porrum* tMT2 enzyme.

SEQ ID NO: 11 sets forth a nucleic acid sequence of a DNA molecule that encodes a *Glycine max* tMT2 enzyme.

SEQ ID NO: 12 sets forth a nucleic acid sequence of a DNA molecule that encodes an *Oryza sativa* tMT2 enzyme.

SEQ ID NO: 13 sets forth a nucleic acid sequence of a DNA molecule that encodes a *Brassica napus* tMT2 enzyme.

SEQ ID NO: 14 sets forth a nucleic acid sequence of a DNA molecule that encodes a *Brassica napus* tMT2 enzyme different in sequence from SEQ ID NO: 13.

SEQ ID NO: 15 sets forth a nucleic acid coding sequence of a wild type *Arabidopsis thaliana* tMT2 enzyme.

SEQ ID NO: 16 sets forth an amino acid sequence of a wild type *Arabidopsis thaliana*, Columbia and Landsberg ecotype, tMT2 enzyme.

SEQ ID NO: 17 sets forth an amino acid sequence of an hdt2 mutant of the *Arabidopsis thaliana*, Landsberg ecotype, tMT2 enzyme.

SEQ ID NO: 18 sets forth an amino acid sequence of an hdt6 mutant of the *Arabidopsis thaliana*, Columbia ecotype, tMT2 enzyme.

SEQ ID NO: 19 sets forth an amino acid sequence of an hdt9 mutant of the *Arabidopsis thaliana*, Columbia ecotype, tMT2 enzyme.

SEQ ID NO: 20 sets forth an amino acid sequence of an hdt10 mutant of the *Arabidopsis thaliana*, Landsberg ecotype, tMT2 enzyme.

SEQ ID NO: 21 sets forth an amino acid sequence of an hdt16 mutant of the *Arabidopsis thaliana*, Columbia ecotype, tMT2 enzyme.

SEQ ID NO: 22 sets forth an amino acid sequence of a *Zea mays* tMT2 enzyme.

SEQ ID NO: 23 sets forth an amino acid sequence of a *Gossypium hirsutum* tMT2 enzyme.

SEQ ID NO: 24 sets forth an amino acid sequence of an *Allium porrum* tMT2 enzyme.

SEQ ID NO: 25 sets forth an amino acid sequence of a *Glycine max* tMT2 enzyme.

SEQ ID NO: 26 sets forth an amino acid sequence of an *Oryza sativa* tMT2 enzyme.

SEQ ID NO: 27 sets forth an amino acid sequence of a *Brassica napus* tMT2 enzyme.

SEQ ID NO: 28 sets forth an amino acid sequence of a mature wild type *Arabidopsis thaliana*, Columbia ecotype, tMT2 enzyme.

SEQ ID NO: 29 sets forth an amino acid sequence of a mature hdt2 mutant of the *Arabidopsis thaliana*, Landsberg ecotype, tMT2 enzyme.

SEQ ID NO: 30 sets forth an amino acid sequence of a mature hdt6 mutant of the *Arabidopsis thaliana*, Columbia ecotype, tMT2 enzyme.

SEQ ID NO: 31 sets forth an amino acid sequence of a mature hdt10 mutant of the *Arabidopsis thaliana*, Landsberg ecotype, tMT2 enzyme.

SEQ ID NO: 32 sets forth an amino acid sequence of a mature hdt16 mutant of the *Arabidopsis thaliana*, Columbia ecotype, tMT2 enzyme.

SEQ ID NO: 33 sets forth an amino acid sequence of a mature *Brassica napus* tMT2 enzyme.

SEQ ID NO: 34 sets forth an amino acid sequence of a mature *Oryza sativa* tMT2 enzyme.

SEQ ID NO: 35 sets forth an amino acid sequence of a mature *Zea mays* tMT2 enzyme.

SEQ ID NO: 36 sets forth an amino acid sequence of a mature *Glycine max* tMT2 enzyme.

SEQ ID NO: 37 sets forth an amino acid sequence of a mature *Allium porrum* tMT2 enzyme.

SEQ ID NO: 38 sets forth an amino acid sequence of a mature *Gossypium hirsutum* tMT2 enzyme.

SEQ ID NO: 39 sets forth a nucleic acid sequence of a DNA molecule that encodes an *Arabidopsis thaliana* γ-tocopherol methyltransferase.

SEQ ID NO: 40 sets forth a nucleic acid sequence of a DNA molecule that encodes an *Arabidopsis thaliana*, Columbia ecotype, γ-tocopherol methyltransferase.

SEQ ID NO: 41 sets forth a nucleic acid sequence of a DNA molecule that encodes an *Oryza sativa* γ-tocopherol methyltransferase.

SEQ ID NO: 42 sets forth a nucleic acid sequence of a DNA molecule that encodes a *Zea mays* γ-tocopherol methyltransferase.

SEQ ID NO: 43 sets forth a nucleic acid sequence of a DNA molecule that encodes a *Gossypium hirsutum* γ-tocopherol methyltransferase.

SEQ ID NO: 44 sets forth a nucleic acid sequence of a DNA molecule that encodes a *Cuphea pulcherrima* γ-tocopherol methyltransferase.

SEQ ID NO: 45 sets forth a nucleic acid sequence of a DNA molecule that encodes a *Brassica napus* S8 γ-tocopherol methyltransferase.

SEQ ID NO: 46 sets forth a nucleic acid sequence of a DNA molecule that encodes a *Brassica napus* P4 γ-tocopherol methyltransferase.

SEQ ID NO: 47 sets forth a nucleic acid sequence of a DNA molecule that encodes a *Lycopersicon esculentum* γ-tocopherol methyltransferase.

SEQ ID NO: 48 sets forth a nucleic acid sequence of a DNA molecule that encodes a *Glycine max* γ-tocopherol methyltransferase 1.

SEQ ID NO: 49 sets forth a nucleic acid sequence of a DNA molecule that encodes a *Glycine max* γ-tocopherol methyltransferase 2.

SEQ ID NO: 50 sets forth a nucleic acid sequence of a DNA molecule that encodes a *Glycine max* γ-tocopherol methyltransferase 3.

SEQ ID NO: 51 sets forth a nucleic acid sequence of a DNA molecule that encodes a *Tagetes erecta* γ-tocopherol methyltransferase.

SEQ ID NO: 52 sets forth a nucleic acid sequence of a DNA molecule that encodes a *Sorghum bicolor* γ-tocopherol methyltransferase SEQ ID NO: 53 sets forth a nucleic acid sequence of a DNA molecule that encodes a *Nostoc punctiforme* γ-tocopherol methyltransferase.

SEQ ID NO: 54 sets forth a nucleic acid sequence of a DNA molecule that encodes an Anabaena γ-tocopherol methyltransferase.

SEQ ID NOs: 55 and 56 set forth nucleic acid sequences of the MAA21_40_1 primer pair.

SEQ ID NOs: 57 and 58 set forth nucleic acid sequences of the MAA21_40_2 primer pair.

SEQ ID NOs: 59 and 60 set forth nucleic acid sequences of the MAA21_40_3 primer pair.

SEQ ID NOs: 61 and 62 set forth nucleic acid sequences of the MAA21_40_4 primer pair.

SEQ ID NOs: 63 and 64 set forth nucleic acid sequences of the MAA21_40_5 primer pair.

SEQ ID NOs: 65 and 66 set forth nucleic acid sequences of the MAA21_40_6 primer pair.

SEQ ID NOs: 67 and 68 set forth nucleic acid sequences of the MAA21_40_7 primer pair.

SEQ ID NOs: 69 and 70 set forth nucleic acid sequences of the MAA21_40_8 primer pair.

SEQ ID NOs: 71 and 72 set forth nucleic acid sequences of the MAA21_40_9 primer pair.

SEQ ID NOs: 73 and 74 set forth nucleic acid sequences of the MAA21_40_10 primer pair.

SEQ ID NOs: 75 and 76 set forth nucleic acid sequences of the MAA21_40_11 primer pair.

SEQ ID NOs: 77 and 78 set forth nucleic acid sequences of primers for use in amplifying a gene encoding a mature *Brassica napus* tMT2 enzyme.

SEQ ID NOs: 79 and 80 set forth nucleic acid sequences of primers for use in amplifying a gene encoding a mature *Oryza sativa* tMT2 enzyme.

SEQ ID NOs: 81 and 82 set forth nucleic acid sequences of primers for use in amplifying a gene encoding a mature *Zea mays* tMT2 enzyme.

SEQ ID NOs: 83 and 84 set forth nucleic acid sequences of primers for use in amplifying a gene encoding a mature *Glycine max* tMT2 enzyme.

SEQ ID NOs: 85 and 86 set forth nucleic acid sequences of primers for use in amplifying a gene encoding a mature *Allium porrum* tMT2 enzyme.

SEQ ID NOs: 87 and 88 set forth nucleic acid sequences of primers for use in amplifying a gene encoding a mature *Gossypium hirsutum* tMT2 enzyme.

SEQ ID NOs: 89 and 90 set forth nucleic acid sequences of primers #17286 and #17181 for use in amplifying a gene encoding a full length *Arabidopsis thaliana* tMT2 enzyme.

SEQ ID NO: 91 sets forth an amino acid sequence of an *Arabidopsis thaliana* γ-tocopherol methyltransferase.

SEQ ID NO: 92 sets forth an amino acid sequence of an *Arabidopsis thaliana*, Columbia ecotype, γ-tocopherol methyltransferase.

SEQ ID NO: 93 sets forth an amino acid sequence of an *Oryza sativa* γ-tocopherol methyltransferase.

SEQ ID NO: 94 sets forth an amino acid sequence of a *Zea mays* γ-tocopherol methyltransferase.

SEQ ID NO: 95 sets forth an amino acid sequence of a *Gossypium hirsutum* γ-tocopherol methyltransferase.

SEQ ID NO: 96 sets forth an amino acid sequence of a *Cuphea pulcherrima* γ-tocopherol methyltransferase.

SEQ ID NO: 97 sets forth an amino acid sequence of a *Brassica napus* S8 γ-tocopherol methyltransferase.

SEQ ID NO: 98 sets forth an amino acid sequence of a *Brassica napus* P4 γ-tocopherol methyltransferase.

SEQ ID NO: 99 sets forth an amino acid sequence of a *Lycopersicon esculentum* γ-tocopherol methyltransferase.

SEQ ID NO: 100 sets forth an amino acid sequence of a *Glycine max* γ-tocopherol methyltransferase 1.

SEQ ID NO: 101 sets forth an amino acid sequence of a *Glycine max* γ-tocopherol methyltransferase 2.

SEQ ID NO: 102 sets forth an amino acid sequence of a *Glycine max* γ-tocopherol methyltransferase 3.

SEQ ID NO: 103 sets forth an amino acid sequence of a *Tagetes erecta* γ-tocopherol methyltransferase.

SEQ ID NO: 104 sets forth an amino acid sequence of a *Sorghum bicolor* γ-tocopherol methyltransferase.

SEQ ID NO: 105 sets forth an amino acid sequence of a *Lilium asiaticum* γ-tocopherol methyltransferase.

SEQ ID NO: 106 sets forth an amino acid sequence of a *Nostoc punctiforme* γ-tocopherol methyltransferase.

SEQ ID NO: 107 sets forth an amino acid sequence of an *Anabaena* γ-tocopherol methyltransferase.

tocopherol methyltransferase.

SEQ ID NO: 108 sets forth an amino acid consensus sequence for the aligned polypeptides shown in FIGS. 3*a* and 3*b*.

BRIEF DESCRIPTION OF THE FIGURES

FIG. 2 represents the results of a TBLASTN homology comparison of the nucleotide sequences of several crop tMT2 genes to the amino acid sequence of a tMT2 gene from *Arabidopsis thaliana* (NCBI General Identifier Number gi7573324).

FIGS. 3*a* and 3*b* represent the Pretty Alignment (Genetics Computer Group, Madison Wis.) of tMT2 protein sequences from different plant species.

DETAILED DESCRIPTION OF THE INVENTION

Figure 1:
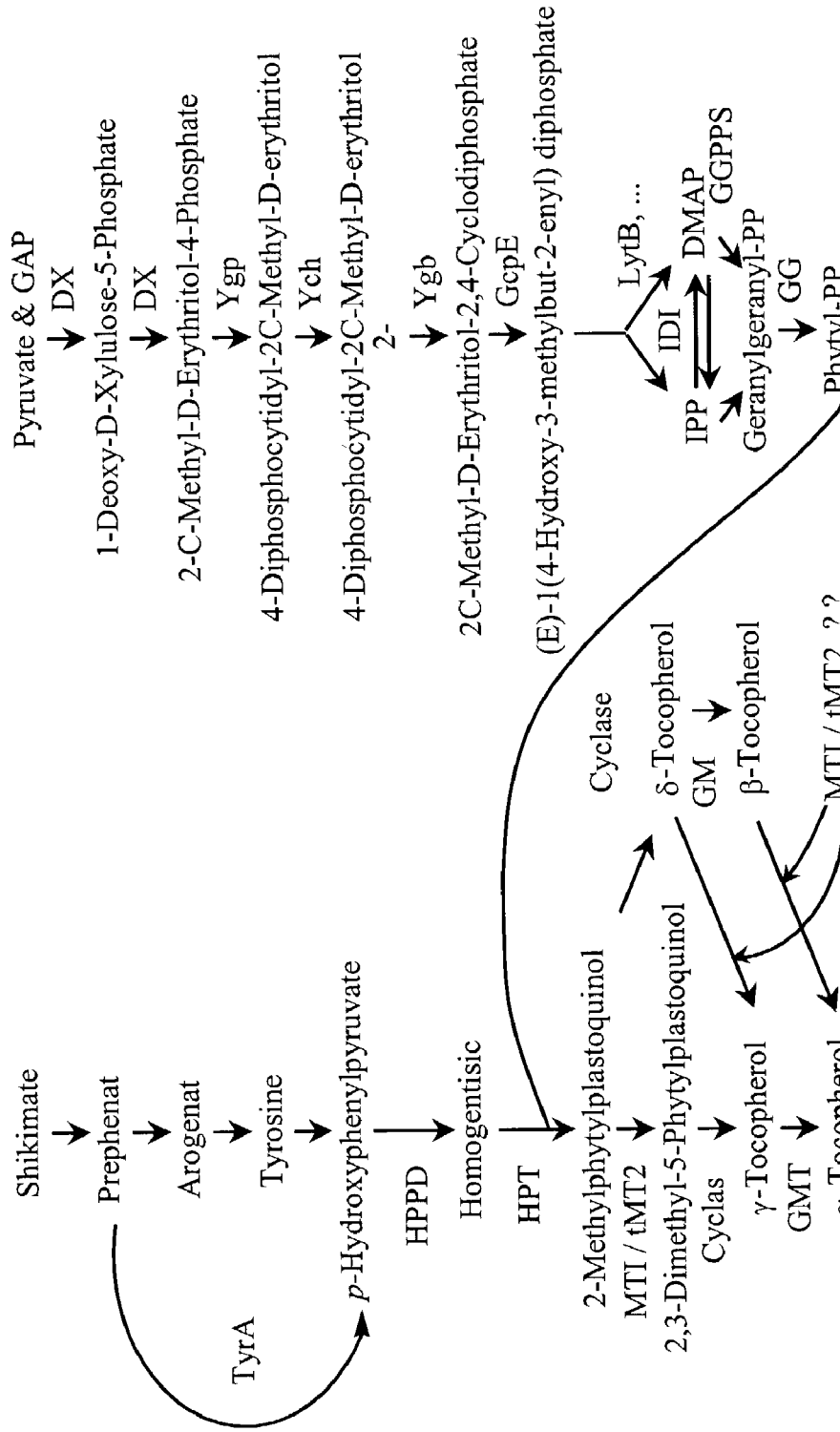
FIG. 1 is a schematic diagram of the tocopherol biosynthetic pathway.
Figure 4:
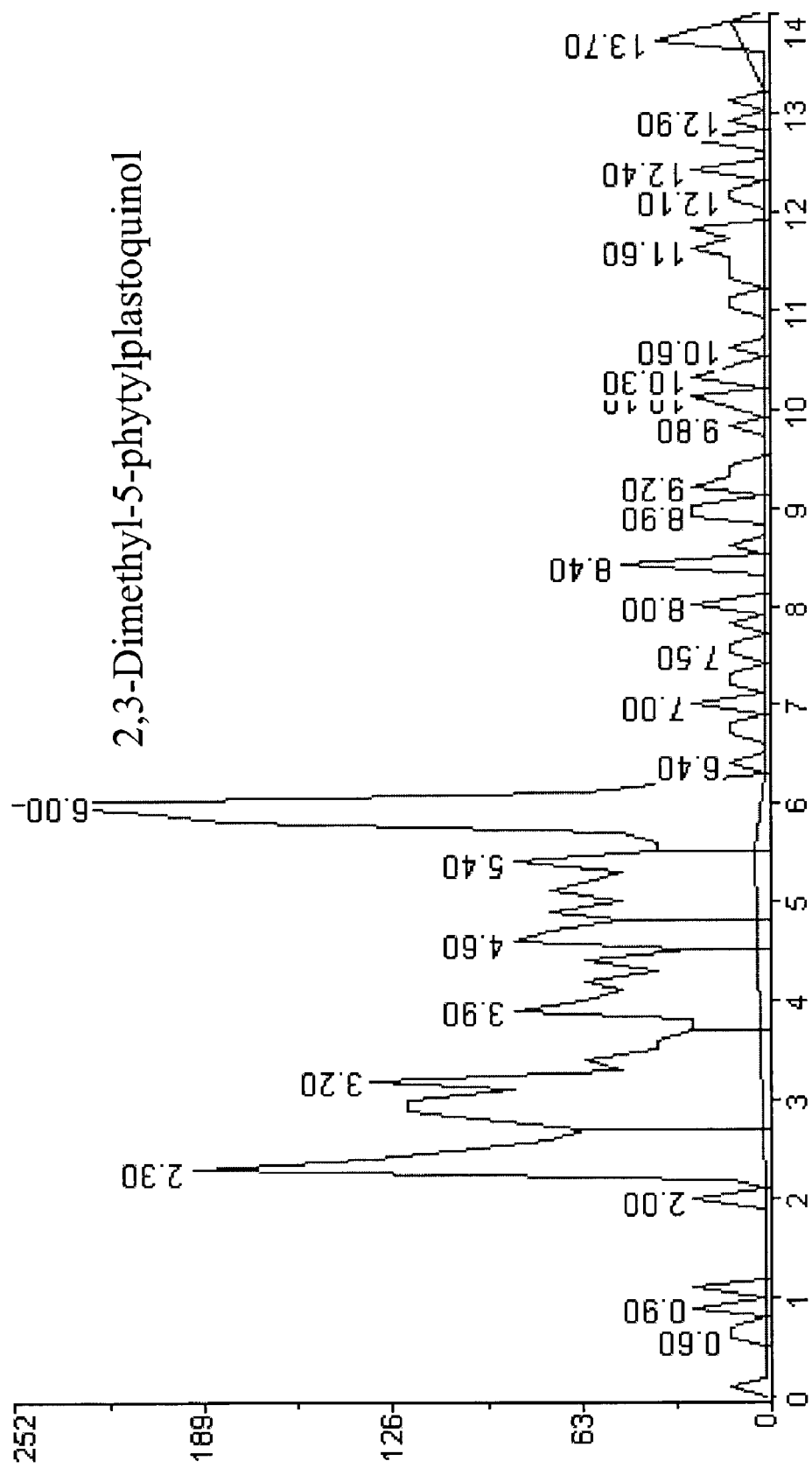
FIG. 4 represents a graph depicting the methyltransferase activity of recombinantly expressed Anabaena MT1 (positive control). Enzyme activity is monitored on crude cell extracts from *E. coli* harboring pMON67174.
Figure 5:
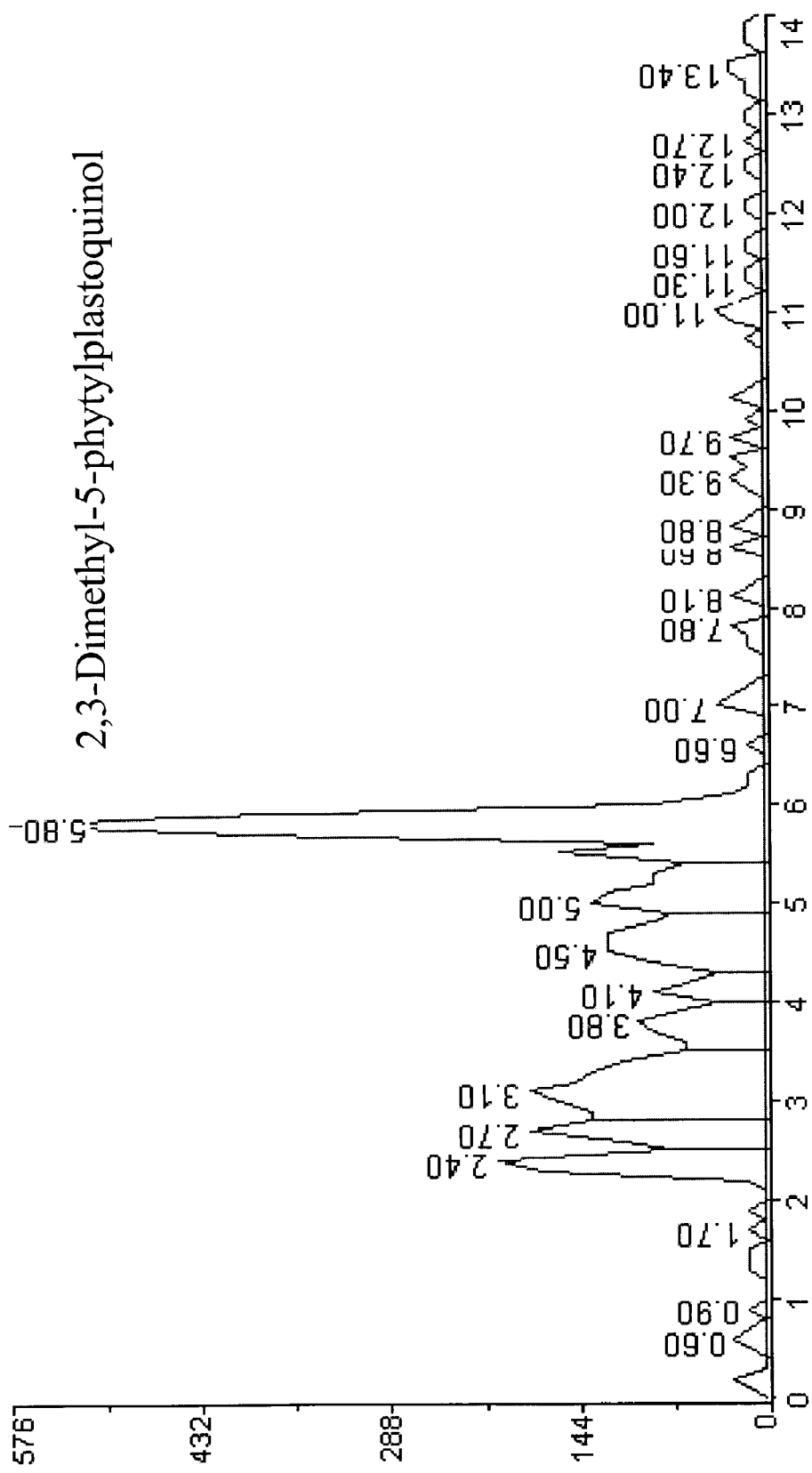
FIG. 5 represents a graph depicting the methyltransferase activity of recombinantly expressed mature Arabidopsis tMT2. Enzyme activity is monitored on crude cell extracts from *E. coli* harboring pMON67191.
Figure 6:
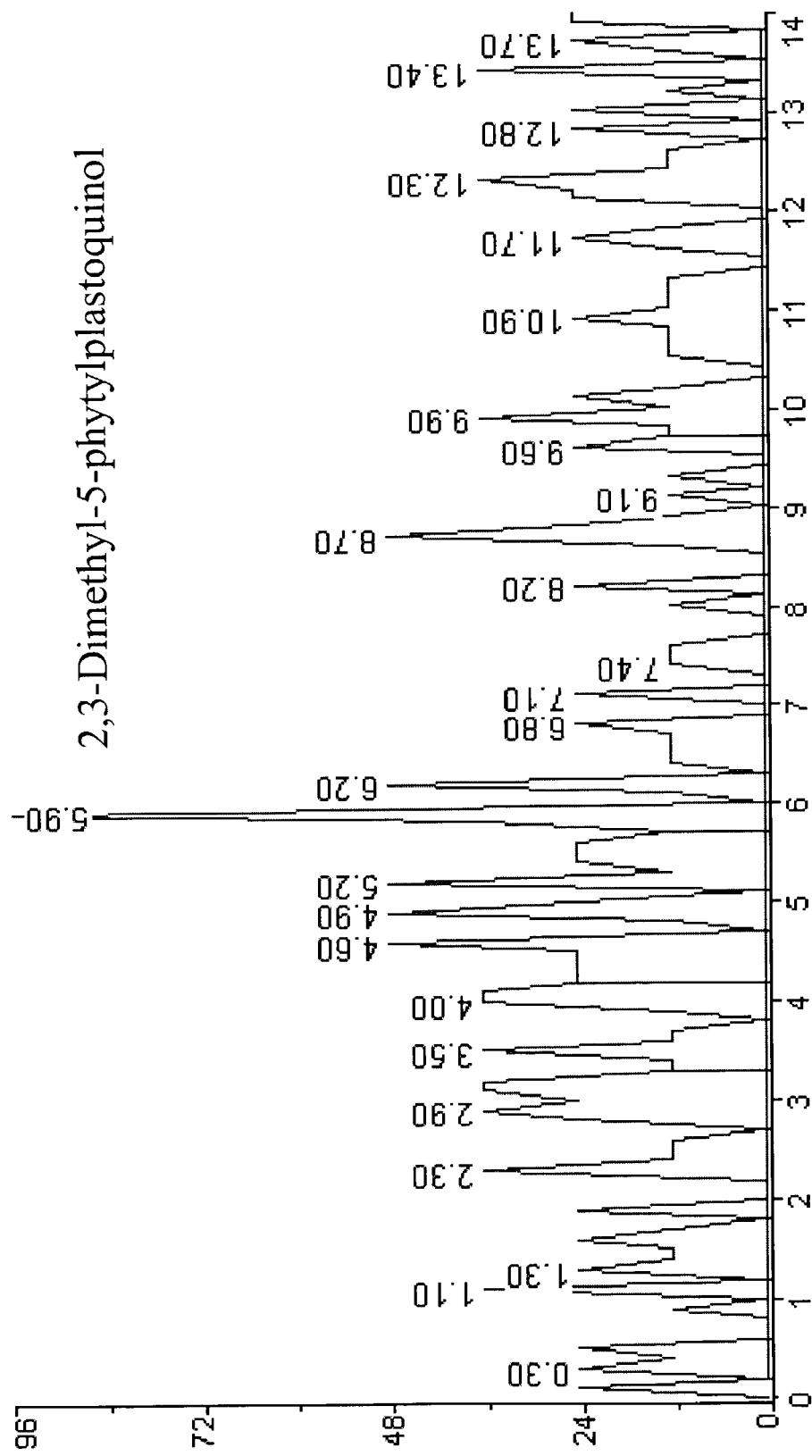
FIG. 6 represents a graph depicting the methyltransferase activity of recombinantly expressed mature Arabidopsis tMT2 hdt2 mutant. Enzyme activity is monitored on crude cell extracts from *E. coli* harboring pMON67207.

The present invention provides a number of agents, for example, nucleic acid molecules and polypeptides associated with the synthesis of tocopherol, and provides uses of such agents.

Agents

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native environmental conditions.

The agents of the invention may also be recombinant. As used herein, the term recombinant means any agent (e.g., DNA, peptide etc.), that is, or results, however indirectly, from human manipulation of a nucleic acid molecule.

It is understood that the agents of the invention may be labeled with reagents that facilitate detection of the agent (e.g., fluorescent labels, Prober et al., Science 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Nucleic Acid Molecules

Agents of the invention include nucleic acid molecules. In a preferred aspect of the present invention the nucleic acid molecule comprises a nucleic acid sequence, which encodes a tocopherol methyltransferase. As used herein, a tocopherol methyltransferase (tMT2) is any plant protein that is capable of specifically catalyzing the methylation of the 3 position of the phenyl ring of 2-methylphytylplastoquinol, 2-methyl-5-phytylplastoquinol, 2-methyl-3-phytylplastoquinol, δ-tocopherol, or β-tocopherol (see, *Photosyn. Research,* 31:99–111 (1992) and *Phytochemistry* 19:215–218 (1980)). A preferred tMT2 is found in an organism selected from the group consisting of *Arabidopsis*, maize, cotton, leek, soybean, rice, and oilseed rape. An example of a more preferred tMT2 is a polypeptide with the amino acid sequence selected from the group consisting of SEQ ID NOs: 16 through 38. In a more preferred embodiment, the tMT2 is encoded by any of SEQ ID NOs: 1 through 15.

In another preferred aspect of the present invention a nucleic acid molecule of the present invention comprises a nucleic acid sequence selected from the group consisting of SEQ ID NOs: 1 through 15, and complements thereof and fragments of either. In another preferred aspect of the present invention, a nucleic acid molecule of the present invention comprises a nucleic acid sequence selected from the group consisting of SEQ ID NOs: 1 and 2, and complements thereof. In another preferred aspect of the present invention the nucleic acid molecule of the invention comprises a nucleic acid sequence selected from the group consisting of SEQ ID NOs: 3 through 7, and complements thereof. In another preferred aspect of the present invention the nucleic acid molecule of the invention comprises a nucleic acid sequence selected from the group consisting of SEQ ID NOs: 8 through 14, and complements thereof. In another preferred aspect of the present invention the nucleic acid molecule of the invention comprises the nucleic acid sequence of SEQ ID NO: 15 and its complement. In a further aspect of the present invention the nucleic acid molecule comprises a nucleic acid sequence encoding an amino acid sequence selected from the group consisting of SEQ ID NOs: 16 through 38, and fragments thereof. In a further aspect of the present invention the nucleic acid molecule comprises a nucleic acid sequence encoding amino acid sequence SEQ ID NO: 16 and fragments thereof.

In another embodiment, the present invention provides nucleic acid molecules comprising a sequence encoding SEQ ID NO: 108, and complements thereof. In another aspect, the present invention provides nucleic acid molecules comprising a sequence encoding residues 83 through 356 of SEQ ID NO: 108, and its complement. In another aspect, the present invention provides nucleic acid molecules comprising a sequence encoding a fragment of residues 83 through 356 of SEQ ID NO: 108, wherein the fragment has a length of at least about 25, 50, 75, 100, 150, 200, or 250 residues, and complements thereof. In yet another aspect, the present invention provides nucleic acid molecules encoding one or more of the following fragments of SEQ ID NO: 108, and complements thereof: 82 through 123, 132 through 146, and 269 through 295.

The present invention includes the use of the above-described sequences and fragments thereof in transgenic plants, other organisms, and for other uses as described below.

In a further aspect of the present invention the nucleic acid molecule comprises a nucleic acid sequence encoding an amino acid sequence selected from the group consisting of SEQ ID NOs: 17 through 21, and fragments thereof. In a further aspect of the present invention the nucleic acid molecule comprises a nucleic acid sequence encoding an amino acid sequence selected from the group consisting of SEQ ID NOs: 22 through 27, and fragments thereof. In a further aspect of the present invention the nucleic acid molecule comprises a nucleic acid sequence encoding an amino acid sequence selected from the group consisting of SEQ ID NOs: 28 through 38, and fragments thereof. In a further aspect of the present invention the nucleic acid molecule comprises a nucleic acid sequence encoding an amino acid of SEQ ID NO: 28 and fragments thereof. In a further aspect of the present invention the nucleic acid molecule comprises a nucleic acid sequence encoding an amino acid sequence selected from the group consisting of SEQ ID NOs: 29 through 32, and fragments thereof. In a further aspect of the present invention the nucleic acid molecule comprises a nucleic acid sequence encoding an amino acid sequence selected from the group consisting of SEQ ID NOs: 33 through 38, and fragments thereof.

In another preferred aspect of the present invention a nucleic acid molecule comprises nucleotide sequences encoding a plastid transit peptide operably fused to a nucleic acid molecule that encodes a protein or fragment of the present invention.

In another preferred embodiment of the present invention, the nucleic acid molecules of the invention encode mutant tMT2 enzymes. As used herein, a "mutant" enzyme or polypeptide is any enzyme or polypeptide that contains an amino acid that is different from the amino acid in the same position of a wild type enzyme of the same type. Examples of suitable mutants of the invention include, but are not limited to, those found in Example 1 of this application.

It is understood that in a further aspect of nucleic acid sequences of the present invention, the nucleic acids can encode a protein that differs from any of the proteins in that one or more amino acids have been deleted, substituted or added without altering the function. For example, it is understood that codons capable of coding for such conservative amino acid substitutions are known in the art.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, without limitation, nucleic acids that have been introduced into cells via transformation, transfection, injection, and projection, and those that have been introduced into an organism via conjugation, endocytosis, phagocytosis, etc.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112–123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 1 through 15, and complements thereof. Nucleic acid molecules of the present invention also include those that specifically hybridize to nucleic acid molecules encoding an amino acid sequence selected from SEQ ID NOs: 16 through 38, and fragments thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989), and by Haymes et al., *Nucleic Acid Hybridization, A Practical Approach, IRL Press*, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0×sodium chloride/sodium citrate (SSC) at about 45° C., followed by a wash of 2.0×SSC at 20–25° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 1 through 15, and complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NOs: 1 through 15, and complements thereof under high stringency conditions such as 0.2×SSC and about 65° C.

In one aspect of the present invention, the nucleic acid molecules of the present invention have one or more of the nucleic acid sequences set forth in SEQ ID NOs: 1 through 15, and complements thereof. In another aspect of the present invention, one or more of the nucleic acid molecules of the present invention share between 100% and 90% sequence identity with one or more of the nucleic acid sequences set forth in SEQ ID NOs: 1 through 15, and complements thereof and fragments of either. In a further aspect of the present invention, one or more of the nucleic acid molecules of the present invention share between 100% and 95% sequence identity with one or more of the nucleic acid sequences set forth in SEQ ID NOs: 1 through 15, complements thereof, and fragments of either. In a more preferred aspect of the present invention, one or more of the nucleic acid molecules of the present invention share between 100% and 98% sequence identity with one or more of the nucleic acid sequences set forth in SEQ ID NOs: 1 through 15, complements thereof and fragments of either. In an even more preferred aspect of the present invention, one or more of the nucleic acid molecules of the present invention share between 100% and 99% sequence identity with one or more of the sequences set forth in SEQ ID NOs: 1 through 15, complements thereof, and fragments of either.

In a preferred embodiment the percent identity calculations are performed using BLASTN or BLASTP (default, parameters, version 2.0.8, Altschul et al., *Nucleic Acids Res.* 25:3389–3402 (1997)).

A nucleic acid molecule of the invention can also encode a homolog polypeptide. As used herein, a homolog polypeptide molecule or fragment thereof is a counterpart protein molecule or fragment thereof in a second species (e.g., corn rubisco small subunit is a homolog of *Arabidopsis* rubisco small subunit). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is selected from the group consisting of alfalfa, *Arabidopsis*, barley, *Brassica campestris*, *Brassica napus*, oilseed rape, broccoli, cabbage, canola, citrus, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, *Phaseolus*, crambe, mustard, castor bean, sesame, cottonseed, linseed, safflower, and oil palm. More particularly, preferred homologs are selected from canola, corn, *Brassica campestris*, *Brassica napus*, oilseed rape, soybean, crambe, mustard, castor bean, peanut, sesame, cottonseed, linseed, rapeseed, safflower, oil palm, flax, and sunflower. In an even more preferred embodiment, the homolog is selected from the group consisting of canola, rapeseed, corn, *Brassica campestris*, *Brassica napus*, oilseed rape, soybean, sunflower, safflower, oil palms, and peanut. In a particularly preferred embodiment, the homolog is soybean. In a particularly preferred embodiment, the homolog is canola. In a particularly preferred embodiment, the homolog is oilseed rape.

In a preferred embodiment, nucleic acid molecules having SEQ ID NOs: 1 through 15, complements thereof, and fragments of either; or more preferably SEQ ID NOs: 1 through 15, and complements thereof, can be utilized to obtain such homologs.

In another further aspect of the present invention, nucleic acid molecules of the present invention can comprise sequences that differ from those encoding a polypeptide or fragment thereof in SEQ ID NOs: 1 through 15 due to the fact that a polypeptide can have one or more conservative amino acid changes, and nucleic acid sequences coding for the polypeptide can therefore have sequence differences. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the polypeptides of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105–132 (1982)). It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157:105–132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.511), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those that are within ±1 are particularly preferred, and those within ±0.5 are even more particularly preferred.

In a further aspect of the present invention, one or more of the nucleic acid molecules of the present invention differ in nucleic acid sequence from those for which a specific sequence is provided herein because one or more codons has been replaced with a codon that encodes a conservative substitution of the amino acid originally encoded.

Agents of the invention include nucleic acid molecules that encode at least about a contiguous 10 amino acid region of a polypeptide of the present invention, more preferably at least about a contiguous 25, 40, 50, 100, or 125 amino acid region of a polypeptide of the present invention.

In a preferred embodiment, any of the nucleic acid molecules of the present invention can be operably linked to a promoter region that functions in a plant cell to cause the production of an mRNA molecule, where the nucleic acid molecule that is linked to the promoter is heterologous with respect to that promoter. As used herein, "heterologous" means not naturally occurring together.

Protein and Peptide Molecules

A class of agents includes one or more of the polypeptide molecules encoded by a nucleic acid agent of the invention. A particular preferred class of proteins is that having an amino acid sequence selected from the group consisting of SEQ ID NOs: 16 through 38, and fragments thereof. In a further aspect of the present invention the polypeptide molecule comprises an amino acid sequence selected from the group consisting of SEQ ID NOs: 17 through 21, and fragments thereof. In a further aspect of the present invention the polypeptide molecule comprises an amino acid sequence selected from the group consisting of SEQ ID NOs: 22 through 27, and fragments thereof. In a further aspect of the present invention the polypeptide molecule comprises an amino acid sequence selected from the group consisting of SEQ ID NOs: 28 through 38, and fragments thereof. In a further aspect of the present invention the polypeptide molecule comprises an amino acid sequence encoding an amino acid of SEQ ID NO: 28 and fragments thereof. In a further aspect of the present invention the polypeptide molecule comprises an amino acid sequence selected from the group consisting of SEQ ID NOs: 29 through 32, and fragments thereof. In a further aspect of the present invention the polypeptide molecule comprises an amino acid sequence selected from the group consisting of SEQ ID NOs: 33 through 38, and fragments thereof.

In another embodiment, the present invention provides a polypeptide comprising the amino acid sequence of SEQ ID NO: 108. In another aspect, the present invention provides a polypeptide comprising the amino acid sequence of residues 83 through 356 of SEQ ID NO: 108. In another aspect, the present invention provides a polypeptide fragment comprising the amino acid sequence of residues 83 through 356 of SEQ ID NO: 108, wherein the fragment has a length of at least about 25, 50, 75, 100, 150, 200, or 250 residues. In yet another aspect, the present invention provides a polypeptide comprising the amino acid sequence of one or more of the following fragments of SEQ ID NO: 108: 82 through 123, 132 through 146, and 269 through 295.

Polypeptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent polypeptides to plastids. In an embodiment of the present invention, any suitable plastid targeting sequence can be used. Where suitable, a plastid targeting sequence can be substituted for a native plastid targeting sequence, for example, for the CTP occurring natively in the tMT2 protein. In a further embodiment, a plastid targeting sequence that is heterologous to any tMT2 protein or fragment described herein can be used. In a further embodiment, any suitable, modified plastid targeting sequence can be used. In another embodiment, the plastid targeting sequence is a CTP1 sequence (see WO 00/61771).

In a preferred aspect a protein of the present invention is targeted to a plastid using either a native transit peptide sequence or a heterologous transit peptide sequence. In the case of nucleic acid sequences corresponding to nucleic acid sequences of non-higher plant organisms such as cynobacteria, such nucleic acid sequences can be modified to attach the coding sequence of the protein to a nucleic acid sequence of a plastid targeting peptide.

As used herein, the term "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation, or oligomerization. Thus, as used herein, the term "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof, peptide molecules, or polypeptide molecules may be produced via chemical synthesis, or more preferably, by expression in a suitable bacterial or eukaryotic host. Suitable methods for expression are described by Sambrook et al., In: *Molecular Cloning, A Laboratory Manual*, 2nd Edition, Cold Spring Harbor Press, Cold Spring Harbor, N.Y. (1989) or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the invention are preferably produced via recombinant means.

Another class of agents comprise protein, peptide molecules, or polypeptide molecules or fragments or fusions thereof comprising SEQ ID NOs: 16 through 38, and fragments thereof in which conservative, non-essential or non-relevant amino acid residues have been added, replaced or deleted. Computerized means for designing modifications in protein structure are known in the art (Dahiyat and Mayo, *Science* 278:82–87 (1997)).

A protein, peptide or polypeptide of the invention can also be a homolog protein, peptide or polypeptide. As used herein, a homolog protein, peptide or polypeptide or fragment thereof is a counterpart protein, peptide or polypeptide or fragment thereof in a second species. A homolog can also be generated by molecular evolution or DNA shuffling techniques, so that the molecule retains at least one functional or structure characteristic of the original (see, for example, U.S. Pat. No. 5,811,238).

In another embodiment, the homolog is selected from the group consisting of alfalfa, *Arabidopsis*, barley, broccoli, cabbage, canola, citrus, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, corn, and *Phaseolus*. More particularly, preferred homologs are selected from canola, rapeseed, corn, *Brassica campestris*, *Brassica napus*, oilseed rape, soybean, crambe, mustard, castor bean, peanut, sesame, cottonseed, linseed, safflower, oil palm, flax, and sunflower. In an even more preferred embodiment, the homolog is selected from the group consisting of canola, rapeseed, corn, *Brassica campestris, Brassica napus*, oilseed rape, soybean, sunflower, safflower, oil palms, and peanut. In a preferred embodiment, the homolog is soybean. In a preferred embodiment, the homolog is canola. In a preferred embodiment, the homolog is oilseed rape.

In a preferred embodiment, the nucleic acid molecules of the present invention or complements and fragments of either can be utilized to obtain such homologs.

Agents of the invention include proteins and fragments thereof comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism.

In a preferred aspect of the present invention the exogenous genetic material comprises a nucleic acid sequence that encodes tocopherol methyltransferase. In another preferred aspect of the present invention the exogenous genetic material of the invention comprises a nucleic acid sequence selected from the group consisting of SEQ ID NOs: 1 through 15, and complements thereof and fragments of either. In a further aspect of the present invention the exogenous genetic material comprises a nucleic acid sequence encoding an amino acid sequence selected from the group consisting of SEQ ID NOs: 16 through 38, and fragments thereof. In a further aspect of the present invention the nucleic acid molecule comprises a nucleic acid sequence encoding an amino acid sequence selected from the group consisting of SEQ ID NOs: 17 through 21, and fragments thereof. In a further aspect of the present invention the nucleic acid molecule comprises a nucleic acid sequence encoding an amino acid sequence selected from the group consisting of SEQ ID NOs: 22 through 27, and fragments thereof. In a further aspect of the present invention the nucleic acid molecule comprises a nucleic acid sequence encoding an amino acid sequence selected from the group consisting of SEQ ID NOs: 28 through 38, and fragments thereof. In a further aspect of the present invention the nucleic acid molecule comprises a nucleic acid sequence encoding an amino acid of SEQ ID NO: 28, and fragments thereof. In a further aspect of the present invention the nucleic acid molecule comprises a nucleic acid sequence encoding an amino acid sequence selected from the group consisting of SEQ ID NOs: 29 through 32, and fragments thereof. In a further aspect of the present invention the nucleic acid molecule comprises a nucleic acid sequence encoding an amino acid sequence selected from the group consisting of SEQ ID NOs: 33 through 38, and fragments thereof. In a further aspect of the present invention, the nucleic acid sequences of the invention also encode peptides involved in intracellular localization, export, or post-translational modification.

In an embodiment of the present invention, exogenous genetic material comprising a tMT2 enzyme or fragment thereof is introduced into a plant with one or more additional genes. In one embodiment, preferred combinations of genes include one or more of the following genes: tyrA, slr1736, HPT, GMT, tocopherol cyclase, dxs, dxr, GGPPS, HPPD, GMT, tMT2, AANT1, slr1737, IDI, GGH, or a plant ortholog thereof, and an antisense construct for homogentisic acid dioxygenase (Kridl et al., *Seed Sci. Res.* 1:209:219 (1991); Keegstra, *Cell* 56(2):247–53 (1989); Nawrath, et al., *Proc. Natl. Acad. Sci. U.S.A.* 91:12760–12764 (1994); Xia et al., *J. Gen. Microbiol.* 138:1309–1316 (1992); Cyanobase, www.kazusa.or.jp/cyanobase; Lois et al., *Proc. Natl. Acad. Sci. U.S.A.* 95 (5):2105–2110 (1998); Takahashi et al. *Proc. Natl. Acad. Sci. U.S.A.* 95 (17), 9879–9884 (1998); Norris et al., *Plant Physiol.* 117:1317–1323 (1998); Bartley and Scolnik, *Plant Physiol.* 104:1469–1470 (1994), Smith et al., *Plant J.* 11:83–92 (1997); WO 00/32757; WO 00/10380; Saint Guily, et al., *Plant Physiol.*, 100(2):1069–1071 (1992); Sato et al., *J. DNA Res.* 7 (1):31–63 (2000)).

In another preferred embodiment, tMT2 is combined with GMT. In any of the embodiments disclosed herein in which a nucleic acid molecule encoding a GMT is used, the nucleic acid molecule is preferably selected from the group consisting of nucleic acid molecules comprising a nucleic acid sequence selected from the group SEQ ID NOs: 39 and 54, and nucleic acids molecules encoding GMTs having an amino acid sequence selected from the group consisting of SEQ ID NOs: 39–54. In another preferred embodiment, tMT2 is combined with GMT and one or more of the genes listed above. In such combinations, one or more of the gene products can be directed to the plastid by the use of a plastid targeting sequence. Alternatively, one or more of the gene products can be localized in the cytoplasm. In a preferred aspect the gene products of tyrA and HPPD are targeted to the cytoplasm. Such genes can be introduced, for example, with the tMT2 or GMT or both, or fragment of either or both on a single construct, introduced on different constructs but the same transformation event, or introduced into separate plants followed by one or more crosses to generate the desired combination of genes. In such combinations, a preferred promoter is a napin promoter and a preferred plastid targeting sequence is a CTP1 sequence. It is preferred that gene products are targeted to the plastid.

In a preferred combination a nucleic acid molecule encoding a tMT2 polypeptide and a nucleic acid molecule encoding any of the following enzymes: tyrA, slr1736, HPT, GMT, tocopherol cyclase, dxs, dxr, GGPPS, HPPD, tMT2, AANT1, slr1737, IDI, GGH or a plant ortholog thereof, and an antisense construct for homogentisic acid dioxygenase are introduced into a plant. A particularly preferred combination that can be introduced is a nucleic acid molecule encoding a tMT2 polypeptide and a nucleic acid molecule encoding a GMT polypeptide, where both polypeptides are targeted to the plastid and where one of such polypeptides is present and the other is introduced. Both nucleic acid sequences encoding such polypeptides can be introduced using a single gene construct, or each polypeptide can be introduced on separate constructs. In a further embodiment, tMT2 is combined with GMT and one or more of tyrA, slr1736, HPT tocopherol cyclase, dxs, dxr, GGPPS, HPPD, AANT1, slr1737, IDI, and GGH.

In a particularly preferred combination, a nucleic acid molecule encoding a tMT2 protein and a nucleic acid molecule encoding a GMT enzyme are introduced into a plant along with a nucleic acid molecule that encodes one or more of tyrA, slr1736, HPT tocopherol cyclase, dxs, dxr, GGPPS, HPPD, AANT1, slr1737, IDI, and GGH.

Another particularly preferred combination that can be introduced is a nucleic acid molecule encoding a tMT2 protein and a nucleic acid molecule that results in the down regulation of a GMT protein. In such an aspect, it is preferred that the plant accumulates either γ-tocopherol or γ-tocotrienol or both.

Such genetic material may be transferred into either monocotyledons or dicotyledons including, but not limited to canola, corn, soybean, *Arabidopsis phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee and dioscorea (Christou, In: *Particle Bombardment for Genetic Engineering of Plants*, Biotechnology Intelligence Unit. Academic Press, San Diego, Calif. (1996)), with canola, corn, *Brassica campestris, Brassica napus*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris, Brassica napus*, oilseed rape, soybean, sunflower, safflower, oil palms, and peanut preferred. In a more preferred embodiment, the genetic material is transferred into canola. In another more preferred embodiment, the genetic material is transferred into oilseed rape. In another particularly preferred embodiment, the genetic material is transferred into soybean.

Transfer of a nucleic acid molecule that encodes a protein can result in expression or overexpression of that polypeptide in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a polypeptide of the present invention in a plant provides in that plant, relative to an untransformed plant with a similar genetic background, an increased level of tocopherols.

In a preferred embodiment, expression or overexpression of a polypeptide of the present invention in a plant provides in that plant, relative to an untransformed plant with a similar genetic background, an increased level of α-tocopherols.

In a preferred embodiment, expression or overexpression of a polypeptide of the present invention in a plant provides in that plant, relative to an untransformed plant with a similar genetic background, an increased level of γ-tocopherols.

In a preferred embodiment, reduction of the expression, expression or overexpression of a polypeptide of the present invention in a plant provides in that plant, relative to an untransformed plant with a similar genetic background, an increased level of δ-tocopherols.

In a preferred embodiment, reduction of the expression, expression or overexpression of a polypeptide of the present invention in a plant provides in that plant, relative to an untransformed plant with a similar genetic background, an increased level of β-tocopherols.

In a preferred embodiment, expression or overexpression of a polypeptide of the present invention in a plant provides in that plant, relative to an untransformed plant with a similar genetic background, an increased level of tocotrienols.

In a preferred embodiment, expression or overexpression of a polypeptide of the present invention in a plant provides in that plant, relative to an untransformed plant with a similar genetic background, an increased level of α-tocotrienols.

In a preferred embodiment, expression or overexpression of a polypeptide of the present invention in a plant provides in that plant, relative to an untransformed plant with a similar genetic background, an increased level of γ-tocotrienols.

In a preferred embodiment, reduction of the expression, expression or overexpression of a polypeptide of the present invention in a plant provides in that plant, relative to an untransformed plant with a similar genetic background, an increased level of δ-tocotrienols.

In a preferred embodiment, reduction of the expression, expression or overexpression of a polypeptide of the present invention in a plant provides in that plant, relative to an untransformed plant with a similar genetic background, an increased level of β-tocotrienols.

In a preferred embodiment, expression or overexpression of a polypeptide of the present invention in combination with a nucleic acid molecule encoding any of the following enzymes: tyrA, slr1736, HPT, GMT, tocopherol cyclase, dxs, dxr, GGPPS, HPPD, tMT2, AANT1, slr1737, IDI, GGH or a plant ortholog thereof, and an antisense construct for homogentisic acid dioxygenase in a plant, provides in that plant, relative to an untransformed plant with a similar genetic background, an increased level of total tocopherols.

In a preferred embodiment, expression or overexpression of a polypeptide of the present invention in a plant provides in that plant, relative to an untransformed plant with a similar genetic background, an increased level of plastoquinols.

In a preferred embodiment, expression or overexpression of a polypeptide of the present invention in a plant provides in that plant, relative to an untransformed plant with a similar genetic background, an increased level of total tocopherols.

In any of the embodiments described herein, an increase in γ-tocopherol, α-tocopherol, or both can lead to a decrease in the relative proportion of β-tocopherol, δ-tocopherol, or both. Similarly, an increase in γ-tocotienol, α-tocotrienol, or both can lead to a decrease in the relative proportion of β-tocotrienol, δ-tocotrienol, or both.

In another embodiment, expression, overexpression of a polypeptide of the present invention in a plant provides in that plant, or a tissue of that plant, relative to an untransformed plant or plant tissue, with a similar genetic background, an increased level of a tMT2 protein or fragment thereof.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are increased by greater than about 10%, or more preferably greater than about 25%, 35%, 50%, 75%, 80%, 90%, 100%, 150%, 200%, 1,000%, 2,000%, or 2,500%. The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds and flowers. A preferred organ is a seed.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are increased so that they constitute greater than about 10%, 20%, 25%, 30%, 35%, 40%, 45%, 50%, 55%, 60%, 65%, 70%, 75%, 80%, 85%, 90%, 95%, 96%, 97%, 98%, or 99% of the total tocopherol content of the organism or tissue. The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds and flowers. A preferred organ is a seed.

In a preferred embodiment, expression of enzymes involved in tocopherol, tocotrienol or plastoquinol synthesis in the seed will result in an increase in δ-tocopherol levels due to the absence of significant levels of GMT activity in those tissues. In another preferred embodiment, expression of enzymes involved in tocopherol, tocotrienol or plastoquinol synthesis in photosynthetic tissues will result in an increase in α-tocopherol due to the higher levels of GMT activity in those tissues relative to the same activity in seed tissue.

In another preferred embodiment, the expression of enzymes involved in tocopherol, tocotrienol or plastoquinol synthesis in the seed will result in an increase in the total tocopherol, tocotrienol or plastoquinol level in the plant.

In some embodiments, the levels of tocopherols or a species such as α-tocopherol may be altered. In some embodiments, the levels of tocotrienols may be altered. Such alteration can be compared to a plant with a similar background.

In another embodiment, either the α-tocopherol level, α-tocotrienol level, or both of plants that natively produce high levels of either α-tocopherol, α-tocotrienol or both (e.g., sunflowers), can be increased by the introduction of a gene coding for a tMT2 enzyme.

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

In another preferred embodiment, reduction of the expression, expression, overexpression of a polypeptide of the present invention in a transformed plant may provide tolerance to a variety of stress, e.g. oxidative stress tolerance such as to oxygen or ozone, UV tolerance, cold tolerance, or fungal/microbial pathogen tolerance.

As used herein in a preferred aspect, a tolerance or resistance to stress is determined by the ability of a plant, when challenged by a stress such as cold to produce a plant having a higher yield than one without such tolerance or resistance to stress. In a particularly preferred aspect of the present invention, the tolerance or resistance to stress is measured relative to a plant with a similar genetic background to the tolerant or resistance plant except that the plant reduces the expression, expresses or over expresses a protein or fragment thereof of the present invention.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y. (1997)).

A construct or vector may include a plant promoter to express the polypeptide of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include the nopaline synthase (NOS) promoter (Ebert et al., *Proc. Natl. Acad. Sci. (U.S.A.)* 84:5745–5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315–324 (1987)) and the CaMV 35S promoter (Odell et al., *Nature* 313: 810–812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624–6628 (1987)), the sucrose synthase promoter (Yang et al., *Proc. Natl. Acad. Sci. (U.S.A.)* 87:4144–4148 (1990)), the R gene complex promoter (Chandler et al., *The Plant Cell* 1:1175–1183 (1989)) and the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci.* (*U.S.A.*) 87:3459–3463 (1990)), the chloroplast fructose-1, 6-biphosphatase (FBPase) promoter from wheat (Lloyd et al., *Mol. Gen. Genet.* 225:209–216 (1991)), the nuclear photosynthetic ST-LS1 promoter from potato (Stockhaus et al., *EMBO J.* 8:2445–2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773–778 (1994)), the promoter for the Cab-1 gene from wheat (Fejes et al., *Plant Mol. Biol.* 15:921–932 (1990)), the promoter for the CAB-1 gene from spinach (Lubberstedt et al., *Plant Physiol.* 104:997–1006 (1994)), the promoter for the cab1R gene from rice (Luan et al., *Plant Cell.* 4:971–981 (1992)), the pyruvate, orthophosphate dikinase (PPDK) promoter from corn (Matsuoka et al., *Proc. Natl. Acad. Sci.* (*U.S.A.*) 90:9586–9590 (1993)), the promoter for the tobacco Lhcb1*2 gene (Cerdan et al., *Plant Mol. Biol.* 33:245–255 (1997)), the *Arabidopsis thaliana* SUC2 sucrose-H+ symporter promoter (Truernit et al., *Planta.* 196:564–570 (1995)) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (Sinapis alba; Kretsch et al., *Plant Mol. Biol.* 28:219–229 (1995)).

For the purpose of expression in sink tissues of the plant, such as the tuber of the potato plant, the fruit of tomato, or the seed of corn, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.* 8:1899–1906 (1986); Jefferson et al., *Plant Mol. Biol.* 14:995–1006 (1990)), the promoter for the potato tuber ADPGPP genes, both the large and small subunits, the sucrose synthase promoter (Salanoubat and Belliard, *Gene* 60:47–56 (1987), Salanoubat and Belliard, *Gene* 84:181–185 (1989)), the promoter for the major tuber proteins including the 22 kd protein complexes and protease inhibitors (Hannapel, *Plant Physiol.* 101:703–704 (1993)), the promoter for the granule-bound starch synthase gene (GBSS) (Visser et al., *Plant Mol. Biol.* 17:691–699 (1991)) and other class I and II patatins promoters (Koster-Topfer et al., *Mol. Gen. Genet.* 219:390–396 (1989); Mignery et al., *Gene.* 62:27–44 (1988)).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos, et al., *Plant Cell,* 1(9):839–853 (1989)), soybean trypsin inhibitor (Riggs, et al., *Plant Cell* 1(6):609–621 (1989)), ACP (Baerson, et al., *Plant Mol. Biol.,* 22(2):255–267 (1993)), stearoyl-ACP desaturase (Slocombe, et al., *Plant Physiol.* 104(4):167–176 (1994)), soybean a' subunit of b-conglycinin (soy 7s, (Chen et al., *Proc. Natl. Acad. Sci.,* 83:8560–8564 (1986))), and oleosin (see, for example, Hong, et al., *Plant Mol. Biol.,* 34(3):549–555 (1997)). Further examples include the promoter for β-conglycinin (Chen et al., *Dev. Genet.* 10:1 12–122 (1989)). Also included are the zeins, which are a group of storage proteins found in corn endosperm. Genomic clones for zein genes have been isolated (Pedersen et al., *Cell* 29:1015–1026 (1982), and Russell et al., *Transgenic Res.* 6(2):157–168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.* 13:5829–5842 (1993)). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins. A preferred promoter for expression in the seed is a napin promoter. Another preferred promoter for expression is an Arcelin5 promoter.

Root specific promoters may also be used. An example of such a promoter is the promoter for the acid chitinase gene (Samac et al., *Plant Mol. Biol.* 25:587–596 (1994)). Expression in root tissue could also be accomplished by utilizing the root specific subdomains of the CaMV35S promoter that have been identified (Lam et al., *Proc. Natl. Acad. Sci.* (*U.S.A.*) 86:7890–7894 (1989)). Other root cell specific promoters include those reported by Conkling et al. (Conkling et al., *Plant Physiol.* 93:1203–1211 (1990)).

Additional promoters that may be utilized are described, for example, in U.S. Pat. Nos. 5,378,619; 5,391,725; 5,428, 147; 5,447,858; 5,608,144; 5,608,144; 5,614,399; 5,633, 441; 5,633,435; and 4,633,436. In addition, a tissue specific enhancer may be used (Fromm et al., *The Plant Cell* 1:977–984 (1989)).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671–680 (1989); Bevan et al., *Nucleic Acids Res.* 11:369–385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183–1200 (1987)), the sucrose synthase intron (Vasil et al., *Plant Physiol.* 91:1575–1579 (1989)) and the TMV omega element (Gallie et al., *The Plant Cell* 1:301–311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183–188 (1985)), which codes for kanamycin resistance and can be selected for using kanamycin, RptII, G418, hpt etc.; a bar gene which codes for bialaphos resistance; a mutant EPSP synthase gene (Hinchee et al., *Bio/Technology* 6:915–922 (1988); Reynaerts et al., Selectable and Screenable Markers. In Gelvin and Schilperoort. Plant Molecular Biology-Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., *Mol. Gen. Genet.* (1987)),) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (European Patent Application 154,204 (Sept. 11, 1985)), ALS (D'Halluin et al., Bio/Technology 10:309–314 (1992)), and a methotrexate resistant DHFR gene (Thillet et al., *J. Biol. Chem.* 263:12500–12508 (1988)).

A vector or construct may also include a transit peptide. Incorporation of a suitable chloroplast transit peptide may also be employed (European Patent Application Publication Number 0218571). Translational enhancers may also be incorporated as part of the vector DNA. DNA constructs could contain one or more 5' non-translated leader sequences, which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393–405 (1996). A preferred transit peptide is CTP1.

A vector or construct may also include a screenable marker. Screenable markers may be used to monitor expression. Exemplary screenable markers include: β-glucuronidase or uidA gene (GUS) which encodes an enzyme for which various chromogenic substrates are known (Jefferson, *Plant Mol. Biol., Rep.* 5:387–405 (1987); Jefferson et al., *EMBO J.* 6:3901–3907 (1987)); an R-locus gene, which encodes a product that regulates the production of anthocyanin pigments (red color) in plant tissues (Dellaporta et al., Stadler Symposium 11:263–282 (1988)); a β-lactamase gene (Sutcliffe et al., *Proc. Natl. Acad. Sci. (U.S.A.)* 75:3737–3741 (1978)), a gene which encodes an enzyme for which various chromogenic substrates are known (e.g., PADAC, a chromogenic cephalosporin); a luciferase gene (Ow et al., *Science* 234:856–859 (1986)); a xylE gene (Zukowsky et al., *Proc. Natl. Acad. Sci. (U.S.A.)* 80:1101–1105 (1983)) which encodes a catechol dioxygenase that can convert chromogenic catechols; an α-amylase gene (Ikatu et al., *Bio/Technol.* 8:241–242 (1990)); a tyrosinase gene (Katz et al., *J. Gen. Microbiol.* 129:2703–2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by Agrobacterium infection or direct delivery of nucleic acid molecules such as, for example, by PEG-mediated transformation, by electroporation or by acceleration of DNA coated particles, and the like. (Potrykus, *Ann. Rev. Plant Physiol. Plant Mol. Biol.* 42:205–225 (1991); Vasil, *Plant Mol. Biol.* 25:925–937 (1994)). For example, electroporation has been used to transform corn protoplasts (Fromm et al., *Nature* 312:791–793 (1986)).

Other vector systems suitable for introducing transforming DNA into a host plant cell include but are not limited to binary artificial chromosome (BIBAC) vectors (Hamilton et al., *Gene* 200:107–116 (1997)); and transfection with RNA viral vectors (Della-Cioppa et al., *Ann. N.Y. Acad. Sci.* (1996), 792 (Engineering Plants for Commercial Products and Applications), 57–61). Additional vector systems also include plant selectable YAC vectors such as those described in Mullen et al., *Molecular Breeding* 4:449–457 (1988).

Technology for introduction of DNA into cells is well known to those of skill in the art. Four general methods for delivering a gene into cells have been described: (1) chemical methods (Graham and van der Eb, *Virology* 54:536–539 (1973)); (2) physical methods such as microinjection (Capecchi, *Cell* 22:479–488 (1980)), electroporation (Wong and Neumann, *Biochem. Biophys. Res. Commun.* 107:584–587 (1982); Fromm et al., *Proc. Natl. Acad. Sci. (U.S.A.)* 82:5824–5828 (1985); U.S. Pat. No. 5,384,253); the gene gun (Johnston and Tang, *Methods Cell Biol.* 43:353–365 (1994)); and vacuum infiltration (Bechtold et al., *C.R. Acad. Sci. Paris, Life Sci.* 316:1194–1199. (1993)); (3) viral vectors (Clapp, *Clin. Perinatol.* 20:155–168 (1993); Lu et al., *J. Exp. Med.* 178:2089–2096 (1993); Eglitis and Anderson, *Biotechniques* 6:608–614 (1988)); and (4) receptor-mediated mechanisms (Curiel et al., *Hum. Gen. Ther.* 3:147–154 (1992), Wagner et al., *Proc. Natl. Acad. Sci. (USA)* 89:6099–6103 (1992)).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994)). Non-biological particles (microprojectiles) may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671–674 (1988)) nor the susceptibility to Agrobacterium infection is required. An illustrative embodiment of a method for delivering DNA into corn cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603–618 (1990)). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, California)(Sanford et al., *Technique* 3:3–16 (1991)).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus that express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (*U.S.A.*) 87:8526–8530 (1990); Svab and Maliga, *Proc. Natl. Acad. Sci.* (*U.S.A.*) 90:913–917 (1993); Staub and Maliga, *EMBO J.* 12:601–606 (1993); U.S. Pat. Nos. 5, 451,513 and 5,545, 818).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629–635 (1985) and Rogers et al., *Methods Enzymol.* 153:253–277 (1987). Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986)).

Modem *Agrobacterum* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179–203 (1985)). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253–277 (1987)). In addition, *Agrobacterum* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterum* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193–200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454–457 (1988)).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Tornyama et al., *Theor. Appl. Genet.* 205:34 (1986); Yamada et al., *Plant Cell Rep.* 4:85 (1986); Abdullah et al., *Biotechnology* 4:1087 (1986)).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988)). In addition, "particle gun" or high-velocity microprojectile technology can be utilized (Vasil et al., *Bio/Technology* 10:667 (1992)).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)* 85:8502–8505 (1988); McCabe et al., *Bio/Technology* 6:923 (1988)). The metal particles penetrate through several layers of cells and thus allow the transformation of cells within tissue explants.

Other methods of cell transformation can also be used and include but are not limited to introduction of DNA into plants by direct DNA transfer into pollen (Hess et al., *Intern Rev. Cytol.* 107:367 (1987); Luo et al., *Plant Mol Biol. Reporter* 6:165 (1988)), by direct injection of DNA into reproductive organs of a plant (Pena et al., *Nature* 325:274 (1987)), or by direct injection of DNA into the cells of immature embryos followed by the rehydration of desiccated embryos (Neuhaus et al., *Theor. Appl. Genet.* 75:30 (1987)).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterum tumefaciens* and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe et al., *Biotechnology* 6:923 (1988); Christou et al., *Plant Physiol.* 87:671–674 (1988)); Brassica (U.S. Pat. No. 5,463,174); peanut (Cheng et al., *Plant Cell Rep.* 15:653–657 (1996), McKently et al., *Plant Cell Rep.* 14:699–703 (1995)); papaya; pea (Grant et al., *Plant Cell Rep.* 15:254–258 (1995)); and *Arabidopsis thaliana* (Bechtold et al., *C.R. Acad. Sci. Paris, Life Sci.* 316:1194–1199 (1993)). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); corn (Rhodes et al., *Science* 240:204 (1988); Gordon-Kamm et al., *Plant Cell* 2:603–618 (1990); Fromm et al., *Bio/Technology* 8:833 (1990); Koziel et al., *Bio/Technology* 11:194 (1993); Armstrong et al., *Crop Science* 35:550–557 (1995)); oat (Somers et al., *Bio/Technology* 10:1589 (1992)); orchard grass (Horn et al., *Plant Cell Rep.* 7:469 (1988)); rice (Tornyama et al., *Theor Appl. Genet.* 205:34 (1986); Part et al., *Plant Mol. Biol.* 32:1135–1148 (1996); Abedinia et al., *Aust. J. Plant Physiol.* 24:133–141 (1997); Zhang and Wu, *Theor. Appl. Genet.* 76:835 (1988); Zhang et al., *Plant Cell Rep.* 7:379 (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al, *Bio/Technology* 10:691 (1992)) and wheat (Vasil et al, *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)). Transient expression systems may be used to functionally dissect gene constructs (see generally, Mailga et al., *Methods in Plant Molecular Biology*, Cold Spring Harbor Press (1995)).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279–289 (1990); van der Krol et al., *Plant Cell* 2:291–299 (1990)). Cosuppression may result from stable transformation with a single copy nucleic acid molecule that is homologous to a nucleic acid sequence found with the cell (Prolls and Meyer, *Plant J.* 2:465–475 (1992)) or with multiple copies of a nucleic acid molecule that is homologous to a nucleic acid sequence found with the cell (Mittlesten et al., *Mol. Gen. Genet.* 244:325–330 (1994)). Genes, even though different, linked to homologous promoters may result in the cosuppression of the linked genes (Vaucheret, *C.R. Acad. Sci. III* 316:1471–1483 (1993); Flavell, *Proc. Natl. Acad. Sci. (U.S.A.)* 91:3490–3496 (1994)); van Blokland et al., *Plant J.* 6:861–877 (1994); Jorgensen, *Trends Biotechnol.* 8:340–344 (1990); Meins and Kunz, In: *Gene Inactivation and Homologous Recombination in Plants*, Paszkowski (ed.), pp. 335–348, Kluwer Academic, Netherlands (1994)).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427–430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49–63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochem.* 55:569–597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155–184 (1990)). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule whose nontranscribed strand encodes a protein or fragment thereof. A preferred protein whose activity can be reduced or depressed, by any method, is tMT2. In such an embodiment of the invention, it is preferred that the concentration of δ-tocopherol or δ-tocotrienol is increased. Another preferred protein whose activity can be reduced or depressed, by any method, is homogentisic acid dioxygenase.

Posttranscriptional gene silencing (PTGS) can result in virus immunity or gene silencing in plants. PTGS is induced by dsRNA and is mediated by an RNA-dependent RNA polymerase, present in the cytoplasm, which requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNase molecules hybridize to the endogene mRNA and cleave the single-stranded RNA adjacent to the hybrid. The cleaved single-stranded RNAs are further degraded by other host RNases because one will lack a capped 5' end and the other will lack a poly(A) tail (Waterhouse et al., *PNAS* 95:13959–13964 (1998)).

It is understood that one or more of the nucleic acids of the invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76–78 (1989); Conrad and Fielder, *Plant Mol. Biol.* 26:1023–1030 (1994)). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489–4496 (1997); Marion-Poll, *Trends in Plant Science* 2:447–448 (1997)). For example, expressed anti-abscisic antibodies have been reported to result in a general perturbation of seed development (Philips et al., *EMBO J.* 16:4489–4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313–1315 (1997); Baca et al., *Ann. Rev. Biophys. Biomol. Struct.* 26:461–493 (1997)). The catalytic abilities of abzymes may be enhanced by site directed mutagenesis. Examples of abzymes are, for example, set forth in U.S. Pat. Nos.: 5,658,753; 5,632,990; 5,631,137; 5,602,015; 5,559,538; 5,576,174; 5,500,358; 5,318,897; 5,298,409; 5,258,289 and 5,194,585.

It is understood that any of the antibodies of the invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed.

In another embodiment, the plant part is a fruit, more preferably a fruit with enhanced shelf life. In another preferred embodiment, the fruit has increased levels of a tocopherol. In another preferred embodiment, the fruit has increased levels of a tocotrienol.

The present invention also provides a container of over about 10,000, more preferably about 20,000, and even more preferably about 40,000 seeds where over about 10%, more preferably about 25%, more preferably about 50% and even more preferably about 75% or 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Any of the plants or parts thereof of the present invention may be processed to produce a feed, meal, protein, or oil preparation, including oil preparations high in total tocopherol content and oil preparations high in any one or more of each tocopherol component listed herein. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than about 5% w/v, more preferably about 10% w/v, and even more preferably about 15% w/v. In a preferred oil preparation, the oil preparation is a high oil preparation with an oil content derived from a plant or part thereof of the present invention of greater than about 5% w/v, more preferably about 10% w/v, and even more preferably about 15% w/v. In a preferred embodiment the oil preparation is a liquid and of a volume greater than about 1, 5, 10 or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than about 0.5%, 1%, 5%, 10%, 25%, 50%, 75% or 90% by volume or weight of the oil component of any product. In another embodiment, the oil preparation may be blended and can constitute greater than about 10%, 25%, 35%, 50% or 75% of the blend by volume. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2–3 (1987))).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryo where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as *Aspergillus*, yeasts, mammals, particularly bovine and porcine, insects, bacteria, and algae. Particularly preferred bacteria are *Agrobacteruim tumefaciens* and *E. coli*.

Methods to transform such cells or organisms are known in the art (EP 0 238 023; Yelton et al., *Proc. Natl. Acad. Sci. (U.S.A.)*, 81:1470–1474 (1984); Malardier et al., *Gene*, 78:147–156 (1989); Becker and Guarente, In: Abelson and Simon (eds.), *Guide to Yeast Genetics and Molecular Biology, Method Enzymol.*, Vol. 194, pp. 182–187, Academic Press, Inc., New York; Ito et al., *J. Bacteriology*, 153:163 (1983) Hinnen et al., *Proc. Natl. Acad. Sci. (U.S.A.)*, 75:1920 (1978); Bennett and LaSure (eds.), *More Gene Manipualtionins in fungi*, Academic Press, CA (1991)). Methods to produce proteins of the present invention are also known (Kudla et al., *EMBO*, 9:1355–1364 (1990); Jarai and Buxton, *Current Genetics*, 26:2238–2244 (1994); Verdier, *Yeast*, 6:271–297 (1990; MacKenzie et al., *Journal of Gen. Microbiol.*, 139:2295–2307 (1993); Hartl et al., *TIBS*, 19:20–25 (1994); Bergenron et al., *TIBS*, 19:124–128 (1994); Demolder et al., *J. Biotechnology*, 32:179–189 (1994); Craig, *Science*, 260:1902–1903 (1993); Gething and Sambrook, *Nature*, 355:33–45 (1992); Puig and Gilbert, *J. Biol. Chem.*, 269:7764–7771 (1994); Wang and Tsou, *FASEB Journal*, 7:1515–1517 (1993); Robinson et al., *Bio/Technology*, 1:381–384 (1994); Enderlin and Ogrydziak, *Yeast*, 10:67–79 (1994); Fuller et al., *Proc. Natl. Acad. Sci. (U.S.A.)*, 86:1434–1438 (1989); Julius et al., *Cell*, 37:1075–1089 (1984); Julius et al., *Cell* 32:839–852 (1983).

In a preferred embodiment, overexpression of a protein or fragment thereof of the present invention in a cell or organism provides in that cell or organism, relative to an untransformed cell or organism with a similar genetic background, an increased level of tocopherols.

In a preferred embodiment, overexpression of a protein or fragment thereof of the present invention in a cell or organism provides in that cell or organism, relative to an untransformed cell or organism with a similar genetic background, an increased level of α-tocopherols.

In a preferred embodiment, overexpression of a protein or fragment thereof of the present invention in a cell or organism provides in that cell or organism, relative to an untransformed cell or organism with a similar genetic background, an increased level of γ-tocopherols.

In another preferred embodiment, overexpression of a protein or fragment thereof of the present invention in a cell or organism provides in that cell or organism, relative to an untransformed cell or organism with a similar genetic background, an increased level of α-tocotrienols.

In another preferred embodiment, overexpression of a protein or fragment thereof of the present invention in a cell or organism provides in that cell or organism, relative to an untransformed cell or organism with a similar genetic background, an increased level of γ-tocotrienols.

Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 16 through 38 or fragments thereof. In another embodiment, the antibody specifically binds to a fusion protein comprising an amino acid sequence selected from the amino acid sequence set forth in SEQ ID NOs: 16 through 38 or fragments thereof. Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials that describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from corn may be utilized to obtain other nucleic acid molecules from corn). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecules of plants and other organisms, including bacteria and fungi, including the nucleic acid molecules that encode, in whole or in part, protein homologues of other plant species or other organisms, sequences of genetic elements, such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of SEQ ID NOs: 1 through 15, and complements thereof because complete complementarity is not needed for stable hybridization. The nucleic acid molecules of the invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143–4146 (1986); Goodchild et al., *Proc. Natl. Acad. Sci.* (*U.S.A.*) 85:5507–5511 (1988); Wickstrom et al., *Proc. Natl. Acad. Sci.* (*U.S.A.*) 85:1028–1032 (1988); Holt et al., *Molec. Cell. Biol.* 8:963–973 (1988); Gerwirtz et al., *Science* 242:1303–1306 (1988); Anfossi et al., *Proc. Natl. Acad. Sci.* (*U.S.A.*) 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof In a second embodiment, methods of "chromosome walking," or inverse PCR may be used to obtain such sequences (Frohman et al., *Proc. Natl. Acad. Sci.* (*U.S.A.*) 85:8998–9002 (1988); Ohara et al., *Proc. Natl. Acad. Sci.* (*U.S.A.*) 86:5673–5677 (1989); Pang et al., *Biotechniques* 22:1046–1048 (1977); Huang et al., *Methods Mol. Biol.* 69:89–96 (1997); Huang et al., *Method Mol. Biol.* 67:287–294 (1997); Benkel et al., *Genet. Anal.* 13:123–127 (1996); Hartl et al., *Methods Mol. Biol.* 58:293–301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers.

The markers can be used in a number of conventional ways in the field of molecular genetics. Such markers include nucleic acid molecules SEQ ID NOs: 1 through 15, complements thereof, and fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, $Ann. Rev. Biochem.$ 55:831–854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a population may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., $FEBS Lett.$ 307:113–115 (1992); Jones et al., $Eur. J. Haematol.$ 39:144–147 (1987); Horn et al., PCT Patent Application WO91/14003; Jeffreys, European Patent Application 370, 719; Jeffreys, U.S. Pat. No. 5,175,082; Jeffreys et al., $Amer. J. Hum. Genet.$ 39:11–24 (1986); Jeffreys et al., $Nature$ 316:76–79 (1985); Gray et al., $Proc. R. Acad. Soc. Lond.$ 243:241–253 (1991); Moore et al., $Genomics$ 10:654–660 (1991); Jeffreys et al., $Anim. Genet.$ 18:1–15 (1987); Hillel et al., $Anim. Genet.$ 20:145–155 (1989); Hillel et al., $Genet.$ 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., $Cytogen. Cell Genet.$ 32:58–67 (1982); Botstein et al., $Ann. J. Hum. Genet.$ 32:314–331 (1980); Fischer et al., (PCT Application WO90/13668; Uhlen, PCT Application WO90/11369).

Polymorphisms can also be identified by Single Strand Conformation Polymorphism (SSCP) analysis (Elles, $Methods in Molecular Medicine: Molecular Diagnosis of Genetic Diseases$, Humana Press (1996)); Orita et al., $Genomics$ 5:874–879 (1989)). A number of protocols have been described for SSCP including, but not limited to, Lee et al., $Anal. Biochem.$ 205:289–293 (1992); Suzuki et al., $Anal. Biochem.$ 192:82–84 (1991); Lo et al., $Nucleic Acids Research$ 20:1005–1009 (1992); Sarkar et al., $Genomics$ 13:441–443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., $Nucleic Acids Res.$ 23:4407–4414 (1995)). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Polymorphisms may also be found using random amplified polymorphic DNA (RAPD) (Williams et al., $Nucl. Acids Res.$ 18:6531–6535 (1990)) and cleaveable amplified polymorphic sequences (CAPS) (Lyamichev et al., $Science$ 260: 778–783 (1993)). It is understood that one or more of the nucleic acid molecules of the invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314–331 (1980); Konieczny and Ausubel, *Plant J.* 4:403–410 (1993)), enzymatic and chemical mismatch assays (Myers et al., *Nature* 313:495–498 (1985)), allele-specific PCR (Newton et al., *Nucl. Acids Res.* 17:2503–2516 (1989); Wu et al., *Proc. Natl. Acad. Sci. USA* 86:2757–2760 (1989)), ligase chain reaction (Barany, *Proc. Natl. Acad. Sci. USA* 88:189–193 (1991)), single-strand conformation polymorphism analysis (Labrune et al., *Am. J. Hum. Genet.* 48:1115–1120 (1991)), single base primer extension (Kuppuswamy et al., *Proc. Natl. Acad. Sci. USA* 88:1143–1147 (1991)), Goelet U.S. Pat. No. 6,004,744; Goelet U.S. Pat. No. 5,888,819), solid-phase ELISA-based oligonucleotide ligation assays (Nikiforov et al., *Nucl. Acids Res.* 22:4167–4175 (1994), dideoxy fingerprinting (Sarkar et al., *Genomics* 13:441–443 (1992)), oligonucleotide fluorescence-quenching assays (Livak et al., *PCR Methods Appl.* 4:357–362 (1995a)), 5'-nuclease allele-specific hybridization TaqMan™ assay (Livak et al., *Nature Genet.* 9:341–342 (1995)), template-directed dye-terminator incorporation (TDI) assay (Chen and Kwok, *Nucl. Acids Res.* 25:347–353 (1997)), allele-specific molecular beacon assay (Tyagi et al., *Nature Biotech.* 16:49–53 (1998)), Pin-Point assay (Haff and Smirnov, *Genome Res.* 7:378–388 (1997)), dCAPS analysis (Neff et al., *Plant J* 14:387–392 (1998)), pyrosequencing (Ronaghi et al, *Analytical Biochemistry* 267:65–71 (1999); Ronaghi et al PCT application WO 98/13523; Nyren et al PCT application WO 98/28440; www.pyrosequencing.com), using mass spectrometry, e.g. the Masscode™ system (Howbert et al PCT application, WO 99/05319; Howbert et al PCT application WO 97/27331; www.rapigene.com; Becker et al PCT application WO 98/26095; Becker et al PCT application; WO 98/12355; Becker et al PCT application WO 97/33000; Monforte et al U.S. Pat. No. 5,965,363), invasive cleavage of oligonucleotide probes (Lyamichev et al *Nature Biotechnology* 1 7:292–296; www.twt.com), and using high density oligonucleotide arrays (Hacia et al *Nature Genetics* 22:164–167; www.affymetrix.com).

Polymorphisms may also be detected using allele-specific oligonucleotides (ASO), which, can be for example, used in combination with hybridization based technology including Southern, Northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide, and temperature. These factors are important both during the hybridization itself and during subsequent washes performed to remove target polynucleotide that is not specifically hybridized. In practice, the conditions of the final, most stringent wash are most critical.

In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula:

$$T_m = 81.5 + 16.6 \times (\log 10[Na+]) + 0.41 \times (\% \ G+C) - 675/n;$$

where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis,* 4:135–186, *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Corn Handbook*, Freeling and Walbot, eds., Springer-Verlag, New York, N.Y. (1994); *Methods in Molecular Medicine: Molecular Diagnosis of Genetic Diseases*, Elles, ed., Humana Press, Totowa, N.J. (1996); Clark, ed., *Plant Molecular Biology: A Laboratory Manual*, Clark, ed., Springer-Verlag, Berlin, Germany (1997).

Factors for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185–199 (1989) and the interval mapping, based on maximum likelihood methods described by Lander and Botstein, *Genetics* 121:185–199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$(MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185–199 (1989) and further described by Arús and Moreno-González, *Plant Breeding*, Hayward et al., (eds.) Chapman & Hall, London, pp. 314–331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered tocopherol levels or compositions or altered tocotrienol levels or compositions.

Additional models can be used. Many modifications and alternative approaches to interval mapping have been reported, including the use of non-parametric methods (Kruglyak and Lander, *Genetics* 139:1421–1428 (1995)). Multiple regression methods or models can also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116–124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447–1455 (1994), and Zeng, *Genetics* 136:1457–1468 (1994). Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195–204 (1994), thereby improving the precision and efficiency of QTL mapping (Zeng, *Genetics* 136:1457–1468 (1994)). These models can be extended to multi-environment experiments to analyze genotype-environment interactions (Jansen et al., *Theo. Appl. Genet.* 91:33–37 (1995)).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed (Tanksley et al., *J.P. Gustafson and R. Appels* (eds.). Plenum Press, New York, pp. 157–173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$ can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter. *Proc. Natl. Acad. Sci.* (*U.S.A.*) 89:1477–1481 (1992)). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477–1481 (1992)). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci. U.S.A.* 88:9828–9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably canola, corn, *Brassica campestris, Brassica napus*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. Derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477–484 (1984); Angerer et al., *Dev. Biol.* 112:157–166 (1985); Dixon et al., *EMBO J.* 10:1317–1324 (1991)). In situ hybridization may be used to measure the steady-state level of RNA accumulation (Hardin et al., *J. Mol. Biol.* 202:417–431 (1989)). A number of protocols have been devised for in situ hybridization, each with tissue preparation, hybridization and washing conditions (Meyerowitz, *Plant Mol. Biol. Rep.* 5:242–250 (1987); Cox and Goldberg, In: *Plant Molecular Biology: A Practical Approach*, Shaw (ed.), pp. 1–35, IRL Press, Oxford (1988); Raikhel et al., *In situ RNA hybridization in plant tissues*, In: *Plant Molecular Biology Manual*, vol. B9:1–32, Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ Hybridization* In: *The Corn Handbook*, Freeling and Walbot (eds.), pp. 165–179, Springer-Verlag, New York (1994)). It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101–109 (1991); Gustafson et al., *Proc. Natl. Acad. Sci. (U.S.A.)* 87:1899–1902 (1990); Mukai and Gill, *Genome* 34:448–452 (1991); Schwarzacher and Heslop-Harrison, *Genome* 34:317–323 (1991); Wang et al., *Jpn. J Genet.* 66:313–316 (1991); Parra and Windle, *Nature Genetics* 5:17–21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta* 112:35–43 (1973); Harris and Chrispeels, *Plant Physiol.* 56:292–299 (1975); Cassab and Varner, *J. Cell. Biol.* 105:2581–2588 (1987); Spruce et al., *Phytochemistry* 26:2901–2903 (1987); Barres et al., *Neuron* 5:527–544 (1990); Reid and Pont-Lezica, *Tissue Printing: Tools for the Study of Anatomy, Histochemistry and Gene Expression*, Academic Press, New York, N.Y. (1992); Reid et al., *Plant Physiol.* 93:160–165 (1990); Ye et al., *Plant J.* 1:175–183 (1991)).

One skilled in the art can refer to general reference texts for detailed descriptions of known techniques discussed herein or equivalent techniques. These texts include *Current Protocols in Molecular Biology* Ausubel, et al., eds., John Wiley & Sons, N.Y. (1989), and supplements through September (1998), *Molecular Cloning, A Laboratory Manual*, Sambrook et al, $2^{nd}$ Ed., Cold Spring Harbor Press, Cold Spring Harbor, N.Y. (1989), *Genome Analysis: A Laboratory Manual* 1: *Analyzing DNA*, Birren et al., Cold Spring Harbor Press, Cold Spring Harbor, N.Y. (1997); *Genome Analysis: A Laboratory Manual* 2: *Detecting Genes*, Birren et al., Cold Spring Harbor Press, Cold Spring Harbor, N.Y. (1998); *Genome Analysis: A Laboratory Manual* 3: *Cloning Systems*, Birren et al., Cold Spring Harbor Press, Cold Spring Harbor, N.Y. (1999); *Genome Analysis: A Laboratory Manual* 4: *Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997), *Methods in Plant Molecular Biology*, Maliga et al, Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples that are provided by way of illustration, and are not intended to be limiting of the present invention, unless specified.

EXAMPLE 1

Identification and characterization of mutant hdt2 *Arabidopsis thaliana*, ecotype Landsberg plants.

Mutagenized ($M_2$) seeds of *Arabidopsis thaliana*, ecotype Landsberg are obtained both by purchase from Lehle Seeds (Round Rock, Tex., U.S.A.) and by standard EMS mutagenesis methodology. The $M_2$ plants are grown from the $M_2$ seeds in greenhouse conditions with one plant per 2.5 inch pot. The resulting $M_3$ seeds are collected from individual $M_2$ plants and analyzed for tocopherol levels.

Seeds from approximately 10,000 $M_3$ lines of *Arabidopsis thaliana*, ecotype Landsberg or Col-O are analyzed for individual tocopherol levels using the following procedure. Five milligrams of seeds from individual plants are ground to a fine powder using a ⅛" steel ball bearing and vigorous shaking. 200 Microliters of 99.5% ethanol/0.5% pyrogallol is added, mixed for 30 seconds and allowed to incubate at 4° C. for 1 h. 50 Microgram/ml of tocol (Matreya, Inc., Pleasant Gap, Pa.) is added to each sample as an injection standard. To remove debris following centrifugation, the supernatant is filtered (PVDF 0.45 µm, Whatman). The filtrate is then analyzed for tocopherol content using high performance liquid chromatography (HPLC) using an isocratic gradient of 90% hexane/10% methyl-t-butyl ether with a Zorbax silica column (4.6×250 mm, Agilent Technologies, Atlanta, Ga.) and fluorescence detection (model 2790 HPLC with model 474 detector; Waters Corporation, Bedford, Mass.) (excitation at 290 nm, emit at 336 nm, 30 nm bandpass and slits). Levels of α, β, γ, and δ-tocopherol are measured in addition to tocol, the injection standard. Individual plant lines that have δ-tocopherol levels higher than wild type are reanalyzed in the next generation (M4), to confirm their inheritability. Five *Arabidopsis* high δ-tocopherol (hdt) mutants possessing increased levels of δ-tocopherols, as compared to wild type, are isolated.

Table 1 below shows the percentage, on a dry weight basis, of δ-tocopherol levels and the relative increases over the appropriate wild type parental ecotype for each of the six mutants. The results show that the six mutants have significant increases in δ-tocopherol levels when compared to the corresponding wild type control. The magnitude of the increases ranged from 2–25 fold.

TABLE 1

| Mutant | WT ecotype | Delta Composition | Increase over WT |
|---|---|---|---|
| hdt2 | Ler | 48% | 25 fold |
| hdt6 | Col-0 | 45% | 20 fold |
| hdt9 | Col-0 | 6% | 2 fold |
| hdt10 | Ler | 25% | 7 fold |
| hdt16 | Col-0 | 50% | 17 fold |

EXAMPLE 2

Identification and sequencing of the mutant hdt2 gene in the *Arabidopsis thaliana*, Landsberg erecta (Ler) high δ-tocopherol mutants.

Using map-based cloning techniques (see, for example, U.S. Ser. No. 09/803,736, Plant Polymorphic Markers and Uses Thereof, filed Mar. 12, 2001) the mutant hdt2 gene is mapped to chromosome 3 telomeric marker T12C14_1563 at 85 cM. This region contains approximately 60 predicted genes. Our analysis of the genes in this region revealed that one of the genes, MAA21_40, possesses homology to known ubiquinone methyltransferases. Based on this homology and the prediction that MAA21_40 is targeted to the chloroplast, this gene is determined to be likely to contain the mutation responsible for the high δ-tocopherol phenotype in hdt2 mutants. The sequences of the MAA21_40 gene locus in the wild types and hdt2 mutants are PCR amplified, and determined by standard sequencing methodology. The gene locus, in each case, is amplified using the sequencing primers as described below:

```
Primer Pair Name MAA21_40_1
Forward Primer TGTAAAACGACGGCCAGTTGCTGAAAGTTGAAAAGAGCAA  (SEQ ID NO: 55)

Reverse Primer CAGGAAACAGCTATGACCCAATTTGATCAATGTTCCACGA  (SEQ ID NO: 56)

Primer Pair Name MAA21_40_2
Forward Primer TGTAAAACGACGGCCAGTAGCTATGCGGATTGATGGTC    (SEQ ID NO: 57)
```

-continued

```
Reverse Primer CAGGAAACAGCTATGACCTCCTCCTGGGAACTCTAGCA    (SEQ ID NO: 58)

Primer Pair Name MAA21_40_3
Forward Primer TGTAAAACGACGGCCAGTTGCTGACTTGCGAGTTTTTG    (SEQ ID NO: 59)

Reverse Primer CAGGAAACAGCTATGACCCCTGTCAACAACCCCTTCTC    (SEQ ID NO: 60)

Primer Pair Name MAA21_40_4
Forward Primer TGTAAAACGACGGCCAGTCCACAAGAGGGGTTTACAATG   (SEQ ID NO: 61)

Reverse Primer CAGGAAACAGCTATGACCACCCAACCTTCTGGCTCTCT    (SEQ ID NO: 62)

Primer Pair Name MAA21_40_5
Forward Primer TGTAAAACGACGGCCAGTGGTCTTTGGGAACGATCTGA    (SEQ ID NO: 63)

Reverse Primer CAGGAAACAGCTATGACCAGGGAAGCGTACAGGGTTCT    (SEQ ID NO: 64)

Primer Pair Name MAA21_40_6
Forward Primer TGTAAAACGACGGCCAGTCCTCTTGAGCTGAACGTCCT    (SEQ ID NO: 65)

Reverse Primer CAGGAAACAGCTATGACCGGCGGAACTGGTTTCACTAC    (SEQ ID NO: 66)

Primer Pair Name MAA21_40_7
Forward Primer TGTAAAACGACGGCCAGTTGTCAGCATAATCGGTTGGA    (SEQ ID NO: 67)

Reverse Primer CAGGAAACAGCTATGACCTCCCCAAAGGTTTAGGTTCC    (SEQ ID NO: 68)

Primer Pair Name MAA21_40_8
Forward Primer TGTAAAACGACGGCCAGTAAGCCTCCTTCTTGTGCTGA    (SEQ ID NO: 69)

Reverse Primer CAGGAAACAGCTATGACCCGACTTTTCCCTTCCATTTG    (SEQ ID NO: 70)

Primer Pair Name MAA21_40_9
Forward Primer TGTAAAACGACGGCCAGTTGGAGGTTCGGGTAACTGAG    (SEQ ID NO: 71)

Reverse Primer CAGGAAACAGCTATGACCCATCCTCTCGCTAGCAGGTC    (SEQ ID NO: 72)

Primer Pair Name MAA21_40_10
Forward Primer TGTAAAACGACGGCCAGTGGAACCAGGGGAACCTAAAC    (SEQ ID NO: 73)

Reverse Primer CAGGAAACAGCTATGACCGCCGTGAGAAACAGACTCCT    (SEQ ID NO: 74)

Primer Pair Name MAA21_40_11
Forward Primer TGTAAAACGACGGCCAGTCAAATGGAAGGGAAAAGTCG    (SEQ ID NO: 75)

Reverse Primer CAGGAAACAGCTATGACCGATCCAAAGAGAACCCAGCA    (SEQ ID NO: 76)
```

The following Polymerase Chain Reaction (PCR) mixture is prepared for each primer pair:

PCR Mixture
5 µl 10×Taq Buffer
5 µl 25 mM MgCl$_2$
4 µl 10 mM dNTPs
2 µl Template DNA
0.5 µl Taq Gold
5 µl F/R Sequencing Primers
28.5 µl dH$_2$O The PCR amplification is carried out using the following Thermocycler program:
1. 94° C. for 10 minutes
2. 94° C. for 15 seconds
3. 56° C. for 15 seconds
4. 72° C. for 1 minute, 30 seconds
5. Repeat Steps 2 through 4 an additional 44 times
6. 72° C. for 10 minutes
7. Hold at 4° C.

The resulting PCR products are sequenced using standard sequencing methodologies.

The wild type Col-0 genomic sequence for the MAA21_40 locus is set forth in SEQ ID NO: 1. The wild type Ler genomic sequence for the MAA21_40 locus is set forth in SEQ ID NO: 2. The wild type coding DNA and peptide sequence for Columbia and Landsberg ecotypes are described in SEQ ID NOs: 15 and 16, respectively.

Once the sequences of the MAA21_40 gene from the hdt2 mutant are determined, they are compared to the sequence of the wild type gene. The high δ-tocopherol mutant identified as hdt2 is determined to have a MAA21_40 gene with the nucleic acid sequence set forth in SEQ ID NO: 3. This sequence has a glutamate to lysine substitution at amino acid position 292, relative to the ATG of the Arabidopsis MAA21_40, as shown in the amino acid sequence of SEQ ID NO: 17.

Another high δ-tocopherol mutant, identified as hdt6, is determined to have a MAA21_40 gene with the nucleic acid sequence set forth in SEQ ID NO: 4. This sequence has a glutamate to a lysine substitution at amino acid 72, relative to the wild type *Arabidopsis* MAA21_40, as shown in the amino acid sequence of SEQ ID NO: 18.

Another high δ-tocopherol mutant, identified as hdt9 is determined to have a MAA21_40 gene with the nucleic acid sequence set forth in SEQ ID NO: 5. This sequence has a proline to a serine substitution at amino acid 13, relative to the *Arabidopsis* MAA21_40, as shown in the amino acid sequence of SEQ ID NO: 19.

Another high δ-tocopherol mutant, identified as hdt10 is determined to have a MAA21_40 gene with the nucleic acid sequence set forth in SEQ ID NO: 6 which encodes MAA21_40 with a aspartate to a asparagine substitution at amino acid 116, relative to the *Arabidopsis* MAA21_40, as shown in the amino acid sequence of SEQ ID NO: 20.

Another high δ-tocopherol mutant hdt16 is determined to have a MAA21_40 gene with the nucleic acid sequence set forth in SEQ ID NO: 7 which encodes MAA21_40 with a threonine to an isoleucine substitution at amino acid 94, relative to the *Arabidopsis* MAA21_40, as shown in the amino acid sequence of SEQ ID NO: 21.

Table 2 summarizes the mutations described above.

TABLE 2

| Mutant | Nucleotide Mutation | Amino Acid Change |
| --- | --- | --- |
| hdt2 | G1041A | E292K |
| hdt6 | G214A | E72K |
| hdt9 | C37T | P13S |
| hdt10 | G346A | D116N |
| hdt16 | C281T | T94I |

EXAMPLE 3

Identification of genes from various sources demonstrating homology to the tMT2 gene from *Arabidopsis thaliana*.

The protein sequence of tMT2 from *Arabidopsis thaliana* (NCBI General Identifier Number gi7573324) is used to search databases for plant sequences with homology to tMT2 using TBLASTN (Altschul et al., *Nucleic Acids Res.* 25:3389–3402 (1997); see also www.ncbi.nlm.nih.gov/BLAST/). Nucleic acid sequences SEQ ID NO: 8 through 15 are found to have high homology with the *Arabidopsis* sequence.

```
>CPR19219 Brassica napus tMT2 homolog 1 - LIB4153-013-R1-K1-B7
ATGGCTTCTCTCATGCTCAACGGGGCCATCACCTTCCCCAAGGGATTAGGCTTCCCCGCTTCCAATCTACACG    (SEQ ID NO: 13)

CCAGACCAAGTCCTCCGCTGAGTCTCGTCTCAAACACAGCCACGCGGAGACTCTCCGTGGCGACAAGATGCAG

CAGCAGCAGCAGCGTGTCGGCGTCAAGGCCATCTGCGCAGCCTAGGTTCATCCAGCACAAGAAAGAGGCCTAC

TGGTTCTACAGGTTCCTGTCCATCGTGTACGACCACATCATCAATCCCGGCCACTGGACGGAGGATATGAGGG

ACGACGCTCTCGAGCCTGCGGATCTGAGCCATCCGGACATGCGAGTTGTCGACGTCGGAGGCGGAACGGGTTT

CACCACGCTGGGAATCGTCAAGACGGTGAAGGCTAAGAACGTGACGATTCTGGACCAGTCGCCGCATCAGCTG

GCAAAGGCGAAGCAGAAGGAGCCGTTGAAGGAGTGCAAGATCGTTGAAGGAGATGCGGAGGATCTCCCTTTTC

CTACTGATTATGCTGACAGATACGTCTCTGCTGGAAGCATTGAGTACTGGCCCGACCCGCAGAGGGGGATAAG

GGAAGCGTACAGAGTTCTCAAGATCGGTGGGAAAGCATGTCTCATTGGCCCTGTCCACCCGACGTTTTGGCTT

TCTCGTTTCTTTGCAGATGTGTGGATGCTTTTCCCCAAGGAGGAGGAGTACATTGAGTGGTTCAAGAATGCTG

GTTTCAAGGACGTTCAGCTTAAGAGGATTGGCCCCAAGTGGTACCGTGGTGTTCGCAGGCACGGACTTATCAT

GGGATGCTCTGTTACTGGTGTCAAACCTGCCTCTGGAGACTCTCCTCTCCAGCTTGGACCAAAGGAAGAGGAC

GTGGAGAAGCCTGTAAACAATCCTTTCTCCTTCTTGGGACGCTTCCTCTTGGGAACCTTAGCGGCTGCCTGGT

TTGTGTTAATCCCAATCTACATGTGGATCAAGGATCAGATCGTTCCCAAAGACCAACCCATCTGA

>Protein sequence Brassica napus tMT2 homolog 1-LIB4153-013-R1-K1-B7
MASLMLNGAITFPKGLGFPASNLHARPSPPLSLVSNTATRRLSVATRCSSSSSVSASRPSAQPRFIQHKKEAY    (SEQ ID NO: 27)

WFYRFLSIVYDHIINPGHWTEDMRDDALEPADLSHPDMRVVDVGGGTGFTTLGIVKTVKAKNVTILDQSPHQL

AKAKQKEPLKECKIVEGDAEDLPFPTDYADRYVSAGSIEYWPDPQRGIREAYRVLKIGGKACLIGPVHPTFWL

SRFFADVWMLFPKEEEYIEWFKNAGFKDVQLKRIGPKWYRGVRRHGLIMGCSVTGVKPASGDSPLQLGPKEED

VEKPVNNPFSFLGRFLLGTLAAAWFVLIPIYMWIKDQIVPKDQPI

>CPR19220 Brassica napus tMT2 homolog 2 - LIB80-011-Q1-E1-E9
ATGGCTTCTCTCATGCTCAACGGGGCCATCACCTTCCCCAAGGGATTAGGCTTCCCCGCTTCCAATCTACACG    (SEQ ID NO: 14)

CCAGACCAAGTCCTCCGCTGAGTCTCGTCTCAAACACAGCCACGCGGAGACTCTCCGTGGCGACAAGATGCAG

CAGCAGCAGCAGCGTGTCGGCGTCAAGGCCATCTGCGCAGCCTAGGTTCATCCAGCACAAGAAAGAGGCCTAC

TGGTTCTACAGGTTCCTGTCCATCGTGTACGACCACATCATCAATCCCGGCCACTGGACGGAGGATATGAGGG
```

```
                                                              -continued
ACGACGCTCTCGAGCCTGCGGATCTGAGCCATCCGGACATGCGAGTTGTCGACGTCGGAGGCGGAACGGGTTT

CACCACGCTGGGAATCGTCAAGACGGTGAAGGCTAAGAACGTGACGATTCTGGACCAGTCGCCGCATCAGCTG

GCAAAGGCGAAGCAGAAGGAGCCGTTGAAGGAGTGCAAGATCGTGGAAGGAGATGCGGAGGATCTCCCTTTTC

CTACTGATTATGCTGACAGATACGTCTCTGCTGGAAGCATTGAGTACTGGCCCGACCCGCAGAGGGGTATAAG

GGAAGCGTACAGAGTTCTCAAGATCGGTGGGAAAGCATGTCTCATTGGCCCTGTCCACCCGACGTTTTGGCTT

TCACGCTTCTTTGCAGATGTGTGGATGCTTTTCCCCAAGGAGGAGGAGTACATTGAGTGGTTCAAGAATGCTG

GTTTCAAGGACGTTCAGCTTAAGAGGATTGGCCCCAAGTGGTACCGTGGTGTTCGCAGGCACGGACTTATCAT

GGGATGCTCTGTTACTGGTGTCAAACCTGCCTCTGGAGACTCTCCTCTCCAGCTTGGACCAAAGGAAGAGGAC

GTGGAGAAGCCTGTAAACAATCCTTTCTCCTTCTTGGGACGCTTCCTCTTGGGTACCCTAGCGGCTGCCTGGT

TTGTGTTAATCCCAATCTACATGTGGATCAAGGATCAGATCGTTCCCAAAGACCAACCCATCTGA

> CPR 193223 Oryza sativa tMT2- LIB4371-041-R1-K1-F7
ATGGCGATGGCCTCCTCCGCCTACGCCCCAGCGGGCGGCGTTGGCACCCACTCCGCGCCGGGCAGGATCAGGC    (SEQ ID NO: 12)

CGCCGCGCGGCCTCGGCTTCTCCACCACCACCACCAAGTCGAGGCCCCTCGTGCTCACCAGGCGTGGGGGAGG

CGGCGGCAACATCTCCGTGGCTCGGCTGAGGTGCGCGGCGTCGTCGTCGTCGGCGGCGGCGAGGCCGATGTCG

CAGCCGCGGTTCATCCAGCACAAGAAGGAGGCGTTCTGGTTCTACCGCTTCCTCTCCATCGTCTACGACCACG

TCATCAACCCGGGCCACTGGACGGAGGACATGCGGGACGACGCCCTCGAGCCCGCCGACCTCTACAGCCGCAA

GCTCAGGGTCGTCGACGTCGGCGGCGGGACGGGGTTCACCACGCTCGGGATCGTCAAGCGCGTCGACCCGGAG

AACGTCACGCTGCTCGACCAGTCCCCGCACCAGCTCGAGAAGGCCCGGGAGAAGGAGGCCCTCAAGGGCGTCA

CCATCATGGAGGGCGACGCCGAGGACCTCCCCTTCCCCACCGACACCTTCGACCGCTACGTCTCCGCCGGCAG

CATCGAGTATTGGCCCGATCCGCAGCGAGGAATCAAGGAAGCTTACAGGGTTTTGAGGCTTGGTGGAGTGGCT

TGCATGATTGGCCCCGTGCACCCAACCTTCTGGCTGTCTCGCTTTTTCGCTGACATGTGGATGCTCTTCCCGA

AGGAAGAGGAGTATATTGAGTGGTTCAAAAAGGCAGGGTTCAAGGATGTCAAGCTCAAAAGGATTGGACCAAA

ATGGTACCGTGGTGTCCGAAGGCATGGCCTGATTATGGGATGCTCTGTGACGGGCGTCAAAAGAGAACATGGA

GACTCCCCTTTGCAGCTTGGTCCAAAGGTTGAGGATGTCAGCAAACCTGTGAATCCTATCACCTTCCTCTTCC

GCTTCCTCATGGGAACAATATGTGCTGCATACTATGTTCTGGTGCCTATCTACATGTGGATAAAGGACCAGAT

TGTGCCCAAAGGCATGCCGATCTAA

> Protein translation Oryza saliva tMT2 - LIB4371-041-R1-K1-F7
MAMASSAYAPAGGVGTHSAPGRIRPPRGLGFSTTTTKSRPLVLTRRGGGGGNISVARLRCAASSSSAAARPMS    (SEQ ID NO: 26)

QPRFIQHKKEAFWFYRFLSIVYDHVINPGHWTEDMRDDALEPADLYSRKLRVVDVGGGTGFTTLGIVKRVDPE

NVTLLDQSPHQLEKAREKEALKGVTIMEGDAEDLPFPTDTFDRYVSAGSIEYWPDPQRGIKEAYRVLRLGGVA

CMIGPVHPTFWLSRFFADMWMLFPKEEEYIEWFKKAGFKDVKLKRIGPKWYRGVRRHGLIMGCSVTGVKREHG

DSPLQLGPKVEDVSKPVNPITFLFRFLMGTICAAYYVLVPIYMWIKDQIVPKGMPI

> CPR193225 and 193226 Zea mays tMT2- LIB3587-273-Q1-K6-C5/ LIB3600-046-
Q1-K6-G1
ATGGCGATGGCCTCCACCTACGCGCCGGGCGGAGGCGCGCGGGCGCTCGCGCAGGGTAGATGCAGGGTCCGCG    (SEQ ID NO: 8)

GTCCCGCGGGGCTGGGCTTCCTCGGCCCCTCCAAGGCCGCCGGCCTCCCCCGCCCCCTCGCCCTCGCCCTCGC

CAGGCGGATGAGCAGCCCCGTCGCGGTGGGCGCCAGGCTGCGATGCGCGGCGTCGTCGTCCCCGCGGCGGCG

CGGCCCGCCACGGCGCCGCGCTTCATCCAGCACAAGAAGGAGGCCTTCTGGTTCTACCGCTTCCTCTCCATCG

TGTACGACCACGTCATCAATCCGGGCCACTGGACCGAGGACATGCGCGACGACGCGCTGGAACCTGCCGACCT

CTTCAGCCGCCACCTCACGGTCGTCGACGTCGGCGGCGGCACGGGGTTCACCACGCTCGGCATCGTCAAGCAC

GTCAACCCGGAGAACGTCACGCTGCTCGACCAGTCCCCGCACCAGCTCGACAAGGCCCGGCAGAAGGAGGCCC

TCAAGGGGGTCACCATCATGGAGGGCGACGCCGAGGACCTCCCGTTCCCCACCGACTCCTTCGACCGATACAT
```

-continued

```
CTCCGCCGGCAGCATCGAGTACTGGCCAGACCCACAGCGGGGGATCAAGGAAGCCTACAGGGTCCTGAGATTT

GGTGGGCTAGCTTGTGTGATCGGCCCGGTCTACCCGACCTTCTGGCTGTCCCGCTTCTTCGCCGACATGTGGA

TGCTCTTCCCCAAGGAGGAAGAGTACATCGAGTGGTTCAAGAAGGCTGGGTTTAGGGATGTCAAGCTGAAGAG

GATTGGACCGAAGTGGTACCGCGGTGTCCGAAGGCATGGCCTCATCATGGGCTGCTCCGTCACAGGCGTCAAG

AGAGAGCGCGGTGACTCTCCCTTGGAGCTTGGTCCCAAGGCGGAGGATGTCAGCAAGCCAGTGAATCCGATCA

CCTTCCTCTTCCGCTTCCTCGTAGGAACGATATGTGCTGCCTACTATGTTCTGGTGCCTATTTACATGTGGAT

AAAGGACCAGATCGTGCCAAAAGGCATGCCAATCTGA
```

> Protein translation *Zea mays* tMT2- LIB3587-273-Q1-K6-C5/LIB3600-046-Q1-K6-G1

```
MAMASTYAPGGGARALAQGRCRVRGPAGLGFLGPSKAAGLPRPLALALARRMSSPVAVGARLRCAASSSPAAA    (SEQ ID NO: 22)

RPATAPRFIQHKKEAFWFYRFLSIVYDHVINPGHWTEDMRDDALEPADLFSRHLTVVDVGGGTGFTTLGIVKH

VNPENVTLLDQSPHQLDKARQKEALKGVTIMEGDAEDLPFPTDSFDRYISAGSIEYWPDPQRGIKEAYRVLRF

GGLACVIGPVYPTFWLSRFFADMWMLFPKEEEYIEWFKKAGFRDVKLKRIGPKWYRGVRRHGLIMGCSVTGVK

RERGDSPLELGPKAEDVSKPVNPITFLFRFLVGTICAAYYVLVPIYMWIKDQIVPKGMPI
```

>CPR193234 *Glycine max* tMT2 - LIB3049-032-Q1-E1-G8

```
ATGGGTTCAGTAATGCTCAGTGGAACTGAAAAGCTCACTCTCAGAACCCTAACCGGGAACGGCTTAGGTTTCA    (SEQ ID NO: 11)

CTGGTTCGGATTTGCACGGTAAGAACTTCCCAAGAGTGAGTTTCGCTGCTACCACTAGTGCTAAAGTTCCCAA

CTTTAGAAGCATAGTAGTACCCAAGTGTAGTGTCTCGGCTTCCAGGCCAAGCTCGCAGCCAAGGTTCATTCAG

CACAAAAAAGAGGCCTTTTGGTTCTATAGGTTTCTCTCAATTGTGTATGACCATGTCATTAACCCTGGCCATT

GGACCGAGGACATGAGGGATGATGCCCTTGAACCCGCTGATCTCAATGACAGGAACATGATTGTGGTGGATGT

TGGTGGCGGCACGGGTTTCACCACTCTTGGTATTGTCAAGCACGTGGATGCCAAGAATGTCACCATTCTTGAC

CAGTCACCCCACCAGCTCGCCAAGGCCAAGCAGAAGGAGCCACTCAAGGAATGCAAAATAATCGAAGGGGATG

CCGAGGATCTCCCCTTTCGAACTGATTATGCCGATAGATATGTATCCGCAGGAAGTATTGAGTACTGGCCGGA

TCCACAGCGTGGCATCAAGGAGGCATACAGGGTTTTGAAACTTGGAGGCAAAGCGTGTCTAATTGGTCCGGTC

TACCCAACATTTTGGTTGTCACGTTTCTTTGCAGATGTTTGGATGCTTTTCCCCAAGGAGGAAGAGTATATTG

AGTGGTTTCAGAAGGCAGGGTTTAAGGACGTCCAACTAAAAAGGATTGGCCCAAAATGGTATCGTGGGGTTCG

CCGTCATGGCTTGATTATGGGTTGTTCAGTGACCGGTGTTAAACCTGCATCTGGAGATTCTCCTTTGCAGCTT

GGTCCAAAGGAAGAAGATGTTGAAAAGCCCGTTAATCCTTTTGTCTTTGCACTGCGCTTCGTTTTGGGTGCCT

TGGCAGCGACATGGTTTGTGTTGGTTCCTATTTACATGTGGCTGAAAGATCAAGTTGTTCCCAAAGGTCAGCC

AATCTAA
```

>Protein translation *Glycine max* tMT2 - LIB3049-032-Q1-E1-G8

```
MGSVMLSGTEKLTLRTLTGNGLGFTGSDLHGKNFPRVSFAATTSAKVPNFRSIVVPKCSVSASRPSSQPRFIQ    (SEQ ID NO: 25)

HKKEAFWFYRFLSIVYDHVINPGHWTEDMRDDALEPADLNDRNMIVVDVGGGTGFTTLGIVKHVDAKNVTILD

QSPHQLAKAKQKEPLKECKIIEGDAEDLPFRTDYADRYVSAGSIEYWPDPQRGIKEAYRVLKLGGKACLIGPV

YPTFWLSRFFADVWMLFPKEEEYIEWFQKAGFKDVQLKRIGPKWYRGVRRHGLIMGCSVTGVKPASGDSPLQL

GPKEEDVEKPVNPFVFALRFVLGALAATWFVLVPIYMWLKDQVVPKGQPI
```

>CPR193236 *Allium Porrum* LIB4521-015-Q1-K1-D6

```
ATGGCTTCCTCCATGCTCAGCGGAGCAGAAAGCCTCTCAATGCTCCGAATCCACCACCAACCCAAACTCACCT    (SEQ ID NO: 10)

TCTCGAGCCCATCCCTCCATTCCAAACCCACAAACCTCAAAATGGATCTCATCCCTTTCGCCACCAAGCATCA

AAAAACGAAAAAGCTTCGATCTTTACATGCAGCGCGTCCTCATCATCCCGACCTGCTTCTCAGCCGAGGTTC

ATCCAGCACAAGCAGGAGGCGTTCTGGTTCTACAGGTTCCTGTCGATAGTGTACGACCATGTGATAAACCCAG

GGCACTGGACCGAGGACATGAGAGACGATGCGTTGGAGCCAGCCGAGCTGTACGATTCCAGGATGAAGGTGGT

GGACGTAGGAGGAGGAACTGGGTTCACCACCTTGGGGATTATAAAGCACATCGACCCTAAAAACGTTACGATT
```

```
CTGGATCAGTCTCCGCATCAGCTTGAGAAGGCTAGGCAGAAGGAGGCTTTGAAGGAGTGTACTATTGTTGAAG

GTGATGCTGAGGATCTCCCTTTTCCTACTGATACTTTCGATCGATATGTATCTGCTGGCAGCATAGAATACTG

GCCAGACCCACAAAGAGGGATAAAGGAAGCATACCGGGTTCTAAAACTGGGAGGCGTTGCCTGCTTGATAGGA

CCCGTGCACCCTACCTTCTGGCTTTCCAGGTTCTTCGCCGACATGTGGATGTTGTTCCCCACCGAAGAAGAAT

ACATAGAGTGGTTTAAAAAGGCCGGGTTCAAAGATGTGAAGTTGAAGAGGATTGGCCCAAAATGGTACCGTGG

TGTGCGTAGACACGGGCTCATCATGGGCTGTTCCGTCACTGGTGTTAAACGTCTCTCTGGTGACTCCCCTCTT

CAGCTTGGACCGAAGGCGGAGGATGTGAAGAAGCCGATCAATCCATTCTCGTTCCTTCTGCGCTTCATTTTGG

GTACGATAGCAGCTACTTACTACGTTTTGGTGCCGATATACATGTGGATAAAGGATCAGATTGTACCGAAAGG

CCAGCCCATATGA

>Protein translation Allium Porrum - LIB4521-015-Q1-K1-D6
MASSMLSGAESLSMLRIHHQPKLTFSSPSLHSKPTNLKMDLIPFATKHQKTKKASIFTCSASSSSRPASQPRF    (SEQ ID NO: 24)

IQHKQEAFWFYRFLSIVYDHVINPGHWTEDMRDDALEPAELYDSRMKVVDVGGGTGFTTLGIIKHIDPKNVTI

LDQSPHQLEKARQKEALKECTIVEGDAEDLPFPTDTFDRYVSAGSIEYWPDPQRGIKEAYRVLKLGGVACLIG

PVHPTFWLSRFFADMWMLFPTEEEYIEWFKKAGFKDVKLKRIGPKWYRGVRRHGLIMGCSVTGVKRLSGDSPL

QLGPKAEDVKKPINPFSFLLRFILGTIAATYYVLVPIYMWIKDQIVPKGQPI

>CPR204065 Gossypium hirsutum tMT2 - LIB3272-054-P1-K1-C11
ATGGCTTCTTCCATGCTGAATGGAGCTGAAACCTTCACTCTCATCCGAGGTGTTACCCCAAAAAGTATTGGTT    (SEQ ID NO: 9)

TTTTGGGGTCAGGTTTACATGGGAAACAGTTTTCCAGTGCGGGTTTAATCTACAGTCCGAAGATGTCCAGGGT

AGGAACGACGATAGCCCCGAGGTGCAGCTTATCAGCGTCAAGGCCAGCTTCACAACCAAGATTCATACAACAC

AAAAAGAGGCCTTTTGGTTCTACAGGTTCCTCTCAATTGTCTATGACCATGTCATAAACCCAGGTCACTGGA

CTGAAGACATGAGGGATGATGCACTTGAGCCGGCTGATCTCAATGACAGGGACATGGTAGTTGTAGATGTTGG

TGGTGGAACTGGTTTCACTACTTTGGGTATTGTTCAGCATGTGGATGCTAAGAATGTTACAATCCTTGACCAA

TCTCCTCACCAGCTTGCAAAGGCTAAACAGAAGGAGCCTCTCAAGGAATGCAACATAATTGAAGGTGATGCAG

AAGATCTTCCTTTTCCTACTGATTATGCCGATAGATATGTGTCTGCTGGAAGCATAGAGTACTGGCCAGACCC

ACAACGGGGATCAAGGAAGCATACAGGGTGTTGAAACAAGGAGGAAAAGCTTGCTTAATTGGTCCTGTGTAC

CCTACATTTTGGTTGTCTCGTTTCTTTGCAGACGTTTGGATGCTTTTCCCTAAGGAGGAAGAATATATAGAGT

GGTTTGAAAAGGCTGGATTTAAGGATGTCCAACTCAAAAGGATTGGCCCTAAATGGTATCGTGGAGTTCGCCG

ACATGGTTTGATCATGGGGTGCTCTGTAACCGGTGTTAAACCCGCATCTGGGGACTCTCCTTTGCAGCTTGGA

CCTAAGGCAGAGGATGTATCAAAGCCGGTAAATCCGTTTGTATTTCTCTTACGCTTCATGTTGGGTGCCACTG

CAGCAGCATATTATGTACTGGTTCCTATCTACATGTGGCTCAAAGATCAAATTGTACCAGAGGGTCAACCAAT

CTAA

>Protein translation Gossypium hirsutum tMT2 -LIB3272-054-P1-K1-C11
MASSMLNGAETFTLIRGVTPKSIGFLGSGLHGKQFSSAGLIYSPKMSRVGTTIAPRCSLSASRPASQPRFIQH    (SEQ ID NO: 23)

KKEAFWFYRFLSIVYDHVINPGHWTEDMRDDALEPADLNDRDMVVVDVGGGTGFTTLGIVQHVDAKNVTILDQ

SPHQLAKAKQKEPLKECNIIEGDAEDLPFPTDYADRYVSAGSIEYWPDPQRGIKEAYRVLKQGGKACLIGPVY

PTFWLSRFFADVWMLFPKEEEYIEWFEKAGFKDVQLKRIGPKWYRGVRRHGLIMGCSVTGVKPASGDSPLQLG

PKAEDVSKPVNPFVFLLRFMLGATAAAYYVLVPIYMWLKDQIVPEGQPI
```

The protein sequence of tMT2 from *Arabidopsis thaliana* is compared against the tMT2 plant protein sequences listed above using BLASTP (Altschul et al., *Nucleic Acids Res.* 25:3389–3402 (1997); see also www.ncbi.nlm.nih.gov/BLAST/). The calculated protein identity of each sequence compared to the *Arabidopsis* sequence is shown in FIG. 2. Also shown is a protein sequence alignment using the Pretty alignment program (Genetics Computer Group, Madison Wis.)(FIG. 3).

EXAMPLE 4

Preparation of constructs to direct the expression of the wild type tMT2 and mutant tMT2 gene sequences of *Arabidopsis thaliana* and tMT2 gene sequences from other crop plant species in a prokaryotic expression system.

A computer program is used to predict the chloroplast targeting peptide cleavage site of the plant tMT2 protein ("ChloroP", Center for Biological Sequence Analysis, Lyngby, Denmark). The result of the search is as follows:

```
#17180 FORWARD-NcoI
5' GGGGACAAGTTTGTACAAAAAAGCAGGCTTAGAAGGAGATAGAACCATGGCTACTAGATGCAGCAGCAGCAGC 3' and    (SEQ ID NO: 79)

#17181 REVERSE-Sse8387i
5' GGGGACCACTTTGTACAAGAAAGCTGGGTCCTGCAGGTCAGATGGGTTGGTCTTTGGGAACG 3'.  (SEQ ID NO: 78)
```

| Name | Length | Score | cTP | CS-score | cTP-length |
|---|---|---|---|---|---|
| *Arabidopsis* | 338 | 0.585 | Y | 6.467 | 51 |

Based on this information, the tMT2 protein from *Arabidopsis thaliana*, ecotype Landsberg is engineered to remove the predicted chloroplast target peptide to allow for the expression of the mature protein in *E. coli*. In order for these proteins to be expressed in a prokaryotic expression system, an amino terminal methionine is required. To make the addition of a 5' ATG the tMT2 coding sequence is amplified from cDNA of wild type and the high δ-tocopherol hdt6, and hdt16 mutant lines of *Arabidopsis thaliana*, ecotype Columbia, and the high δ-tocopherol hdt2 and hdt10 mutant lines of *Arabidopsis thaliana*, ecotype Landsberg.

PolyA+RNA is isolated from each source using an adapted biotin/streptavadin procedure based on the "mRNA Capture Kit" by Roche Molecular Biochemicals (Indianapolis, Ind.). A young plantlet, approximately 1 cm tall, with root tissue removed is homogenized in CTAB buffer (50 mM Tris-HCl pH 9, 0.8M NaCl, 0.5% CTAB, 10 mM EDTA), extracted with chloroform, and pelleted with centrifugation. As specified by the manufacturer's instructions, polyA+ RNA in the soluble fraction is hybridized to biotin-labeled oligo-dT, immobilized on streptavadin-coated PCR tubes and washed. The first strand cDNA is synthesized using the "1$^{st}$ strand cDNA synthesis kit for RT-PCR" (Roche Molecular Biochemicals) in a 50 µl volume according to the manufacturer's protocol. Following the cDNA synthesis, the soluble contents of the tube are replaced with equal volume amplification reaction mixture. The components of the mixture at final concentration consist of:

1×Buffer 2 (Expand™ High Fidelity PCR System, Roche Molecular Biochemicals)

200 µM dNTPs 300 nM each synthetic oligonucleotide primers;

Each primer contains regions for GATEWAY™ cloning (Life Technologies Division, Invitrogen Corporation) as well as conventional restriction enzyme sites.

0.4 µl Expand™ High Fidelity Polymerase (Roche Molecular Biochemicals)

Constructs are also prepared to direct expression of the engineered *Brassica napus*, *Oryza sativa*, *Zea mays*, *Glycine max*, *Allium Porrum*, and *Gossypium hirsutum* tMT2 sequences in a prokaryotic expression vector. The mature protein coding region of each tMT2 with the aminoterminal methionine, as described above, is amplified from plasmid DNA using the following oligonucleotide primers in the polymerase chain reaction.

The mature *Brassica napus* tMT2 coding sequence is amplified from LIB4153–013-R1-K1-B7 (SEQ ID NO: 13) using the synthetic oligonucleotide primers:

```
Brassica forward (17509)
    GGGACAAGTTTGTACAAAAAAGCAGGCTTAGAAGGAGATAGAACCATGGCGACAAGATGCAGCAGCAGCAG.  (SEQ ID NO: 77)

Brassica reverse (17181)
    GGGGACCACTTTGTACAAGAAAGCTGGGTCCTGCAGGTCAGATGGGTTGGTCTTTGGGAACG.            (SEQ ID NO: 78)
```

The mature *Oryza sativa* tMT2 coding sequence is amplified from LIB4371–041-R1-K1-F7 (SEQ ID NO: 12) using the synthetic oligonucleotide primers:

```
Rice forward (17512)
    GGGACAAGTTTGTACAAAAAAGCAGGCTTAGAAGGAGATAGAACCATGCCGCTGAGGTGCGCGGCGTCGTCG. (SEQ ID NO: 79)

Rice reverse (17513)
    GGGGACCACTTTGTACAAGAAAGCTGGGTCCTGCAGGTTAGATCGGCATGCCTTTGGGCAC.             (SEQ ID NO: 80)
```

The mature *Zea mays* tMT2 coding sequence is amplified from LIB3587–273-Q1-K6-C5 (SEQ ID NO: 8) using the synthetic oligonucleotide primers:

```
Corn forward (17510)
GGGACAAGTTTGTACAAAAAAGCAGGCTTAGAAGGAGATAGAACCATCAGGCTGCGATGCGCGGCGTCGTCG.  (SEQ ID NO: 81)

Corn reverse (17511)
GGGGACCACTTTGTACAAGAAAGCTGGGTCCTGCAGGTCAGATTGCCATGCCTTTTGGCACG.            (SEQ ID NO: 82)
```

The mature *Glycine max* tMT2 coding sequence is amplified from LIB3049-032-Q1-E1-G8 (SEQ ID NO: 11) using the synthetic oligonucleotide primers:

```
Soy forward (17516)
GGGACAAGTTTGTACAAAAAAGCAGGCTTAGAAGGAGATAGAACCATGGTACCCAAGTGTAGTGTCTCGGC.  (SEQ ID NO: 83)

Soy reverse (17517)
GGGGACCACTTTGTACAAGAAAGCTGGGTCCTGCAGGTTAGATTGGCTGACCTTTGGGAAC.             (SEQ ID NO: 84)
```

The mature *Allium porrum* tMT2 coding sequence is amplified from LIB4521–015-Q1-K1-D6 (SEQ ID NO: 10) using the synthetic oligonucleotide primers:

```
Leek forward (17518)
GGGACAAGTTTGTACAAAAAAGCAGGCTTAGAAGGAGATAGAACCATGATCTTTACATGCAGCGCGTCCT.   (SEQ ID NO: 85)

Leek reverse (17519)
GGGGACCACTTTGTACAAGAAAGCTGGGTCCTGCAGGTCATATGGGCTGGCCTTTCGGTAC.             (SEQ ID NO: 86)
```

The mature *Gossypium hirsutum* tMT2 coding sequence is amplified from LIB3272-054-P1-K1-C11 (SEQ ID NO: 9) using the synthetic oligonucleotide primers:

```
Cotton forward (17514)
GGGACAAGTTTGTACAAAAAAGCAGGCTTAGAAGGAGATAGAACCATGGCCCCGAGGTGCAGCTTATCAGCG. (SEQ ID NO: 87)

Cotton reverse (17515)
GGGGACCACTTTGTACAAGAAAGCTGGGTCCTGCAGGTTAGATTGGTTGACCCTCTGGTAC.             (SEQ ID NO: 88)
```

The components of each 100 µl PCR reaction at final concentration consisted of:

0.5 µl plasmid DNA diluted 1:20 with water

1×Buffer 2 (Expand™ High Fidelity PCR System, Roche Molecular Biochemicals)

200 µM dNTPs 300 nM each, synthetic oligonucleotide primers 0.8 µl Expand™ High Fidelity Polymerase (Roche Molecular Biochemicals)

The tMT2 gene from each source is PCR amplified for 30 cycles using the following "touchdown" cycling profile. For each reaction the reaction mix is pre-incubated for 5 minutes at 95° C., during which the polymerase is spiked in. The product is then amplified for 15 cycles, each cycle consisting of denaturation at 94° C. for 30 sec, annealing at 60° C. for 30 sec, and elongation at 72° C. for 1.5 minutes. The annealing temperature is decreased by 1° C. per cycle for each of the previous 15 cycles. An additional 15 cycles follow, consisting of 94° C. for 30 seconds, 45° C. for 30 seconds, and 72° C. for 1.5 minute, followed by a 7 minute hold at 72° C. The resulting amplification product is visualized as a clean band of the appropriate size for each species on a 0.8% agarose gel.

The resulting PCR products are subcloned into pDONR™201 (Life Technologies, A Division of Invitrogen Corp., Rockville, Md.) using the GATEWAY cloning system (Life Technologies, A Division of Invitrogen Corp., Rockville, Md.).

To verify that no errors are introduced by the PCR amplification, the double stranded DNA sequence is obtained using standard sequencing methodology. The tMT2 sequences are then recombined behind the T7 promoter in the prokaryotic expression vector pET-DEST42 (Life Technologies, A Division of Invitrogen Corp., Rockville, Md.) using the GATEWAY cloning system (Life Technologies, A Division of Invitrogen Corp., Rockville, Md.).

The following sequences represent the mature amino acid sequences of the wild type and mutant genes which may be expressed in *E. Coli*, following the addition of an amino terminal methionine. The bolded and italicized amino acid residues represent the location of the substitution in each of the mutants.

Mature wildtype Arabidopsis tMT2 protein as expressed in E. coli:
ATRCSSSSVSSSRPSAQPRFIQHKKEAYWFYRFLSIVYDHVINPGHWTEDMRDDALEPADLSHPDMRVVDVGG  (SEQ ID NO: 28)

GTGFTTLGIVKTVKAKNVTILDQSPHQLAKAKQKEPLKECKIVEGDAEDLPFPTDYADRYVSAGSIEYWPDPQ

RGIREAYRVLKIGGKACLIGPVYPTFWLSRFFSDVWMLFPKEEEYIEWFKNAGFKDVQLKRIGPKWYRGVRRH

GLIMGCSVTGVKPASGDSPLQLGPKEEDVEKPVNNPFSFLGRFLLGTLAAAWFVLIPIYMWIKDQIVPKDQPI

Mature mutant hdt2 Arabidopsis tmt2 protein as expressed in E. coli
ATRCSSSSVSSSRPSAQPRFIQHKKEAYWFYRFLSIVYDHVINPGHWTEDMRDDALEPADLSHPDMRVVDVGG  (SEQ ID NO: 29)

GTGFTTLGIVKTVKAKNVTILDQSPHQLAKAKQKEPLKECKIVEGDAEDLPFPTDYADRYVSAGSIEYWPDPQ

RGIREAYRVLKIGGKACLIGPVYPTFWLSRFFSDVWMLFPKEEEYIEWFKNAGFKDVQLKRIGPKWYRGVRRH

GLIMGCSVTGVKPASGDSPLQLGPKEKDVEKPVNNPFSFLGRFLLGTLAAAWFVLIPIYMWIKDQIVPKDQPI

Mature mutant hdt6 Arabidopsis tmt2 protein as expressed in E. coli
ATRCSSSSVSSSRPSAQPRFIQHKKKAYWFYRFLSIVYDHVINPGHWTEDMRDDALEPADLSHPDMRVVDVGG  (SEQ ID NO: 30)

GTGFTTLGIVKTVKAKNVTILDQSPHQLAKAKQKEPLKECKIVEGDAEDLPFPTDYADRYVSAGSIEYWPDPQ

RGIREAYRVLKIGGKACLIGPVYPTFWLSRFFSDVWMLFPKEEEYIEWFKNAGFKDVQLKRIGPKWYRGVRRH

GLIMGCSVTGVKPASGDSPLQLGPKEEDVEKPVNNPFSFLGRFLLGTLAAAWFVLIPIYMWIKDQIVPKDQPI

Mature mutant hdt10 Arabidopsis tmt2 protein as expressed in E. coli
ATRCSSSSVSSSRPSAQPRFIQHKKEAYWFYRFLSIVYDHVINPGHWTEDMRDDALEPADLSHPDMRVVNVGG  (SEQ ID NO: 31)

GTGFTTLGIVKTVKAKNVTILDQSPHQLAKAKQKEPLKECKIVEGDAEDLPFPTDYADRYVSAGSIEYWPDPQ

RGIREAYRVLKIGGKACLIGPVYPTFWLSRFFSDVWMLFPKEEEYIEWFKNAGFKDVQLKRIGPKWYRGVRRH

GLIMGCSVTGVKPASGDSPLQLGPKEEDVEKPVNNPFSFLGRFLLGTLAAAWFVLIPIYMWIKDQIVPKDQPI

Mature mutant hdt16 Arabidopsis tmt2 protein as expressed in E. coli
ATRCSSSSVSSSRPSAQPRFIQHKKEAYWFYRFLSIVYDHVINPGHWIEDMRDDALEPADLSHPDMRVVDVGG  (SEQ ID NO: 32)

GTGFTTLGIVKTVKAKNVTILDQSPHQLAKAKQKEPLKECKIVEGDAEDLPFPTDYADRYVSAGSIEYWPDPQ

RGIREAYRVLKIGGKACLIGPVYPTFWLSRFFSDVWMLFPKEEEYIEWFKNAGFKDVQLKRIGPKWYRGVRRH

GLIMGCSVTGVKPASGDSPLQLGPKEEDVEKPVNNPFSFLGRFLLGTLAAAWFVLIPIYMWIKDQIVPKDQPI

Mature Brassica napus tMT2 as expressed in E. coli
ATRCSSSSSVSASRPSAQPRFIQHKKEAYWFYRFLSIVYDHIINPGHWTEDMRDDALEPADLSHPDMRVVDVG  (SEQ ID NO: 33)

GGTGFTTLGIVKTVKAKNVTILDQSPHQLAKAKQKEPLKECKIVEGDAEDLPFPTDYADRYVSAGSIEYWPDP

QRGIREAYRVLKIGGKACLIGPVHPTFWLSRFFADVWMLFPKEEEYIEWFKNAGFKDVQLKRIGPKWYRGVRR

HGLIMGCSVTGVKPASGDSPLQLGPKEEDVEKPVNNPESFLGRFLLGTLAAAWFVLIPIYMWIKDQIVPKDQP

I.

Mature Oryza sativa tMT2 as expressed in E. coli
RLRCAASSSAAARPMSQPRFIQHKKEAFWFYRFLSIVYDHVINPGHWTEDMRDDALEPADLYSRKLRVVDVG  (SEQ ID NO: 34)

GGTGFTTLGIVKRVDPENVTLLDQSPHQLEKAREKEALKGVTIMEGDAEDLPFPTDTFDRYVSAGSIEYWPDP

QRGIKEAYRVLRLGGVACMIGPVHPTFWLSRFFADMWMLPPKEEEYIEWFKKAGFKDVKLKRIGPKWYRGVRR

HGLIMGCSVTGVKREHGDSPLQLGPKVEDVSKPVNPITFLFRFLMGTICAAYYVLVPIYMWIKDQIVPKGMPI.

Mature Zea mays tMT2 as expressed In E. coli
RLRCAASSSPAAARPATAPRFIQHKKEAFWFYRFLSIVYDHVINPGHWTEDMRDDALEPADLFSRHLTVVDVG  (SEQ ID NO: 35)

GGTGETTLGIVKHVNPENVTLLDQSPHQLDKARQKEALKGVTIMEGDAEDLPFPTDSFDRYISAGSIEYWPDP

QRGIKEAYRVLRFGGLACVIGPVYPTFWLSRFFADMWMLFPKEEEYIEWFKKAGFRDVKLKRIGPKWYRGVRR

HGLIMGCSVTGVKRERGDSPLELGPKAEDVSKPVNPITFLFRFLVGTICAAYYVLVPIYMWIKDQIVFKGMPI

Mature Glycine max tMT2 as expressed in E. coli
VPKCSVSASRPSSQPRFIQHKKEAFWFYRFLSIVYDHVINPGHWTEDMRDDALEPADLNDRNMIVVDVGGGTG  (SEQ ID NO: 36)

FTTLGIVKHVDAKNVTILDQSPHQLAKAKQKEPLKECKIIEGDAEDLPFRTDYADRYVSAGSIEYWPDPQRGI

KEAYRVLKLGGKACLIGPVYPTFWLSRFFADVWMLFPKEEEYIEWFQKAGFKDVQLKRIGPKWYRGVRRHGLI

-continued

MGCSVTGVKPASGDSPLQLGPKEEDVEKPVNPFVFALRFVLGALAATWFVLVPIYMWLKDQVVPKGQPI

Mature *Allium Porrum* as expressed in *E. coli*
IFTCSASSSSRPASQPRFIQHKQEAFWFYRFLSIVYDHVINPGHWTEDMRDDALEPAELYDSRMKVVDVGGGT       (SEQ ID NO: 37)

GFTTLGIIKHIDPKNVTILDQSPHQLEKARQKEALKECTIVEGDAEDLPFPTDTFDRYVSAGSIEYWPDPQRG

IKEAYRVLKLGGVACLIGPVHPTFWLSRFFADMWMLFPTEEEYIEWFKKAGFKDVKLKRIGPKWYRGVRRHGL

IMGCSVTGVKRLSGDSPLQLGPKAEDVKKPINPFSFLLRFILGTIAATYYVLVPIYMWIKDQIVPKGQPI.

Mature *Gossypium hirsutum* tMT2 as expressed in *E. coli*
APRCSLSASRPASQPRFIQHKKEAFWFYRELSIVYDHVINPGHWTEDMRDDALEPADLNDRDMVVVDVGGGTG       (SEQ ID NO: 38)

FTTLGIVQHVDAKNVTILDQSPHQLAKAKQKEPLKECNIIEGDAEDLPFPTDYADRYVSAGSIEYWPDPQRGI

KEAYRVLKQGGKACLIGPVYPTFWLSRFFADVWMLFPKEEEYIEWFEKAGFKDVQLKRIGPKWYRGVRRHGLI

MGCSVTGVKPASGDSPLQLGPKAEDVSKPVNPFVFLLRFMLGATAAAYYVLVPIYMWLKDQIVPEGQPI

EXAMPLE 5

A 2-methylphytylplastoquinol methyltransferase enzymatic assay is performed on the mature cloned genes expressed in *E. coli* to test for functionality of the encoded proteins.

A culture is started by inoculating 100 mL of LB media with appropriate antibiotics with an overnight starter culture of *E. coli* BL21(DE3) cells that is previously transformed with prokaryotic expression constructs described in Example 4. The initial inoculation results in an optical density of $OD_{600}$=0.1 and the culture is grown at 25° C. to a final density of $OD_{600}$=0.6. An amount corresponding to a final concentration of 0.4 mM IPTG is added to induce protein expression, and the cells are then incubated at 25° C. for 3 hours until harvest.

The cells are chilled on ice for 5 minutes and then spun down at 5000×g for 10 minutes. The cell pellet is stored at −80° C. overnight after thoroughly aspirating off the supernatant.

The cell pellet is thawed on ice and resuspended in 4 mL of extraction buffer XB (10 mM HEPES-KOH pH7.8,5 mM DTT, 1 mM AEBSF, 0.1 mM aprotinin, 1 mg/ml leupeptin). Cells are disrupted using a French press by making two passes through the pressure cell at 20,000 psi. Triton X-100 is added to a final concentration of 1% and the extract is incubated on ice for one hour. The cell homogenate is then centrifuged at 5000×g for 10 minutes at 4° C.

The enzyme assays are run on the same day that the cells are extracted. The assays are run in 10 mL polypropylene culture tubes with a final volume of 1 mL. A reaction mixture consisting of the following is prepared and brought to a final volume of 950 µL with distilled water.

Reaction Mixture
50 mM Tris-HCl pH 8.0
5 mM dithiothreitol (DTT, 100 mM stock solution in water)
100 µM 2-methylphytylplastoquinol (404 g/mol)
0.5% Tween 80 (added directly to phytylplastoquinol after evaporating off solvent)
1.7 µM $^{14}$C-SAM (58 µCi/µmole)

2-Methyl-phytylplastoquinol and 2-methyl-geranylgeranylplastoquinol are synthesized as follows:

Fresh $BF_3$-etherate (0.3 ml) is added drop by drop to a solution of 400 mg methylquinol, 1000 mg isophytol in 10 ml dry dioxane. The mixture is stirred under $N_2$ in the dark and is maintained at 50° C. for 2 hours. The reaction mixture is hydrolyzed with ice, extracted with 3×15 ml petroleum ether/diethyl ether (1:1), the extract is washed several times with water to remove unused methylquinol, and dried with $MgSO_4$. The solvent is evaporated off with a rotavapor to yield an oil like crude reaction product containing a mixture of methylplastoquinols. At this stage the reaction mixture is either separated into various methylphytylplastoquinols by flash chromatography followed by HPLC purification or alternatively oxidized to yield the more stable methylplastoquinones. This is achieved by addition of a small amount of $Ag_2O$ (200 mg) to the reaction product dissolved in diethyl ether for 1 hour. Removal of the $Ag_2O$ by filtration provides the methylphytylplastoquinone mixture.

The synthesis of methylphytylplastoquinol as described above gives six isomers, namely 2'-cis and 2'-trans isomers of 2-methyl-3-phytylplastoquinol, 2-methyl-5-phytylplastoquinol 2-methyl-6-phytylplastoquinol. Purification of the six isomers is achieved by an initial separation of the methylphytylplastoquinol mixture into two bands on TLC (PSC-Fertigplatten Kieselgel 60 $F_{254+366}$, Merck, Darmstadt), using solvent system petroleum ether:diethyl ether (7:3). The final purification of isomers of methylplastoquinols is achieved by semi-preparative HPLC.

HPLC is performed on a HP1100 series HPLC system consisting of HP G1329A Auto Sampler, HP G1311A Quaternary Pump, HP G1315A Diode Array Detector, HP G1321A Fluorescence Detector. Excitation is performed at 290 nm, emission is measured at 336 nm. In parallel, absorption is measured using a diode array detector set at 210 and 254 nm. The flow rate is kept at 5 mL/min. Plastoquinols are separated on isocratic HPLC using 90% Hexane:Methyl-Tertbutyl-Ether (90:10) on an Agilent Zorbax Silica 9.4×250 mm column.

Synthesis of 2-methyl-6-geranylgeranylplastoquinol is performed as the synthesis of 2-methyl-6-phytylplastoquinol, except geranyllinalool is used instead of isophytol for synthesis. The pure product is obtained from flash chromatography followed by repetitive TLC as described above.

To perform the methyltransferase assay 50 µL of the cell extract is added to the assay mixture and mixed well. The reaction is initiated by adding $^{14}$C-SAM (ICN) and incubating for one hour at 30° C. in the dark. The reactions are then transferred to 15 mL glass screw cap tubes equipped with Teflon coated caps. The reaction mixture is extracted with 4 mL 2:1 $CHCl_3$/MeOH with 1 mg/mL butylated hydroxy toluene (BHT) and mixed by vortex for 30 seconds. The tubes are centrifuged for 5 minutes to separate layers and the organic phase (bottom) is transferred to fresh 15 mL glass tube. The $CHCl_3$ is evaporated off under a stream of nitrogen gas at 37° C. for about 15 minutes. The residue is dissolved in 200 µL of EtOH containing 1% pyrogallol and then mixed by vortex for 30 seconds. The resuspension is filtered into a brown LC vial equipped with an insert and analyzed by HPLC using a normal phase column (Agilent 4.6×250 mm Zorbax Sil, Agilent Technologies). The elution program is an isocratic flow of 10% methyl-tert-butyl-ether (MTBE) in hexane at 1.5 ml/minute for 12 minutes. Prior to each injection, a clean up run of 75% MTBE in hexane for 3 minutes is done, followed by a re-equilibration step of 10% MTBE in hexane for 3 minutes.

As a positive control, a pea chloroplast concentrate, which is known to have tMT2 activity, is prepared according to the procedure described by Arango and Heise, *Biochem J.* 336:531–533 (1998).

Figure 7:
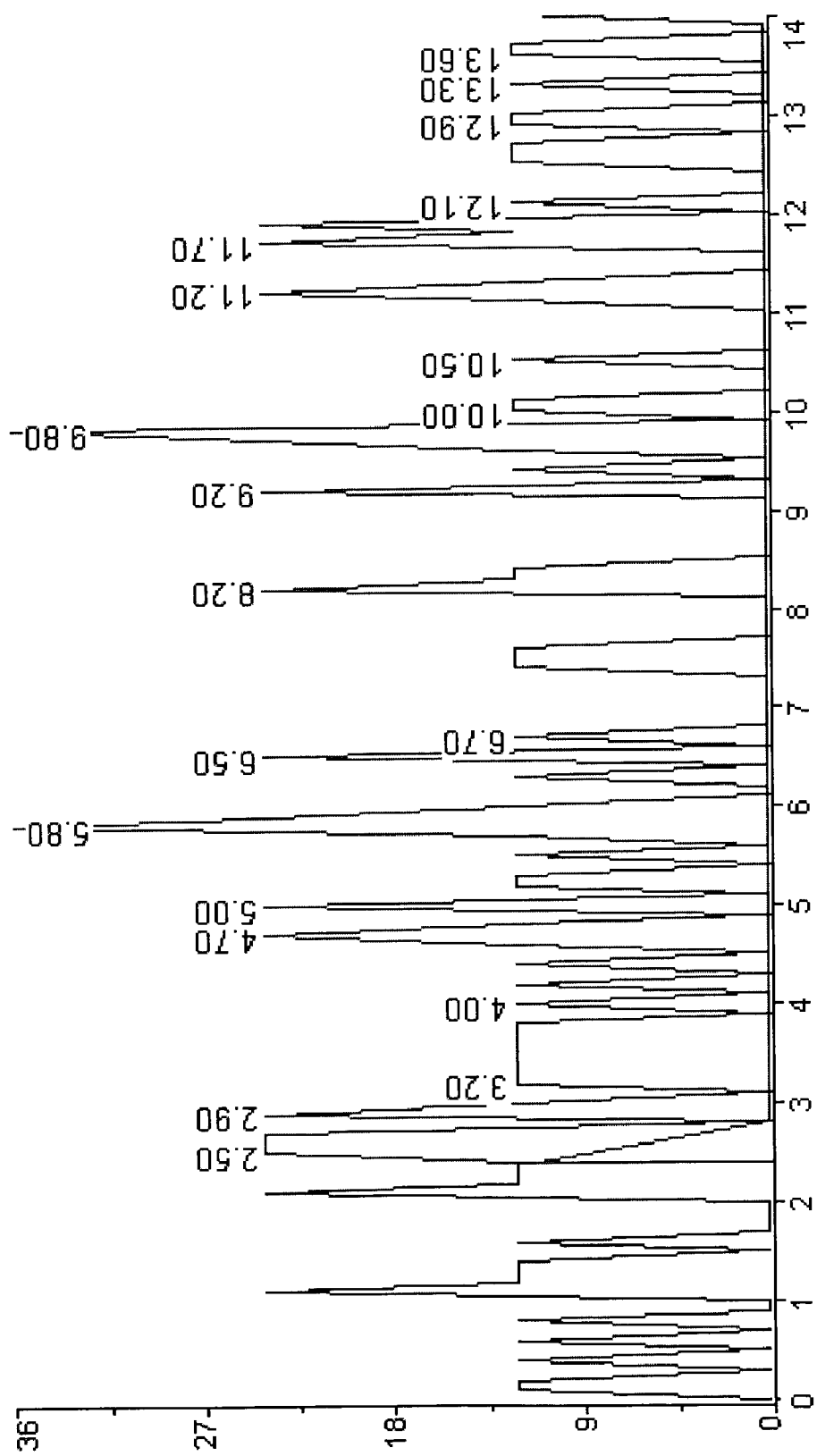
FIG. 7 represents a graph depicting the methyltransferase activity of recombinantly expressed Anabaena MT1 without 2-methylphytylplastoquinol substrate (negative control). Enzyme activity is monitored on crude cell extracts from *E. coli* harboring pMON67174.
Figure 8:
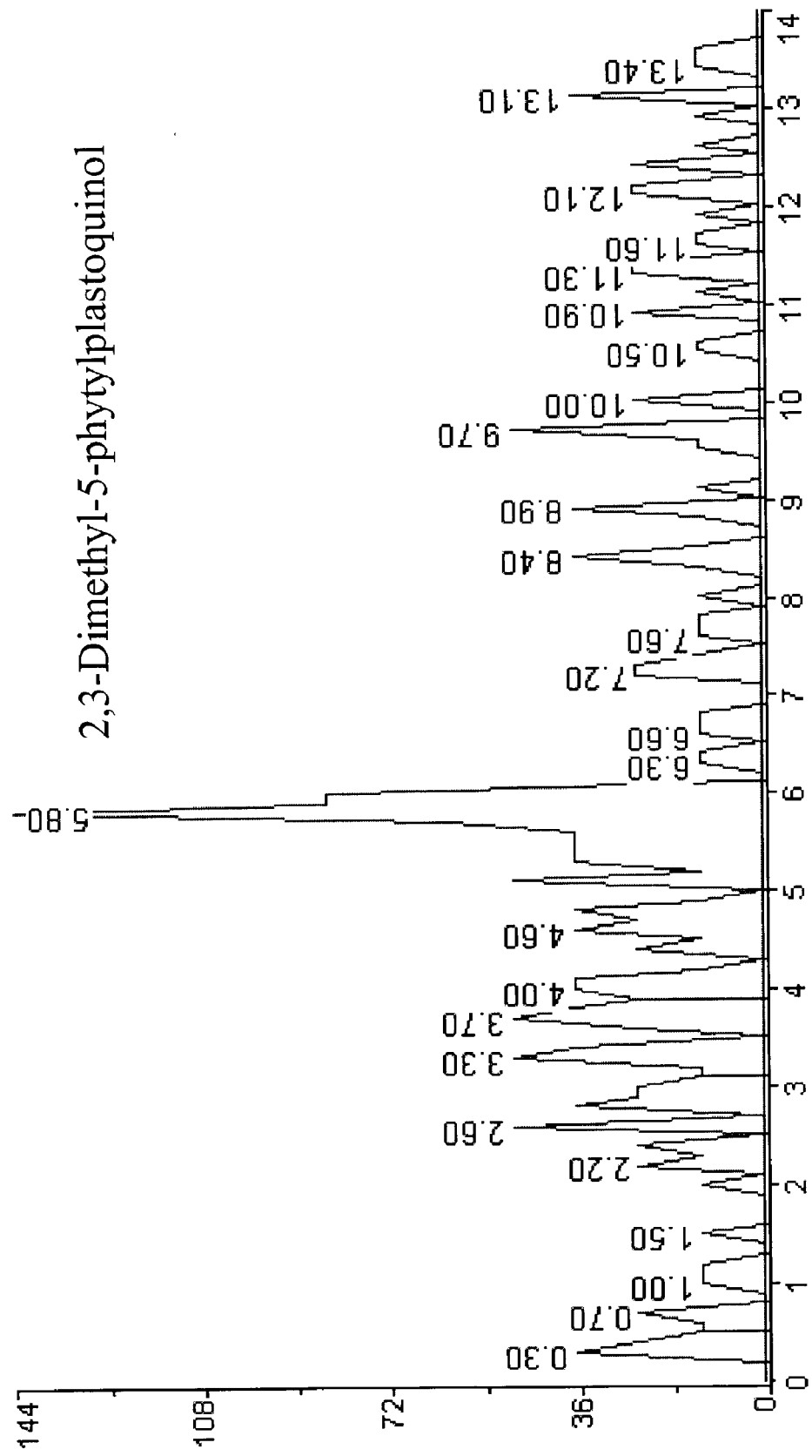
FIG. 8 represents a graph depicting the methyltransferase I activity in isolated pea chloroplasts (positive control).

The results of these enzyme assays are shown in FIGS. 4–8. The series of HPLC chromatograms demonstrate that the cells transformed with the MT1 from *Anabaena*, which is known to have tMT2 activity (FIG. 4) and the tMT2 from *Arabidopsis* (FIG. 5) accumulate methylated products comigrating with a 2,3-dimethyl-5-phytylplastoquinone standard. The mutated tMT2 gene from *Arabidopsis* (hdt2) accumulated significantly less methylated products (FIG. 6) than the wildtype tMT2 gene (FIG. 5), showing that it has a decreased tMT2 activity. By way of comparison, the negative control where substrate is withheld from the cells transformed with the MT1 from *Anabaena* did not show a significant peak corresponding to the methylated products (FIG. 7). Furthermore, the positive control of pea chloroplasts showed peaks corresponding to the methylated products obtained in the assays using *E. coli* extracts from strains harboring the MT1 and tMT2 expression constructs (FIG. 8).

Expression and enzyme assay of crop tMT2 orthologs tMT2 orthologs from *Brassica* (pMON67233), corn (pMON67234), leek (pMON67235), soybean (pMON67245), rice (pMON67232), and cotton (pMON67244), as well as the wild type *Arabidopsis* tMT2 (pMON67191), the hdt2 mutant (pMON67207), and the hdt10 mutant (pMON67243) are expressed as mature proteins in *E. coli* (Example 4). An *Anabaena* hdt2 otholog is expressed from pMON67190. The *Anabaena* MT1 (pMON67174) and empty vector (pMON67179) are used as positive and negative controls, respectively. Cell growth, cell harvest, cell disruption, and enzyme assay are performed as described in Example 5. HPLC-purified 2-methyl-6-phytylplastoquinol is used as methyl group acceptor.

TABLE 3

2-Methyl-6-phytylplastoquinol activity of recombinant expressed tMT2 genes

| pMON # | Gene | Enzyme activity [µU/mg protein] |
|---|---|---|
| 67174 | *Anabaena* MT1 | 6.5 |
| 67179 | Plasmid control | <1 |
| 67190 | *Anabaena* tMT2 ortholog | <1 |
| 67191 | *Arabidopsis* tMT2 | 10 |
| 67207 | *Arabidopsis* hdt2 mutant | 1.1 |
| 67232 | Rice tMT2 ortholog | 4 |
| 67233 | *Brassica* tMT2 ortholog | 2 |
| 67234 | Corn tMT2 ortholog | <1 |
| 67235 | Leek tMT2 ortholog | <1 |
| 67243 | *Arabidopsis* hdt10 mutant | <1 |
| 67244 | Cotton tMT2 ortholog | 23.4 |
| 67245 | Soy tMT2 ortholog | 16.8 |

Figure 24:
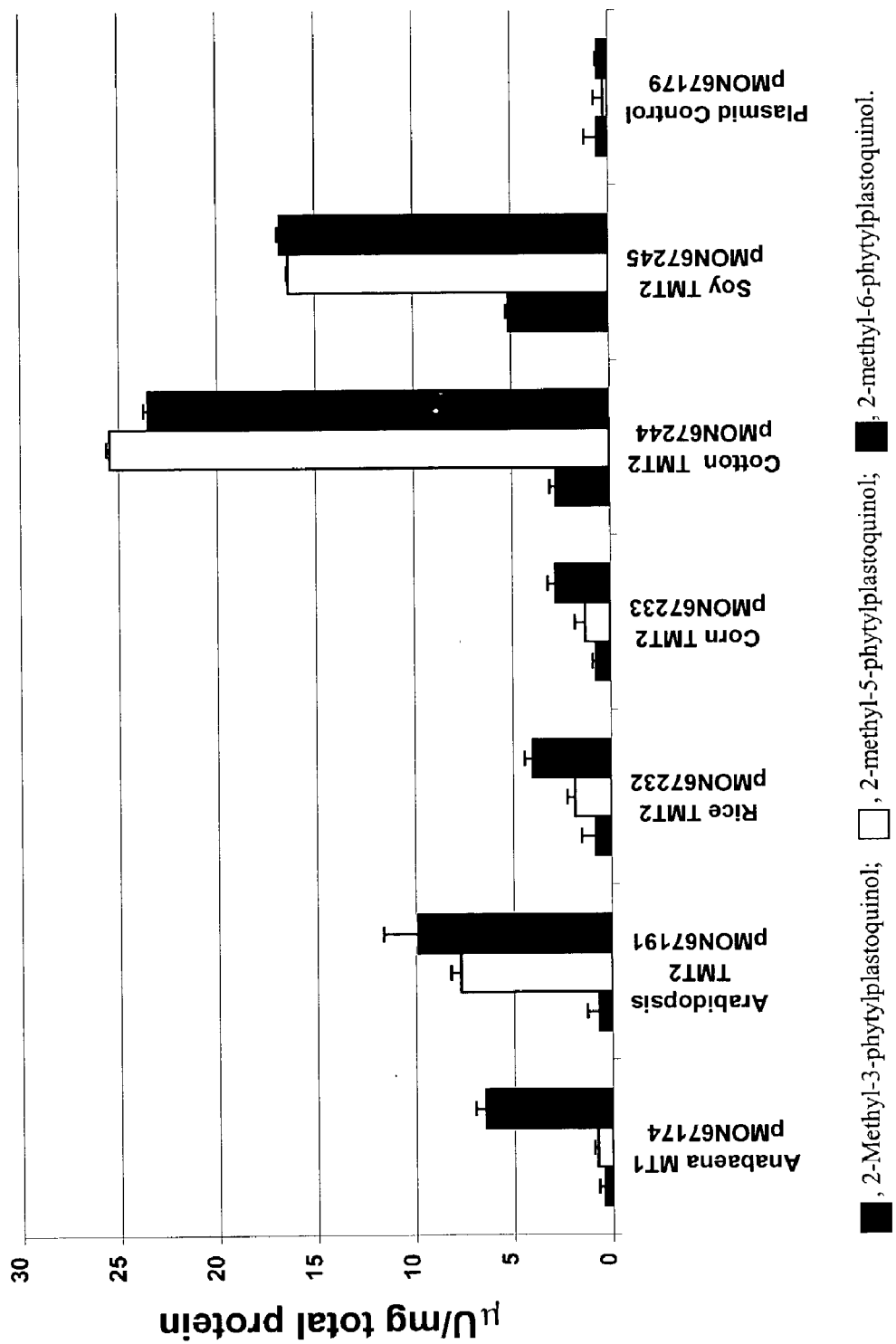
FIG. 24 depicts the results of various 2-methylphytylplastoquinol methyltransferase assays.

*E. coli* extracts expressing the *Anabaena* MT1, as well as mature proteins of the *Arabidopsis* tMT2, rice tMT2, cotton tMT2, and the soybean tMT2 are assayed as described in Example 5 using HPLC-purified 2-methyl-6-phytylplastoquinol, 2-methyl-5-phytylplastoquinol, or 2-methyl-3-phytylplastoquinol as methyl group acceptor. The assay demonstrates that tMT2 orthologs have a broader substrate range than the bacterial MT1 (FIG. 24).

Methyltransferase assays are performed using cell free *E. coli* extracts used in the experiments described above, expressing the *Anabaena* MT 1, as well as the mature *Arabidopsis*, rice, cotton, and soybean tMT2s and 2-methyl-6-gernanylplastoquinol, δ-tocopherol, γ-tocopherol, or β-tocopherol as methyl group accepting substrates. Enzyme activities are below the limit of detection with all four substrates.

EXAMPLE 6

Transformation and expression of a wild type *Arabidopsis* tMT2 gene in *Arabidopsis thialiana*.

The coding region of tMT2 is amplified from the EST clone Lib 3177-021-P1-K1-A3 (SEQ ID NO: 1) using the synthetic oligonucleotide primers;

```
#17286 FORWARD
GGGGACAAGTTTGTACAAAAAAGCAGGCTGCGGCCGCTGAACAATGGCCTCTTTGATGCTCAACG and   (SEQ ID NO: 89)

#17181 REVERSE
GGGGACCACTTTGTACAAGAAAGCTGGGTCCTGCAGGTCAGATGGGTTGGTCTTTGGGAACG.        (SEQ ID NO: 90)
```

The amplification reaction consists of 1.0 µl of EST template, 2.5 µl 20×dNTPs, 2.5 µl of each oligonucleotide primers, 5 µl 10×PCR buffer, 35.75 µl H20 and 0.75 µl Expand High Fidelity DNA Polymerase. PCR conditions for amplification are as follows:
  1 cycle of 94° for 2 minutes, 10 cycles of 94°—15 seconds; 55°—30 seconds; and 72°—1.5 minutes,
  15 cycles of 94°—15 seconds; 55°—30 seconds; and 72°—1.5 minutes adding 5 seconds to the 72° extension with each cycle,
  1 cycle of 72° for 7 minutes.

After amplification, the samples are purified using a Qiagen PCR cleanup column (Qiagen Company, Valencia, Calif.), suspended in 30 μl water. The PCR reaction products are separated on an agarose gel and visualized according to standard methodologies. The resulting PCR products are subcloned into pDONR™201 (Life Technologies, A Division of Invitrogen Corp., Rockville, Md.) using the GATEWAY cloning system (Life Technologies, A Division of Invitrogen Corp., Rockville, Md.). The resultant intermediate plasmid is named pMON67204 and the tMT2 sequence is confirmed by DNA sequencing using standard methodologies.

Figure 9:
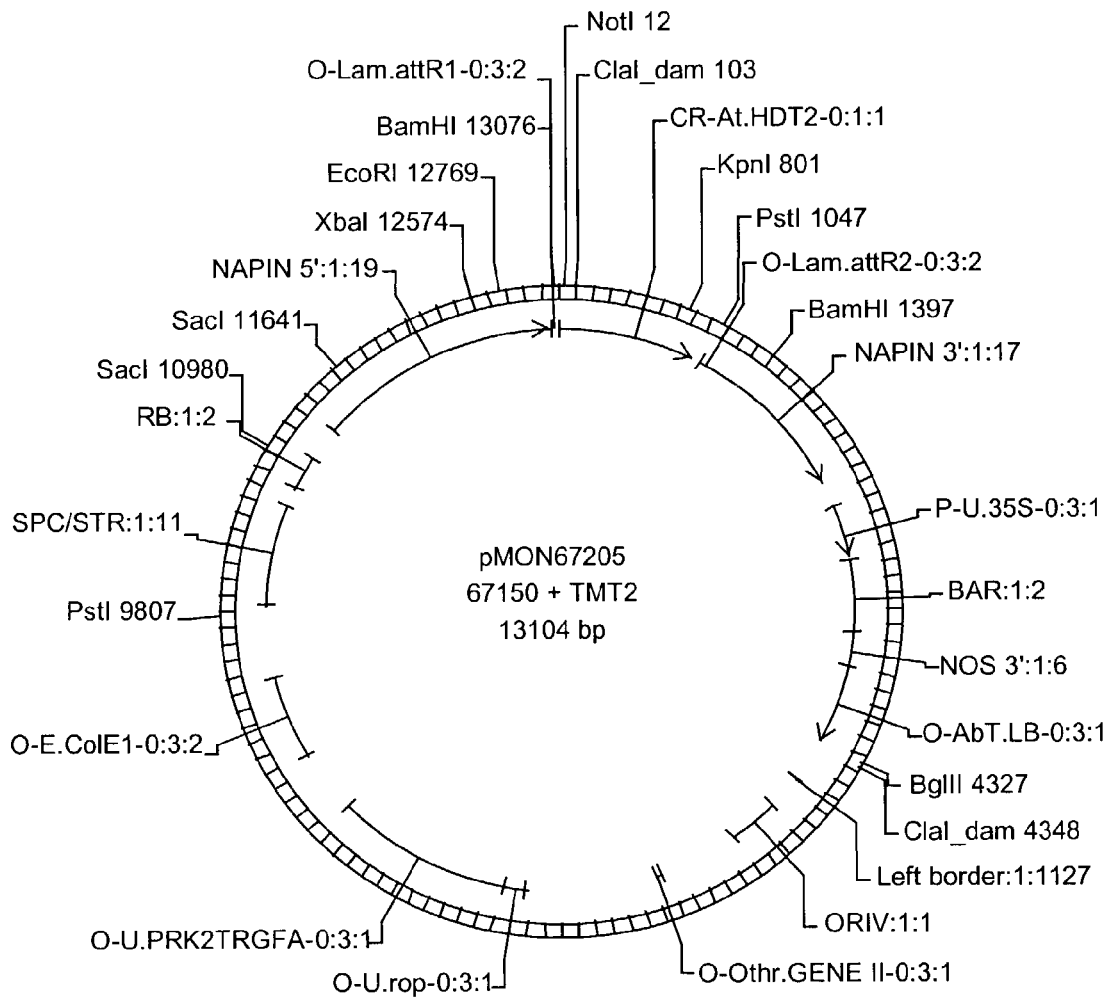
FIG. 9 is a plasmid map of pMON67205.

The wild type Arabidopsis tMT2 sequence is then cloned from the pMON67204 donor vector into the pMON67150 destination vector using the GATEWAY Technology kit (Life Technologies, a Division of Invitrogen Corporation, Rockville, Md.) according to the manufacturer's instructions. This destination vector is a GATEWAY compatible binary vector containing the napin cassette derived from pCGN3223 (described in U.S. Pat. No. 5,639,790). The resultant expression vector is named pMON67205 (FIG. 9) and is used to drive the expression of the tMT2 sequence in seeds.

The plant binary construct described above is used in Arabidopsis thaliana plant transformation to direct the expression of the tMT2 gene in the embryo. The binary vector construct is transformed into ABI strain Agrobacterium cells by the method of Holsters et al. *Mol. Gen. Genet.* 163:181–187 (1978). Transgenic Arabidopsis thaliana plants are obtained by Agrobacterium-mediated transformation of Arabidopsis wild type and the high δ-tocopherol mutants hdt2, hdt10, and hdt16 as described by Valverkens et al., *Proc. Nat. Acad. Sci.* 85:5536–5540 (1988), Bent et al., *Science* 265:1856–1860 (1994), and Bechtold et al., *C. R. Acad. Sci., Life Sciences* 316:1194–1199 (1993). Transgenic plants are selected by sprinkling the transformed $T_1$ seeds directly onto soil and then vernalizing them at 4° C. in the absence of light for 4 days. The seeds are transferred to 21° C., 16 hours light and sprayed with a 1:200 dilution of Finale (AgrEvo Environmental Health, Montvale, N.J.) at 7 days and 14 days after seeding. Transformed plants are grown to maturity and the $T_2$ seed that is produced is analyzed for tocopherol content. The resulting tocopherol data shown in Tables 4 and 5 confirm a reduction of δ-tocopherol in favor of γ and α-tocopherol production in the high δ-tocopherol mutants and in wild type Arabidopsis lines. Tables 4 and 5 contain the results of HPLC analysis using the methodology (with minor modifications) described in Savidge et al., *Plant Phys.* 129:321–332 (2000), Isolation and Characterization of Homogentisate Phytltransferase Genes from Synechocystis sp PCC 6803 and Arabidopsis.

Table 4 below details the results of the $T_2$ seed analysis.

TABLE 4

| ng alpha toco./mg seed | ng beta toco./mg seed | ng gamma toco./mg seed | ng delta toco./mg seed | ng total toco./mg seed | Serial Number | Pedigree | Line # | | % Delta | Average % Delta |
|---|---|---|---|---|---|---|---|---|---|---|
| 5.88 | 0.00 | 529.64 | 18.87 | 554.39 | 69000076011 | 9979-AT00002-81:@.0001. | 1 | | 3.4 | 3.2 |
| 5.45 | 0.00 | 525.89 | 17.44 | 548.78 | 69000076009 | 9979-AT00002-81:@.0004. | 4 | | 3.2 | |
| 5.74 | 0.00 | 511.61 | 16.32 | 533.67 | 69000075994 | 9979-AT00002-81:@.0003. | 3 | | 3.1 | |
| 5.04 | 0.00 | 507.38 | 16.10 | 528.52 | 69000076023 | 9979-AT00002-81:@.0002. | 2 | | 3.0 | |
| 7.74 | 0.00 | 466.14 | 11.53 | 485.41 | 69000075463 | 67205-AT00002:0010. | 10 | T2 | 2.4 | 1.2 |
| 8.76 | 0.00 | 460.36 | 7.00 | 476.12 | 69000075540 | 67205-AT00002:0001. | 1 | T2 | 1.5 | |
| 8.33 | 0.00 | 445.02 | 6.71 | 460.06 | 69000075564 | 67205-AT00002:0004. | 4 | T2 | 1.5 | |
| 8.46 | 0.00 | 443.94 | 6.67 | 459.06 | 69000075502 | 67205-AT00002:0014. | 14 | T2 | 1.5 | |
| 11.13 | 0.00 | 447.27 | 6.35 | 464.75 | 69000075526 | 67205-AT00002:0016. | 16 | T2 | 1.4 | |
| 9.07 | 0.00 | 470.64 | 6.49 | 486.19 | 69000075552 | 67205-AT00002:0003. | 3 | T2 | 1.3 | |
| 8.10 | 0.00 | 422.89 | 5.82 | 436.81 | 69000075538 | 67205-AT00002:0002. | 2 | T2 | 1.3 | |
| 8.64 | 0.00 | 473.01 | 6.47 | 488.12 | 69000075603 | 67205-AT00002:0008. | 8 | T2 | 1.3 | |
| 9.25 | 0.00 | 488.63 | 6.43 | 504.32 | 69000075590 | 67205-AT00002:0007. | 7 | T2 | 1.3 | |
| 7.71 | 0.00 | 475.80 | 6.21 | 489.72 | 69000075588 | 67205-AT00002:0006. | 6 | T2 | 1.3 | |
| 7.77 | 0.00 | 458.67 | 5.71 | 472.15 | 69000075475 | 67205-AT00002:0011. | 11 | T2 | 1.2 | |
| 8.85 | 0.00 | 455.97 | 5.59 | 470.41 | 69000075576 | 67205-AT00002:0005. | 5 | T2 | 1.2 | |
| 10.27 | 0.00 | 349.67 | 3.05 | 362.98 | 69000075514 | 67205-AT00002:0015. | 15 | T2 | 0.8 | |
| 9.22 | 0.00 | 371.75 | 2.84 | 383.81 | 69000075499 | 67205-AT00002:0013. | 13 | T2 | 0.7 | |
| 8.68 | 0.00 | 348.97 | 2.53 | 360.18 | 69000075451 | 67205-AT00002:0009. | 9 | T2 | 0.7 | |
| 7.96 | 0.00 | 413.19 | 2.40 | 423.55 | 69000075487 | 67205-AT00002:0012. | 12 | T2 | 0.6 | |

TABLE 4-continued

| ng alpha toco./mg seed | ng beta toco./mg seed | ng gamma toco./mg seed | ng delta toco./mg seed | ng total toco./mg seed | Serial Number | Pedigree | Line # | | % Delta | Average % Delta |
|---|---|---|---|---|---|---|---|---|---|---|
| 7.00 | 0.00 | 277.36 | 286.49 | 570.84 | 69000077835 | hdt2:@.0001. | 1 | | 50.2 | 49.7 |
| 6.57 | 0.00 | 273.89 | 278.92 | 559.38 | 69000077809 | hdt2:@.0004. | 4 | | 49.9 | |
| 6.90 | 0.00 | 277.90 | 279.96 | 564.77 | 69000077811 | hdt2:@.0003. | 3 | | 49.6 | |
| 6.93 | 0.00 | 275.20 | 273.89 | 556.01 | 69000077823 | hdt2:@.0002. | 2 | | 49.3 | |
| 8.35 | 0.00 | 365.85 | 143.68 | 517.88 | 69000075639 | 67205-hdt2.0011. | 11 | T2 | 27.7 | 20.5 |
| 7.75 | 0.00 | 384.44 | 127.60 | 519.79 | 69000075689 | 67205-hdt2:0016. | 16 | T2 | 24.5 | |
| 7.05 | 0.00 | 358.91 | 105.17 | 471.13 | 69000075627 | 67205-hdt2 0010. | 10 | T2 | 22.3 | |
| 8.33 | 0.00 | 342.11 | 98.01 | 448.45 | 69000075665 | 67205-hdt2:0014. | 14 | T2 | 21.9 | |
| 6.73 | 0.00 | 410.18 | 112.97 | 529.88 | 69000075716 | 67205-hdt2:0006. | 6 | T2 | 21.3 | |
| 6.89 | 0.00 | 357.86 | 98.47 | 463.22 | 69000075704 | 67205-hdt2:0007. | 7 | T2 | 21.3 | |
| 6.85 | 0.00 | 352.48 | 96.71 | 456.04 | 69000075691 | 67205-hdt2:0008. | 8 | T2 | 21.2 | |
| 8.06 | 0.00 | 356.89 | 96.10 | 461.05 | 69000075754 | 67205-hdt2:0002. | 2 | T2 | 20.8 | |
| 7.60 | 0.00 | 311.53 | 82.55 | 401.68 | 69000075677 | 67205-hdt2:0015. | 15 | T2 | 20.6 | |
| 7.81 | 0.00 | 344.03 | 88.44 | 440.28 | 69000075615 | 67205-hdt2:0009. | 9 | T2 | 20.1 | |
| 7.50 | 0.00 | 368.30 | 88.66 | 464.46 | 69000075641 | 67205-hdt2:0012. | 12 | T2 | 19.1 | |
| 7.13 | 0.00 | 336.24 | 80.34 | 423.71 | 69000075728 | 67205-hdt2:0005. | 5 | T2 | 19.0 | |
| 7.78 | 0.00 | 345.26 | 81.26 | 434.30 | 69000075766 | 67205-hdt2:0001. | 1 | T2 | 18.7 | |
| 8.82 | 0.00 | 340.61 | 72.71 | 422.15 | 69000075730 | 67205-hdt2:0004. | 4 | T2 | 17.2 | |
| 8.11 | 0.00 | 418.69 | 81.01 | 507.81 | 69000075742 | 67205-hdt2:0003. | 3 | T2 | 16.0 | |
| 6.08 | 0.00 | 365.54 | 69.78 | 441.40 | 69000075653 | 67205-hdt2:0013. | 13 | T2 | 15.8 | |
| 3.36 | | 262.76 | 180.18 | 446.30 | 69000157140 | hdt16:@.0007. | Control | M5 | 40.4 | 38.2 |
| 3.36 | | 290.12 | 177.76 | 471.24 | 69000157114 | hdt16:@.0003. | Control | M5 | 37.7 | |
| 2.54 | | 305.52 | 178.20 | 486.25 | 69000157099 | hdt16:@.0005. | Control | M5 | 36.6 | |
| 4.93 | | 248.24 | 67.78 | 320.95 | 69000156403 | AT_G119:@. | PMON67205 | R2 | 21.1 | 16.0 |
| 3.55 | | 232.71 | 62.01 | 298.26 | 69000156667 | AT_G36:@. | PMON67205 | R2 | 20.8 | |
| 5.55 | | 282.81 | 64.06 | 352.42 | 69000156679 | AT_G37:@. | PMON67205 | R2 | 18.2 | |
| 6.79 | | 273.40 | 55.90 | 336.09 | 69000156617 | AT_G31:@. | PMON67205 | R2 | 16.6 | |
| 5.65 | | 377.29 | 52.27 | 435.22 | 69000156631 | AT_G33:@. | PMON67205 | R2 | 12.0 | |
| 5.82 | | 256.67 | 20.04 | 282.53 | 69000156655 | AT_G35:@. | PMON67205 | R2 | 7.1 | |
| 4.32 | | 356.41 | 71.85 | 432.59 | 69000157037 | hdt10:@.0001. | Control | M6 | 16.6 | 9.6 |
| 5.73 | | 469.11 | 12.79 | 487.62 | 69000157049 | hdt10:@.0002. | Control | M6 | 2.6 | |
| 3.39 | | 308.41 | 27.44 | 339.24 | 69000156528 | AT_G22:@. | PMON67205 | R2 | 8.1 | 2.9 |
| 5.53 | | 350.19 | 28.83 | 384.55 | 69000156592 | AT_G29:@. | PMON67205 | R2 | 7.5 | |
| 4.33 | | 329.32 | 23.29 | 356.94 | 69000156489 | AT_G18:@. | PMON67205 | R2 | 6.5 | |
| 5.20 | | 344.82 | 19.81 | 369.84 | 69000156566 | AT_G26:@. | PMON67205 | R2 | 5.4 | |
| 6.14 | | 348.51 | 19.38 | 374.03 | 69000156453 | AT_G15:@. | PMON67205 | R2 | 5.2 | |
| 5.12 | | 394.47 | 14.59 | 414.19 | 69000156578 | AT_G27:@. | PMON67205 | R2 | 3.5 | |
| 7.01 | | 473.37 | 13.03 | 493.40 | 69000156530 | AT_G23:@. | PMON67205 | R2 | 2.6 | |
| 6.82 | | 355.34 | 3.94 | 366.10 | 69000156580 | AT_G28:@. | PMON67205 | R2 | 1.1 | |
| 4.41 | | 395.46 | 3.82 | 403.69 | 69000156477 | AT_G17:@. | PMON67205 | R2 | 0.9 | |
| 4.64 | | 383.13 | 2.46 | 390.23 | 69000156542 | AT_G24:@. | PMON67205 | R2 | 0.6 | |
| 6.21 | | 319.67 | 1.91 | 327.79 | 69000156465 | AT_G16:@. | PMON67205 | R2 | 0.6 | |
| 4.79 | | 291.39 | 1.59 | 297.77 | 69000156441 | AT_G14:@. | PMON67205 | R2 | 0.5 | |
| 4.72 | | 393.79 | 1.89 | 400.40 | 69000156491 | AT_G19:@. | PMON67205 | R2 | 0.5 | |
| 5.97 | | 378.05 | 1.59 | 385.62 | 69000156516 | AT_G21:@. | PMON67205 | R2 | 0.4 | |
| 6.16 | | 358.64 | 0.00 | 364.80 | 69000156554 | AT_G25:@. | PMON67205 | R2 | 0.0 | | mp: indicates "metabolic profiling".

Table 1 below depicts the results of the analysis of T3 seed data from pMON67205 in hdt2 mutant lines.

TABLE 5

| Crop | Biotype | Serial Number | mp:aT | mp:gT | mp:dT | total toco. | % delta | Gen | Pedigree | Construct |
|---|---|---|---|---|---|---|---|---|---|---|
| AT | SEED | 69000357524 | 2 | 280 | 190 | 472 | 40.3 | M7 | hdt2:@.0001.0001. | |
| AT | SEED | 69000357512 | 3 | 262 | 208 | 473 | 44.0 | M7 | hdt2:@.0001.0002. | |
| AT | SEED | 69000357625 | 4 | 263 | 204 | 471 | 43.3 | M7 | hdt2:@.0001.0003. | |
| AT | SEED | 69000357613 | 4 | 271 | 220 | 495 | 44.4 | M7 | hdt2:@.0001.0004. | |
| AT | SEED | 69000357803 | 6 | 436 | 26 | 468 | 5.6 | R3 | 67205-hdt2:0003.0001. | 67205 |
| AT | SEED | 69000357790 | 4 | 336 | 149 | 489 | 30.5 | R3 | 67205-hdt2:0003.0002. | 67205 |
| AT | SEED | 69000357788 | 4 | 332 | 112 | 448 | 25.0 | R3 | 67205-hdt2:0003.0003. | 67205 |
| AT | SEED | 69000357776 | 3 | 334 | 140 | 477 | 29.4 | R3 | 67205-hdt2:0003.0004. | 67205 |
| AT | SEED | 69000357764 | 4 | 324 | 128 | 456 | 28.1 | R3 | 67205-hdt2:0003.0005. | 67205 |
| AT | SEED | 69000357598 | 3 | 363 | 97 | 463 | 21.0 | R3 | 67205-hdt2:0003.0006. | 67205 |
| AT | SEED | 69000357586 | 4 | 339 | 145 | 488 | 29.7 | R3 | 67205-hdt2:0003.0007. | 67205 |
| AT | SEED | 69000357574 | 4 | 372 | 99 | 475 | 20.8 | R3 | 67205-hdt2:0003.0008. | 67205 |
| AT | SEED | 69000357562 | 5 | 388 | 72 | 465 | 15.5 | R3 | 67205-hdt2:0003.0009. | 67205 |
| AT | SEED | 69000357550 | 4 | 341 | 63 | 408 | 15.4 | R3 | 67205-hdt2:0013.0001. | 67205 |
| AT | SEED | 69000357548 | 3 | 352 | 60 | 415 | 14.5 | R3 | 67205-hdt2:0013.0002. | 67205 |
| AT | SEED | 69000357536 | 4 | 386 | 54 | 444 | 12.2 | R3 | 67205-hdt2:0013.0003. | 67205 |
| AT | SEED | 69000358209 | 4 | 381 | 54 | 439 | 12.3 | R3 | 67205-hdt2:0013.0004. | 67205 |
| AT | SEED | 69000358196 | 6 | 413 | 73 | 492 | 14.8 | R3 | 67205-hdt2:0013.0005. | 67205 |
| AT | SEED | 69000358184 | 3 | 379 | 62 | 444 | 14.0 | R3 | 67205-hdt2:0013.0006. | 67205 |
| AT | SEED | 69000358172 | 5 | 382 | 63 | 450 | 14.0 | R3 | 67205-hdt2:0013.0007. | 67205 |
| AT | SEED | 69000358160 | 5 | 359 | 49 | 413 | 11.9 | R3 | 67205-hdt2:0013.0008. | 67205 |
| AT | SEED | 69000357601 | 4 | 371 | 4 | 379 | 1.1 | R3 | 67205-hdt2:0013.0009. | 67205 |

EXAMPLE 7

Method to prepare double gene constructs for expression in soybean and *Arabidopsis*.

Figure 14:
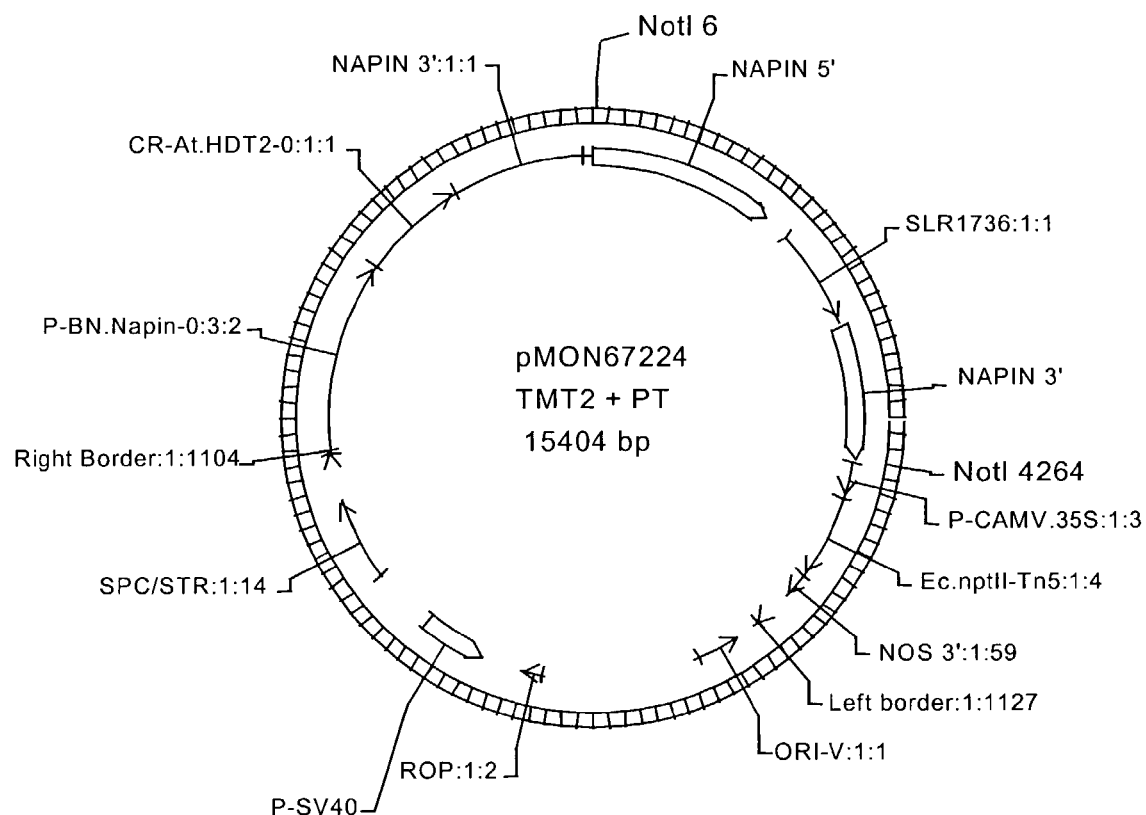
FIG. 14 is a plasmid map of pMON67224.
Figure 15:
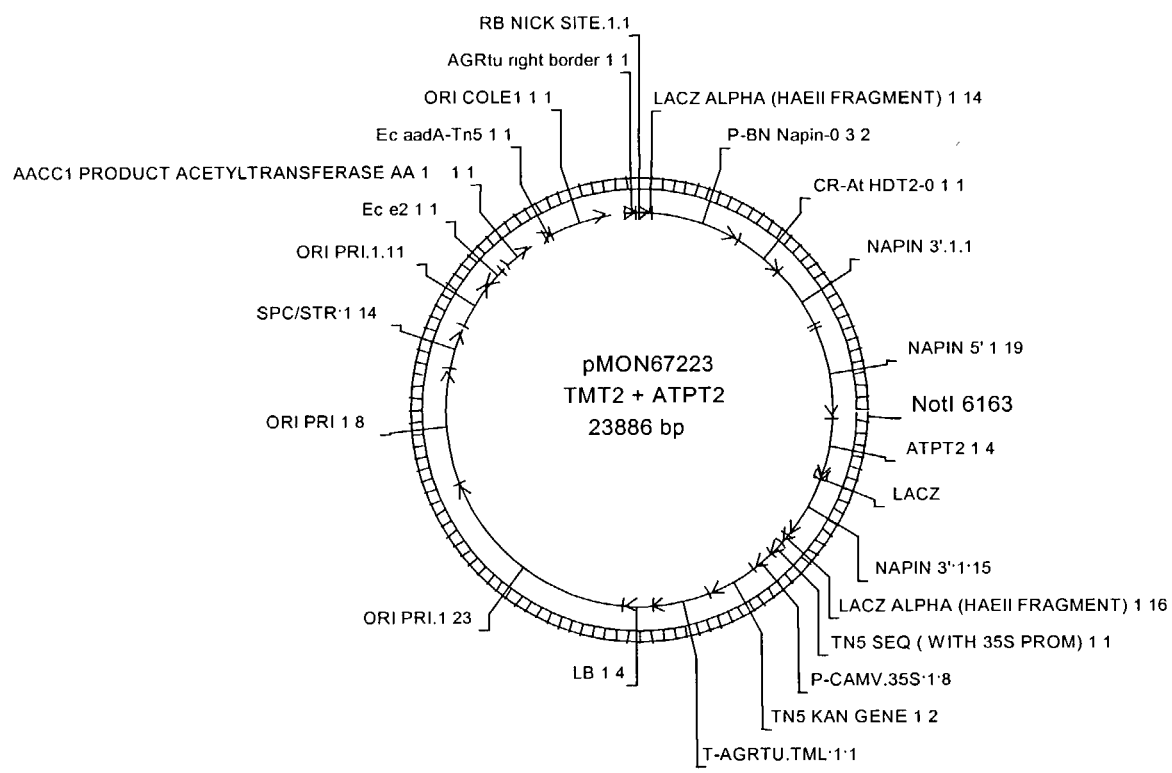
FIG. 15 is a plasmid map of pMON67223.
Figure 16A:
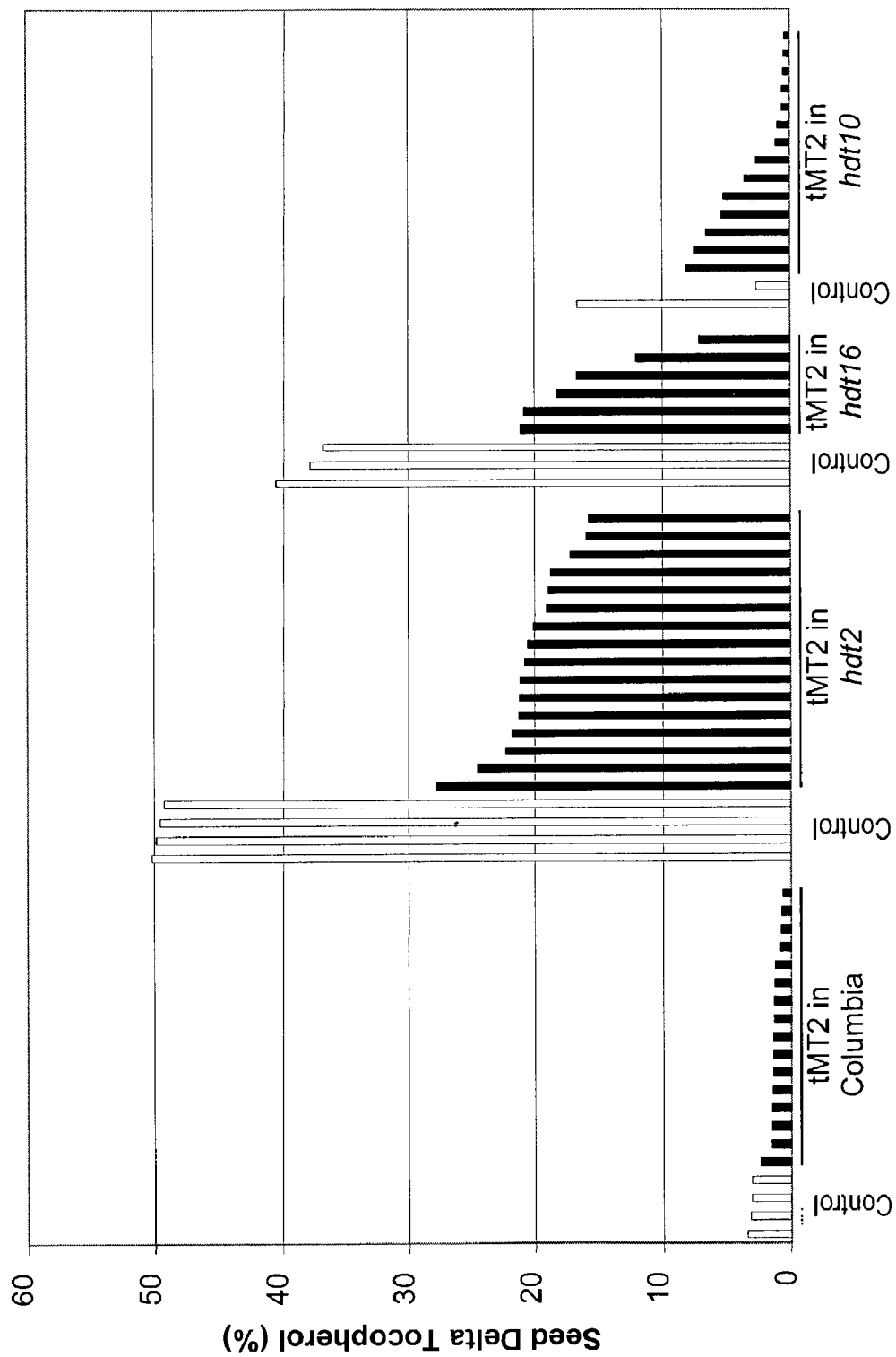
FIGS. 16*a* and 16*b* depict the levels of expression of δ-tocopherol in various types of *Arabidopsis*.
Figure 16B:
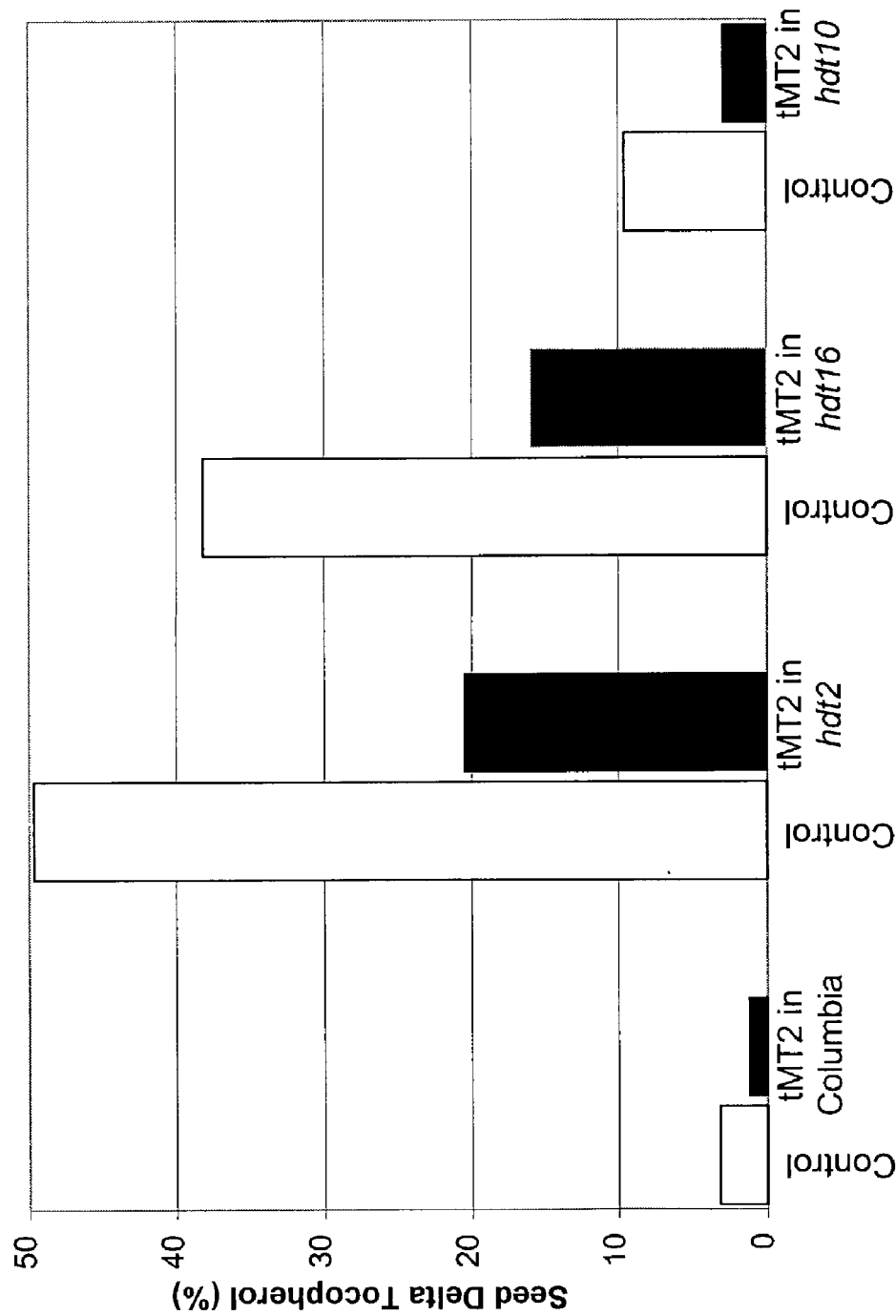
Figure 17:
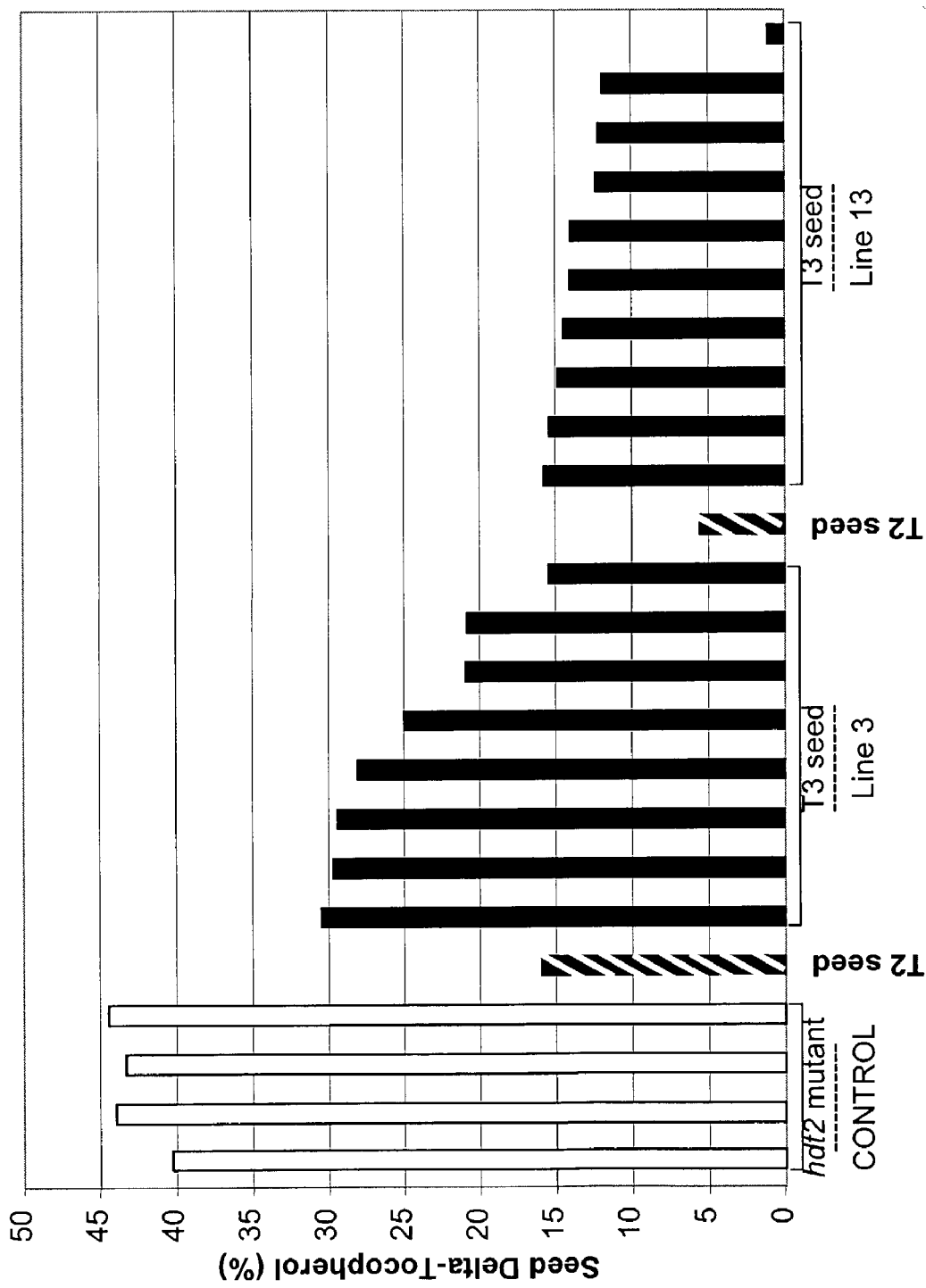
FIG. 17 depicts T3 seed δ-tocopherol (%) from two lines expressing tMT2 under the control of the napin promoter (pMON67205) in the hdt2 mutant line.
Figure 18A:
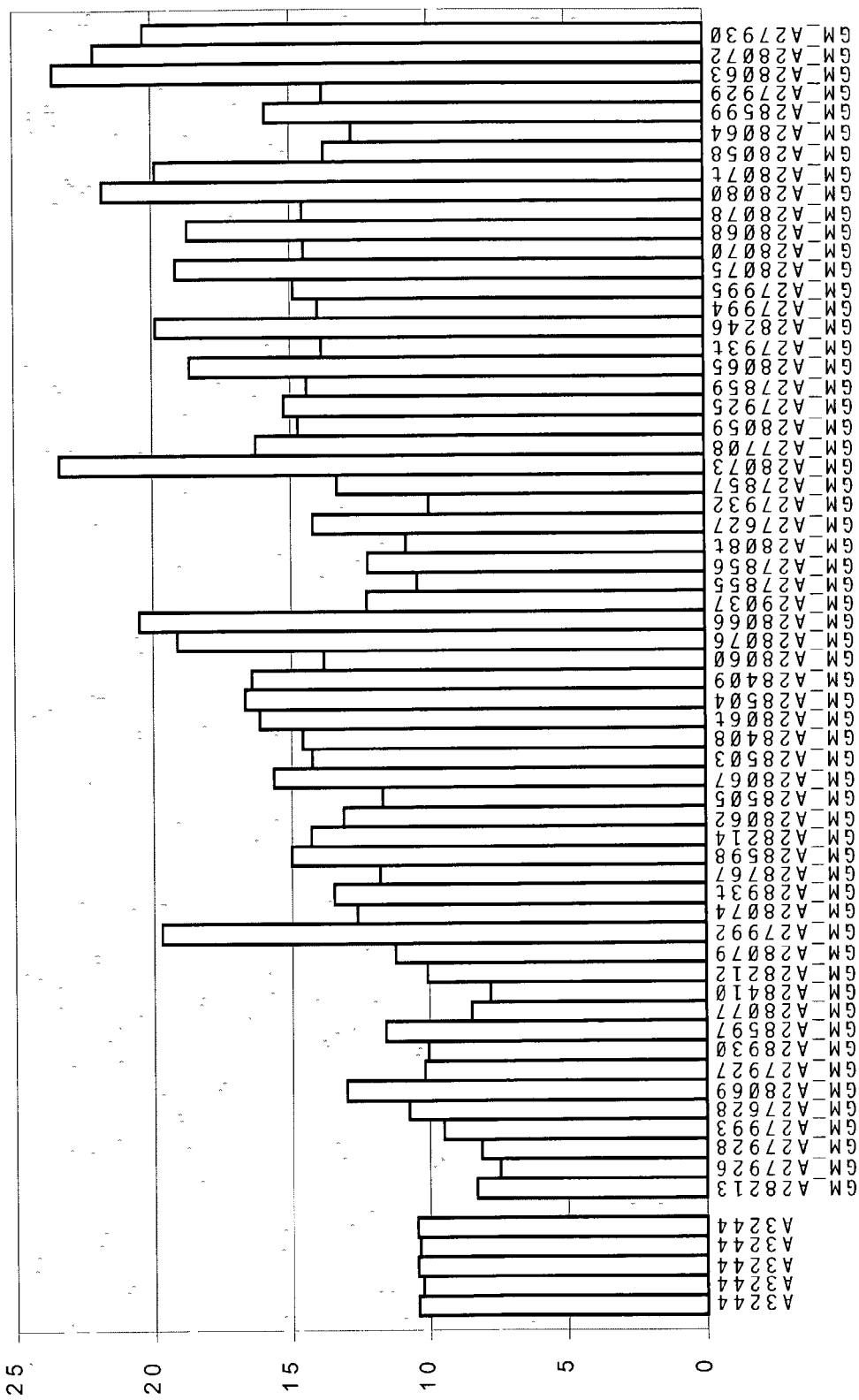
FIGS. 18*a–d* depict the levels of α, β, γ, and δ-tocopherol in tMT2 pools of 10 seeds.
Figure 18B:
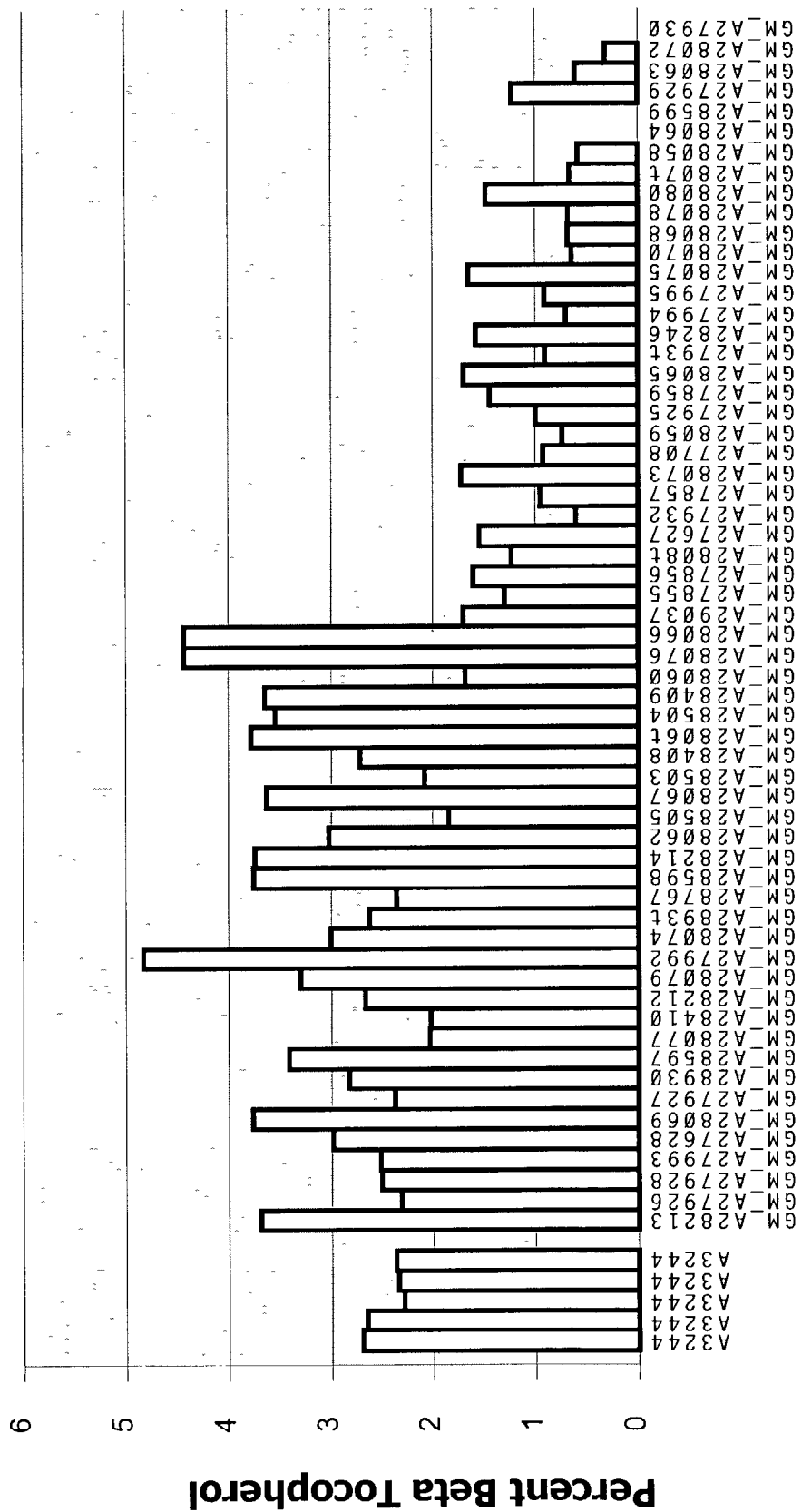
Figure 18C:
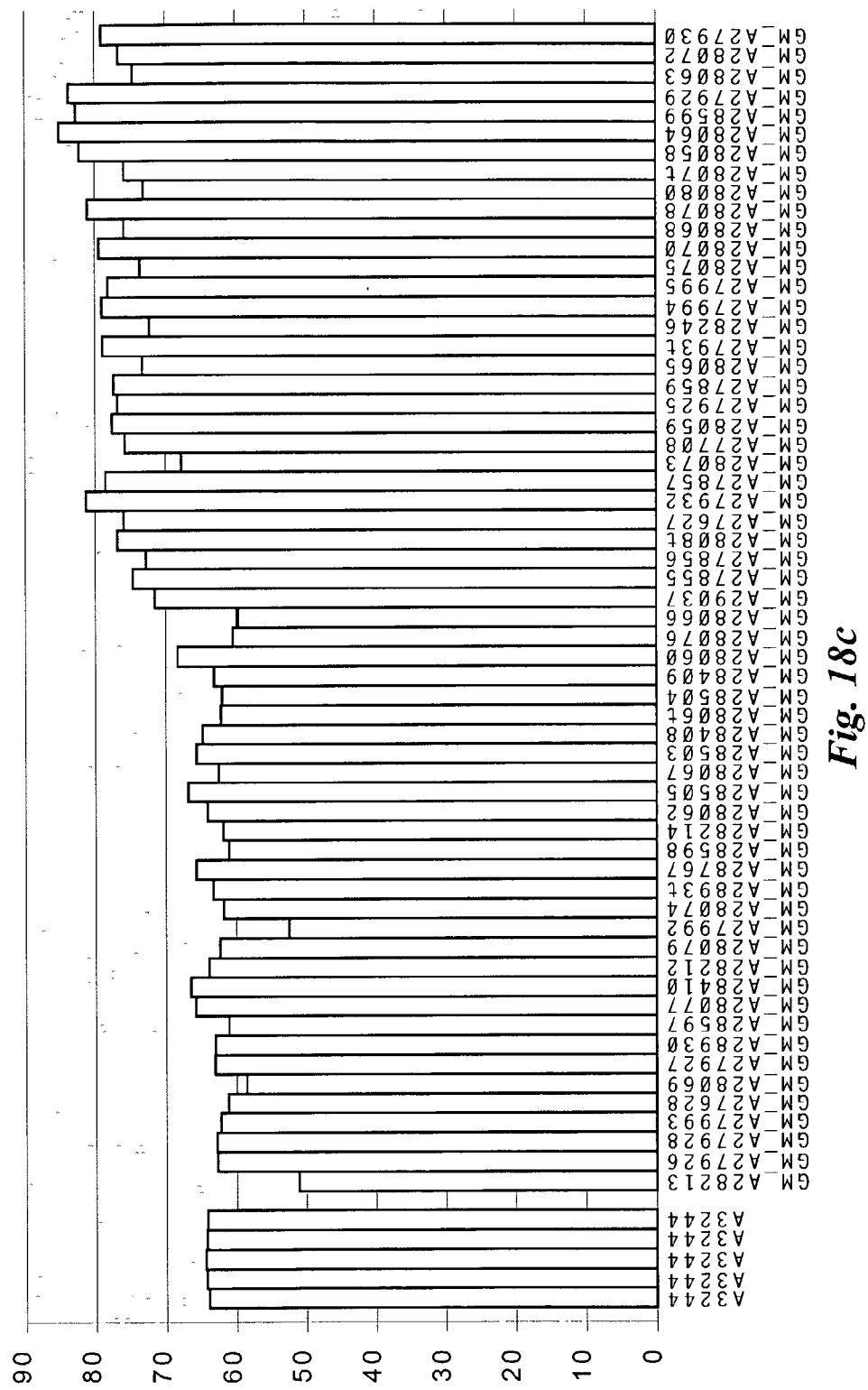
Figure 18D:
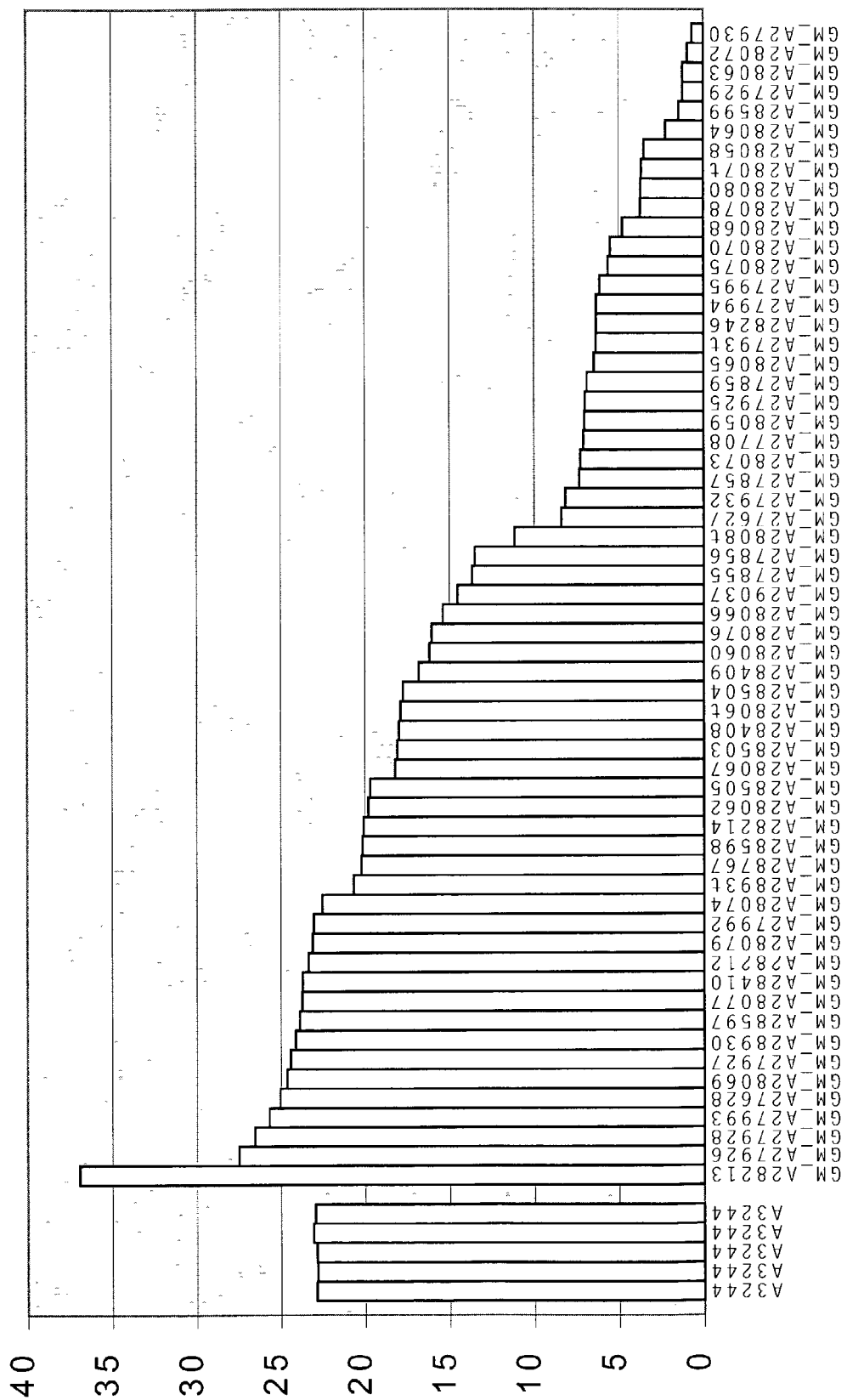
Figure 19A:
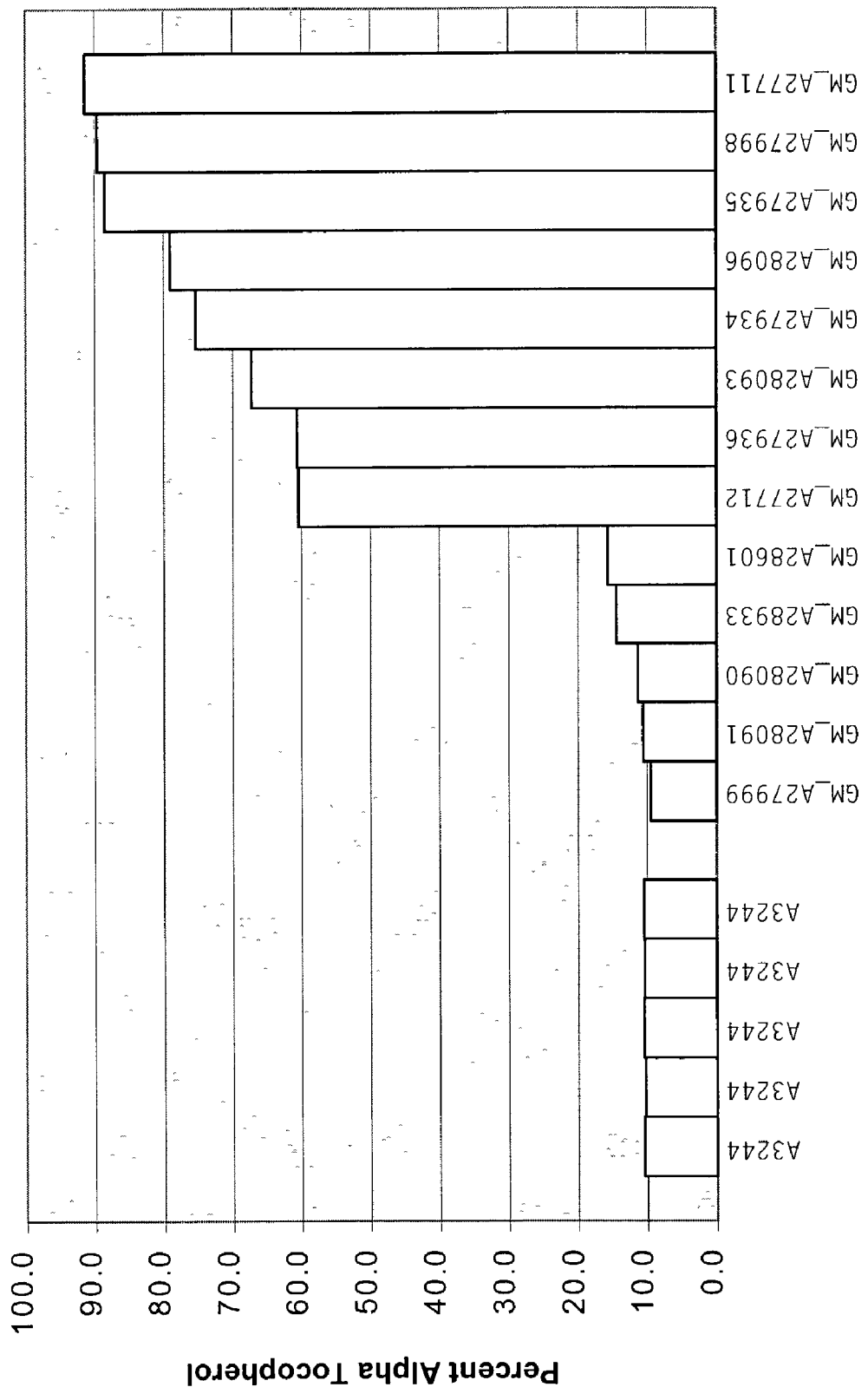
FIGS. 19*a–d* depict the levels of α, β, γ, and δ-tocopherol in tMT2/GMT pools of 10 seeds.
Figure 19B:
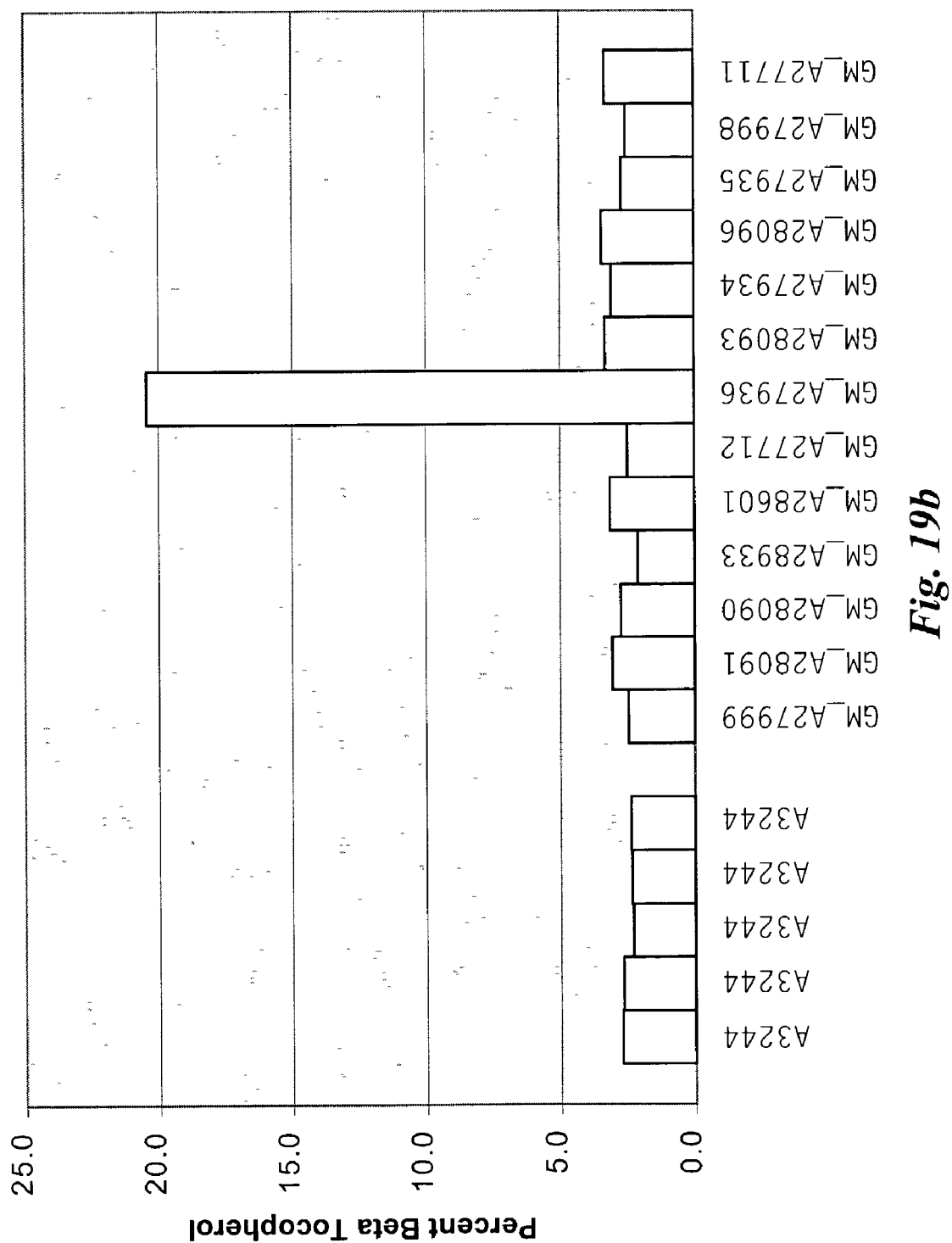
Figure 19C:
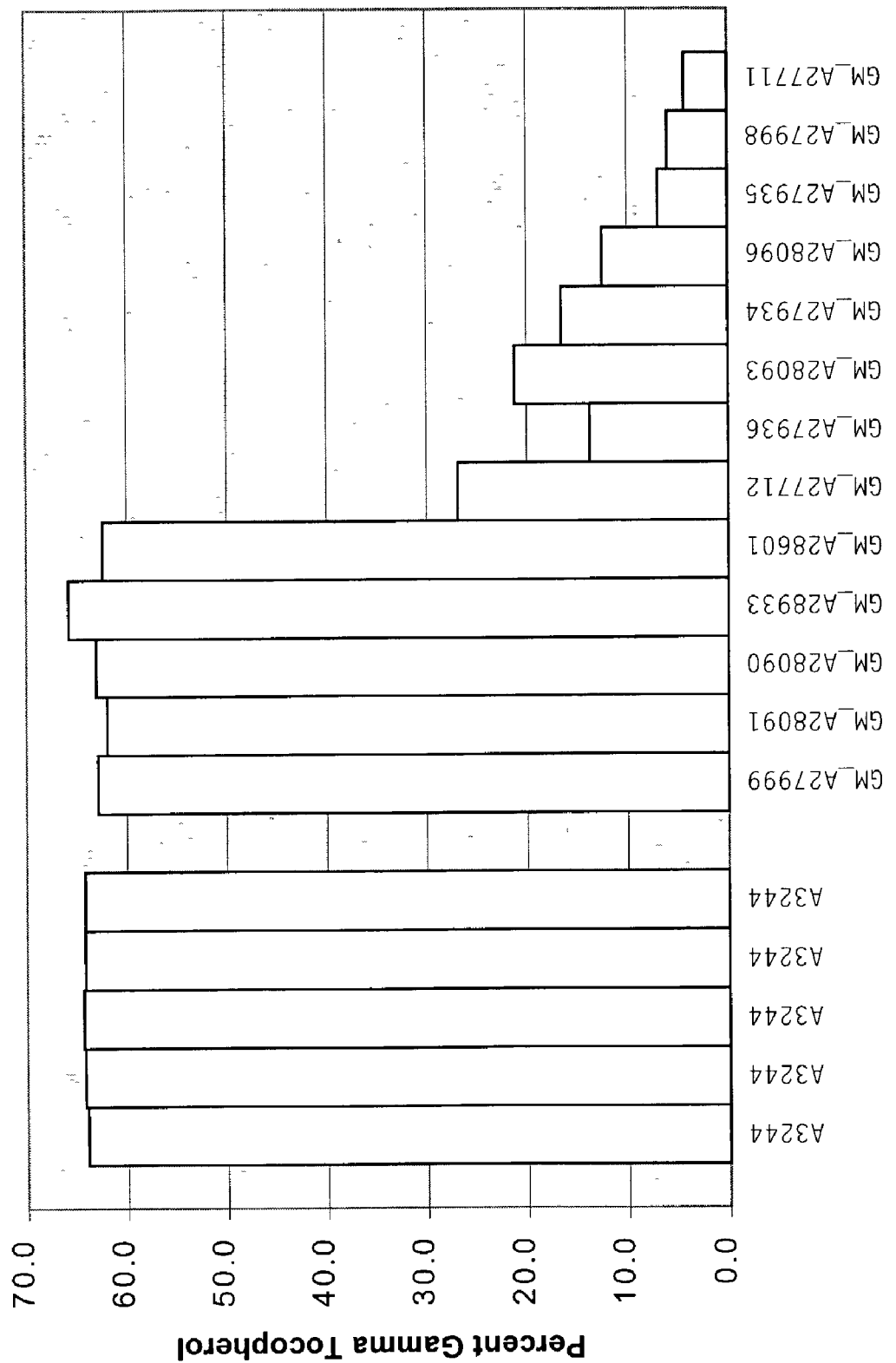
Figure 19D:
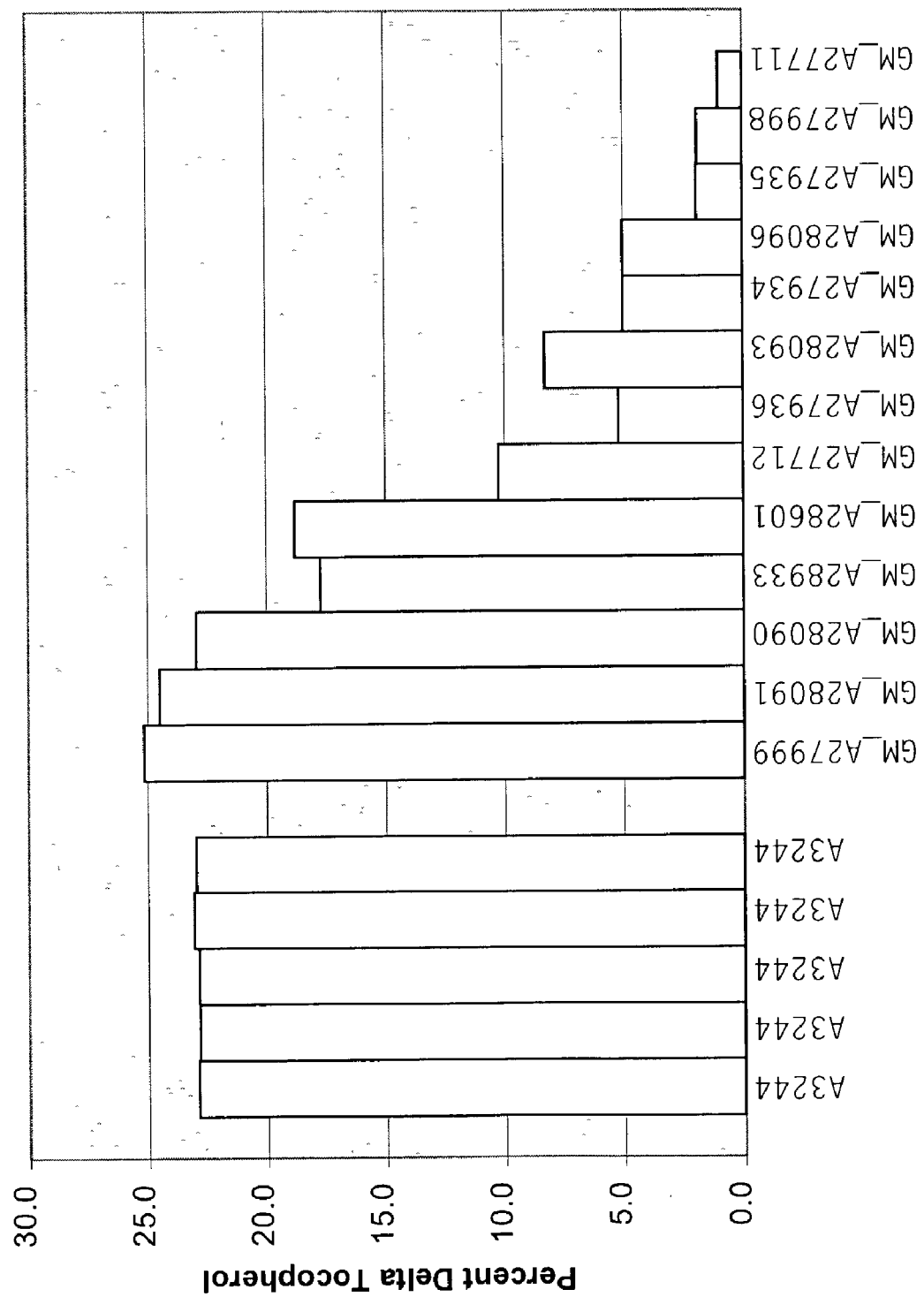
Figure 20:
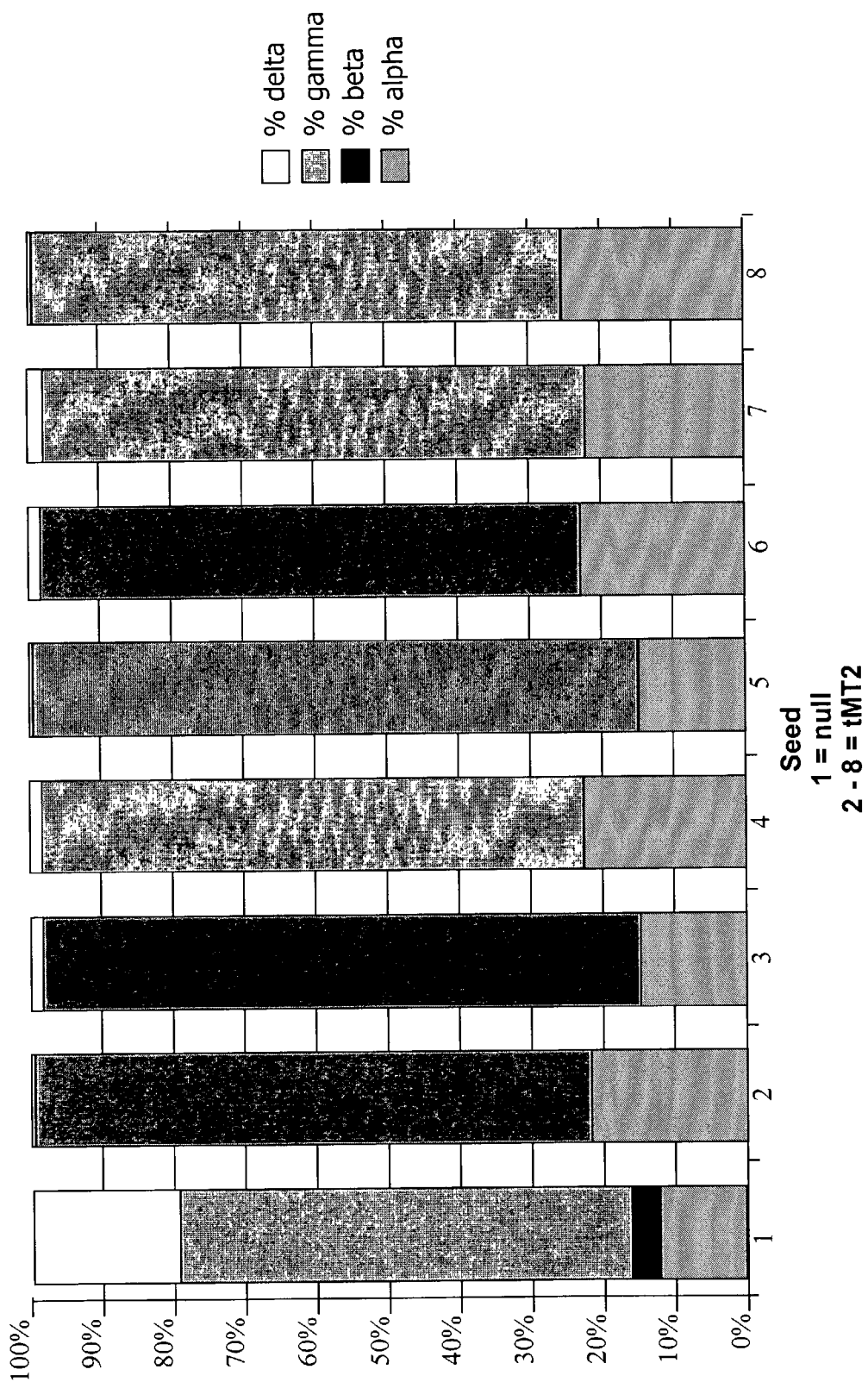
FIG. 20 depicts the tocopherol composition of single seeds from one line of soybean (28072) transformed with pMON67226.
Figure 21B:
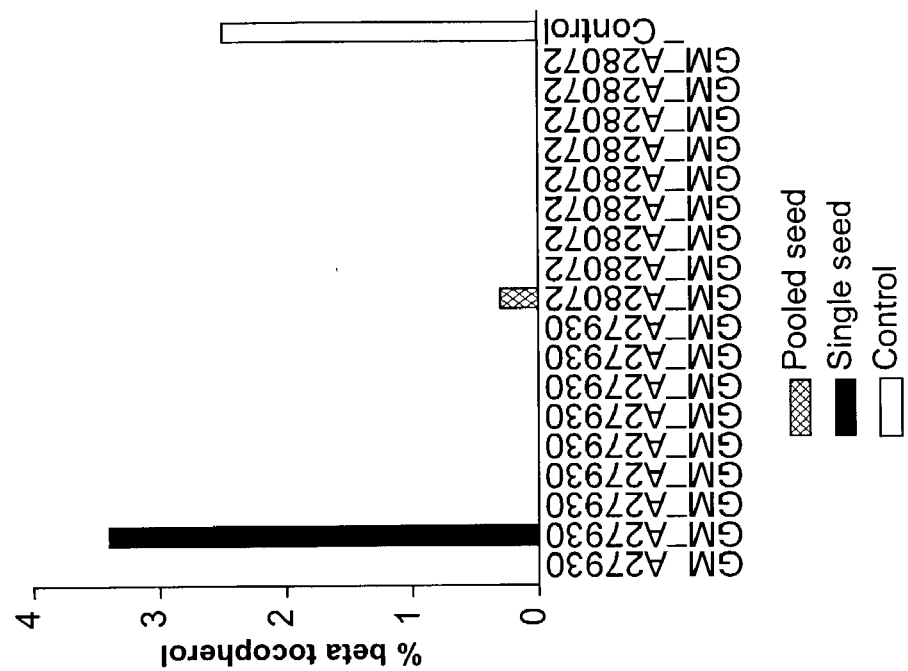
FIGS. 21*a–d* depict the levels of α, β, γ, and δ-tocopherol in R1 Soy Single Seed from pMON67226.
Figure 21A:
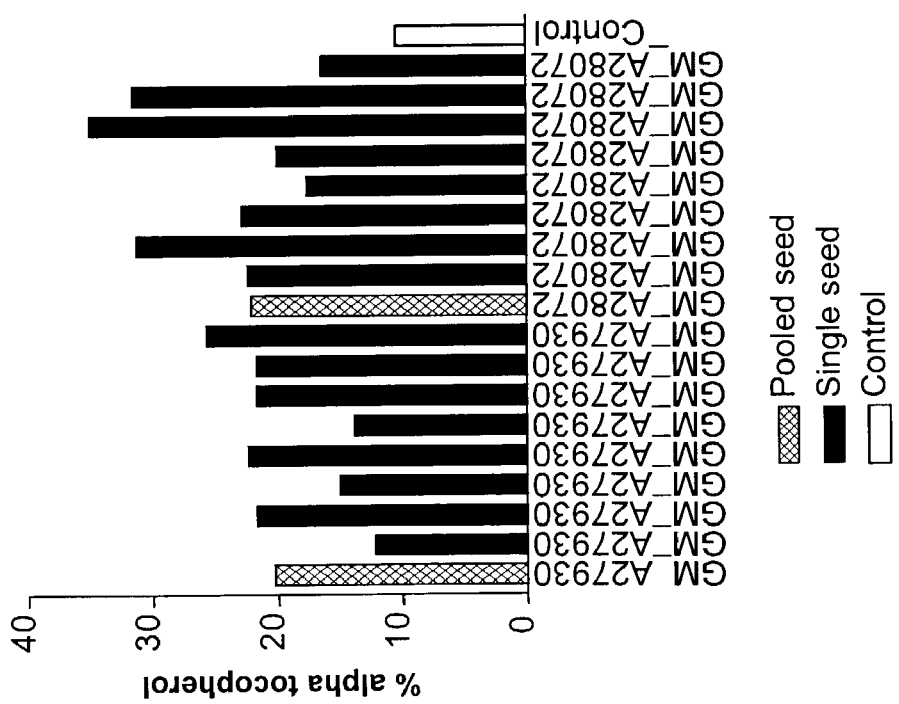
Figure 21D:
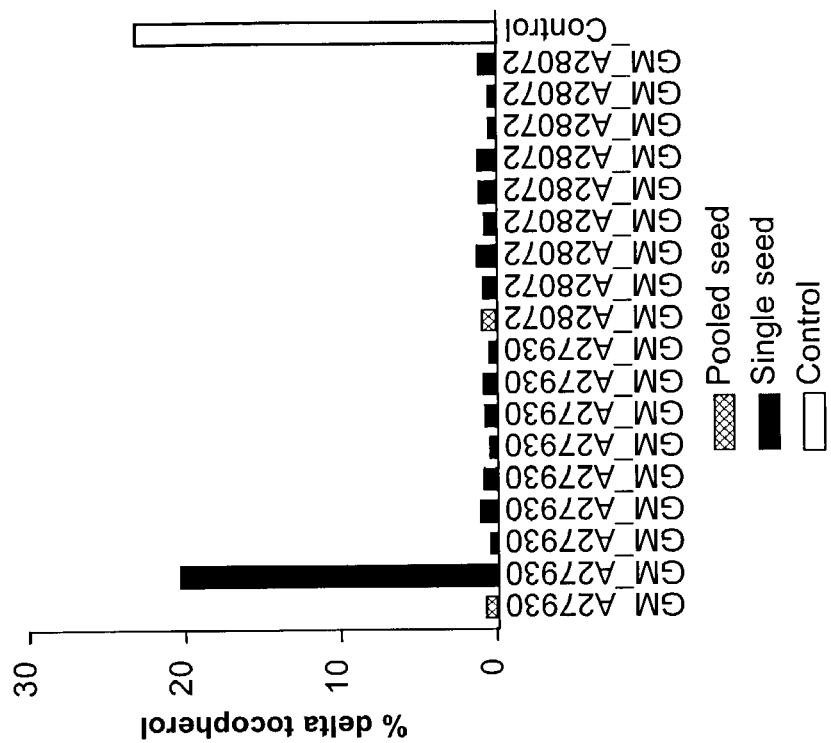
Figure 21C:
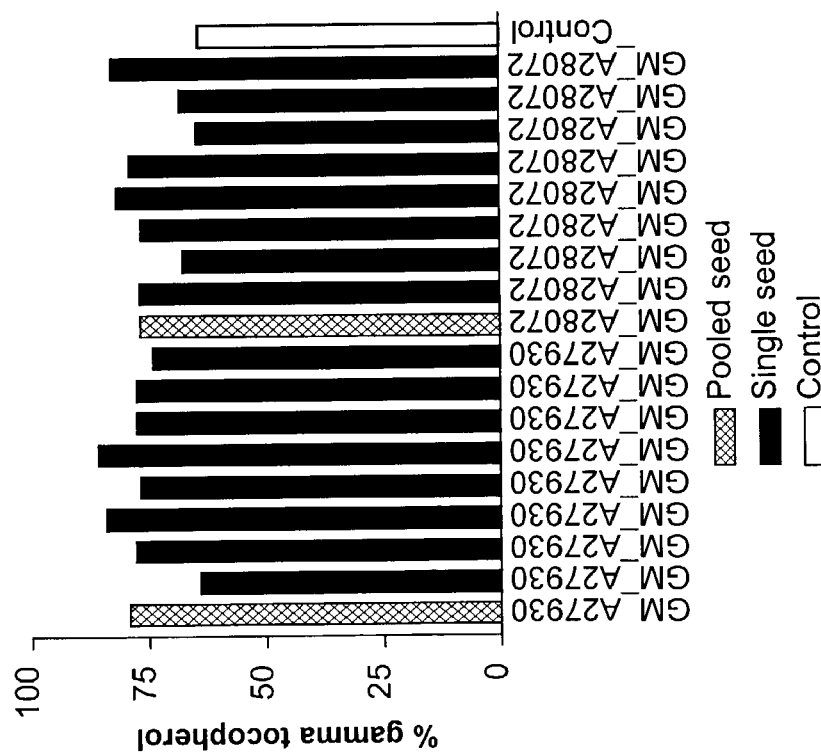
Figure 22:
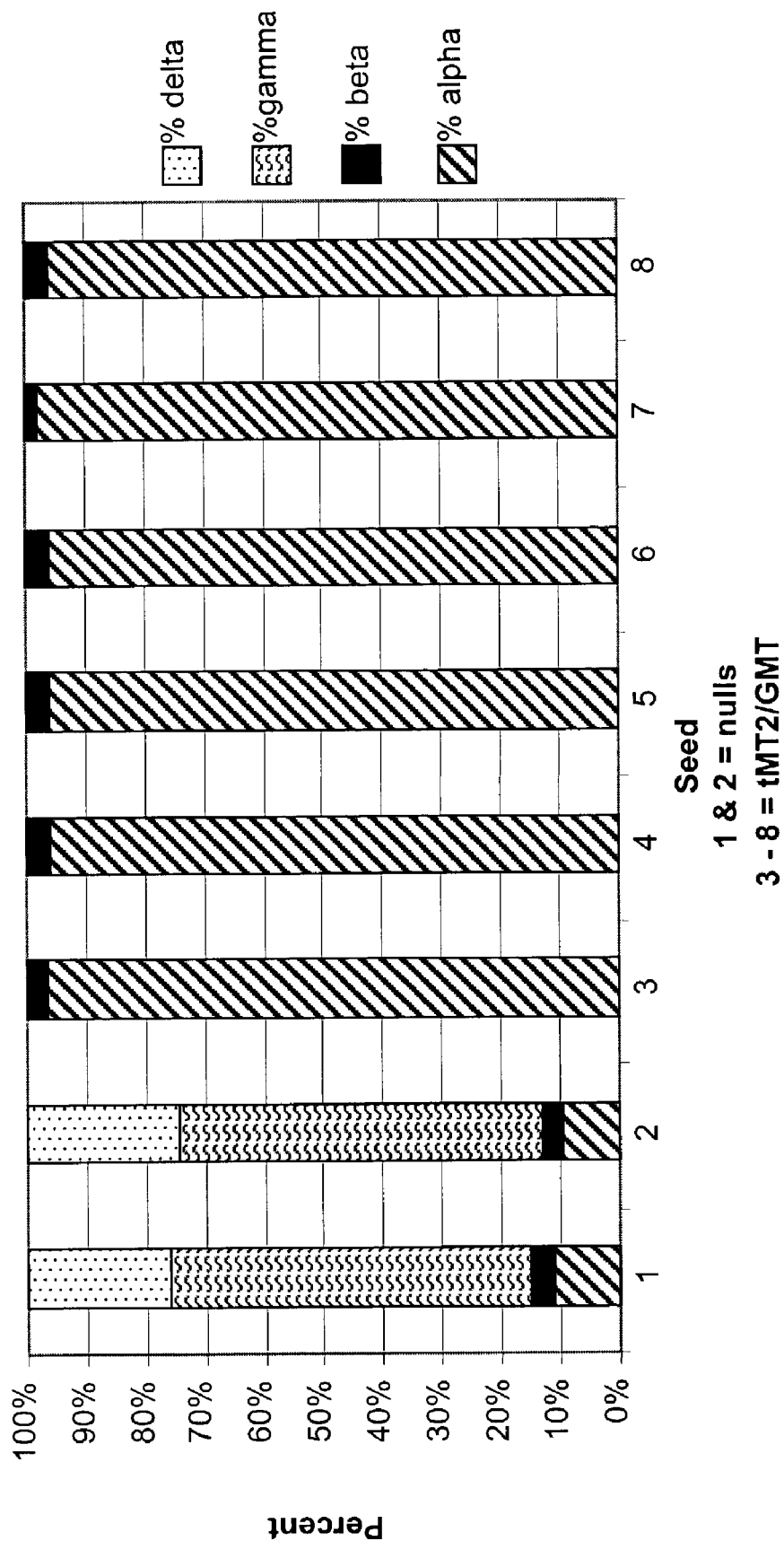
FIG. 22 depicts the tocopherol composition of single seeds from one line of soybean (28906) transformed with pMON67227.
Figure 23A:
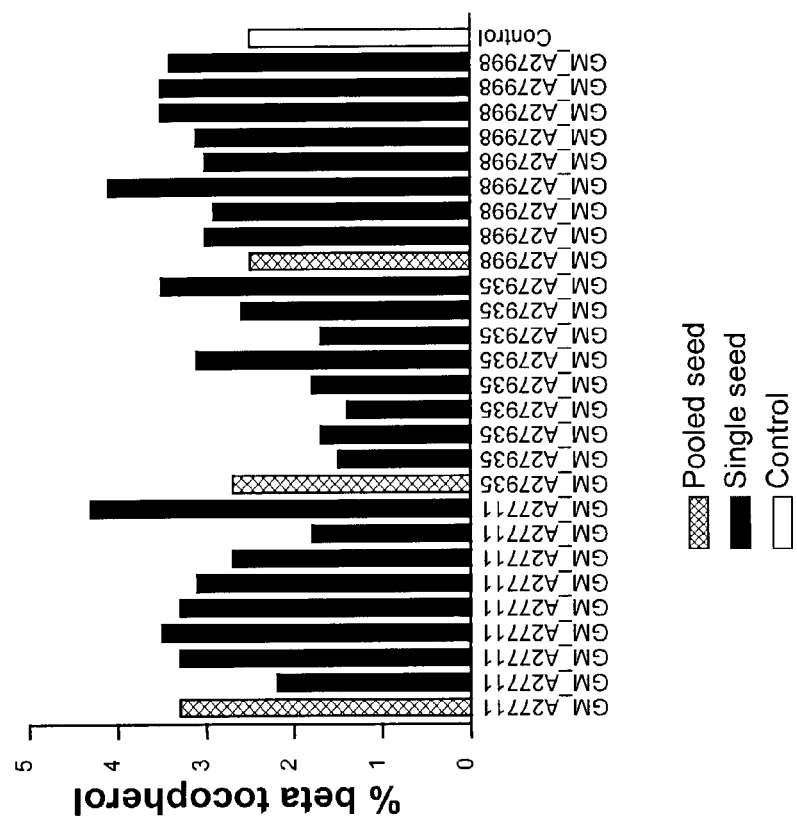
FIGS. 23*a–d* depict the levels of α, β, γ, and δ-tocopherol in R1 Soy Single Seed from pMON67227.
Figure 23B:
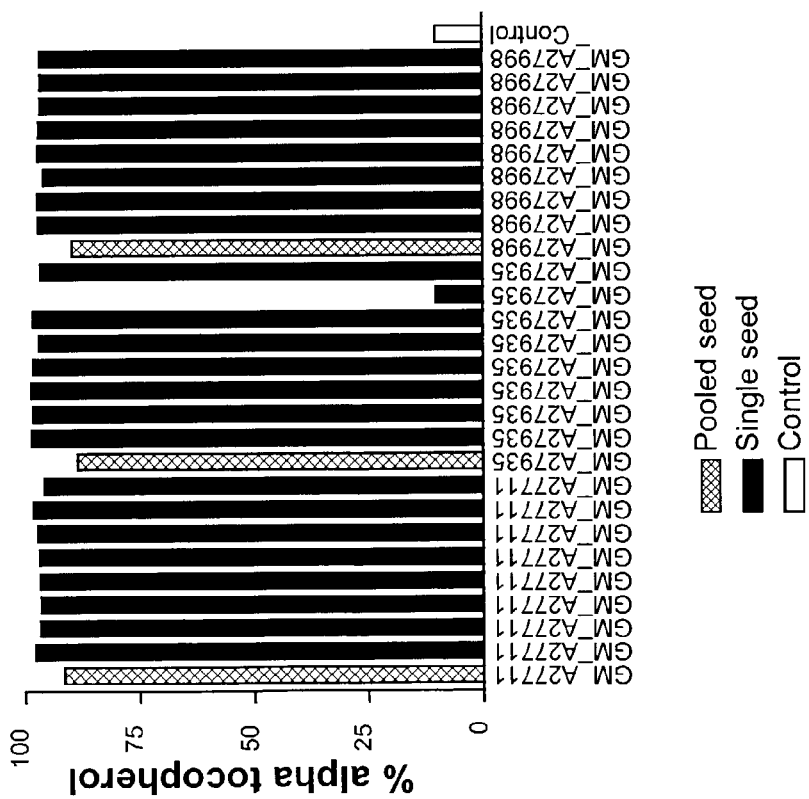
Figure 23D:
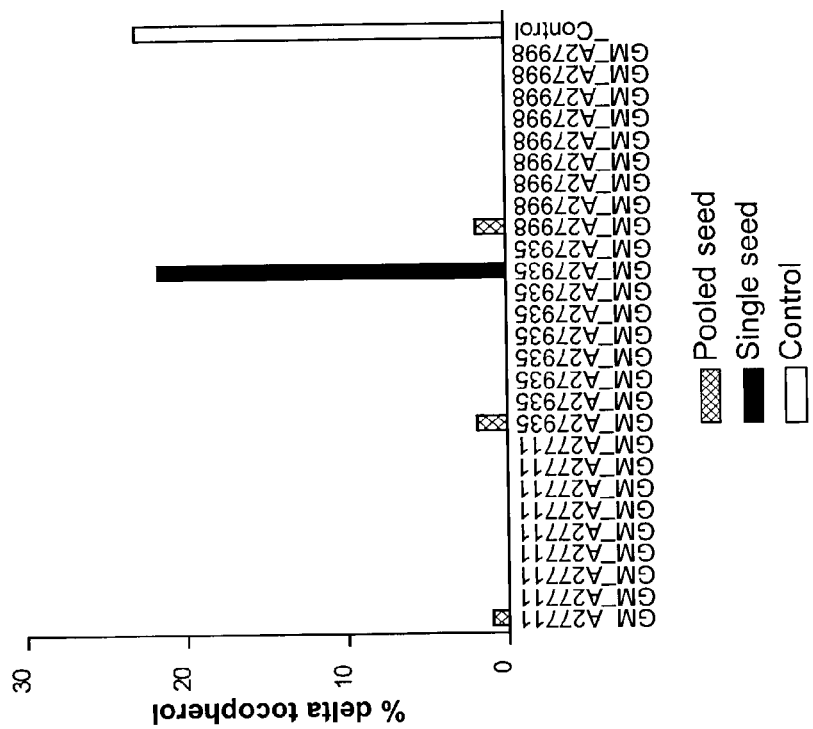
Figure 23C:
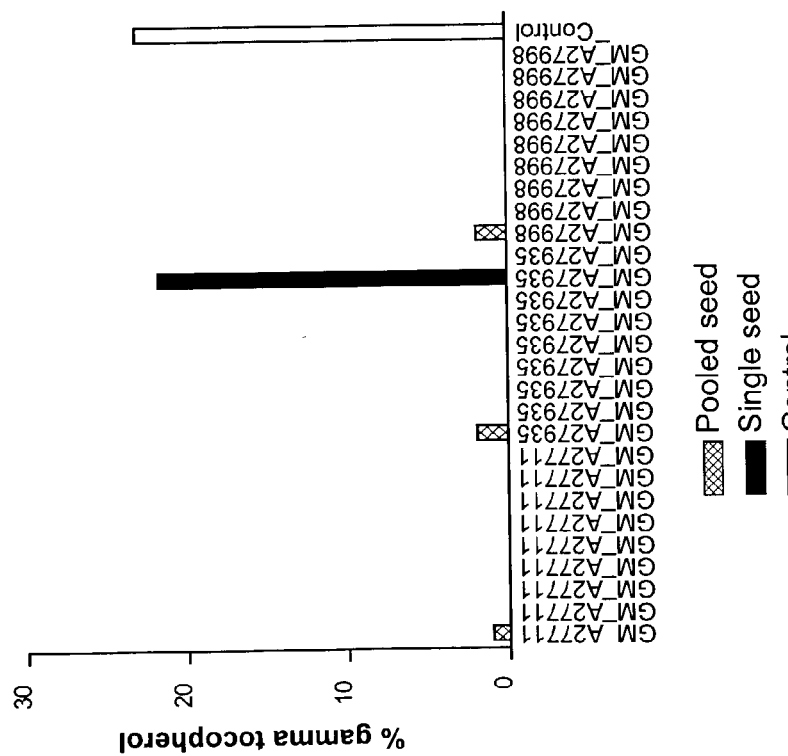

Constructs are made containing promoters that provide seed-specific expression of the tMT2 gene alone and in combination with the GMT gene in soybean. Additionally the tMT2 gene is cloned behind the napin promoter and cloned into a binary vector with the HPT gene from *Arabidopsis* and in another double gene construct with the prenyltransferase (PT) gene (slr1736) from *Synechocystis* (pMON67224 and pMON67223 as shown in FIGS. 14 and 15, respectively).

Soybean Constructs

Figure 10:
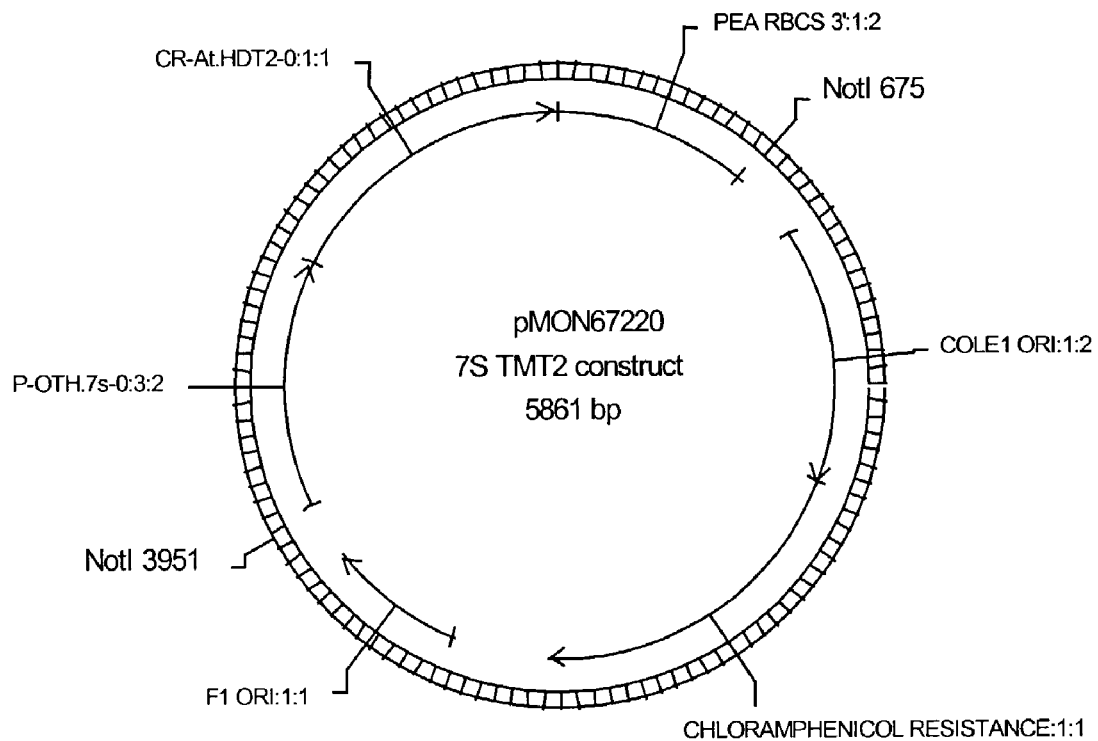
FIG. 10 is a plasmid map of pMON67220.
Figure 11:
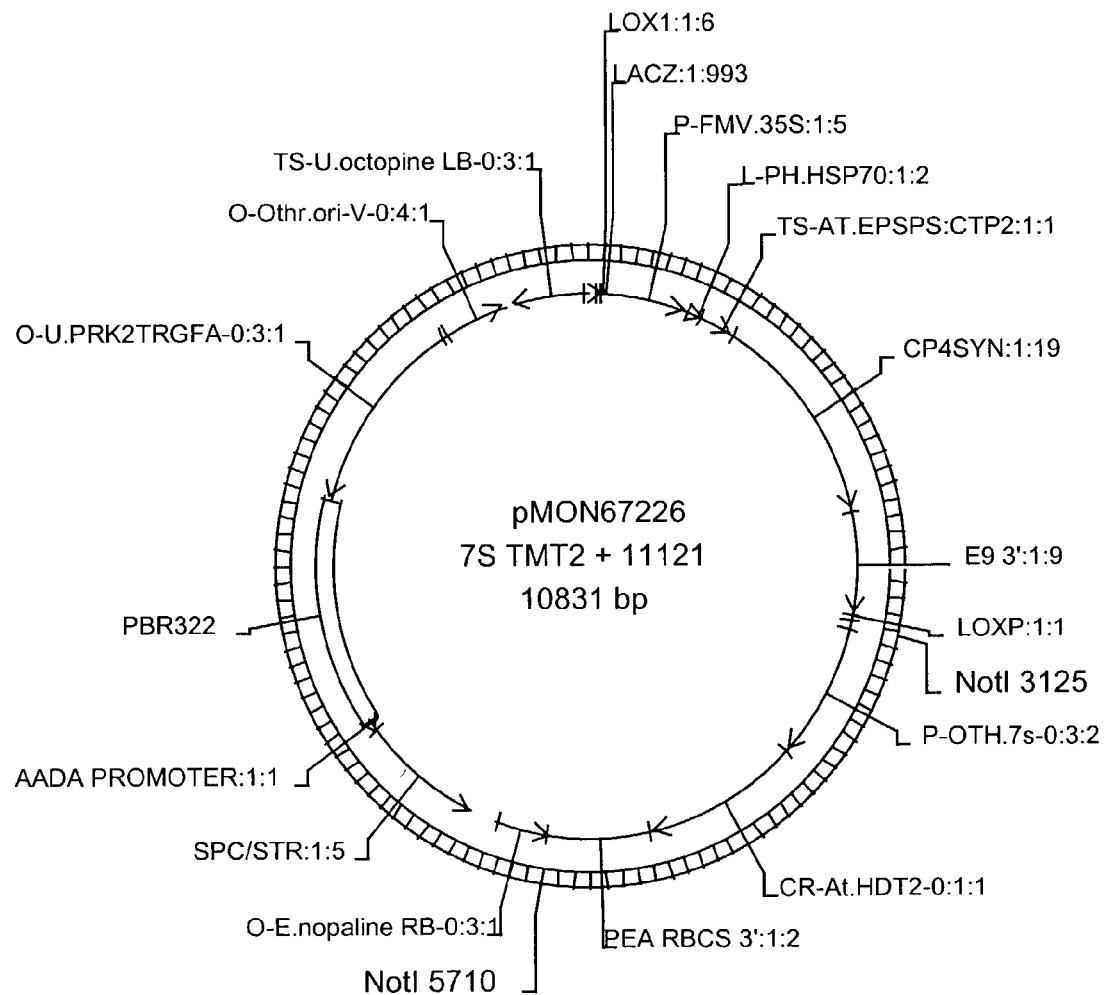
FIG. 11 is a plasmid map of pMON67226.
Figure 12:
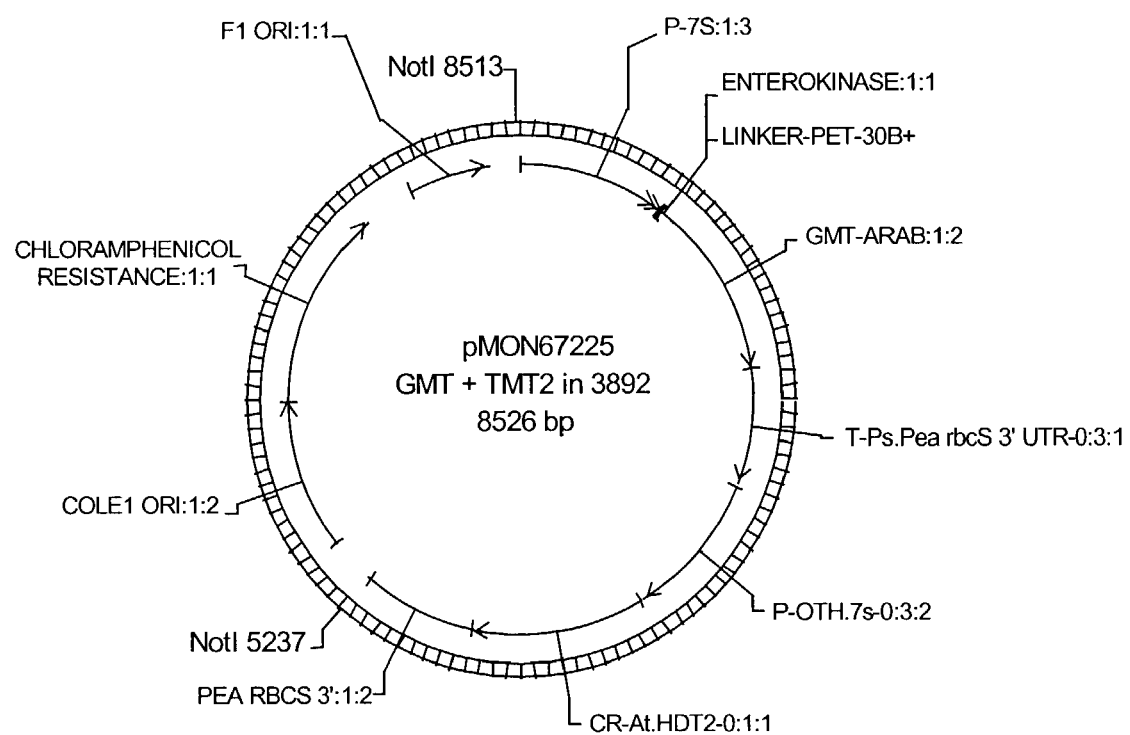
FIG. 12 is a plasmid map of pMON67225.
Figure 13:
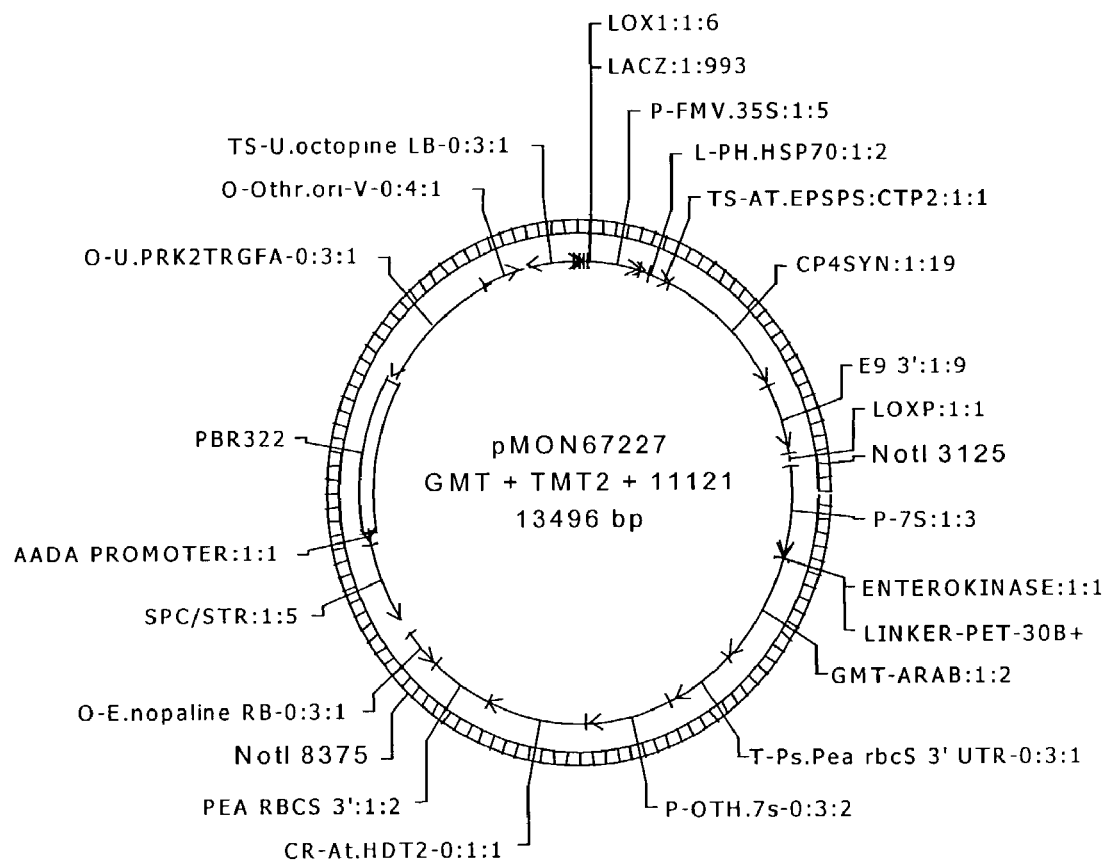
FIG. 13 is a plasmid map of pMON67227.

The wild type *Arabidopsis* tMT2 gene is cloned in between the 7S promoter and the pea SSU Rubisco 3' UTR in the vector pCGN3892 to create pMON67220 (FIG. 10). This clone is then digested with Not I and the expression cassette is subcloned into the plant binary expression vector pCGN11121 to create pMON67226 (FIG. 11). This construct is used to transform soybean. Additionally, the *Arabidopsis* GMT between the 7S promoter and the pea SSU Rubisco 3' UTR is cut out from pMON36503 and then cloned into pMON67220 to create pMON67225 (FIG. 12). These two genes under the control of 7S promoters are then cut out of pMON67225 with NotI and cloned into the Not site of pCGN11121 to create pMON67227 (FIG. 13). This double gene construct is then used to transform soybean according to the procedure set forth in WO 00/61771 A3 on pages 99–100. Transformed plants are grown to maturity and seed that is produced is analyzed for total tocopherol content and composition.

The tocopherol data presented in Tables 3 and 5 demonstrate the reduction of β-tocopherol and more so, δ-tocopherol in favor of γ and α-tocopherol production in soybean seeds harboring a tMT2 expression construct. Tables 4 and 6 demonstrate a nearly complete (98% in the RO generation) conversion of tocopherols into α-tocopherol in soybean seed harboring a double gene expression construct for tMT2 and a γ-methyltransferase.

Table 6 below depicts the results of the analysis of various soybean lines transformed with pMon67226 Soy. Tables 6 and 9 contain the results of HPLC analysis using the methodology (with minor modifications) described in Savidge et al., *Plant Phys.* 129:321–332 (2000), Isolation and Characterization of Homogentisate Phytltransferase Genes from *Synechocystis* sp PCC 6803 and *Arabidopsis*.

TABLE 6

| Pedigree | % delta | % gamma | % alpha | % beta* | mp:aT | mp:bT | mp:gT | mp:dT | total toco. |
|---|---|---|---|---|---|---|---|---|---|
| A3244 | 22.90 | 63.97 | 10.44 | 2.69 | 31 | 8 | 190 | 68 | 297 |
| A3244 | 22.85 | 64.24 | 10.26 | 2.65 | 31 | 8 | 194 | 69 | 302 |
| A3244 | 22.88 | 64.38 | 10.46 | 2.29 | 32 | 7 | 197 | 70 | 306 |
| A3244 | 23.08 | 64.21 | 10.37 | 2.34 | 31 | 7 | 192 | 69 | 299 |
| A3244 | 22.97 | 64.19 | 10.47 | 2.36 | 31 | 7 | 190 | 68 | 296 |
| GM_A28213:@. | 36.92 | 51.08 | 8.31 | 3.69 | 27 | 12 | 166 | 120 | 325 |
| GM_A27926:@. | 27.51 | 62.72 | 7.46 | 2.31 | 29 | 9 | 244 | 107 | 389 |
| GM_A27928:@. | 26.56 | 62.81 | 8.13 | 2.50 | 26 | 8 | 201 | 85 | 320 |
| GM_A27993:@. | 25.70 | 62.29 | 9.50 | 2.51 | 34 | 9 | 223 | 92 | 358 |
| GM_A27628:@. | 25.07 | 61.19 | 10.75 | 2.99 | 36 | 10 | 205 | 84 | 335 |
| GM_A28069:@. | 24.66 | 58.56 | 13.01 | 3.77 | 38 | 11 | 171 | 72 | 292 |

TABLE 6-continued

| Pedigree | % delta | % gamma | % alpha | % beta* | mp:aT | mp:bT | mp:gT | mp:dT | total toco. |
|---|---|---|---|---|---|---|---|---|---|
| GM_A27927:@. | 24.41 | 63.05 | 10.17 | 2.37 | 30 | 7 | 186 | 72 | 295 |
| GM_A28930:@. | 24.14 | 63.01 | 10.03 | 2.82 | 32 | 9 | 201 | 77 | 319 |
| GM_A28597:@. | 23.89 | 61.09 | 11.60 | 3.41 | 34 | 10 | 179 | 70 | 293 |
| GM_A28077:@. | 23.73 | 65.76 | 8.47 | 2.03 | 25 | 6 | 194 | 70 | 295 |
| GM_A28410:@. | 23.70 | 66.47 | 7.80 | 2.02 | 27 | 7 | 230 | 82 | 346 |
| GM_A28212:@. | 23.37 | 63.91 | 10.06 | 2.66 | 34 | 9 | 216 | 79 | 338 |
| GM_A28079:@. | 23.10 | 62.38 | 11.22 | 3.30 | 34 | 10 | 189 | 70 | 303 |
| GM_A27992:@. | 23.05 | 52.42 | 19.70 | 4.83 | 53 | 13 | 141 | 62 | 269 |
| GM_A28074:@. | 22.52 | 61.86 | 12.61 | 3.00 | 42 | 10 | 206 | 75 | 333 |
| GM_A28931:@. | 20.66 | 63.28 | 13.44 | 2.62 | 41 | 8 | 193 | 63 | 305 |
| GM_A28767:@. | 20.20 | 65.66 | 11.78 | 2.36 | 35 | 7 | 195 | 60 | 297 |
| GM_A28598:@. | 20.14 | 61.09 | 15.02 | 3.75 | 44 | 11 | 179 | 59 | 293 |
| GM_A28214:@. | 20.07 | 61.90 | 14.29 | 3.74 | 42 | 11 | 182 | 59 | 294 |
| GM_A28062:@. | 19.80 | 64.09 | 13.09 | 3.02 | 39 | 9 | 191 | 59 | 298 |
| GM_A28505:@. | 19.69 | 66.77 | 11.69 | 1.85 | 38 | 6 | 217 | 64 | 325 |
| GM_A28067:@. | 18.18 | 62.55 | 15.64 | 3.64 | 43 | 10 | 172 | 50 | 275 |
| GM_A28503:@. | 18.06 | 65.63 | 14.24 | 2.08 | 41 | 6 | 189 | 52 | 288 |
| GM_A28408:@. | 17.97 | 64.75 | 14.58 | 2.71 | 43 | 8 | 191 | 53 | 295 |
| GM_A28061:@. | 17.87 | 62.20 | 16.15 | 3.78 | 47 | 11 | 181 | 52 | 291 |
| GM_A28504:@. | 17.73 | 62.06 | 16.67 | 3.55 | 47 | 10 | 175 | 50 | 282 |
| GM_A28409:@. | 16.79 | 63.14 | 16.42 | 3.65 | 45 | 10 | 173 | 46 | 274 |
| GM_A28060:@. | 16.16 | 68.35 | 13.80 | 1.68 | 41 | 5 | 203 | 48 | 297 |
| GM_A28076:@. | 16.04 | 60.41 | 19.11 | 4.44 | 56 | 13 | 177 | 47 | 293 |
| GM_A28066:@. | 15.36 | 59.73 | 20.48 | 4.44 | 60 | 13 | 175 | 45 | 293 |
| GM_A29037:@. | 14.49 | 71.59 | 12.22 | 1.70 | 43 | 6 | 252 | 51 | 352 |
| GM_A27855:@. | 13.64 | 74.68 | 10.39 | 1.30 | 32 | 4 | 230 | 42 | 308 |
| GM_A27856:@. | 13.46 | 72.76 | 12.18 | 1.60 | 38 | 5 | 227 | 42 | 312 |
| GM_A28081:@. | 11.11 | 76.85 | 10.80 | 1.23 | 35 | 4 | 249 | 36 | 324 |
| GM_A27627:@. | 8.33 | 75.93 | 14.20 | 1.54 | 46 | 5 | 246 | 27 | 324 |
| GM_A27932:@. | 8.13 | 81.33 | 9.94 | 0.60 | 33 | 2 | 270 | 27 | 332 |
| GM_A27857:@. | 7.28 | 78.48 | 13.29 | 0.95 | 42 | 3 | 248 | 23 | 316 |
| GM_A28073:@. | 7.22 | 67.70 | 23.37 | 1.72 | 68 | 5 | 197 | 21 | 291 |
| GM_A27708:@. | 7.06 | 75.77 | 16.26 | 0.92 | 53 | 3 | 247 | 23 | 326 |
| GM_A28059:@. | 6.99 | 77.57 | 14.71 | 0.74 | 40 | 2 | 211 | 19 | 272 |
| GM_A27925:@. | 6.95 | 76.82 | 15.23 | 0.99 | 46 | 3 | 232 | 21 | 302 |
| GM_A27859:@. | 6.83 | 77.34 | 14.39 | 1.44 | 40 | 4 | 215 | 19 | 278 |
| GM_A28065:@. | 6.44 | 73.22 | 18.64 | 1.69 | 55 | 5 | 216 | 19 | 295 |
| GM_A27931:@. | 6.33 | 78.92 | 13.86 | 0.90 | 46 | 3 | 262 | 21 | 332 |
| GM_A28246:@. | 6.31 | 72.24 | 19.87 | 1.58 | 63 | 5 | 229 | 20 | 317 |
| GM_A27994:@. | 6.29 | 79.02 | 13.99 | 0.70 | 40 | 2 | 226 | 18 | 286 |
| GM_A27995:@. | 6.08 | 78.12 | 14.89 | 0.91 | 49 | 3 | 257 | 20 | 329 |
| GM_A28075:@. | 5.61 | 73.60 | 19.14 | 1.65 | 58 | 5 | 223 | 17 | 303 |
| GM_A28070:@. | 5.47 | 79.42 | 14.47 | 0.64 | 45 | 2 | 247 | 17 | 311 |
| GM_A28068:@. | 4.76 | 75.85 | 18.71 | 0.68 | 55 | 2 | 223 | 14 | 294 |
| GM_A28078:@. | 3.72 | 81.08 | 14.53 | 0.68 | 43 | 2 | 240 | 11 | 296 |
| GM_A28080:@. | 3.69 | 73.06 | 21.77 | 1.48 | 59 | 4 | 198 | 10 | 271 |
| GM_A28071:@. | 3.64 | 75.83 | 19.87 | 0.66 | 60 | 2 | 229 | 11 | 302 |
| GM_A28058:@. | 3.51 | 82.16 | 13.74 | 0.58 | 47 | 2 | 281 | 12 | 342 |
| GM_A28064:@. | 2.23 | 85.03 | 12.74 | 0.00 | 40 | 0 | 267 | 7 | 314 |
| GM_A28599:@. | 1.47 | 82.65 | 15.88 | 0.00 | 54 | 0 | 281 | 5 | 340 |
| GM_A27929:@. | 1.23 | 83.74 | 13.80 | 1.23 | 45 | 4 | 273 | 4 | 326 |
| GM_A28063:@. | 1.22 | 74.62 | 23.55 | 0.61 | 77 | 2 | 244 | 4 | 327 |
| GM_A28072:@. | 0.95 | 76.66 | 22.08 | 0.32 | 70 | 1 | 243 | 3 | 317 |
| GM_A27930:@. | 0.68 | 79.05 | 20.27 | 0.00 | 60 | 0 | 234 | 2 | 296 |

Table 7 below sets forth the results of the analysis of various soybean lines transformed with pMON 67227.

TABLE 7

| Pedigree | % alpha | % beta* | % gamma | % delta | mp:aT | mp:bT | mp:gT | mp:dT | total toco. |
|---|---|---|---|---|---|---|---|---|---|
| A3244 | 10.4 | 2.7 | 64.0 | 22.9 | 31 | 8 | 190 | 68 | 297 |
| A3244 | 10.3 | 2.6 | 64.2 | 22.8 | 31 | 8 | 194 | 69 | 302 |
| A3244 | 10.5 | 2.3 | 64.4 | 22.9 | 32 | 7 | 197 | 70 | 306 |
| A3244 | 10.4 | 2.3 | 64.2 | 23.1 | 31 | 7 | 192 | 69 | 299 |
| A3244 | 10.5 | 2.4 | 64.2 | 23.0 | 31 | 7 | 190 | 68 | 296 |
| GM_A27999:@. | 9.5 | 2.5 | 62.9 | 25.2 | 31 | 8 | 205 | 82 | 326 |
| GM_A28091:@. | 10.5 | 3.1 | 61.9 | 24.5 | 31 | 9 | 182 | 72 | 294 |
| GM_A28090:@. | 11.3 | 2.7 | 63.0 | 22.9 | 33 | 8 | 184 | 67 | 292 |
| GM_A28933:@. | 14.4 | 2.1 | 65.8 | 17.7 | 48 | 7 | 219 | 59 | 333 |
| GM_A28601:@. | 15.7 | 3.1 | 62.4 | 18.8 | 45 | 9 | 179 | 54 | 287 |

TABLE 7-continued

| Pedigree | % alpha | % beta* | % gamma | % delta | mp:aT | mp:bT | mp:gT | mp:dT | total toco. |
|---|---|---|---|---|---|---|---|---|---|
| GM__A27712:@. | 60.4 | 2.5 | 26.9 | 10.2 | 171 | 7 | 76 | 29 | 283 |
| GM__A27936:@. | 60.6 | 20.4 | 13.8 | 5.2 | 163 | 55 | 37 | 14 | 269 |
| GM__A28093:@. | 67.2 | 3.3 | 21.2 | 8.3 | 203 | 10 | 64 | 25 | 302 |
| GM__A27934:@. | 75.4 | 3.1 | 16.5 | 5.0 | 196 | 8 | 43 | 13 | 260 |
| GM__A28096:@. | 79.1 | 3.4 | 12.5 | 5.0 | 253 | 11 | 40 | 16 | 320 |
| GM__A27935:@. | 88.5 | 2.7 | 6.9 | 1.9 | 231 | 7 | 18 | 5 | 261 |
| GM__A27998:@. | 89.6 | 2.5 | 6.0 | 1.9 | 285 | 8 | 19 | 6 | 318 |
| GM__A27711:@. | 91.4 | 3.3 | 4.3 | 1.0 | 276 | 10 | 13 | 3 | 302 |

Table 8 below sets for the results of the analysis of single seeds of soybean transformed with pMON 67226.

TABLE 8

| Pedigree | % alpha | % beta* | % gamma | % delta | mp:aT | mp:bT | mp:gT | mp:dT | total toco. |
|---|---|---|---|---|---|---|---|---|---|
| GM__A27930:@. | 12.2 | 3.4 | 64.1 | 20.3 | 29 | 8 | 152 | 48 | 237 |
| GM__A27930:@. | 21.7 | 0.0 | 77.9 | 0.4 | 55 | 0 | 197 | 1 | 253 |
| GM__A27930:@. | 15.0 | 0.0 | 84.0 | 1.0 | 46 | 0 | 257 | 3 | 306 |
| GM__A27930:@. | 22.4 | 0.0 | 76.8 | 0.8 | 58 | 0 | 199 | 2 | 259 |
| GM__A27930:@. | 13.9 | 0.0 | 85.7 | 0.4 | 33 | 0 | 204 | 1 | 238 |
| GM__A27930:@. | 21.7 | 0.0 | 77.6 | 0.7 | 63 | 0 | 225 | 2 | 290 |
| GM__A27930:@. | 21.7 | 0.0 | 77.6 | 0.8 | 55 | 0 | 197 | 2 | 254 |
| GM__A27930:@. | 25.7 | 0.0 | 74.0 | 0.4 | 68 | 0 | 196 | 1 | 265 |
| GM__A28072:@. | 22.4 | 0.0 | 76.8 | 0.8 | 57 | 0 | 195 | 2 | 254 |
| GM__A28072:@. | 31.3 |  | 67.6 | 1.2 | 80 | 0 | 173 | 3 | 256 |
| GM__A28072:@. | 22.8 | 0.0 | 76.5 | 0.7 | 64 | 0 | 215 | 2 | 281 |
| GM__A28072:@. | 17.6 | 0.0 | 81.5 | 1.0 | 55 | 0 | 255 | 3 | 313 |
| GM__A28072:@. | 20.0 | 0.0 | 78.9 | 1.1 | 55 | 0 | 217 | 3 | 275 |
| GM__A28072:@. | 35.0 | 0.0 | 64.6 | 0.4 | 97 | 0 | 179 | 1 | 277 |
| GM__A28072:@. | 31.5 | 0.0 | 68.1 | 0.4 | 80 | 0 | 173 | 1 | 254 |
| GM__A28072:@. | 16.4 | 0.0 | 82.6 | 1.0 | 51 | 0 | 257 | 3 | 311 |

Table 9 below sets forth the results of the analysis of single seeds of soybean transformed with pMON 67227.

TABLE 9

| Pedigree | % alpha | % beta* | % gamma | % delta | mp:aT | mp:bT | mp:gT | mp:dT | total toco. |
|---|---|---|---|---|---|---|---|---|---|
| GM__A27711:@. | 97.8 | 2.2 | 0.0 | 0.0 | 263 | 6 | 0 | 0 | 269 |
| GM__A27711:@. | 96.7 | 3.3 | 0.0 | 0.0 | 320 | 11 | 0 | 0 | 331 |
| GM__A27711:@. | 96.5 | 3.5 | 0.0 | 0.0 | 301 | 11 | 0 | 0 | 312 |
| GM__A27711:@. | 96.7 | 3.3 | 0.0 | 0.0 | 295 | 10 | 0 | 0 | 305 |
| GM__A27711:@. | 96.9 | 3.1 | 0.0 | 0.0 | 308 | 10 | 0 | 0 | 318 |
| GM__A27711:@. | 97.3 | 2.7 | 0.0 | 0.0 | 287 | 8 | 0 | 0 | 295 |
| GM__A27711:@. | 98.2 | 1.8 | 0.0 | 0.0 | 272 | 5 | 0 | 0 | 277 |
| GM__A27711:@. | 95.7 | 4.3 | 0.0 | 0.0 | 287 | 13 | 0 | 0 | 300 |
| GM__A27935:@. | 10.3 | 2.6 | 65.4 | 21.7 | 28 | 7 | 178 | 59 | 272 |
| GM__A27935:@. | 98.5 | 1.5 | 0.0 | 0.0 | 261 | 4 | 0 | 0 | 265 |
| GM__A27935:@. | 98.3 | 1.7 | 0.0 | 0.0 | 230 | 4 | 0 | 0 | 234 |
| GM__A27935:@. | 98.6 | 1.4 | 0.0 | 0.0 | 272 | 4 | 0 | 0 | 276 |
| GM__A27935:@. | 98.2 | 1.8 | 0.0 | 0.0 | 267 | 5 | 0 | 0 | 272 |
| GM__A27935:@. | 96.9 | 3.1 | 0.0 | 0.0 | 277 | 9 | 0 | 0 | 286 |
| GM__A27935:@. | 98.3 | 1.7 | 0.0 | 0.0 | 337 | 6 | 0 | 0 | 343 |
| GM__A27935:@. | 96.5 | 3.5 | 0.0 | 0.0 | 276 | 10 | 0 | 0 | 286 |
| GM__A27998:@. | 97.0 | 3.0 | 0.0 | 0.0 | 318 | 10 | 0 | 0 | 328 |
| GM__A27998:@. | 97.1 | 2.9 | 0.0 | 0.0 | 300 | 9 | 0 | 0 | 309 |
| GM__A27998:@. | 95.9 | 4.1 | 0.0 | 0.0 | 324 | 14 | 0 | 0 | 338 |
| GM__A27998:@. | 97.0 | 3.0 | 0.0 | 0.0 | 292 | 9 | 0 | 0 | 301 |
| GM__A27998:@. | 96.9 | 3.1 | 0.0 | 0.0 | 314 | 10 | 0 | 0 | 324 |
| GM__A27998:@. | 96.5 | 3.5 | 0.0 | 0.0 | 359 | 13 | 0 | 0 | 372 |
| GM__A27998:@. | 96.5 | 3.5 | 0.0 | 0.0 | 335 | 12 | 0 | 0 | 347 |
| GM__A27998:@. | 96.6 | 3.4 | 0.0 | 0.0 | 310 | 11 | 0 | 0 | 321 |
| GM__A28096:@. | 11.1 | 3.7 | 61.0 | 24.1 | 36 | 12 | 197 | 78 | 323 |
| GM__A28096:@. | 9.5 | 3.3 | 61.4 | 25.8 | 29 | 10 | 188 | 79 | 306 |
| GM__A28096:@. | 96.8 | 3.2 | 0.0 | 0.0 | 299 | 10 | 0 | 0 | 309 |
| GM__A28096:@. | 96.0 | 4.0 | 0.0 | 0.0 | 288 | 12 | 0 | 0 | 300 |
| GM__A28096:@. | 95.8 | 4.2 | 0.0 | 0.0 | 319 | 14 | 0 | 0 | 333 |
| GM__A28096:@. | 95.8 | 4.2 | 0.0 | 0.0 | 295 | 13 | 0 | 0 | 308 |

TABLE 9-continued

| Pedigree | % alpha | % beta* | % gamma | % delta | mp:aT | mp:bT | mp:gT | mp:dT | total toco. |
|---|---|---|---|---|---|---|---|---|---|
| GM_A28096:@. | 97.8 | 2.2 | 0.0 | 0.0 | 316 | 7 | 0 | 0 | 323 |
| GM_A28096:@. | 95.8 | 4.2 | 0.0 | 0.0 | 300 | 13 | 0 | 0 | 313 |

The * next to % beta in Tables 6 through 9 is a label to indicate that β-tocopherol comigrates with an unknown compound, making it difficult to quantify.

*Arabidopsis* double constructs

The tMT2 gene is cut out of the vector pMON67204 using the restriction enzymes Not I (blunt)/Pst I and then cloned into the napin shuttle vector pCGN3223 which is digested with Sal (blunt)/Pst I. This napin cassette containing the tMT2 gene is then cut out from this vector with Not I and the ends are filled in with dNTPs using a Klenow procedure. The resulting fragment is inserted into the vectors pMON16602 (digested with PmeI) and pCGN10822 (digested with SnaBI) to make pMON67224 and pMON67223, respectively (FIGS. 14 and 15). The vectors pMON16602 and pCGN10822 are described in PCT application WO 0063391.

These double constructs express the tMT2 gene and the prenyltransferase from either *Arabidopsis* (HPT) or *Synechocystis* (slr1736) under the control of the napin seed-specific promoter. These constructs are used to transform *Arabidopsis* and transformed plants are grown to maturity, as detailed in Example 6. The resulting $T_2$ seed is analyzed for total tocopherol content and composition using analytical procedures described in Example 1.

What is claimed is:

1. A substantially purified nucleic acid molecule encoding a vascular plant polypeptide having 2-methylphytylplastoquinol methytransferase activity operably linked to an introduced promoter region which functions in plant cells wherein the polypeptide comprises the polypeptide of SEQ ID NO: 16 or a variant thereof selected from the group consisting of hdt2 (SEQ ID NO:17), hdt6 (SEQ ID NO:18), hdt9 (SEQ ID NO:19), hdt10(SEQ ID NO:20) and hdt16 (SEQ ID NO:21).

2. A transformed plant comprising the nucleic acid sequence of claim 1.

3. The transformed plant of claim 2, wherein said plant is selected from the group consisting of alfalfa, *Arabidopsis thaliana*, barley, *Brassica cainpestris, Brossica napus*, oilseed rape, broccoli, cabbage, citrus, canola, cotton, garlic, oat, *Alliurn*, fiax, peanut, pepper, potato, rapeseed, rice, rye, sorghum, strawberry, sugarcane, sugarbeet, tomato, wheat, poplar, pine, fir, eucalyptus, apple, lettuce, lentils, rape, banana, tea, turf grasses, sunflower, soybean, chick peas, corn, *Phaseolus*, cranibe, mustard, castor bean, sesame, cottonseed, linseed, safflower, and oil palm.

4. The transformed plant of claim 2, wherein said transformed plant produces a seed with an increased γ-tocopherol level relative to a plant with an isogenic genetic background except lacking said nucleic acid molecule.

5. The transformed plant of claim 2, wherein said promoter is a seed specific promoter.

6. Seed derived from the transformed plant of claim 2, comprising the nucleic acid sequence of claim 1.

7. The seed of claim 6, wherein said seed an exhibits an increased γ-tocopherol level relative to a seed from a plant having an isogenic genetic background except lacking said substantially purified nucleic acid molecule.

* * * * *

UNITED STATES PATENT AND TRADEMARK OFFICE
CERTIFICATE OF CORRECTION

PATENT NO. : 7,262,339 B2  Page 1 of 1
APPLICATION NO. : 10/279029
DATED : August 28, 2007
INVENTOR(S) : Susan R. Norris et al.

It is certified that error appears in the above-identified patent and that said Letters Patent is hereby corrected as shown below:

In claim 3, column 207, line 44, delete "cainpestris" and insert --campestris--.

In claim 3, column 207, line 44, delete "Brossica" and insert --Brassica--.

In claim 3, column 207, line 46, delete "Alliurn" and insert --Allium--.

In claim 3, column 207, line 46, delete "fiax" and insert --flax--.

In claim 3, column 208, line 30, delete "rape" and insert --grape--.

In claim 3, column 208, line 32, delete "cranibe" and insert --crambe--.

In claim 7, column 208, line 42, delete "an exhibits" and insert --exhibits--.

Signed and Sealed this

Twenty-ninth Day of April, 2008

JON W. DUDAS
*Director of the United States Patent and Trademark Office*

SEQUENCE LISTING

```
<160> NUMBER OF SEQ ID NOS: 108
<210> SEQ ID NO 1
<211> LENGTH: 1184
<212> TYPE: DNA
<213> ORGANISM: Arabidopsis thaliana

<400> SEQUENCE: 1
atggcctctt tgatgctcaa cggggccatt accttcccca aaggtttagg ttcccctggt      60
tccaatttgc atgccagatc gattcctcgg ccgaccttac tctcagttac ccgaacctcc     120
acacctagac tctcggtggc tactagatgc agcagcagca gcgtgtcgtc ttcccggcca     180
tcggcgcaac ctaggttcat tcagcacaag aaggaggctt actggttcta caggttctta     240
tccatcgtat acgaccatgt catcaatcct gggcattgga ccgaggatat gagagacgac     300
gctcttgagc cagcggatct cagccatccg gacatgcgag tggtcgatgt cggcggcgga     360
actggtttca ctactctggg catagtcaag acagtgaagg ccaagaatgt gaccattctg     420
gaccagtcgc cacatcagct ggccaaagca aagcaaaagg agccgttgaa agaatgcaag     480
atcgtcgagg gagatgctga ggatcttcct tttccaaccg attatgctga cagatacgtt     540
tctgctggaa ggtatccttt tcttcttctt cttcttcttc ttcttcttct tcttataatc     600
gtcttctttc cggtgggttt gattgtgtgt ctcatcatca cacagcattg agtactggcc     660
ggacccgcag aggggaataa gggaagcgta cagggttctc aagatcggtg gcaaagcgtg     720
tctcatcggc cctgtctacc caaccttctg gctctctcgc ttcttttctg atgtctggat     780
gctcttcccc aaggaggaag agtacattga gtggttcaag aatgccggtt tcaaggacgt     840
tcagctcaag aggattggcc ccaagtggta ccgtggtgtt cgcaggcacg gccttatcat     900
gggatgttct gtcactggtg ttaaacctgc ctccggtgac tctcctctcc aggtctttta     960
cctcccactt cacctttttt actttcttct ctctttgata cactaaactt atcactcaaa    1020
tgctgcagct tggtccaaag gaagaggacg tagagaagcc tgtcaacaac cccttctcct    1080
tcttgggacg cttcctcctg ggaactctag cagctgcctg gtttgtgtta atccctatct    1140
acatgtggat caaggatcag atcgttccca aagaccaacc catc                     1184
```

<210> SEQ ID NO 2

<211> LENGTH: 1181
<212> TYPE: DNA
<213> ORGANISM: Arabidopsis thaliana

<400> SEQUENCE: 2

| | | |
|---|---|---|
| atggcctctt tgatgctcaa cggggccatt accttcccca aaggtttagg ttcccctggt | 60 |
| tccaatttgc atgccagatc gattcctcgg ccgaccttac tctcagttac ccgaacctcc | 120 |
| acacctagac tctcggtggc tactagatgc agcagcagca gcgtgtcgtc ttcccggcca | 180 |
| tcggcgcaac ctaggttcat tcagcacaag aaggaggctt actggttcta caggttctta | 240 |
| tccatcgtat acgaccatgt catcaatcct gggcattgga ccgaggatat gagagacgac | 300 |
| gctcttgagc cagcggatct cagccatccg gacatgcgag tggtcgatgt cggcggcgga | 360 |
| actggtttca ctactctggg catagtcaag acagtgaagg ccaagaatgt gaccattctg | 420 |
| gaccagtcgc cacatcagct ggccaaagca aagcaaaagg agccgttgaa agaatgcaag | 480 |
| atcgtcgagg gagatgctga ggatcttcct tttccaaccg attatgctga cagatacgtt | 540 |
| tctgctggaa ggtatccttt tcttcttctt cttcttcttc ttcttcttct tataatcgtc | 600 |
| ttctttccgg tgggtttgat tgtgtgtctc atcatcacac agcattgagt actggccgga | 660 |
| cccgcagagg ggaataaggg aagcgtacag ggttctcaag atcggtggca aagcgtgtct | 720 |
| catcggccct gtctacccaa ccttctggct ctctcgcttc ttttctgatg tctggatgct | 780 |
| cttccccaag gaggaagagt acattgagtg gttcaagaat gccggtttca aggacgttca | 840 |
| gctcaagagg attggcccca gtggtaccg tggtgttcgc aggcacggcc ttatcatggg | 900 |
| atgttctgtc actggtgtta aacctgcctc cggtgactct cctctccagg tcttttacct | 960 |
| cccacttcac ctttttttact ttcttctctc tttgatacac taaacttatc actcaaatgc | 1020 |
| tgcagcttgg tccaaaggaa gaggacgtag agaagcctgt caacaacccc ttctccttct | 1080 |
| tgggacgctt cctcctggga actctagcag ctgcctggtt tgtgttaatc cctatctaca | 1140 |
| tgtggatcaa ggatcagatc gttcccaaag accaacccat c | 1181 |

<210> SEQ ID NO 3
<211> LENGTH: 1181
<212> TYPE: DNA
<213> ORGANISM: Arabidopsis thaliana

<400> SEQUENCE: 3

| | | |
|---|---|---|
| atggcctctt tgatgctcaa cggggccatt accttcccca aaggtttagg ttcccctggt | 60 |
| tccaatttgc atgccagatc gattcctcgg ccgaccttac tctcagttac ccgaacctcc | 120 |
| acacctagac tctcggtggc tactagatgc agcagcagca gcgtgtcgtc ttcccggcca | 180 |
| tcggcgcaac ctaggttcat tcagcacaag aaggaggctt actggttcta caggttctta | 240 |
| tccatcgtat acgaccatgt catcaatcct gggcattgga ccgaggatat gagagacgac | 300 |
| gctcttgagc cagcggatct cagccatccg gacatgcgag tggtcgatgt cggcggcgga | 360 |
| actggtttca ctactctggg catagtcaag acagtgaagg ccaagaatgt gaccattctg | 420 |
| gaccagtcgc cacatcagct ggccaaagca aagcaaaagg agccgttgaa agaatgcaag | 480 |
| atcgtcgagg gagatgctga ggatcttcct tttccaaccg attatgctga cagatacgtt | 540 |
| tctgctggaa ggtatccttt tcttcttctt cttcttcttc ttcttcttct tataatcgtc | 600 |
| ttctttccgg tgggtttgat tgtgtgtctc atcatcacac agcattgagt actggccgga | 660 |
| cccgcagagg ggaataaggg aagcgtacag ggttctcaag atcggtggca aagcgtgtct | 720 |
| catcggccct gtctacccaa ccttctggct ctctcgcttc ttttctgatg tctggatgct | 780 |

```
cttccccaag gaggaagagt acattgagtg gttcaagaat gccggtttca aggacgttca      840
gctcaagagg attggcccca agtggtaccg tggtgttcgc aggcacggcc ttatcatggg      900
atgttctgtc actggtgtta aacctgcctc cggtgactct cctctccagg tcttttacct      960
cccacttcac cttttttact ttcttctctc tttgatacac taaacttatc actcaaatgc     1020
tgcagcttgg tccaaaggaa aaggacgtag agaagcctgt caacaacccc ttctccttct     1080
tgggacgctt cctcctggga actctagcag ctgcctggtt tgtgttaatc cctatctaca     1140
tgtggatcaa ggatcagatc gttcccaaag accaacccat c                         1181

<210> SEQ ID NO 4
<211> LENGTH: 1184
<212> TYPE: DNA
<213> ORGANISM: Arabidopsis thaliana

<400> SEQUENCE: 4
atggcctctt tgatgctcaa cggggccatt accttcccca aaggtttagg ttcccctggt       60
tccaatttgc atgccagatc gattcctcgg ccgaccttac tctcagttac ccgaacctcc      120
acacctagac tctcggtggc tactagatgc agcagcagca gcgtgtcgtc ttcccggcca      180
tcggcgcaac ctaggttcat tcagcacaag aagaaggctt actggttcta caggttctta      240
tccatcgtat acgaccatgt catcaatcct gggcattgga ccgaggatat gagagacgac      300
gctcttgagc cagcggatct cagccatccg gacatgcgag tggtcgatgt cggcggcgga      360
actggtttca ctactctggg catagtcaag acagtgaagg ccaagaatgt gaccattctg      420
gaccagtcgc cacatcagct ggccaaagca aagcaaaagg agccgttgaa agaatgcaag      480
atcgtcgagg gagatgctga ggatcttcct tttccaaccg attatgctga cagatacgtt      540
tctgctggaa ggtatccttt tcttcttctt cttcttcttc ttcttcttct tcttataatc      600
gtcttctttc cggtgggttt gattgtgtgt ctcatcatca cacagcattg agtactggcc      660
ggacccgcag aggggaataa gggaagcgta cagggttctc aagatcggtg caaagcgtg      720 tctcatcggc cctgtctacc caaccttctg gctctctcgc ttcttttctg atgtctggat      780
gctcttcccc aaggaggaag agtacattga gtggttcaag aatgccggtt tcaaggacgt      840
tcagctcaag aggattggcc ccaagtggta ccgtggtgtt cgcaggcacg gcttatcat      900 gggatgttct gtcactggtg ttaaacctgc ctccggtgac tctcctctcc aggtctttta     960
cctcccactt caccttttttt actttcttct ctctttgata cactaaactt atcactcaaa    1020
tgctgcagct tggtccaaag gaagaggacg tagagaagcc tgtcaacaac cccttctcct     1080
tcttgggacg cttcctcctg gaactctag cagctgcctg gtttgtgtta atccctatct     1140
acatgtggat caaggatcag atcgttccca aagaccaacc catc                      1184

<210> SEQ ID NO 5
<211> LENGTH: 1184
<212> TYPE: DNA
<213> ORGANISM: Arabidopsis thaliana

<400> SEQUENCE: 5
atggcctctt tgatgctcaa cggggccatt accttctcca aaggtttagg ttcccctggt       60
tccaatttgc atgccagatc gattcctcgg ccgaccttac tctcagttac ccgaacctcc      120
acacctagac tctcggtggc tactagatgc agcagcagca gcgtgtcgtc ttcccggcca      180
tcggcgcaac ctaggttcat tcagcacaag aaggaggctt actggttcta caggttctta      240
```

```
tccatcgtat acgaccatgt catcaatcct gggcattgga ccgaggatat gagagacgac      300
gctcttgagc cagcggatct cagccatccg gacatgcgag tggtcgatgt cggcggcgga      360
actggtttca ctactctggg catagtcaag acagtgaagg ccaagaatgt gaccattctg      420
gaccagtcgc cacatcagct ggccaaagca aagcaaaagg agccgttgaa agaatgcaag      480
atcgtcgagg gagatgctga ggatcttcct tttccaaccg attatgctga cagatacgtt      540
tctgctggaa ggtatccttt tcttcttctt cttcttcttc ttcttcttct tcttataatc      600
gtcttctttc cggtgggttt gattgtgtgt ctcatcatca cacagcattg agtactggcc      660
ggacccgcag aggggaataa gggaagcgta cagggttctc aagatcggtg gcaaagcgtg      720
tctcatcggc cctgtctacc caaccttctg gctctctcgc ttcttttctg atgtctggat      780
gctcttcccc aaggaggaag agtacattga gtggttcaag aatgccggtt tcaaggacgt      840
tcagctcaag aggattggcc ccaagtggta ccgtggtgtt cgcaggcacg gccttatcat      900
gggatgttct gtcactggtg ttaaacctgc ctccggtgac tcctctctcc aggtctttta      960
cctcccactt caccttttttt actttcttct ctctttgata cactaaactt atcactcaaa     1020
tgctgcagct tggtccaaag gaagaggacg tagagaagcc tgtcaacaac cccttctcct     1080
tcttgggacg cttcctcctg ggaactctag cagctgcctg gtttgtgtta atccctatct     1140
acatgtggat caaggatcag atcgttccca aagaccaacc catc                      1184
```

<210> SEQ ID NO 6
<211> LENGTH: 1181
<212> TYPE: DNA
<213> ORGANISM: Arabidopsis thaliana

<400> SEQUENCE: 6

```
atggcctctt tgatgctcaa cggggccatt accttcccca aaggtttagg ttcccctggt       60
tccaatttgc atgccagatc gattcctcgg ccgaccttac tctcagttac ccgaaccctcc     120 acacctagac tctcggtggc tactagatgc agcagcagca gcgtgtcgtc ttcccggcca      180
tcggcgcaac ctaggttcat tcagcacaag aaggaggctt actggttcta caggttctta      240
tccatcgtat acgaccatgt catcaatcct gggcattgga ccgaggatat gagagacgac      300
gctcttgagc cagcggatct cagccatccg gacatgcgag tggtcaatgt cggcggcgga      360
actggtttca ctactctggg catagtcaag acagtgaagg ccaagaatgt gaccattctg      420
gaccagtcgc cacatcagct ggccaaagca aagcaaaagg agccgttgaa agaatgcaag      480
atcgtcgagg gagatgctga ggatcttcct tttccaaccg attatgctga cagatacgtt      540
tctgctggaa ggtatccttt tcttcttctt cttcttcttc ttcttcttct tataatcgtc      600
ttctttccgg tgggtttgat tgtgtgtctc atcatcacac agcattgagt actggccgga      660
cccgcagagg ggaataaggg aagcgtacag ggttctcaag atcggtggca aagcgtgtct      720 catcggcccct gtctacccaa ccttctggct ctctcgcttc ttttctgatg tctggatgct     780
cttccccaag gaggaagagt acattgagtg gttcaagaat gccggtttca aggacgttca      840
gctcaagagg attggcccca gtggtaccgt ggtgttcgc aggcacggcc ttatcatggg       900
atgttctgtc actggtgtta aacctgcctc cggtgactct cctctccagg tcttttacct      960
cccacttcac ctttttttact tcttctctc tttgatacac taaacttatc actcaaatgc     1020
tgcagcttgg tccaaaggaa gaggacgtag agaagcctgt caacaacccc ttctccttct     1080
tgggacgctt cctcctggga actctagcag ctgcctggtt tgtgttaatc cctatctaca     1140
tgtggatcaa ggatcagatc gttcccaaag accaacccat c                         1181
```

<210> SEQ ID NO 7
<211> LENGTH: 1184
<212> TYPE: DNA
<213> ORGANISM: Arabidopsis thaliana

<400> SEQUENCE: 7

| | | | | | |
|---|---|---|---|---|---|
| atggcctctt | tgatgctcaa | cggggccatt | accttcccca | aaggtttagg | ttccctggt | 60 |
| tccaatttgc | atgccagatc | gattcctcgg | ccgaccttac | tctcagttac | ccgaacctcc | 120 |
| acacctagac | tctcggtggc | tactagatgc | agcagcagca | gcgtgtcgtc | ttcccggcca | 180 |
| tcggcgcaac | ctaggttcat | tcagcacaag | aaggaggctt | actggttcta | caggttctta | 240 |
| tccatcgtat | acgaccatgt | catcaatcct | gggcattgga | tcgaggatat | gagagacgac | 300 |
| gctcttgagc | cagcggatct | cagccatccg | gacatgcgag | tggtcgatgt | cggcggcgga | 360 |
| actggtttca | ctactctggg | catagtcaag | acagtgaagg | ccaagaatgt | gaccattctg | 420 |
| gaccagtcgc | cacatcagct | ggccaaagca | agcaaaagg | agccgttgaa | agaatgcaag | 480 |
| atcgtcgagg | gagatgctga | ggatcttcct | tttccaaccg | attatgctga | cagatacgtt | 540 |
| tctgctggaa | ggtatccttt | tcttcttctt | cttcttcttc | ttcttcttct | tcttataatc | 600 |
| gtcttctttc | cggtgggttt | gattgtgtgt | ctcatcatca | cacagcattg | agtactggcc | 660 |
| ggacccgcag | agggaataa | gggaagcgta | cagggttctc | aagatcggtg | gcaaagcgtg | 720 |
| tctcatcggc | cctgtctacc | caaccttctg | ctctctcgc | ttcttttctg | atgtctggat | 780 |
| gctcttcccc | aaggaggaag | agtacattga | gtggttcaag | aatgccggtt | tcaaggacgt | 840 |
| tcagctcaag | aggattggcc | ccaagtggta | ccgtggtgtt | cgcaggcacg | gccttatcat | 900 |
| gggatgttct | gtcactggtg | ttaaacctgc | tccggtgac | tctcctctcc | aggtcttta | 960 |
| cctcccactt | cacctttttt | actttcttct | ctctttgata | cactaaactt | atcactcaaa | 1020 |
| tgctgcagct | tggtccaaag | gaagaggacg | tagagaagcc | tgtcaacaac | ccttctcct | 1080 |
| tcttgggacg | cttcctcctg | ggaactctag | cagctgcctg | gtttgtgtta | atccctatct | 1140 |
| acatgtggat | caaggatcag | atcgttccca | agaccaacc | catc | | 1184 |

<210> SEQ ID NO 8
<211> LENGTH: 1059
<212> TYPE: DNA
<213> ORGANISM: Arabidopsis thaliana

<400> SEQUENCE: 8

| | | | | | |
|---|---|---|---|---|---|
| atggcgatgg | cctccaccta | cgcgccgggc | ggaggcgcgc | gggcgctcgc | gcagggtaga | 60 |
| tgcagggtcc | gcggtcccgc | ggggctgggc | ttcctcggcc | cctccaaggc | cgccggcctc | 120 |
| ccccgccccc | tcgccctcgc | cctcgccagg | cggatgagca | gccccgtcgc | ggtgggcgcc | 180 |
| aggctgcgat | gcgggcgtc | gtcgtccccc | gcggcggcgc | ggcccgccac | ggcgccgcgc | 240 |
| ttcatccagc | acaagaagga | ggccttctgg | ttctaccgct | tcctctccat | cgtgtacgac | 300 |
| cacgtcatca | atccgggcca | ctggaccgag | gacatgcgcg | acgacgcgct | ggaacctgcc | 360 |
| gacctcttca | gccgccacct | cacggtcgtc | gacgtcggcg | gcggcacggg | gttcaccacg | 420 |
| ctcggcatcg | tcaagcacgt | caacccggag | aacgtcacgc | tgctcgacca | gtccccgcac | 480 |
| cagctcgaca | aggcccggca | gaaggaggcc | ctcaagggg | tcaccatcat | ggaggcgac | 540 |
| gccgaggacc | tccgttccc | caccgactcc | ttcgaccgat | acatctccgc | cggcagcatc | 600 |
| gagtactggc | cagacccaca | gcgggggatc | aaggaagcct | acagggtcct | gagatttggt | 660 |

```
gggctagctt gtgtgatcgg cccggtctac ccgaccttct ggctgtcccg cttcttcgcc      720
gacatgtgga tgctcttccc caaggaggaa gagtacatcg agtggttcaa gaaggctggg      780
tttagggatg tcaagctgaa gaggattgga ccgaagtggt accgcggtgt ccgaaggcat      840
ggcctcatca tgggctgctc cgtcacaggc gtcaagagag agcgcggtga ctctcccttg      900
gagcttggtc ccaaggcgga ggatgtcagc aagccagtga atccgatcac cttcctcttc      960
cgcttcctcg taggaacgat atgtgctgcc tactatgttc tggtgcctat ttacatgtgg     1020
ataaaggacc agatcgtgcc aaaaggcatg ccaatctga                            1059
```

<210> SEQ ID NO 9
<211> LENGTH: 1026
<212> TYPE: DNA
<213> ORGANISM: Arabidopsis thaliana

<400> SEQUENCE: 9

```
atggcttctt ccatgctgaa tggagctgaa accttcactc tcatccgagg tgttacccca       60
aaaagtattg gttttttggg gtcaggttta catgggaaac agttttccag tgcgggttta      120
atctacagtc cgaagatgtc cagggtagga acgacgatag ccccgaggtg cagcttatca      180
gcgtcaaggc cagcttcaca accaagattc atacaacaca aaaaagaggc cttttggttc      240
tacaggttcc tctcaattgt ctatgaccat gtcataaacc caggtcactg gactgaagac      300
atgagggatg atgcacttga gccggctgat ctcaatgaca gggacatggt agttgtagat      360
gttggtggtg gaactggttt cactactttg ggtattgttc agcatgtgga tgctaagaat      420
gttacaatcc ttgaccaatc tcctcaccag cttgcaaagg ctaaacagaa ggagcctctc      480
aaggaatgca acataattga aggtgatgca gaagatcttc cttttcctac tgattatgcc      540
gatagatatg tgtctgctgg aagcatagag tactggccag acccacaacg ggggatcaag      600
gaagcataca gggtgttgaa acaaggagga aaagcttgct taattggtcc tgtgtaccct      660
acattttggt tgtctcgttt cttttgcagac gtttggatgc ttttccctaa ggaggaagaa      720
tatatagagt ggtttgaaaa ggctggattt aaggatgtcc aactcaaaag gattggccct      780
aaatggtatc gtggagttcg ccgacatggt ttgatcatgg ggtgctctgt aaccggtgtt      840
aaacccgcat ctggggactc tccttttgcag cttggaccta aggcagagga tgtatcaaag      900
ccggtaaatc cgtttgtatt tctcttacgc ttcatgttgg gtgccactgc agcagcatat      960
tatgtactgg ttcctatcta catgtggctc aaagatcaaa ttgtaccaga gggtcaacca     1020
atctaa                                                                1026
```

<210> SEQ ID NO 10
<211> LENGTH: 1035
<212> TYPE: DNA
<213> ORGANISM: Arabidopsis thaliana

<400> SEQUENCE: 10

```
atggcttcct ccatgctcag cggagcagaa agcctctcaa tgctccgaat ccaccaccaa       60
cccaaactca ccttctcgag cccatccctc cattccaaac ccacaaacct caaaatggat      120
ctcatccctt tcgccaccaa gcatcaaaaa acgaaaaaag cttcgatctt tacatgcagc      180
gcgtcctcat catcccgacc tgcttctcag ccgaggttca tccagcacaa gcaggaggcg      240
ttctggttct acaggttcct gtcgatagtg tacgaccatg tgataaaccc agggcactgg      300
accgaggaca tgagagacga tgcgttggag ccagccgagc tgtacgattc caggatgaag      360
gtggtggacg taggaggagg aactgggttc accaccttgg ggattataaa gcacatcgac      420
```

```
cctaaaaacg ttacgattct ggatcagtct ccgcatcagc ttgagaaggc taggcagaag       480
gaggctttga aggagtgtac tattgttgaa ggtgatgctg aggatctccc ttttcctact       540
gatactttcg atcgatatgt atctgctggc agcatagaat actggccaga cccacaaaga       600
gggataaagg aagcataccg ggttctaaaa ctggagcgcg ttgcctgctt gataggaccc       660 gtgcaccta ccttctggct ttccaggttc ttcgccgaca tgtggatgtt gttccccacc       720
gaagaagaat acatagagtg gtttaaaaag gccgggttca agatgtgaa gttgaagagg        780 attggcccaa aatggtaccg tggtgtgcgt agacacgggc tcatcatggg ctgttccgtc       840
actggtgtta aacgtctctc tggtgactcc cctcttcagc ttggaccgaa ggcggaggat       900
gtgaagaagc cgatcaatcc attctcgttc cttctgcgct tcattttggg tacgatagca       960
gctacttact acgttttggt gccgatatac atgtggataa aggatcagat tgtaccgaaa      1020
ggccagccca tatga                                                        1035

<210> SEQ ID NO 11
<211> LENGTH: 1029
<212> TYPE: DNA
<213> ORGANISM: Arabidopsis thaliana

<400> SEQUENCE: 11
atgggttcag taatgctcag tggaactgaa aagctcactc tcagaaccct aaccgggaac        60
ggcttaggtt tcactggttc ggatttgcac ggtaagaact tcccaagagt gagtttcgct       120
gctaccacta gtgctaaagt tcccaacttt agaagcatag tagtacccaa gtgtagtgtc       180
tcggcttcca ggccaagctc gcagccaagg ttcattcagc acaaaaaaga ggcctttgg        240 ttctataggt ttctctcaat tgtgtatgac catgtcatta accctggcca ttggaccgag       300
gacatgaggg atgatgccct tgaaccgct gatctcaatg caggaacat gattgtggtg         360 gatgttggtg gcggcacggg tttcaccact cttggtattg tcaagcacgt ggatgccaag       420
aatgtcacca ttcttgacca gtcaccccac cagctcgcca aggccaagca gaaggagcca       480
ctcaaggaat gcaaaataat cgaaggggat gccgaggatc tccccttcg aactgattat       540 gccgatagat atgtatccgc aggaagtatt gagtactggc cggatccaca gcgtggcatc       600
aaggaggcat acaggtttt gaaacttgga ggcaaagcgt gtctaattgg tccggtctac       660
ccaacatttt ggttgtcacg tttctttgca gatgtttgga tgcttttccc caaggaggaa       720
gagtatattg agtggtttca gaaggcaggg tttaaggacg tccaactaaa aaggattggc       780
ccaaaatggt atcgtggggt tcgccgtcat ggcttgatta tgggttgttc agtgaccggt       840
gttaaacctg catctggaga ttctcctttg cagcttggtc caaaggaaga agatgttgaa       900
aagcccgtta atccttttgt ctttgcactg cgcttcgttt tgggtgcctt ggcagcgaca       960
tggtttgtgt tggttcctat ttacatgtgg ctgaaagatc aagttgttcc caaaggtcag      1020
ccaatctaa                                                              1029

<210> SEQ ID NO 12
<211> LENGTH: 1047
<212> TYPE: DNA
<213> ORGANISM: Arabidopsis thaliana

<400> SEQUENCE: 12
atggcgatgg cctcctccgc ctacgcccca gcgggcggcg ttggcaccca ctccgcgccg        60
ggcaggatca ggccgccgcg cggcctcggc ttctccacca ccaccaccaa gtcgaggccc       120
```

```
ctcgtgctca ccaggcgtgg gggaggcggc ggcaacatct ccgtggctcg gctgaggtgc      180
gcggcgtcgt cgtcgtcggc ggcggcgagg ccgatgtcgc agccgcggtt catccagcac      240
aagaaggagg cgttctggtt ctaccgcttc ctctccatcg tctacgacca cgtcatcaac      300
ccgggccact ggacggagga catgcgggac gacgccctcg agcccgccga cctctacagc      360
cgcaagctca gggtcgtcga cgtcggcggc gggacgggt tcaccacgct cgggatcgtc      420
aagcgcgtcg acccggagaa cgtcacgctg ctcgaccagt ccccgcacca gctcgagaag      480
gcccgggaga aggaggccct caagggcgtc accatcatgg agggcgacgc cgaggacctc      540
cccttcccca ccgacacctt cgaccgctac gtctccgccg cagcatcga gtattggccc      600 gatccgcagc gaggaatcaa ggaagcttac agggttttga ggcttggtgg agtggcttgc      660
atgattggcc ccgtgcaccc aaccttctgg ctgtctcgct ttttcgctga catgtggatg      720
ctcttcccga aggaagagga gtatattgag tggttcaaaa aggcagggtt caaggatgtc      780
aagctcaaaa ggattggacc aaaatggtac cgtggtgtcc gaaggcatgg cctgattatg      840
ggatgctctg tgacgggcgt caaaagagaa catggagact cccctttgca gcttggtcca      900
aaggttgagg atgtcagcaa acctgtgaat cctatcacct tcctcttccg cttcctcatg      960
ggaacaatat gtgctgcata ctatgttctg gtgcctatct acatgtggat aaaggaccag     1020
attgtgccca aaggcatgcc gatctaa                                         1047

<210> SEQ ID NO 13
<211> LENGTH: 1014
<212> TYPE: DNA
<213> ORGANISM: Arabidopsis thaliana

<400> SEQUENCE: 13
atggcttctc tcatgctcaa cggggccatc accttcccca agggattagg cttcccgct       60 tccaatctac acgccagacc aagtcctccg ctgagtctcg tctcaaacac agccacgcgg      120
agactctccg tggcgacaag atgcagcagc agcagcagcg tgtcggcgtc aaggccatct      180
gcgcagccta ggttcatcca gcacaagaaa gaggcctact ggttctacag gttcctgtcc      240
atcgtgtacg accacatcat caatcccggc cactggacgg aggatatgag ggacgacgct      300
ctcgagcctg cggatctgag ccatccggac atgcgagttg tcgacgtcgg aggcggaacg      360
ggtttcacca cgctgggaat cgtcaagacg gtgaaggcta agaacgtgac gattctggac      420
cagtcgccgc atcagctggc aaaggcgaag cagaaggagc cgttgaagga gtgcaagatc      480
gttgaaggag atgcggagga tctcccttt cctactgatt atgctgacag atacgtctct      540
gctggaagca ttgagtactg gcccgacccg cagaggggga taaggaaagc gtacagagtt      600
ctcaagatcg gtgggaaagc atgtctcatt ggccctgtcc acccgacgtt ttggcttct      660 cgtttctttg cagatgtgtg gatgcttttc cccaaggagg aggagtacat tgagtggttc      720
aagaatgctg gtttcaagga cgttcagctt aagaggattg gccccaagtg gtaccgtggt      780
gttcgcaggc acggacttat catgggatgc tctgttactg gtgtcaaacc tgcctctgga      840
gactctcctc tccagcttgg accaaaggaa gaggacgtgg agaagcctgt aaacaatcct      900
ttctccttct tgggacgctt cctcttggga accttagcgg ctgcctggtt tgtgttaatc      960
ccaatctaca tgtggatcaa ggatcagatc gttcccaaag accaacccat ctga          1014

<210> SEQ ID NO 14
<211> LENGTH: 1014
<212> TYPE: DNA
<213> ORGANISM: Arabidopsis thaliana
```

```
<400> SEQUENCE: 14
atggcttctc tcatgctcaa cggggccatc accttcccca agggattagg cttccccgct      60
tccaatctac acgccagacc aagtcctccg ctgagtctcg tctcaaacac agccacgcgg     120
agactctccg tggcgacaag atgcagcagc agcagcagcg tgtcggcgtc aaggccatct     180
gcgcagccta ggttcatcca gcacaagaaa gaggcctact ggttctacag gttcctgtcc     240
atcgtgtacg accacatcat caatcccggc cactggacgg aggatatgag ggacgacgct     300
ctcgagcctg cggatctgag ccatccggac atgcgagttg tcgacgtcgg aggcggaacg     360
ggtttcacca cgctgggaat cgtcaagacg gtgaaggcta agaacgtgac gattctggac     420
cagtcgccgc atcagctggc aaaggcgaag cagaaggagc cgttgaagga gtgcaagatc     480
gtggaaggag atgcggagga tctcccttt cctactgatt atgctgacag atacgtctct      540
gctggaagca ttgagtactg gcccgacccg cagaggggta agggaagc gtacagagtt       600 ctcaagatcg gtgggaaagc atgtctcatt ggccctgtcc acccgacgtt ttggctttca    660
cgcttctttg cagatgtgtg gatgcttttc cccaaggagg aggagtacat tgagtggttc    720
aagaatgctg gtttcaagga cgttcagctt aagaggattg gccccaagtg gtaccgtggt   780
gttcgcaggc acggacttat catgggatgc tctgttactg gtgtcaaacc tgcctctgga   840
gactctcctc tccagcttgg accaaaggaa gaggacgtga gaagcctgt aaacaatcct    900 ttctccttct tgggacgctt cctcttgggt accctagcgg ctgcctggtt tgtgttaatc    960
ccaatctaca tgtggatcaa ggatcagatc gttcccaaag accaacccat ctga         1014

<210> SEQ ID NO 15
<211> LENGTH: 1017
<212> TYPE: DNA
<213> ORGANISM: Arabidopsis thaliana

<400> SEQUENCE: 15
atggcctctt tgatgctcaa cggggccatt accttcccca aggtttagg ttccctggt       60 tccaatttgc atgccagatc gattcctcgg ccgaccttac tctcagttac ccgaacctcc    120
acacctagac tctcggtggc tactagatgc agcagcagca gcgtgtcgtc ttcccggcca   180
tcggcgcaac ctaggttcat tcagcacaag aaggaggctt actggttcta caggttctta   240
tccatcgtat acgaccatgt catcaatcct gggcattgga ccgaggatat gagagacgac   300
gctcttgagc cagcggatct cagccatccg gacatgcgag tggtcgatgt cggcggcgga   360
actggtttca ctactctggg catagtcaag acagtgaagg ccaagaatgt gaccattctg   420
gaccagtcgc cacatcagct ggccaaagca aagcaaaagg agccgttgaa gaatgcaag    480 atcgtcgagg gagatgctga ggatcttcct tttccaaccg attatgctga cagatacgtt   540
tctgctggaa gcattgagta ctggccggac ccgcagaggg gaataaggga agcgtacagg   600
ttctcaagat cggtggcaa agcgtgtctc atcggccctg tctacccaac cttctggctc   660
tctcgcttct tttctgatgt ctggatgctc ttccccaagg aggaagagta cattgagtgg   720
ttcaagaatg ccggtttcaa ggacgttcag ctcaagagga ttggccccaa gtggtaccgt   780
ggtgttcgca ggcacggcct tatcatggga tgttctgtca ctggtgttaa acctgcctcc   840
ggtgactctc ctctccagct tggtccaaag gaagaggacg tagagaagcc tgtcaacaac   900
cccttctcct tcttgggacg cttcctcctg ggaactctag cagctgcctg gtttgtgtta   960
atccctatct acatgtggat caaggatcag atcgttccca agaccaacc catctga      1017
```

```
<210> SEQ ID NO 16
<211> LENGTH: 338
<212> TYPE: PRT
<213> ORGANISM: Arabidopsis thaliana

<400> SEQUENCE: 16

Met Ala Ser Leu Met Leu Asn Gly Ala Ile Thr Phe Pro Lys Gly Leu
1               5                   10                  15

Gly Ser Pro Gly Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
        35                  40                  45

Arg Cys Ser Ser Ser Val Ser Ser Ser Arg Pro Ser Ala Gln Pro
    50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Thr Glu Asp
                85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
        115                 120                 125

Val Lys Thr Val Lys Ala Lys Asn Val Thr Ile Leu Asp Gln Ser Pro
    130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
        195                 200                 205

Cys Leu Ile Gly Pro Val Tyr Pro Thr Phe Trp Leu Ser Arg Phe Phe
    210                 215                 220

Ser Asp Val Trp Met Leu Phe Pro Lys Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Cys Ser
            260                 265                 270

Val Thr Gly Val Lys Pro Ala Ser Gly Asp Ser Pro Leu Gln Leu Gly
        275                 280                 285

Pro Lys Glu Glu Asp Val Glu Lys Pro Val Asn Asn Pro Phe Ser Phe
    290                 295                 300

Leu Gly Arg Phe Leu Leu Gly Thr Leu Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile

<210> SEQ ID NO 17
<211> LENGTH: 338
<212> TYPE: PRT
<213> ORGANISM: Arabidopsis thaliana
```

```
<400> SEQUENCE: 17

Met Ala Ser Leu Met Leu Asn Gly Ala Ile Thr Phe Pro Lys Gly Leu
1               5                   10                  15

Gly Ser Pro Gly Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
        35                  40                  45

Arg Cys Ser Ser Ser Val Ser Ser Ser Arg Pro Ser Ala Gln Pro
    50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Thr Glu Asp
                85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
            115                 120                 125

Val Lys Thr Val Lys Ala Lys Asn Val Thr Ile Leu Asp Gln Ser Pro
130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
            195                 200                 205

Cys Leu Ile Gly Pro Val Tyr Pro Thr Phe Trp Leu Ser Arg Phe Phe
        210                 215                 220

Ser Asp Val Trp Met Leu Phe Pro Lys Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Cys Ser
            260                 265                 270

Val Thr Gly Val Lys Pro Ala Ser Gly Asp Ser Pro Leu Gln Leu Gly
            275                 280                 285

Pro Lys Glu Lys Asp Val Glu Lys Pro Val Asn Pro Phe Ser Phe
    290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile

<210> SEQ ID NO 18
<211> LENGTH: 338
<212> TYPE: PRT
<213> ORGANISM: Arabidopsis thaliana

<400> SEQUENCE: 18

Met Ala Ser Leu Met Leu Asn Gly Ala Ile Thr Phe Pro Lys Gly Leu
1               5                   10                  15

Gly Ser Pro Gly Ser Asn Leu His Ala Arg Ser Ile Pro Arg Pro Thr
```

```
                    20                  25                  30
Leu Leu Ser Val Thr Arg Thr Ser Thr Pro Arg Leu Ser Val Ala Thr
                35                  40                  45
Arg Cys Ser Ser Ser Ser Val Ser Ser Ser Arg Pro Ser Ala Gln Pro
         50                  55                  60
Arg Phe Ile Gln His Lys Lys Ala Tyr Trp Phe Tyr Arg Phe Leu
 65                  70                  75                  80
Ser Ile Val Tyr Asp His Val Ile Asn Pro Gly His Trp Thr Glu Asp
                 85                  90                  95
Met Arg Asp Asp Ala Leu Glu Pro Ala Asp Leu Ser His Pro Asp Met
             100                 105                 110
Arg Val Val Asp Val Gly Gly Gly Thr Gly Phe Thr Thr Leu Gly Ile
             115                 120                 125
Val Lys Thr Val Lys Ala Lys Asn Val Thr Ile Leu Asp Gln Ser Pro
         130                 135                 140
His Gln Leu Ala Lys Ala Gln Lys Glu Pro Leu Lys Glu Cys Lys
145                 150                 155                 160
Ile Val Glu Gly Asp Ala Glu Asp Leu Pro Phe Pro Thr Asp Tyr Ala
                 165                 170                 175
Asp Arg Tyr Val Ser Ala Gly Ser Ile Glu Tyr Trp Pro Asp Pro Gln
             180                 185                 190
Arg Gly Ile Arg Glu Ala Tyr Arg Val Leu Lys Ile Gly Gly Lys Ala
             195                 200                 205
Cys Leu Ile Gly Pro Val Tyr Pro Thr Phe Trp Leu Ser Arg Phe Phe
         210                 215                 220
Ser Asp Val Trp Met Leu Phe Pro Lys Glu Glu Tyr Ile Glu Trp
225                 230                 235                 240
Phe Lys Asn Ala Gly Phe Lys Asp Val Gln Leu Lys Arg Ile Gly Pro
                 245                 250                 255
Lys Trp Tyr Arg Gly Val Arg Arg His Gly Leu Ile Met Gly Cys Ser
             260                 265                 270
Val Thr Gly Val Lys Pro Ala Ser Gly Asp Ser Pro Leu Gln Leu Gly
             275                 280                 285
Pro Lys Glu Glu Asp Val Glu Lys Pro Val Asn Asn Pro Phe Ser Phe
         290                 295                 300
Leu Gly Arg Phe Leu Leu Gly Thr Leu Ala Ala Trp Phe Val Leu
305                 310                 315                 320
Ile Pro Ile Tyr Met Trp Ile Lys Asp Gln Ile Val Pro Lys Asp Gln
                 325                 330                 335
Pro Ile

<210> SEQ ID NO 19
<211> LENGTH: 338
<212> TYPE: PRT
<213> ORGANISM: Arabidopsis thaliana

<400> SEQUENCE: 19

Met Ala Ser Leu Met Leu Asn Gly Ala Ile Thr Phe Ser Lys Gly Leu
 1               5                  10                  15
Gly Ser Pro Gly Ser Asn Leu His Ala Arg Ser Ile Pro Arg Pro Thr
                 20                  25                  30
Leu Leu Ser Val Thr Arg Thr Ser Thr Pro Arg Leu Ser Val Ala Thr
                 35                  40                  45
Arg Cys Ser Ser Ser Ser Val Ser Ser Ser Arg Pro Ser Ala Gln Pro
```

```
            50                  55                  60
Arg Phe Ile Gln His Lys Lys Glu Ala Tyr Trp Phe Tyr Arg Phe Leu
 65                  70                  75                  80

Ser Ile Val Tyr Asp His Val Ile Asn Pro Gly His Trp Thr Glu Asp
                 85                  90                  95

Met Arg Asp Asp Ala Leu Glu Pro Ala Asp Leu Ser His Pro Asp Met
                100                 105                 110

Arg Val Val Asp Val Gly Gly Thr Gly Phe Thr Thr Leu Gly Ile
                115                 120                 125

Val Lys Thr Val Lys Ala Lys Asn Val Thr Ile Leu Asp Gln Ser Pro
130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
                180                 185                 190

Arg Gly Ile Arg Glu Ala Tyr Arg Val Leu Lys Ile Gly Gly Lys Ala
                195                 200                 205

Cys Leu Ile Gly Pro Val Tyr Pro Thr Phe Trp Leu Ser Arg Phe Phe
    210                 215                 220

Ser Asp Val Trp Met Leu Phe Pro Lys Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Cys Ser
                260                 265                 270

Val Thr Gly Val Lys Pro Ala Ser Gly Asp Ser Pro Leu Gln Leu Gly
                275                 280                 285

Pro Lys Glu Glu Asp Val Glu Lys Pro Val Asn Asn Pro Phe Ser Phe
    290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile

<210> SEQ ID NO 20
<211> LENGTH: 338
<212> TYPE: PRT
<213> ORGANISM: Arabidopsis thaliana

<400> SEQUENCE: 20

Met Ala Ser Leu Met Leu Asn Gly Ala Ile Thr Phe Pro Lys Gly Leu
 1               5                  10                  15

Gly Ser Pro Gly Ser Asn Leu His Ala Arg Ser Ile Pro Arg Pro Thr
                20                  25                  30

Leu Leu Ser Val Thr Arg Thr Ser Thr Pro Arg Leu Ser Val Ala Thr
             35                  40                  45

Arg Cys Ser Ser Ser Val Ser Ser Arg Pro Ser Ala Gln Pro
 50                  55                  60

Arg Phe Ile Gln His Lys Lys Glu Ala Tyr Trp Phe Tyr Arg Phe Leu
 65                  70                  75                  80

Ser Ile Val Tyr Asp His Val Ile Asn Pro Gly His Trp Thr Glu Asp
```

```
                     85                  90                  95
Met Arg Asp Asp Ala Leu Glu Pro Ala Asp Leu Ser His Pro Asp Met
            100                 105                 110

Arg Val Val Asn Val Gly Gly Gly Thr Gly Phe Thr Thr Leu Gly Ile
            115                 120                 125

Val Lys Thr Val Lys Ala Lys Asn Val Thr Ile Leu Asp Gln Ser Pro
            130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
            195                 200                 205

Cys Leu Ile Gly Pro Val Tyr Pro Thr Phe Trp Leu Ser Arg Phe Phe
            210                 215                 220

Ser Asp Val Trp Met Leu Phe Pro Lys Glu Glu Tyr Ile Glu Trp
225                 230                 235                 240

Phe Lys Asn Ala Gly Phe Lys Asp Val Gln Leu Lys Arg Ile Gly Pro
            245                 250                 255

Lys Trp Tyr Arg Gly Val Arg Arg His Gly Leu Ile Met Gly Cys Ser
            260                 265                 270

Val Thr Gly Val Lys Pro Ala Ser Gly Asp Ser Pro Leu Gln Leu Gly
            275                 280                 285

Pro Lys Glu Glu Asp Val Glu Lys Pro Val Asn Asn Pro Phe Ser Phe
            290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile

<210> SEQ ID NO 21
<211> LENGTH: 338
<212> TYPE: PRT
<213> ORGANISM: Arabidopsis thaliana

<400> SEQUENCE: 21

Met Ala Ser Leu Met Leu Asn Gly Ala Ile Thr Phe Pro Lys Gly Leu
1                5                  10                  15

Gly Ser Pro Gly Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
            35                  40                  45

Arg Cys Ser Ser Ser Val Ser Ser Ser Arg Pro Ser Ala Gln Pro
50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Ile Glu Asp
                85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
```

```
                115                 120                 125
Val Lys Thr Val Lys Ala Lys Asn Val Thr Ile Leu Asp Gln Ser Pro
    130                 135                 140
His Gln Leu Ala Lys Ala Lys Gln Lys Glu Pro Leu Lys Glu Cys Lys
145                 150                 155                 160
Ile Val Glu Gly Asp Ala Glu Asp Leu Pro Phe Pro Thr Asp Tyr Ala
                165                 170                 175
Asp Arg Tyr Val Ser Ala Gly Ser Ile Glu Tyr Trp Pro Asp Pro Gln
                180                 185                 190
Arg Gly Ile Arg Glu Ala Tyr Arg Val Leu Lys Ile Gly Gly Lys Ala
                195                 200                 205
Cys Leu Ile Gly Pro Val Tyr Pro Thr Phe Trp Leu Ser Arg Phe Phe
    210                 215                 220
Ser Asp Val Trp Met Leu Phe Pro Lys Glu Glu Tyr Ile Glu Trp
225                 230                 235                 240
Phe Lys Asn Ala Gly Phe Lys Asp Val Gln Leu Lys Arg Ile Gly Pro
                245                 250                 255
Lys Trp Tyr Arg Gly Val Arg Arg His Gly Leu Ile Met Gly Cys Ser
                260                 265                 270
Val Thr Gly Val Lys Pro Ala Ser Gly Asp Ser Pro Leu Gln Leu Gly
    275                 280                 285
Pro Lys Glu Asp Val Glu Lys Pro Val Asn Asn Pro Phe Ser Phe
    290                 295                 300
Leu Gly Arg Phe Leu Leu Gly Thr Leu Ala Ala Ala Trp Phe Val Leu
305                 310                 315                 320
Ile Pro Ile Tyr Met Trp Ile Lys Asp Gln Ile Val Pro Lys Asp Gln
                325                 330                 335
Pro Ile

<210> SEQ ID NO 22
<211> LENGTH: 352
<212> TYPE: PRT
<213> ORGANISM: Arabidopsis thaliana

<400> SEQUENCE: 22

Met Ala Met Ala Ser Thr Tyr Ala Pro Gly Gly Gly Ala Arg Ala Leu
1               5                   10                  15
Ala Gln Gly Arg Cys Arg Val Arg Gly Pro Ala Gly Leu Gly Phe Leu
                20                  25                  30
Gly Pro Ser Lys Ala Ala Gly Leu Pro Arg Pro Leu Ala Leu Ala Leu
                35                  40                  45
Ala Arg Arg Met Ser Ser Pro Val Ala Val Gly Ala Arg Leu Arg Cys
    50                  55                  60
Ala Ala Ser Ser Pro Ala Ala Arg Pro Ala Thr Ala Pro Arg
65                  70                  75                  80
Phe Ile Gln His Lys Lys Glu Ala Phe Trp Phe Tyr Arg Phe Leu Ser
                85                  90                  95
Ile Val Tyr Asp His Val Ile Asn Pro Gly His Trp Thr Glu Asp Met
                100                 105                 110
Arg Asp Asp Ala Leu Glu Pro Ala Asp Leu Phe Ser Arg His Leu Thr
                115                 120                 125
Val Val Asp Val Gly Gly Gly Thr Gly Phe Thr Thr Leu Gly Ile Val
    130                 135                 140
Lys His Val Asn Pro Glu Asn Val Thr Leu Leu Asp Gln Ser Pro His
```

```
               145                 150                 155                 160
Gln Leu Asp Lys Ala Arg Gln Lys Glu Ala Leu Lys Gly Val Thr Ile
                165                 170                 175
Met Glu Gly Asp Ala Glu Asp Leu Pro Phe Pro Thr Asp Ser Phe Asp
            180                 185                 190
Arg Tyr Ile Ser Ala Gly Ser Ile Glu Tyr Trp Pro Asp Pro Gln Arg
        195                 200                 205
Gly Ile Lys Glu Ala Tyr Arg Val Leu Arg Phe Gly Gly Leu Ala Cys
    210                 215                 220
Val Ile Gly Pro Val Tyr Pro Thr Phe Trp Leu Ser Arg Phe Phe Ala
225                 230                 235                 240
Asp Met Trp Met Leu Phe Pro Lys Glu Glu Tyr Ile Glu Trp Phe
                245                 250                 255
Lys Lys Ala Gly Phe Arg Asp Val Lys Leu Lys Arg Ile Gly Pro Lys
                260                 265                 270
Trp Tyr Arg Gly Val Arg Arg His Gly Leu Ile Met Gly Cys Ser Val
            275                 280                 285
Thr Gly Val Lys Arg Glu Arg Gly Asp Ser Pro Leu Glu Leu Gly Pro
    290                 295                 300
Lys Ala Glu Asp Val Ser Lys Pro Val Asn Pro Ile Thr Phe Leu Phe
305                 310                 315                 320
Arg Phe Leu Val Gly Thr Ile Cys Ala Ala Tyr Tyr Val Leu Val Pro
                325                 330                 335
Ile Tyr Met Trp Ile Lys Asp Gln Ile Val Pro Lys Gly Met Pro Ile
                340                 345                 350

<210> SEQ ID NO 23
<211> LENGTH: 341
<212> TYPE: PRT
<213> ORGANISM: Arabidopsis thaliana

<400> SEQUENCE: 23

Met Ala Ser Ser Met Leu Asn Gly Ala Glu Thr Phe Thr Leu Ile Arg
1               5                   10                  15
Gly Val Thr Pro Lys Ser Ile Gly Phe Leu Gly Ser Gly Leu His Gly
                20                  25                  30
Lys Gln Phe Ser Ser Ala Gly Leu Ile Tyr Ser Pro Lys Met Ser Arg
            35                  40                  45
Val Gly Thr Thr Ile Ala Pro Arg Cys Ser Leu Ser Ala Ser Arg Pro
    50                  55                  60
Ala Ser Gln Pro Arg Phe Ile Gln His Lys Lys Glu Ala Phe Trp Phe
65                  70                  75                  80
Tyr Arg Phe Leu Ser Ile Val Tyr Asp His Val Ile Asn Pro Gly His
                85                  90                  95
Trp Thr Glu Asp Met Arg Asp Asp Ala Leu Glu Pro Ala Asp Leu Asn
                100                 105                 110
Asp Arg Asp Met Val Val Val Asp Val Gly Gly Gly Thr Gly Phe Thr
            115                 120                 125
Thr Leu Gly Ile Val Gln His Val Asp Ala Lys Asn Val Thr Ile Leu
    130                 135                 140
Asp Gln Ser Pro His Gln Leu Ala Lys Ala Lys Gln Lys Glu Pro Leu
145                 150                 155                 160
Lys Glu Cys Asn Ile Ile Glu Gly Asp Ala Glu Asp Leu Pro Phe Pro
                165                 170                 175
```

-continued

```
Thr Asp Tyr Ala Asp Arg Tyr Val Ser Ala Gly Ser Ile Glu Tyr Trp
            180                 185                 190

Pro Asp Pro Gln Arg Gly Ile Lys Glu Ala Tyr Arg Val Leu Lys Gln
        195                 200                 205

Gly Gly Lys Ala Cys Leu Ile Gly Pro Val Tyr Pro Thr Phe Trp Leu
    210                 215                 220

Ser Arg Phe Phe Ala Asp Val Trp Met Leu Phe Pro Lys Glu Glu
225                 230                 235                 240

Tyr Ile Glu Trp Phe Glu Lys Ala Gly Phe Lys Asp Val Gln Leu Lys
                245                 250                 255

Arg Ile Gly Pro Lys Trp Tyr Arg Gly Val Arg His Gly Leu Ile
            260                 265                 270

Met Gly Cys Ser Val Thr Gly Val Lys Pro Ala Ser Gly Asp Ser Pro
        275                 280                 285

Leu Gln Leu Gly Pro Lys Ala Glu Asp Val Ser Lys Pro Val Asn Pro
    290                 295                 300

Phe Val Phe Leu Leu Arg Phe Met Leu Gly Ala Thr Ala Ala Ala Tyr
305                 310                 315                 320

Tyr Val Leu Val Pro Ile Tyr Met Trp Leu Lys Asp Gln Ile Val Pro
                325                 330                 335

Glu Gly Gln Pro Ile
            340
```

<210> SEQ ID NO 24
<211> LENGTH: 344
<212> TYPE: PRT
<213> ORGANISM: Arabidopsis thaliana

<400> SEQUENCE: 24

```
Met Ala Ser Ser Met Leu Ser Gly Ala Glu Ser Leu Ser Met Leu Arg
1               5                   10                  15

Ile His His Gln Pro Lys Leu Thr Phe Ser Ser Pro Ser Leu His Ser
            20                  25                  30

Lys Pro Thr Asn Leu Lys Met Asp Leu Ile Pro Phe Ala Thr Lys His
        35                  40                  45

Gln Lys Thr Lys Lys Ala Ser Ile Phe Thr Cys Ser Ala Ser Ser Ser
    50                  55                  60

Ser Arg Pro Ala Ser Gln Pro Arg Phe Ile Gln His Lys Gln Glu Ala
65                  70                  75                  80

Phe Trp Phe Tyr Arg Phe Leu Ser Ile Val Tyr Asp His Val Ile Asn
                85                  90                  95

Pro Gly His Trp Thr Glu Asp Met Arg Asp Asp Ala Leu Glu Pro Ala
            100                 105                 110

Glu Leu Tyr Asp Ser Arg Met Lys Val Val Asp Val Gly Gly Gly Thr
        115                 120                 125

Gly Phe Thr Thr Leu Gly Ile Ile Lys His Ile Asp Pro Lys Asn Val
    130                 135                 140

Thr Ile Leu Asp Gln Ser Pro His Gln Leu Glu Lys Ala Arg Gln Lys
145                 150                 155                 160

Glu Ala Leu Lys Glu Cys Thr Ile Val Glu Gly Asp Ala Glu Asp Leu
                165                 170                 175

Pro Phe Pro Thr Asp Thr Phe Asp Arg Tyr Val Ser Ala Gly Ser Ile
            180                 185                 190

Glu Tyr Trp Pro Asp Pro Gln Arg Gly Ile Lys Glu Ala Tyr Arg Val
        195                 200                 205
```

```
Leu Lys Leu Gly Gly Val Ala Cys Leu Ile Gly Pro Val His Pro Thr
            210                 215                 220

Phe Trp Leu Ser Arg Phe Phe Ala Asp Met Trp Met Leu Phe Pro Thr
225                 230                 235                 240

Glu Glu Glu Tyr Ile Glu Trp Phe Lys Lys Ala Gly Phe Lys Asp Val
                245                 250                 255

Lys Leu Lys Arg Ile Gly Pro Lys Trp Tyr Arg Gly Val Arg Arg His
            260                 265                 270

Gly Leu Ile Met Gly Cys Ser Val Thr Gly Val Lys Arg Leu Ser Gly
            275                 280                 285

Asp Ser Pro Leu Gln Leu Gly Pro Lys Ala Glu Asp Val Lys Lys Pro
            290                 295                 300

Ile Asn Pro Phe Ser Phe Leu Leu Arg Phe Ile Leu Gly Thr Ile Ala
305                 310                 315                 320

Ala Thr Tyr Tyr Val Leu Val Pro Ile Tyr Met Trp Ile Lys Asp Gln
                325                 330                 335

Ile Val Pro Lys Gly Gln Pro Ile
            340
```

<210> SEQ ID NO 25
<211> LENGTH: 342
<212> TYPE: PRT
<213> ORGANISM: Arabidopsis thaliana

<400> SEQUENCE: 25

```
Met Gly Ser Val Met Leu Ser Gly Thr Glu Lys Leu Thr Leu Arg Thr
1               5                   10                  15

Leu Thr Gly Asn Gly Leu Gly Phe Thr Gly Ser Asp Leu His Gly Lys
            20                  25                  30

Asn Phe Pro Arg Val Ser Phe Ala Ala Thr Thr Ser Ala Lys Val Pro
            35                  40                  45

Asn Phe Arg Ser Ile Val Val Pro Lys Cys Ser Val Ser Ala Ser Arg
50                  55                  60

Pro Ser Ser Gln Pro Arg Phe Ile Gln His Lys Lys Glu Ala Phe Trp
65                  70                  75                  80

Phe Tyr Arg Phe Leu Ser Ile Val Tyr Asp His Val Ile Asn Pro Gly
                85                  90                  95

His Trp Thr Glu Asp Met Arg Asp Asp Ala Leu Glu Pro Ala Asp Leu
            100                 105                 110

Asn Asp Arg Asn Met Ile Val Val Asp Val Gly Gly Gly Thr Gly Phe
            115                 120                 125

Thr Thr Leu Gly Ile Val Lys His Val Asp Ala Lys Asn Val Thr Ile
130                 135                 140

Leu Asp Gln Ser Pro His Gln Leu Ala Lys Ala Lys Gln Lys Glu Pro
145                 150                 155                 160

Leu Lys Glu Cys Lys Ile Ile Glu Gly Asp Ala Glu Asp Leu Pro Phe
                165                 170                 175

Arg Thr Asp Tyr Ala Asp Arg Tyr Val Ser Ala Gly Ser Ile Glu Tyr
            180                 185                 190

Trp Pro Asp Pro Gln Arg Gly Ile Lys Glu Ala Tyr Arg Val Leu Lys
            195                 200                 205

Leu Gly Gly Lys Ala Cys Leu Ile Gly Pro Val Tyr Pro Thr Phe Trp
210                 215                 220

Leu Ser Arg Phe Phe Ala Asp Val Trp Met Leu Phe Pro Lys Glu Glu
```

```
                    225                 230                 235                 240

Glu Tyr Ile Glu Trp Phe Gln Lys Ala Gly Phe Lys Asp Val Gln Leu
                245                 250                 255

Lys Arg Ile Gly Pro Lys Trp Tyr Arg Gly Val Arg Arg His Gly Leu
            260                 265                 270

Ile Met Gly Cys Ser Val Thr Gly Val Lys Pro Ala Ser Gly Asp Ser
            275                 280                 285

Pro Leu Gln Leu Gly Pro Lys Glu Glu Asp Val Glu Lys Pro Val Asn
        290                 295                 300

Pro Phe Val Phe Ala Leu Arg Phe Val Leu Gly Ala Leu Ala Ala Thr
305                 310                 315                 320

Trp Phe Val Leu Val Pro Ile Tyr Met Trp Leu Lys Asp Gln Val Val
                325                 330                 335

Pro Lys Gly Gln Pro Ile
                340

<210> SEQ ID NO 26
<211> LENGTH: 348
<212> TYPE: PRT
<213> ORGANISM: Arabidopsis thaliana

<400> SEQUENCE: 26

Met Ala Met Ala Ser Ser Ala Tyr Ala Pro Ala Gly Gly Val Gly Thr
1               5                   10                  15

His Ser Ala Pro Gly Arg Ile Arg Pro Pro Arg Gly Leu Gly Phe Ser
            20                  25                  30

Thr Thr Thr Thr Lys Ser Arg Pro Leu Val Leu Thr Arg Arg Gly Gly
        35                  40                  45

Gly Gly Gly Asn Ile Ser Val Ala Arg Leu Arg Cys Ala Ala Ser Ser
    50                  55                  60

Ser Ser Ala Ala Ala Arg Pro Met Ser Gln Pro Arg Phe Ile Gln His
65                  70                  75                  80

Lys Lys Glu Ala Phe Trp Phe Tyr Arg Phe Leu Ser Ile Val Tyr Asp
                85                  90                  95

His Val Ile Asn Pro Gly His Trp Thr Glu Asp Met Arg Asp Asp Ala
            100                 105                 110

Leu Glu Pro Ala Asp Leu Tyr Ser Arg Lys Leu Arg Val Val Asp Val
        115                 120                 125

Gly Gly Gly Thr Gly Phe Thr Thr Leu Gly Ile Val Lys Arg Val Asp
    130                 135                 140

Pro Glu Asn Val Thr Leu Leu Asp Gln Ser Pro His Gln Leu Glu Lys
145                 150                 155                 160

Ala Arg Glu Lys Glu Ala Leu Lys Gly Val Thr Ile Met Glu Gly Asp
                165                 170                 175

Ala Glu Asp Leu Pro Phe Pro Thr Asp Thr Phe Asp Arg Tyr Val Ser
            180                 185                 190

Ala Gly Ser Ile Glu Tyr Trp Pro Asp Pro Gln Arg Gly Ile Lys Glu
        195                 200                 205

Ala Tyr Arg Val Leu Arg Leu Gly Gly Val Ala Cys Met Ile Gly Pro
    210                 215                 220

Val His Pro Thr Phe Trp Leu Ser Arg Phe Phe Ala Asp Met Trp Met
225                 230                 235                 240

Leu Phe Pro Lys Glu Glu Glu Tyr Ile Glu Trp Phe Lys Lys Ala Gly
                245                 250                 255
```

```
Phe Lys Asp Val Lys Leu Lys Arg Ile Gly Pro Lys Trp Tyr Arg Gly
            260                 265                 270

Val Arg Arg His Gly Leu Ile Met Gly Cys Ser Val Thr Gly Val Lys
            275                 280                 285

Arg Glu His Gly Asp Ser Pro Leu Gln Leu Gly Pro Lys Val Glu Asp
            290                 295                 300

Val Ser Lys Pro Val Asn Pro Ile Thr Phe Leu Phe Arg Phe Leu Met
305                 310                 315                 320

Gly Thr Ile Cys Ala Ala Tyr Tyr Val Leu Val Pro Ile Tyr Met Trp
            325                 330                 335

Ile Lys Asp Gln Ile Val Pro Lys Gly Met Pro Ile
            340                 345

<210> SEQ ID NO 27
<211> LENGTH: 337
<212> TYPE: PRT
<213> ORGANISM: Arabidopsis thaliana

<400> SEQUENCE: 27

Met Ala Ser Leu Met Leu Asn Gly Ala Ile Thr Phe Pro Lys Gly Leu
1               5                   10                  15

Gly Phe Pro Ala Ser Asn Leu His Ala Arg Pro Ser Pro Pro Leu Ser
            20                  25                  30

Leu Val Ser Asn Thr Ala Thr Arg Arg Leu Ser Val Ala Thr Arg Cys
            35                  40                  45

Ser Ser Ser Ser Val Ser Ala Ser Arg Pro Ser Ala Gln Pro Arg
    50                  55                  60

Phe Ile Gln His Lys Lys Glu Ala Tyr Trp Phe Tyr Arg Phe Leu Ser
65                  70                  75                  80

Ile Val Tyr Asp His Ile Ile Asn Pro Gly His Trp Thr Glu Asp Met
            85                  90                  95

Arg Asp Asp Ala Leu Glu Pro Ala Asp Leu Ser His Pro Asp Met Arg
            100                 105                 110

Val Val Asp Val Gly Gly Gly Thr Gly Phe Thr Thr Leu Gly Ile Val
            115                 120                 125

Lys Thr Val Lys Ala Lys Asn Val Thr Ile Leu Asp Gln Ser Pro His
            130                 135                 140

Gln Leu Ala Lys Ala Lys Gln Lys Glu Pro Leu Lys Glu Cys Lys Ile
145                 150                 155                 160

Val Glu Gly Asp Ala Glu Asp Leu Pro Phe Pro Thr Asp Tyr Ala Asp
            165                 170                 175

Arg Tyr Val Ser Ala Gly Ser Ile Glu Tyr Trp Pro Asp Pro Gln Arg
            180                 185                 190

Gly Ile Arg Glu Ala Tyr Arg Val Leu Lys Ile Gly Gly Lys Ala Cys
            195                 200                 205

Leu Ile Gly Pro Val His Pro Thr Phe Trp Leu Ser Arg Phe Phe Ala
            210                 215                 220

Asp Val Trp Met Leu Phe Pro Lys Glu Glu Tyr Ile Glu Trp Phe
225                 230                 235                 240

Lys Asn Ala Gly Phe Lys Asp Val Gln Leu Lys Arg Ile Gly Pro Lys
            245                 250                 255

Trp Tyr Arg Gly Val Arg Arg His Gly Leu Ile Met Gly Cys Ser Val
            260                 265                 270

Thr Gly Val Lys Pro Ala Ser Gly Asp Ser Pro Leu Gln Leu Gly Pro
            275                 280                 285
```

```
Lys Glu Glu Asp Val Glu Lys Pro Val Asn Asn Pro Phe Ser Phe Leu
    290                 295                 300

Gly Arg Phe Leu Leu Gly Thr Leu Ala Ala Ala Trp Phe Val Leu Ile
305                 310                 315                 320

Pro Ile Tyr Met Trp Ile Lys Asp Gln Ile Val Pro Lys Asp Gln Pro
                325                 330                 335

Ile

<210> SEQ ID NO 28
<211> LENGTH: 292
<212> TYPE: PRT
<213> ORGANISM: Arabidopsis thaliana

<400> SEQUENCE: 28

Ala Thr Arg Cys Ser Ser Ser Val Ser Ser Arg Pro Ser Ala
1               5                   10                  15

Gln Pro Arg Phe Ile Gln His Lys Lys Glu Ala Tyr Trp Phe Tyr Arg
                20                  25                  30

Phe Leu Ser Ile Val Tyr Asp His Val Ile Asn Pro Gly His Trp Thr
            35                  40                  45

Glu Asp Met Arg Asp Asp Ala Leu Glu Pro Ala Asp Leu Ser His Pro
        50                  55                  60

Asp Met Arg Val Val Asp Val Gly Gly Gly Thr Gly Phe Thr Thr Leu
65                  70                  75                  80

Gly Ile Val Lys Thr Val Lys Ala Lys Asn Val Thr Ile Leu Asp Gln
                85                  90                  95

Ser Pro His Gln Leu Ala Lys Ala Lys Gln Lys Glu Pro Leu Lys Glu
            100                 105                 110

Cys Lys Ile Val Glu Gly Asp Ala Glu Asp Leu Pro Phe Pro Thr Asp
        115                 120                 125

Tyr Ala Asp Arg Tyr Val Ser Ala Gly Ser Ile Glu Tyr Trp Pro Asp
    130                 135                 140

Pro Gln Arg Gly Ile Arg Glu Ala Tyr Arg Val Leu Lys Ile Gly Gly
145                 150                 155                 160

Lys Ala Cys Leu Ile Gly Pro Val Tyr Pro Thr Phe Trp Leu Ser Arg
                165                 170                 175

Phe Phe Ser Asp Val Trp Met Leu Phe Pro Lys Glu Glu Tyr Ile
            180                 185                 190

Glu Trp Phe Lys Asn Ala Gly Phe Lys Asp Val Gln Leu Lys Arg Ile
        195                 200                 205

Gly Pro Lys Trp Tyr Arg Gly Val Arg Arg His Gly Leu Ile Met Gly
    210                 215                 220

Cys Ser Val Thr Gly Val Lys Pro Ala Ser Gly Asp Ser Pro Leu Gln
225                 230                 235                 240

Leu Gly Pro Lys Glu Glu Asp Val Glu Lys Pro Val Asn Asn Pro Phe
                245                 250                 255

Ser Phe Leu Gly Arg Phe Leu Leu Gly Thr Leu Ala Ala Ala Trp Phe
            260                 265                 270

Val Leu Ile Pro Ile Tyr Met Trp Ile Lys Asp Gln Ile Val Pro Lys
        275                 280                 285

Asp Gln Pro Ile
    290

SEQ ID NO 29
```

```
LENGTH: 292
TYPE: PRT
ORGANISM: Arabidopsis thaliana

<400> SEQUENCE: 29

Ala Thr Arg Cys Ser Ser Ser Val Ser Ser Arg Pro Ser Ala
1               5                   10                  15

Gln Pro Arg Phe Ile Gln His Lys Lys Glu Ala Tyr Trp Phe Tyr Arg
            20                  25                  30

Phe Leu Ser Ile Val Tyr Asp His Val Ile Asn Pro Gly His Trp Thr
                35                  40                  45

Glu Asp Met Arg Asp Asp Ala Leu Glu Pro Ala Asp Leu Ser His Pro
    50                  55                  60

Asp Met Arg Val Val Asp Val Gly Gly Thr Gly Phe Thr Thr Leu
65                  70                  75                  80

Gly Ile Val Lys Thr Val Lys Ala Lys Asn Val Thr Ile Leu Asp Gln
                85                  90                  95

Ser Pro His Gln Leu Ala Lys Ala Lys Gln Lys Glu Pro Leu Lys Glu
            100                 105                 110

Cys Lys Ile Val Glu Gly Asp Ala Glu Asp Leu Pro Phe Pro Thr Asp
            115                 120                 125

Tyr Ala Asp Arg Tyr Val Ser Ala Gly Ser Ile Glu Tyr Trp Pro Asp
130                 135                 140

Pro Gln Arg Gly Ile Arg Glu Ala Tyr Arg Val Leu Lys Ile Gly Gly
145                 150                 155                 160

Lys Ala Cys Leu Ile Gly Pro Val Tyr Pro Thr Phe Trp Leu Ser Arg
                165                 170                 175

Phe Phe Ser Asp Val Trp Met Leu Phe Pro Lys Glu Glu Tyr Ile
            180                 185                 190

Glu Trp Phe Lys Asn Ala Gly Phe Lys Asp Val Gln Leu Lys Arg Ile
            195                 200                 205

Gly Pro Lys Trp Tyr Arg Gly Val Arg Arg His Gly Leu Ile Met Gly
    210                 215                 220

Cys Ser Val Thr Gly Val Lys Pro Ala Ser Gly Asp Ser Pro Leu Gln
225                 230                 235                 240

Leu Gly Pro Lys Glu Lys Asp Val Glu Lys Pro Val Asn Asn Pro Phe
                245                 250                 255

Ser Phe Leu Gly Arg Phe Leu Leu Gly Thr Leu Ala Ala Trp Phe
            260                 265                 270

Val Leu Ile Pro Ile Tyr Met Trp Ile Lys Asp Gln Ile Val Pro Lys
                275                 280                 285

Asp Gln Pro Ile
    290

<210> SEQ ID NO 30
<211> LENGTH: 292
<212> TYPE: PRT
<213> ORGANISM: Arabidopsis thaliana

<400> SEQUENCE: 30

Ala Thr Arg Cys Ser Ser Ser Val Ser Ser Arg Pro Ser Ala
1               5                   10                  15

Gln Pro Arg Phe Ile Gln His Lys Lys Lys Ala Tyr Trp Phe Tyr Arg
            20                  25                  30

Phe Leu Ser Ile Val Tyr Asp His Val Ile Asn Pro Gly His Trp Thr
                35                  40                  45
```

```
Glu Asp Met Arg Asp Asp Ala Leu Glu Pro Ala Asp Leu Ser His Pro
     50                  55                  60

Asp Met Arg Val Val Asp Val Gly Gly Thr Gly Phe Thr Thr Leu
 65                  70                  75                  80

Gly Ile Val Lys Thr Val Lys Ala Lys Asn Val Thr Ile Leu Asp Gln
                 85                  90                  95

Ser Pro His Gln Leu Ala Lys Ala Lys Gln Lys Glu Pro Leu Lys Glu
                100                 105                 110

Cys Lys Ile Val Glu Gly Asp Ala Glu Asp Leu Pro Phe Pro Thr Asp
                115                 120                 125

Tyr Ala Asp Arg Tyr Val Ser Ala Gly Ser Ile Glu Tyr Trp Pro Asp
    130                 135                 140

Pro Gln Arg Gly Ile Arg Glu Ala Tyr Arg Val Leu Lys Ile Gly Gly
145                 150                 155                 160

Lys Ala Cys Leu Ile Gly Pro Val Tyr Pro Thr Phe Trp Leu Ser Arg
                165                 170                 175

Phe Phe Ser Asp Val Trp Met Leu Phe Pro Lys Glu Glu Tyr Ile
                180                 185                 190

Glu Trp Phe Lys Asn Ala Gly Phe Lys Asp Val Gln Leu Lys Arg Ile
        195                 200                 205

Gly Pro Lys Trp Tyr Arg Gly Val Arg Arg His Gly Leu Ile Met Gly
        210                 215                 220

Cys Ser Val Thr Gly Val Lys Pro Ala Ser Gly Asp Ser Pro Leu Gln
225                 230                 235                 240

Leu Gly Pro Lys Glu Glu Asp Val Glu Lys Pro Val Asn Asn Pro Phe
                245                 250                 255

Ser Phe Leu Gly Arg Phe Leu Leu Gly Thr Leu Ala Ala Trp Phe
            260                 265                 270

Val Leu Ile Pro Ile Tyr Met Trp Ile Lys Asp Gln Ile Val Pro Lys
            275                 280                 285

Asp Gln Pro Ile
        290

<210> SEQ ID NO 31
<211> LENGTH: 292
<212> TYPE: PRT
<213> ORGANISM: Arabidopsis thaliana

<400> SEQUENCE: 31

Ala Thr Arg Cys Ser Ser Ser Val Ser Ser Arg Pro Ser Ala
 1               5                  10                  15

Gln Pro Arg Phe Ile Gln His Lys Lys Glu Ala Tyr Trp Phe Tyr Arg
                20                  25                  30

Phe Leu Ser Ile Val Tyr Asp His Val Ile Asn Pro Gly His Trp Thr
            35                  40                  45

Glu Asp Met Arg Asp Asp Ala Leu Glu Pro Ala Asp Leu Ser His Pro
     50                  55                  60

Asp Met Arg Val Val Asn Val Gly Gly Thr Gly Phe Thr Thr Leu
 65                  70                  75                  80

Gly Ile Val Lys Thr Val Lys Ala Lys Asn Val Thr Ile Leu Asp Gln
                 85                  90                  95

Ser Pro His Gln Leu Ala Lys Ala Lys Gln Lys Glu Pro Leu Lys Glu
                100                 105                 110

Cys Lys Ile Val Glu Gly Asp Ala Glu Asp Leu Pro Phe Pro Thr Asp
```

```
            115                 120                 125
Tyr Ala Asp Arg Tyr Val Ser Ala Gly Ser Ile Glu Tyr Trp Pro Asp
    130                 135                 140

Pro Gln Arg Gly Ile Arg Glu Ala Tyr Arg Val Leu Lys Ile Gly Gly
145                 150                 155                 160

Lys Ala Cys Leu Ile Gly Pro Val Tyr Pro Thr Phe Trp Leu Ser Arg
                165                 170                 175

Phe Phe Ser Asp Val Trp Met Leu Phe Pro Lys Glu Glu Tyr Ile
            180                 185                 190

Glu Trp Phe Lys Asn Ala Gly Phe Lys Asp Val Gln Leu Lys Arg Ile
        195                 200                 205

Gly Pro Lys Trp Tyr Arg Gly Val Arg Arg His Gly Leu Ile Met Gly
    210                 215                 220

Cys Ser Val Thr Gly Val Lys Pro Ala Ser Gly Asp Ser Pro Leu Gln
225                 230                 235                 240

Leu Gly Pro Lys Glu Glu Asp Val Glu Lys Pro Val Asn Asn Pro Phe
                245                 250                 255

Ser Phe Leu Gly Arg Phe Leu Leu Gly Thr Leu Ala Ala Ala Trp Phe
            260                 265                 270

Val Leu Ile Pro Ile Tyr Met Trp Ile Lys Asp Gln Ile Val Pro Lys
        275                 280                 285

Asp Gln Pro Ile
    290

<210> SEQ ID NO 32
<211> LENGTH: 292
<212> TYPE: PRT
<213> ORGANISM: Arabidopsis thaliana

<400> SEQUENCE: 32

Ala Thr Arg Cys Ser Ser Ser Val Ser Ser Arg Pro Ser Ala
1               5                   10                  15

Gln Pro Arg Phe Ile Gln His Lys Lys Glu Ala Tyr Trp Phe Tyr Arg
                20                  25                  30

Phe Leu Ser Ile Val Tyr Asp His Val Ile Asn Pro Gly His Trp Ile
            35                  40                  45

Glu Asp Met Arg Asp Asp Ala Leu Glu Pro Ala Asp Leu Ser His Pro
    50                  55                  60

Asp Met Arg Val Val Asp Val Gly Gly Thr Gly Phe Thr Thr Leu
65                  70                  75                  80

Gly Ile Val Lys Thr Val Lys Ala Lys Asn Val Thr Ile Leu Asp Gln
                85                  90                  95

Ser Pro His Gln Leu Ala Lys Ala Lys Gln Lys Glu Pro Leu Lys Glu
            100                 105                 110

Cys Lys Ile Val Glu Gly Asp Ala Glu Asp Leu Pro Phe Pro Thr Asp
        115                 120                 125

Tyr Ala Asp Arg Tyr Val Ser Ala Gly Ser Ile Glu Tyr Trp Pro Asp
    130                 135                 140

Pro Gln Arg Gly Ile Arg Glu Ala Tyr Arg Val Leu Lys Ile Gly Gly
145                 150                 155                 160

Lys Ala Cys Leu Ile Gly Pro Val Tyr Pro Thr Phe Trp Leu Ser Arg
                165                 170                 175

Phe Phe Ser Asp Val Trp Met Leu Phe Pro Lys Glu Glu Tyr Ile
            180                 185                 190
```

-continued

Glu Trp Phe Lys Asn Ala Gly Phe Lys Asp Val Gln Leu Lys Arg Ile
            195                 200                 205

Gly Pro Lys Trp Tyr Arg Gly Val Arg Arg His Gly Leu Ile Met Gly
        210                 215                 220

Cys Ser Val Thr Gly Val Lys Pro Ala Ser Gly Asp Ser Pro Leu Gln
225                 230                 235                 240

Leu Gly Pro Lys Glu Glu Asp Val Glu Lys Pro Val Asn Asn Pro Phe
                245                 250                 255

Ser Phe Leu Gly Arg Phe Leu Leu Gly Thr Leu Ala Ala Ala Trp Phe
            260                 265                 270

Val Leu Ile Pro Ile Tyr Met Trp Ile Lys Asp Gln Ile Val Pro Lys
            275                 280                 285

Asp Gln Pro Ile
    290

<210> SEQ ID NO 33
<211> LENGTH: 293
<212> TYPE: PRT
<213> ORGANISM: Arabidopsis thaliana

<400> SEQUENCE: 33

Ala Thr Arg Cys Ser Ser Ser Ser Val Ser Ala Ser Arg Pro Ser
1               5                   10                  15

Ala Gln Pro Arg Phe Ile Gln His Lys Lys Glu Ala Tyr Trp Phe Tyr
            20                  25                  30

Arg Phe Leu Ser Ile Val Tyr Asp His Ile Ile Asn Pro Gly His Trp
        35                  40                  45

Thr Glu Asp Met Arg Asp Asp Ala Leu Glu Pro Ala Asp Leu Ser His
    50                  55                  60

Pro Asp Met Arg Val Val Asp Val Gly Gly Gly Thr Gly Phe Thr Thr
65                  70                  75                  80

Leu Gly Ile Val Lys Thr Val Lys Ala Lys Asn Val Thr Ile Leu Asp
                85                  90                  95

Gln Ser Pro His Gln Leu Ala Lys Ala Lys Gln Lys Glu Pro Leu Lys
            100                 105                 110

Glu Cys Lys Ile Val Glu Gly Asp Ala Glu Asp Leu Pro Phe Pro Thr
        115                 120                 125

Asp Tyr Ala Asp Arg Tyr Val Ser Ala Gly Ser Ile Glu Tyr Trp Pro
130                 135                 140

Asp Pro Gln Arg Gly Ile Arg Glu Ala Tyr Arg Val Leu Lys Ile Gly
145                 150                 155                 160

Gly Lys Ala Cys Leu Ile Gly Pro Val His Pro Thr Phe Trp Leu Ser
                165                 170                 175

Arg Phe Phe Ala Asp Val Trp Met Leu Phe Pro Lys Glu Glu Glu Tyr
            180                 185                 190

Ile Glu Trp Phe Lys Asn Ala Gly Phe Lys Asp Val Gln Leu Lys Arg
        195                 200                 205

Ile Gly Pro Lys Trp Tyr Arg Gly Val Arg Arg His Gly Leu Ile Met
    210                 215                 220

Gly Cys Ser Val Thr Gly Val Lys Pro Ala Ser Gly Asp Ser Pro Leu
225                 230                 235                 240

Gln Leu Gly Pro Lys Glu Glu Asp Val Glu Lys Pro Val Asn Asn Pro
                245                 250                 255

Phe Ser Phe Leu Gly Arg Phe Leu Leu Gly Thr Leu Ala Ala Ala Trp
            260                 265                 270

```
Phe Val Leu Ile Pro Ile Tyr Met Trp Ile Lys Asp Gln Ile Val Pro
        275                 280                 285

Lys Asp Gln Pro Ile
        290

<210> SEQ ID NO 34
<211> LENGTH: 292
<212> TYPE: PRT
<213> ORGANISM: Arabidopsis thaliana

<400> SEQUENCE: 34

Arg Leu Arg Cys Ala Ala Ser Ser Ser Ala Ala Arg Pro Met
1               5                   10                  15

Ser Gln Pro Arg Phe Ile Gln His Lys Lys Glu Ala Phe Trp Phe Tyr
            20                  25                  30

Arg Phe Leu Ser Ile Val Tyr Asp His Val Ile Asn Pro Gly His Trp
        35                  40                  45

Thr Glu Asp Met Arg Asp Asp Ala Leu Glu Pro Ala Asp Leu Tyr Ser
    50                  55                  60

Arg Lys Leu Arg Val Val Asp Val Gly Gly Thr Gly Phe Thr Thr
65                  70                  75                  80

Leu Gly Ile Val Lys Arg Val Asp Pro Glu Asn Val Thr Leu Leu Asp
                85                  90                  95

Gln Ser Pro His Gln Leu Glu Lys Ala Arg Glu Lys Glu Ala Leu Lys
            100                 105                 110

Gly Val Thr Ile Met Glu Gly Asp Ala Glu Asp Leu Pro Phe Pro Thr
        115                 120                 125

Asp Thr Phe Asp Arg Tyr Val Ser Ala Gly Ser Ile Glu Tyr Trp Pro
    130                 135                 140

Asp Pro Gln Arg Gly Ile Lys Glu Ala Tyr Arg Val Leu Arg Leu Gly
145                 150                 155                 160

Gly Val Ala Cys Met Ile Gly Pro Val His Pro Thr Phe Trp Leu Ser
                165                 170                 175

Arg Phe Phe Ala Asp Met Trp Met Leu Phe Pro Lys Glu Glu Tyr
            180                 185                 190

Ile Glu Trp Phe Lys Lys Ala Gly Phe Lys Asp Val Lys Leu Lys Arg
        195                 200                 205

Ile Gly Pro Lys Trp Tyr Arg Gly Val Arg Arg His Gly Leu Ile Met
    210                 215                 220

Gly Cys Ser Val Thr Gly Val Lys Arg Glu His Gly Asp Ser Pro Leu
225                 230                 235                 240

Gln Leu Gly Pro Lys Val Glu Asp Val Ser Lys Pro Val Asn Pro Ile
                245                 250                 255

Thr Phe Leu Phe Arg Phe Leu Met Gly Thr Ile Cys Ala Ala Tyr Tyr
            260                 265                 270

Val Leu Val Pro Ile Tyr Met Trp Ile Lys Asp Gln Ile Val Pro Lys
        275                 280                 285

Gly Met Pro Ile
        290

<210> SEQ ID NO 35
<211> LENGTH: 292
<212> TYPE: PRT
<213> ORGANISM: Arabidopsis thaliana

<400> SEQUENCE: 35
```

-continued

```
Arg Leu Arg Cys Ala Ala Ser Ser Pro Ala Ala Arg Pro Ala
 1               5                  10                  15

Thr Ala Pro Arg Phe Ile Gln His Lys Lys Glu Ala Phe Trp Phe Tyr
             20                  25                  30

Arg Phe Leu Ser Ile Val Tyr Asp His Val Ile Asn Pro Gly His Trp
             35                  40                  45

Thr Glu Asp Met Arg Asp Asp Ala Leu Glu Pro Ala Asp Leu Phe Ser
     50                  55                  60

Arg His Leu Thr Val Val Asp Val Gly Gly Thr Gly Phe Thr Thr
65                  70                  75                  80

Leu Gly Ile Val Lys His Val Asn Pro Glu Asn Val Thr Leu Leu Asp
                 85                  90                  95

Gln Ser Pro His Gln Leu Asp Lys Ala Arg Gln Lys Glu Ala Leu Lys
             100                 105                 110

Gly Val Thr Ile Met Glu Gly Asp Ala Glu Asp Leu Pro Phe Pro Thr
             115                 120                 125

Asp Ser Phe Asp Arg Tyr Ile Ser Ala Gly Ser Ile Glu Tyr Trp Pro
130                 135                 140

Asp Pro Gln Arg Gly Ile Lys Glu Ala Tyr Arg Val Leu Arg Phe Gly
145                 150                 155                 160

Gly Leu Ala Cys Val Ile Gly Pro Val Tyr Pro Thr Phe Trp Leu Ser
                 165                 170                 175

Arg Phe Phe Ala Asp Met Trp Met Leu Phe Pro Lys Glu Glu Glu Tyr
             180                 185                 190

Ile Glu Trp Phe Lys Lys Ala Gly Phe Arg Asp Val Lys Leu Lys Arg
             195                 200                 205

Ile Gly Pro Lys Trp Tyr Arg Gly Val Arg Arg His Gly Leu Ile Met
             210                 215                 220

Gly Cys Ser Val Thr Gly Val Lys Arg Glu Arg Gly Asp Ser Pro Leu
225                 230                 235                 240

Glu Leu Gly Pro Lys Ala Glu Asp Val Ser Lys Pro Val Asn Pro Ile
                 245                 250                 255

Thr Phe Leu Phe Arg Phe Leu Val Gly Thr Ile Cys Ala Ala Tyr Tyr
             260                 265                 270

Val Leu Val Pro Ile Tyr Met Trp Ile Lys Asp Gln Ile Val Pro Lys
             275                 280                 285

Gly Met Pro Ile
        290
```

<210> SEQ ID NO 36
<211> LENGTH: 288
<212> TYPE: PRT
<213> ORGANISM: Arabidopsis thaliana

<400> SEQUENCE: 36

```
Val Pro Lys Cys Ser Val Ser Ala Ser Arg Pro Ser Ser Gln Pro Arg
 1               5                  10                  15

Phe Ile Gln His Lys Lys Glu Ala Phe Trp Phe Tyr Arg Phe Leu Ser
             20                  25                  30

Ile Val Tyr Asp His Val Ile Asn Pro Gly His Trp Thr Glu Asp Met
             35                  40                  45

Arg Asp Asp Ala Leu Glu Pro Ala Asp Leu Asn Asp Arg Asn Met Ile
     50                  55                  60

Val Val Asp Val Gly Gly Gly Thr Gly Phe Thr Thr Leu Gly Ile Val
```

```
65                  70                  75                  80
Lys His Val Asp Ala Lys Asn Val Thr Ile Leu Asp Gln Ser Pro His
                85                  90                  95
Gln Leu Ala Lys Ala Lys Gln Lys Glu Pro Leu Lys Glu Cys Lys Ile
            100                 105                 110
Ile Glu Gly Asp Ala Glu Asp Leu Pro Phe Arg Thr Asp Tyr Ala Asp
            115                 120                 125
Arg Tyr Val Ser Ala Gly Ser Ile Glu Tyr Trp Asp Pro Gln Arg
            130                 135                 140
Gly Ile Lys Glu Ala Tyr Arg Val Leu Lys Leu Gly Lys Ala Cys
145                 150                 155                 160
Leu Ile Gly Pro Val Tyr Pro Thr Phe Trp Leu Ser Arg Phe Phe Ala
                165                 170                 175
Asp Val Trp Met Leu Phe Pro Lys Glu Glu Tyr Ile Glu Trp Phe
                180                 185                 190
Gln Lys Ala Gly Phe Lys Asp Val Gln Leu Lys Arg Ile Gly Pro Lys
            195                 200                 205
Trp Tyr Arg Gly Val Arg Arg His Gly Leu Ile Met Gly Cys Ser Val
210                 215                 220
Thr Gly Val Lys Pro Ala Ser Gly Asp Ser Pro Leu Gln Leu Gly Pro
225                 230                 235                 240
Lys Glu Glu Asp Val Glu Lys Pro Val Asn Pro Phe Val Phe Ala Leu
                245                 250                 255
Arg Phe Val Leu Gly Ala Leu Ala Ala Thr Trp Phe Val Leu Val Pro
                260                 265                 270
Ile Tyr Met Trp Leu Lys Asp Gln Val Val Pro Lys Gly Gln Pro Ile
            275                 280                 285

<210> SEQ ID NO 37
<211> LENGTH: 289
<212> TYPE: PRT
<213> ORGANISM: Arabidopsis thaliana

<400> SEQUENCE: 37

Ile Phe Thr Cys Ser Ala Ser Ser Ser Arg Pro Ala Ser Gln Pro
1               5                   10                  15
Arg Phe Ile Gln His Lys Gln Glu Ala Phe Trp Phe Tyr Arg Phe Leu
                20                  25                  30
Ser Ile Val Tyr Asp His Val Ile Asn Pro Gly His Trp Thr Glu Asp
            35                  40                  45
Met Arg Asp Asp Ala Leu Glu Pro Ala Glu Leu Tyr Asp Ser Arg Met
        50                  55                  60
Lys Val Val Asp Val Gly Gly Gly Thr Gly Phe Thr Thr Leu Gly Ile
65                  70                  75                  80
Ile Lys His Ile Asp Pro Lys Asn Val Thr Ile Leu Asp Gln Ser Pro
                85                  90                  95
His Gln Leu Glu Lys Ala Arg Gln Lys Glu Ala Leu Lys Glu Cys Thr
            100                 105                 110
Ile Val Glu Gly Asp Ala Glu Asp Leu Pro Phe Pro Thr Asp Thr Phe
            115                 120                 125
Asp Arg Tyr Val Ser Ala Gly Ser Ile Glu Tyr Trp Pro Asp Pro Gln
            130                 135                 140
Arg Gly Ile Lys Glu Ala Tyr Arg Val Leu Lys Leu Gly Gly Val Ala
145                 150                 155                 160
```

```
Cys Leu Ile Gly Pro Val His Pro Thr Phe Trp Leu Ser Arg Phe Phe
                165                 170                 175

Ala Asp Met Trp Met Leu Phe Pro Thr Glu Glu Tyr Ile Glu Trp
            180                 185                 190

Phe Lys Lys Ala Gly Phe Lys Asp Val Lys Leu Lys Arg Ile Gly Pro
        195                 200                 205

Lys Trp Tyr Arg Gly Val Arg Arg His Gly Leu Ile Met Gly Cys Ser
210                 215                 220

Val Thr Gly Val Lys Arg Leu Ser Gly Asp Ser Pro Leu Gln Leu Gly
225                 230                 235                 240

Pro Lys Ala Glu Asp Val Lys Lys Pro Ile Asn Pro Phe Ser Phe Leu
                245                 250                 255

Leu Arg Phe Ile Leu Gly Thr Ile Ala Ala Thr Tyr Tyr Val Leu Val
            260                 265                 270

Pro Ile Tyr Met Trp Ile Lys Asp Gln Ile Val Pro Lys Gly Gln Pro
        275                 280                 285

Ile

<210> SEQ ID NO 38
<211> LENGTH: 288
<212> TYPE: PRT
<213> ORGANISM: Arabidopsis thaliana

<400> SEQUENCE: 38

Ala Pro Arg Cys Ser Leu Ser Ala Ser Arg Pro Ala Ser Gln Pro Arg
1               5                   10                  15

Phe Ile Gln His Lys Lys Glu Ala Phe Trp Phe Tyr Arg Phe Leu Ser
            20                  25                  30

Ile Val Tyr Asp His Val Ile Asn Pro Gly His Trp Thr Glu Asp Met
        35                  40                  45

Arg Asp Asp Ala Leu Glu Pro Ala Asp Leu Asn Asp Arg Asp Met Val
    50                  55                  60

Val Val Asp Val Gly Gly Gly Thr Gly Phe Thr Thr Leu Gly Ile Val
65                  70                  75                  80

Gln His Val Asp Ala Lys Asn Val Thr Ile Leu Asp Gln Ser Pro His
                85                  90                  95

Gln Leu Ala Lys Ala Lys Gln Lys Glu Pro Leu Lys Glu Cys Asn Ile
            100                 105                 110

Ile Glu Gly Asp Ala Glu Asp Leu Pro Phe Pro Thr Asp Tyr Ala Asp
        115                 120                 125

Arg Tyr Val Ser Ala Gly Ser Ile Glu Tyr Trp Pro Asp Pro Gln Arg
    130                 135                 140

Gly Ile Lys Glu Ala Tyr Arg Val Leu Lys Gln Gly Gly Lys Ala Cys
145                 150                 155                 160

Leu Ile Gly Pro Val Tyr Pro Thr Phe Trp Leu Ser Arg Phe Phe Ala
                165                 170                 175

Asp Val Trp Met Leu Phe Pro Lys Glu Glu Tyr Ile Glu Trp Phe
            180                 185                 190

Glu Lys Ala Gly Phe Lys Asp Val Gln Leu Lys Arg Ile Gly Pro Lys
        195                 200                 205

Trp Tyr Arg Gly Val Arg Arg His Gly Leu Ile Met Gly Cys Ser Val
    210                 215                 220

Thr Gly Val Lys Pro Ala Ser Gly Asp Ser Pro Leu Gln Leu Gly Pro
225                 230                 235                 240
```

```
Lys Ala Glu Asp Val Ser Lys Pro Val Asn Pro Phe Val Phe Leu Leu
                245                 250                 255

Arg Phe Met Leu Gly Ala Thr Ala Ala Ala Tyr Tyr Val Leu Val Pro
            260                 265                 270

Ile Tyr Met Trp Leu Lys Asp Gln Ile Val Pro Glu Gly Gln Pro Ile
        275                 280                 285

<210> SEQ ID NO 39
<211> LENGTH: 1047
<212> TYPE: DNA
<213> ORGANISM: Arabidopsis thaliana

<400> SEQUENCE: 39
atgaaagcaa ctctagcagc accctcttct ctcacaagcc tcccttatcg aaccaactct      60
tctttcggct caaagtcatc gcttctcttt cggtctccat cctcctcctc ctcagtctct     120
atgacgacaa cgcgtggaaa cgtggctgtg gcggctgctg ctacatccac tgaggcgcta     180
agaaaaggaa tagcggagtt ctacaatgaa acttcgggtt tgtgggaaga gatttgggga     240
gatcatatgc atcatggctt ttatgaccct gattcttctg ttcaactttc tgattctggt     300
cacaaggaag ctcagatccg tatgattgaa gagtctctcc gtttcgccgg tgttactgat     360
gaagaggagg agaaaaagat aaagaaagta gtggatgttg ggtgtgggat tggaggaagc     420
tcaagatatc ttgcctctaa atttggagct gaatgcattg gcattactct cagccctgtt     480
caggccaaga gagccaatga tctcgcggct gctcaatcac tctctcataa ggcttccttc     540
caagttgcgg atgcgttgga tcagccattc gaagatggaa attcgatct agtgtggtcg      600 atggagagtg gtgagcatat gcctgacaag gccaagtttg taaaagagtt ggtacgtgtg     660
gcggctccag gaggtaggat aataatagtg acatggtgcc atagaaatct atctgcgggg     720
gaggaagctt tgcagccgtg ggagcaaaac atcttggaca aaatctgtaa gacgttctat     780
ctcccggctt ggtgctccac cgatgattat gtcaacttgc ttcaatccca ttctctccag     840
gatattaagt gtgcggattg gtcagagaac gtagctcctt tctggcctgc ggttatacgg     900
actgcattaa catggaaggg ccttgtgtct ctgcttcgta gtggtatgaa agtattaaa      960 ggagcattga caatgccatt gatgattgaa ggttacaaga aggtgtcat taagtttggt     1020 atcatcactt gccagaagcc actctaa                                        1047

<210> SEQ ID NO 40
<211> LENGTH: 1047
<212> TYPE: DNA
<213> ORGANISM: Arabidopsis thaliana

<400> SEQUENCE: 40
atgaaagcaa ctctagcagc accctcttct ctcacaagcc tcccttatcg aaccaactct      60
tctttcggct caaagtcatc gcttctcttt cggtctccat cctcctcctc ctcagtctct     120
atgacgacaa cgcgtggaaa cgtggctgtg gcggctgctg ctacatccac tgaggcgcta     180
agaaaaggaa tagcggagtt ctacaatgaa acttcgggtt tgtgggaaga gatttgggga     240
gatcatatgc atcatggctt ttatgaccct gattcttctg ttcaactttc tgattctggt     300
cacaaggaag ctcagatccg tatgattgaa gagtctctcc gttttgccgg tgttactgat     360
gaagaggagg agaaaaagat aaagaaagta gtggatgttg ggtgtgggat tggaggaagc     420
tcaagatatc ttgcctctaa atttggagct gaatgcattg gcattactct cagccctgtt     480
caggccaaga gagccaatga tctcgcggct gctcaatcac tcgctcataa ggcttccttc     540
```

| | |
|---|---:|
| caagttgcgg atgcgttgga tcagccattc gaagatggaa aattcgatct agtgtggtcg | 600 |
| atggagagtg gtgagcatat gcctgacaag gccaagtttg taaaagagtt ggtacgtgtg | 660 |
| gcggctccag gaggtaggat aataatagtg acatggtgcc atagaaatct atctgcgggg | 720 |
| gaggaagctt tgcagccgtg ggagcaaaac atcttggaca aaatctgtaa gacgttctat | 780 |
| ctcccggctt ggtgctccac cgatgattat gtcaacttgc ttcaatccca ttctctccag | 840 |
| gatattaagt gtgcggattg gtcagagaac gtagctcctt tctggcctgc ggttatacgg | 900 |
| actgcattaa catggaaggg ccttgtgtct ctgcttcgta gtggtatgaa agtattaaa | 960 |
| ggagcattga caatgccatt gatgattgaa ggttacaaga aggtgtcat taagtttggt | 1020 |
| atcatcactt gccagaagcc actctaa | 1047 |

<210> SEQ ID NO 41
<211> LENGTH: 1095
<212> TYPE: DNA
<213> ORGANISM: Arabidopsis thaliana

<400> SEQUENCE: 41

| | |
|---|---:|
| atggcccacg ccgccgcggc cacgggcgca ctggcaccgc tgcatccact gctccgctgc | 60 |
| acgagccgtc atctctgcgc ctcggcttcc cctcgcgccg gcctctgcct ccaccaccac | 120 |
| cgccgccgcc gccgcagcag ccggaggacg aaactcgccg tgcgcgcgat ggcaccgacg | 180 |
| ttgtcctcgt cgtcgacggc ggcggcagct cccccggggc tgaaggaggg catcgcgggg | 240 |
| ctctacgacg agtcgtccgg cgtgtgggag agcatctggg gcgagcacat gcaccacggc | 300 |
| ttctacgacg ccggcgaggc cgcctccatg tccgaccacc gccgcgccca gatccgcatg | 360 |
| atcgaggaat ccctcgcctt cgccgccgtc ccggtgcag atgatgcgga gaagaaaccc | 420 |
| aaaagtgtag ttgatgttgg ctgtggcatt ggtggtagct caagatactt ggcgaacaaa | 480 |
| tacgagcgc aatgctacgg catcacgttg agtccggtgc aggctgaaag aggaaatgcc | 540 |
| ctcgcggcag agcaagggtt atcagacaag gtgcgtattc aagttggtga tgcattggag | 600 |
| cagccttttc ctgatgggca gtttgatctt gtctggtcca tggagagtgg cgagcacatg | 660 |
| ccagacaaac ggcagtttgt aagcgagctg gcacgcgtcg cagctcctgg ggcgagaata | 720 |
| atcattgtga cctggtgcca taggaacctc gagccatccg aagagtccct gaaacctgat | 780 |
| gagctgaatc tcctgaaaag gatatgcgat gcatattatc tcccagactg gtgctctcct | 840 |
| tctgattatg tcaaaattgc cgagtcactg tctcttgagg atataaggac agctgattgg | 900 |
| tcagagaacg tcgccccatt ctggcctgcg gttataaaat cagcattgac atggaaaggt | 960 |
| ttaacttctc tgctaagaag tgggtggaag acgataagag gtgcaatggt gatgcctctg | 1020 |
| atgatcgaag gatacaagaa agggctcatc aaattccaca tcatcacctg tcgcaagccc | 1080 |
| gaaacaacgc agtag | 1095 |

<210> SEQ ID NO 42
<211> LENGTH: 1059
<212> TYPE: DNA
<213> ORGANISM: Arabidopsis thaliana

<400> SEQUENCE: 42

| | |
|---|---:|
| atggctcacg cggcgctgct ccattgctcc cagtcctcca ggagcctcgc agcctgccgc | 60 |
| cgcggcagcc actaccgcgc cccttcgcac gtcccgcgcc actccgccg tctccgacgc | 120 |
| gccgtcgtca gctgcgctcc gatggcctcg tcgacggctc aggcccccgc gacggcgccg | 180 |
| ccgggtctga aggagggcat cgcggggctg tacgacgagt cgtcggggct gtgggagaac | 240 |

```
atctggggcg accacatgca ccacggcttc tacgactcga gcgaggccgc ctccatggcc      300
gatcaccgcc gcgcccagat ccgcatgatc gaggaggcgc tcgccttcgc cggtgtccca      360
gcctcagatg atccagagaa gacaccaaaa acaatagtcg atgtcggatg tggcattggt      420
ggtagctcaa ggtacttggc gaagaaatac ggagcgcagt gcactgggat cacgttgagc      480
cctgttcaag ccgagagagg aaatgctctc gctgcagcgc aggggttgtc ggatcaggtt      540
actctgcaag ttgctgatgc tctggagcaa ccgtttcctg acgggcagtt cgatctggtg      600
tggtccatgg agagtggcga gcacatgccg gacaagagaa agtttgttag tgagctagca      660
cgcgtggcgg ctcctggagg gacaataatc atcgtgacat ggtgccatag gaacctggat      720
ccatccgaaa cctcgctaaa gcccgatgaa ctgagcctcc tgaggaggat atgcgacgcg      780
tactacctcc cggactggtg ctcaccttca gactatgtga acattgccaa gtcactgtct      840
ctcgaggata tcaagacagc tgactggtcg gagaacgtgg ccccgttttg gcccgccgtg      900
ataaaatcag cgctaacatg gaagggcttc acctctctgc tgacgaccgg atggaagacg      960
atcagaggcg cgatggtgat gccgctaatg atccagggct acaagaaggg gctcatcaaa     1020
ttcaccatca tcacctgtcg caagcctgga gccgcgtag                            1059

<210> SEQ ID NO 43
<211> LENGTH: 1038
<212> TYPE: DNA
<213> ORGANISM: Arabidopsis thaliana

<400> SEQUENCE: 43
atggctgccg cgttacaatt acaaacacac ccttgcttcc atggcacgtg ccaactctca       60
cctccgccac gaccttccgt ttccttccct tcttcctccc gctcgtttcc atctagcaga      120
cgttccctgt ccgcgcatgt gaaggcggcg gcgtcgtctt tgtccaccac caccttgcag      180
gaagggatag cggagttttta cgatgagtcg tcggggattt gggaagacat atggggtgac      240
catatgcacc atggatatta cgagccgggt tccgatattt cgggttcaga tcatcgtgcc      300
gctcagattc gaatggtcga agaatcgctc cgttttgctg gaatatcaga ggacccagca      360
aacaggccca agagaatagt tgatgttggg tgtgggatag gaggcagttc taggtatcta      420
gcaaggaaat atgggcaaa tgccaaggc attactttga gccctgttca agctggaaga      480
gccaatgctc ttgctaatgc tcaaggacta gcagaacagg tttgttttga agttgcagat      540
gccttgaacc aaccattccc tgatgaccaa tttgatcttg tttggtctat ggaaagcgga      600
gaacacatgc ctgacaaacc caagtttgtt aaagagctgg tgcgagtggc agctccagga      660
ggcacaataa tagtagtgac atggtgccat agggatcttg gtccatctga agagtctttg      720
cagccatggg agcaaaagct tttaaacaga atatgtgatg cttactattt accagagtgg      780
tgttctactt ctgattatgt caaattattt cagtccctat ctctccagga tataaaggca      840
ggagactgga ctgagaatgt agcacccttt tggccagcag tgatacgttc agcattgaca      900
tggaagggct tcacatcgct gctacgaagt ggattaaaaa caataaaagg tgcactggtg      960
atgccattga tgatcgaagg tttccagaaa ggggtgataa agtttgccat cattgcttgc     1020
cggaagccag ctgagtag                                                   1038

<210> SEQ ID NO 44
<211> LENGTH: 1131
<212> TYPE: DNA
<213> ORGANISM: Arabidopsis thaliana
```

```
<400> SEQUENCE: 44
atgccgataa catctatttc cgcaaaccaa aggccattct tcccctcacc ttatagaggc      60
agctccaaga acatggcacc gcccgaactg gctcagtcgc aagtacctat gggaagtaac     120
aagagcaaca agaaccacgg cttggtcggt tcggtttctg gttggagaag gatgtttggg     180
acatgggcta ctgccgacaa gactcagagt accgatacgt ctaatgaagg cgtggttagt     240
tacgatactc aggtcttgca gaagggtata gcggagttct atgacgagtc gtcgggtata     300
tgggaggata tatggggaga tcacatgcat catggctact atgatggttc cactcctgtc     360
tccctcccag accatcgctc tgcgcagatc cgaatgattg acgaggctct ccgctttgcc     420
tcggttcctt caggagaaga agatgagtcc aagtctaaga ttccaaagag gatagtggat     480
gtcgggtgtg ggatagggg aagctccaga tacctggcta gaaaatatgg cgccgagtgt      540
cggggcatca ctctcagtcc tgtccaggct gagagggca attcacttgc acggtctcaa      600 ggtcttctg acaaggtctc ctttcaagtc gccgatgctt tggcacagcc atttcccgat      660
ggacagtttg atttggtctg gtccatggag agcgggaac acatgcccga caagagcaag      720
tttgtcaatg agctagtaag agtagcagct ccgggtggca cgataataat tgtcacatgg      780
tgccatagag atctcaggga agacgaagat gcgctgcagc ctcgggagaa agagatattg     840
gacaagatat gcaaccccctt ttatcttccc gcctggtgtt ctgctgccga ctatgttaag    900
ttgctccagt cacttgatgt cgaggacatt aaatctgcgg actggactcc atatgttgcc     960 ccatttggc cagctgtgct gaagtccgct tcactataa agggcttcgt gtctctattg       1020
aggagcggaa tgaagaccat aaagggagca tttgcaatgc cgctgatgat cgaaggatac     1080
aagaaaggtg tcatcaagtt ttccatcatc acatgccgta agcccgaata g              1131

<210> SEQ ID NO 45
<211> LENGTH: 2045
<212> TYPE: DNA
<213> ORGANISM: Arabidopsis thaliana

<400> SEQUENCE: 45
atgaaagcga ctctcgcacc ctcctctctc ataagcctcc ccaggcacaa agtatcttct      60
ctccgttcac cgtcgcttct ccttcagtcc caacggccat cctcagcctt aatgacgacg     120
acgacggcat cacgtggaag cgtggctgtg acggctgctg ctacctcctc cgttgaggcg     180
ctgcgggaag aatagcgga attctacaac gagacgtcgg gattatggga ggagatttgg     240
ggagatcata tgcatcacgg cttctacgat cctgattcct ctgttcaact ttcagattcc     300
ggtcaccggg aagctcagat ccggatgatc gaagagtctc tacgtttcgc cggcgttact     360
ggttcgcttc tcatgctata cagttagagt ttgattcgtt gtttgttatg aatgataaac     420
ctacacatga acactttcta gatttattat aaacattctt tttgaactta tattataaac     480
aattcttaca aacaaaatgc tctttgaact cttaaaaata taacaatg gtttagtttt       540 gatttgtcgg taagagaaat gagtagggat gtttgaagcc agataaagcc tttcttttat     600
ccctggggag aggcttacag taagccacgt cccatccaga agcagaccca ttccctaact     660
aggctggatg atgataaata agttcttcct catttcaaga ttaagaaaac aatctaaact     720
gaaataataa cgcgcagtcg gtgaaaatat ctttatgctt gggattgttg ttgttattat     780
taatttatat tataaacaca tgacctttt aagaagagg agaaaagat aaagagagta        840 gtggatgttg ggtgtgggat cggcggaagc tcaaggtata ttgcctctaa atttggtgcc     900
gaatgcattg gcatcacact cagtcccgtt caagccaaga gagccaatga tctcgccgcc     960
```

```
gctcaatcac tctctcataa ggtgtcttct tgtacattcg accattttt tctgcggaat    1020 ctgagctaac tgagacgcca ctggaccagg tttccttcca agttgcagat gcactggagc    1080
aaccatttga agatggtata ttcgatcttg tgtggtcaat ggaaagcggt gagcatatgc    1140
ctgacaaggc caaggtatac tacctagctc accataatct ttatactaga tttagtagac    1200
aatatccatc ttttggatgt caatgatgtc cattaatttt taaataaaca aaataaaaaa    1260
tgagagtaaa attttttttt gtcaaactta tctaataaat attatgtaat ataccacgt     1320 ttttctattt aattatggca tggtttcttt ttttttgtc taaaaaaat tgtagtatct     1380 gttagaaaac agaatctaag tatgatattt ttgaaactca ttcagtcttc gttgtggaag    1440
tatatttacc gtgtgtgcga aatgagtgta gttcgtgaag gaattggtac gtgtggcggc    1500
tccaggagga aggataataa tagtgacatg gtgccacaga aatctatctc caggggaaga    1560
ggctttgcag ccatgggagc agaacctctt ggacagaatc tgcaaaacat tttatctccc    1620
agcctggtgc tccacctcgg attatgtcga tttgcttcag tccctctcgc tccaggttat    1680
tatatttctc acgctccaat tgctaaaatt agtacttgga gctagttaag tagtgtctca    1740
aatatatgtg tgtttgtagg atattaagtg tgcagattgg tcagagaacg tagctccttt    1800
ctggccggcg gttatacgaa ccgcattaac gtggaagggc cttgtgtctc tgcttcgtag    1860
tggtatgttt ccgcaatgtt gttcacattc atgattttta taagattaga actaaggttg    1920
ttgggtgtcg gaaacgcaca ggtatgaaga gtataaaagg agcattgaca atgccattga    1980
tgattgaagg gtacaagaaa ggtgtcatta agtttggcat catcacttgc cagaagcctc    2040
tctaa                                                                 2045
```

<210> SEQ ID NO 46
<211> LENGTH: 2973
<212> TYPE: DNA
<213> ORGANISM: Arabidopsis thaliana

<400> SEQUENCE: 46

```
atgaaagcga cactcgcacc accctcctct ctcataagcc tccccaggca caaagtatct      60
tccctccgtt caccgtcgct tctccttcag tcccaacggc gatcctcagc cttaatgacg     120
acgacggcat cacgtggaag cgtggctgtg acggctgctg ctacctcctc cgctgaggcg     180
ctgcgagaag gaatagcgga attctacaac gagacgtcgg gattatggga ggagatttgg    240
ggagatcata tgcatcacgg cttctacgat cccgattcct ctgttcaact ttcagattcc     300
ggtcaccggg aagctcagat ccggatgatt gaagagtctc tacgtttcgc cggcgttact     360
ggttcgcttc tcatgctcta cacttgagtt tgatacgttg tttattataa acattttttt     420 gaactttat tataaacaat tcttacaaac aaattactct ttgaactctt taaaatctat     480
aacaaaggtt tagttttact tttatttgt tgttggtaac agaaatgagt agggatgttt      540
gaagtcagat atagcctttc tgtttatccc ttgggaagaa aggcttacag taagccacgt     600
cccatccaga agcagaccca ttccctaact aatcattttt atgaacaatt tgtaacacta     660
ttattcctag atatttttt tttacgttta gttaccctaa ctctttgtat ataagacaag     720
aggtgatttt tcacattata tatcaaaaca tagacatagt tttttgaga aaatatatca     780 tacatagttg taacttagaa ttatatattt ttgagaaaaa aactcagtaa taattttctt    840
ataattattc atagttttat atttattaat aataagattt tgtaagctct ttttgaaact    900
attatggata atgaataagt tccccatttc aagattaaga aaacaattta aactgaaata    960
```

-continued

```
ataatgcgca ttcggtgaaa atatctttct gcttgggatt gttgttgtta atctatatta    1020
ttaaaactga agtacatttt ggtactgttt ggaaacttag atagtagatt aaatgaaaat    1080
tgtttggaaa caaggatagc agattaaata tttttttatt tacatatttta gtcactgtat    1140 ttctttctca tttacagatt ctgtcgtttg gaaacttgga tagcagatta aatgaaaaat    1200
gtttggaaac acagttaaca tattaaatat ctattttttat ttcatatttta gccattgcat    1260 ttctttctta tttacaaatc tgccacttca cttaaaataa aaaaattaaa ttaattacaa    1320
tgaattgtta tttcttttttg ctgaaaataa aaacgcaaac tgcaatatat agtatatatt    1380
aatctgctac aatacaattt tcaagaaaac caaatatcat aaaattaata ataatttata    1440
aaaacctaca gtaaaaaaat aaatcatttt taaataaata aacaaaaaaa atcaataggt    1500
tgatatatga atattacaat tacatcaaat tgcatcaagt tataaaatta taaatataat    1560
attacgtaca aataaaaatt attatcaaac atctattttta taatataata tattctactc    1620
taaatatatt tacaaaacat aaaaatataa atggacattt tataaaatca atggtttata    1680
agtttacatt gaacgcaagt taaattccaa catccgcgcg gggcgcgggt caagatctag    1740
tattaattta tattataaac acatgacttt ttttaaagaa gaggagaaaa agataaagag    1800
agtggtggat gttgggtgtg ggatcggagg aagctcaagg tatattgcct ctaaatttgg    1860
tgccgaatgc attggcatca cactcagtcc cgttcaagcc aagagagcaa atgatctcgc    1920
caccgctcaa tcactctctc ataaggtgtc ttctcgtaca ttcgaccatt ctttctgcgg    1980
ataatctgat ctaactgaga cgccattgga ccaggtttcc ttccaagttg cagatgcatt    2040
ggaccaacca tttgaagatg gtatatccga tcttgtttgg tcaatggaaa gcggtgagca    2100
tatgcctgac aaggccaagg tatactagct cagcataact tttatactag atttactaga    2160
caatatctat cttttcatgt caatgatgtc caataatttt aaaataaaca aaagaaggat    2220
gtgagggtaa aatttttgtca aatttatata acaacacgtt ttctatttag ttatgtcatg    2280
gtttcttttt gtctaaaaaa ttttaggcag agtttacaaa agaaaattg tagtatctgt    2340 tcgaaaacag aatcttagtg tggtatttta gaaactcatt cagtcttcct tgtggaagca    2400
tatttactgt gtgtgcgaaa tgagtgtagt tcgtgaagga attggtacgt gtgacggctc    2460
caggaggaag gataataata gtgacatggt gccacagaaa tctatctcaa ggggaagaat    2520 cttttgcagcc atgggagcag aacctcttgg acagaatctg caaaacattt tatctcccgg    2580
cctggtgctc caccactgat tatgtcgagt tgcttcaatc cctctcgctc caggttatta    2640
tatttctcac gctccgatgc taaaatcagt aagtattgtc tcaaatatat gtgtgtttgt    2700
aggatattaa gtatgcagat tggtcagaga acgtagctcc tttctggccg gcggttatac    2760
gaaccgcatt aacgtggaag ggccttgtgt ctctgcttcg tagtggtatg tttccgcaat    2820
gttgtttaca ttcatgattc caaatgtttta taagattaga aacatacagg tatgaagagt    2880 ataaaggag cattgacaat gccattgatg attgaagggt acaagaaagg tgtcattaag    2940
tttggcatca tcacttgcca gaagcctcta taa                                 2973
```

<210> SEQ ID NO 47
<211> LENGTH: 933
<212> TYPE: DNA
<213> ORGANISM: Arabidopsis thaliana

<400> SEQUENCE: 47

```
atggctagtg ttgctgcgat gaatgctgtg tcttcgtcat ctgtagaagt tggaatacag      60
aatcaacagg agctgaaaaa aggaattgca gatttatatg atgagtcttc tgggatttgg     120
```

-continued

```
gaagatattt ggggtgacca tatgcatcat ggatattatg aacctaaatc ctctgtggaa      180
ctttcagatc atcgtgctgc tcagatccgt atgattgaac aggctctaag ttttgctgct      240
atttctgaag atccagcgaa gaaaccaacg tccatagttg atgttggatg tggcatcggt      300
ggcagttcta ggtaccttgc aaagaaatat ggcgctacag ctaaaggtat cactttgagt      360
cctgtacaag cagagagggc tcaagctctt gctgatgctc aaggattagg tgataaggtt      420
tcatttcaag tagcagacgc cttgaatcag ccttttccag atgggcaatt cgacttggtt      480
tggtccatgg agagtggaga acacatgccg aacaaagaaa agtttgttgg cgaattagct      540
cgagtggcag caccaggagg cacaatcatc cttgtcacat ggtgccacag ggacctttcc      600
ccttcggagg aatctctgac tccagaggag aaagagctgt taaataagat atgcaaagcc      660
ttctatcttc cggcttggtg ttccactgct gattatgtga agttacttca atccaattct      720
cttcaggata tcaaggcaga agactggtct gagaatgttg ctccattttg ccagcagtc       780 ataaagtcag cactgacatg gaagggcttc acatcagtac tacgcagtgg atggaagaca      840
atcaaagctg cactggcaat gccactgatg attgaaggat acaagaaagg tctcatcaaa      900
tttgccatca tcacatgtcg aaaacctgaa taa                                   933

<210> SEQ ID NO 48
<211> LENGTH: 909
<212> TYPE: DNA
<213> ORGANISM: Arabidopsis thaliana

<400> SEQUENCE: 48
atgtcggtgg agcagaaagc agcagggaag gaggaggagg gaaaactgca gaagggaatt      60
gcagagttct acgacgagtc gtctggcata tgggagaaca tttggggcga tcacatgcac      120
cacggctttt atgacccgga ttccaccgtt tctgtttctg atcatcgcgc tgctcagatc      180
cgaatgatcc aagaatctct tcgttttgcc tctctgcttt ctgagaaccc ttctaaatgg      240
cccaagagta tagttgatgt tgggtgtggc ataggggca gctccagata cctggccaag      300
aaatttggag caacgagcgt aggcattact ctgagtcctg ttcaagctca aagagcaaat      360
gctcttgctg ctgctcaagg attggctgat aaggtttcct ttcaggttgc tgacgctcta      420
cagcaaccat tctctgacgg ccagtttgat ctggtgtggt ccatggagag tggagagcat      480
atgcctgaca aagctaagtt tgttggagag ttagctcggg tagcagcacc aggtgccact      540
ataataatag taacatggtg ccacagggat cttggccctg acgaacaatc cttacatcca      600
tgggagcaag atctcttaaa gaagatttgc gatgcatatt acctccctgc ctggtgctca      660
acttctgatt atgttaagtt gctccaatcc ctgtcacttc aggacatcaa gtcagaagat      720
tggtctcgct tgttgctcc attttggcca gcagtgatac gctcagcctt cacatggaag      780
ggtctaactt cactcttgag cagtggacaa aaaacgataa aaggagcttt ggctatgcca      840
ttgatgatag agggatacaa gaaagatcta attaagtttg ccatcattac atgtcgaaaa      900
cctgaataa                                                             909

<210> SEQ ID NO 49
<211> LENGTH: 1053
<212> TYPE: DNA
<213> ORGANISM: Arabidopsis thaliana

<400> SEQUENCE: 49
atggccaccg tggtgaggat cccaacaatc tcatgcatcc acatccacac gttccgttcc      60
```

```
caatcccctc gcactttcgc cagaatccgg gtcggaccca ggtcgtgggc tcctattcgg      120
gcatcggcag cgagctcgga gagagggag atagtattgg agcagaagcc gaagaaggag      180
gaggagggga aactgcagaa gggaatcgca gagttctacg acgagtcgtc tggcttatgg     240
gagaacattt ggggcgacca catgcaccat ggcttttatg acccggattc cactgtttct     300
gtttctgatc atcgcgctgc tcagatccga atgatccaag agtctcttcg ctttgcctct     360
gtttctgagg agcgtagtaa atggcccaag agtatagttg atgttgggtg tggcataggt     420
ggcagctcca gatacctggc caagaaattt ggagcaacca gcgtaggcat tactctgagt     480
cctgttcaag ctcaaagagc aaatgctctt gctgctgctc aaggattggc tgataaggtt     540
tcctttcagg ttgctgacgc tctacagcaa ccattctctg acggccagtt tgatctggtg     600
tggtccatgg agagtggaga gcatatgcct gacaaagcta gtttgttgg agagttagct      660 cgggtagcag caccaggtgc cactataata atagtaacat ggtgccacag ggatcttggc     720
cctgacgaac aatccttaca tccatgggag caagatctct aaagaagat ttgcgatgca      780 tattaccttc ctgcctggtg ctcaacttct gattatgtta agttgctcca atccctgtca     840
cttcaggaca tcaagtcaga agattggtct cgctttgttg ctccattttg ccagcagtg     900 atacgctcag ccttcacatg gaagggtcta acttcactct tgagcagtgg acttaaaacc     960 ataaaggag ctttggctat gccattgatg atagagggat acaagaaaga tctaattaag    1020
tttgccatca ttacatgtcg aaaacctgaa taa                                 1053

<210> SEQ ID NO 50
<211> LENGTH: 1053
<212> TYPE: DNA
<213> ORGANISM: Arabidopsis thaliana

<400> SEQUENCE: 50
atggccaccg tggtgaggat cccaacaatc tcatgcatcc acatccacac gttccgttcc      60
caatcccctc gcactttcgc cagaatccgg gtcggaccca ggtcgtgggc tcctattcgg    120
gcatcggcag cgagctcgga gagagggag atagtattgg agcagaagcc gaagaaggat     180
gacaaggaga aactgcagaa gggaatcgca gagttttacg acgagtcttc tggcttatgg    240
gagaacattt ggggcgacca catgcaccat ggcttttatg acccggattc cactgtttcg    300
ctttcggatc atcgtgctgc tcagatccga atgatccaag agtctcttcg ctttgcctct    360
gtttctgagg agcgtagtaa atggcccaag agtatagttg atgttgggtg tggcataggt    420
ggcagctcca gatacctggc caagaaattt ggagcaacca gtgtaggcat cactctgagt    480
cctgttcaag ctcaaagagc aaatgctctt gctgctgctc aaggattggc tgataaggtt    540
tcctttcagg ttgctgacgc tctacagcaa ccattctctg acggccagtt tgatctggtg    600
tggtccatgg agagtggaga gcatatgcct gacaaagcta gtttgttgg agagttagct     660 cgggtagcag caccaggtgc cactataata atagtaacat ggtgccacag ggatcttggc    720
cctgacgaac aatccttaca tccatgggag caagatctct aaagaagat ttgcgatgca     780 tattaccttc ctgcctggtg ctcaacttct gattatgtta agttgctcca atccctgtca    840
cttcaggaca tcaagtcaga agattggtct cgctttggtg ctccattttg ccagcagtg    900 atacgctcag ccttcacatg gaagggtcta acttcactct tgagcagtgg ccaaaaacg    960 ataaaggag ctttggctat gccattgatg atagagggat acaagaaaga tctaattaag   1020
tttgccatca ttacatgtcg aaaacctgaa taa                                1053
```

<210> SEQ ID NO 51
<211> LENGTH: 933
<212> TYPE: DNA
<213> ORGANISM: Arabidopsis thaliana

<400> SEQUENCE: 51

| | | | | | |
|---|---|---|---|---|---|
| gcccttagcg | tggtcgcggc | cgaggtacca | gttacggtta | ctccggcgac | gacgaaggcg | 60 |
| gaggatgtgg | agctgaagaa | aggaattgca | gagttctacg | atgaatcgtc | ggagatgtgg | 120 |
| gagaatatat | ggggagaaca | catgcatcat | ggatactata | acactaatgc | cgttgttgaa | 180 |
| ctctccgatc | atcgttctgc | tcagatccgt | atgattgaac | aagccctact | tttcgcatct | 240 |
| gtttcagatg | atccagtaaa | gaaacctaga | agcatcgttg | atgttgggtg | tggcataggt | 300 |
| ggtagctcaa | ggtatctggc | aaagaaatac | gaagctgaat | gccatggaat | cactctcagc | 360 |
| cctgtgcaag | ctgagagagc | tcaagctcta | gctgctgctc | aaggattggc | cgataaggct | 420 |
| tcatttcaag | ttgctgatgc | tttagaccaa | ccatttcctg | atggaaagtt | tgatctggtc | 480 |
| tggtcaatgg | agagtggtga | acacatgcct | gacaaactaa | agtttgttag | tgagttggtt | 540 |
| cgggttgctg | ccccaggagc | cacgattatc | atagttacat | ggtgccatag | ggatctttct | 600 |
| cctggtgaaa | agtcccttcg | acccgatgaa | gaaaaaatct | tgaaaaagat | tgttccagc | 660 |
| ttttatcttc | ctgcttggtg | ttcaacatct | gattatgtaa | aattactaga | gtccctttct | 720 |
| cttcaggaca | tcaaagctgc | agactggtca | gcaaacgtgg | ctccattttg | gcctgctgta | 780 |
| ataaaaacag | cattatcttg | gaagggcatt | acttcgctac | ttcgtagtgg | atggaagtca | 840 |
| ataagagggg | caatggtaat | gccattgatg | attgaaggat | ttaagaagga | tataatcaaa | 900 |
| ttctccatca | tcacatgcaa | aaagcctgaa | taa | | | 933 |

<210> SEQ ID NO 52
<211> LENGTH: 1230
<212> TYPE: DNA
<213> ORGANISM: Sorghum bicolor

<400> SEQUENCE: 52

| | | | | | |
|---|---|---|---|---|---|
| cgaacggcga | gcagcaggag | ggcgtcgcga | acccttgggc | ggcggatcgg | tacccgtagg | 60 |
| cagccactac | tactaccgcg | ccccttcgca | cgtcccgcgc | cgctcccgcc | cccgcggacg | 120 |
| cggcggcgtc | gtcagcctgc | gtccgatggc | ctcgtcgacg | gcggctcagc | ccccccgcgcc | 180 |
| ggcgccccccg | ggcctgaagg | agggcatcgc | ggggctgtac | gacgagtctt | cggggctgtg | 240 |
| ggagaacatc | tgggggcgacc | acatgcacca | cggcttctac | gactcgggcg | aggccgcgtc | 300 |
| catggccgac | caccgacgcg | cccagatccg | catgatcgag | gaggcgctcg | ccttcgccgc | 360 |
| cgtcccatcc | ccagatgatc | cggagaaggc | accaaaaacc | atagtagatg | ttggatgtgg | 420 |
| cattggtggt | agctcaaggt | acttggctaa | gaaatacgga | gcacagtgca | agggatcac | 480 |
| attgagccct | gttcaagctg | aaagaggaaa | tgctcttgct | acagcgcagg | ggttgtcgga | 540 |
| tcaggttact | ctgcaagttg | ctgatgctct | ggagcaaccg | tttcctgatg | gcagtttga | 600 |
| tctggtatgg | tccatggaga | gtggcgagca | catgccggac | aagagaaagt | ttgttagtga | 660 |
| gctggcacgc | gtcgctgctc | ctggagggac | aataatcatc | gtgacatggt | gccataggaa | 720 |
| cctcgaacca | tctgagactt | cgctaaaacc | cgatgaactg | agtctcttga | agaggatttg | 780 |
| cgatgcgtac | tacctcccag | actggtgctc | accttcagac | tatgtgaaca | tcgccaaatc | 840 |
| actgtctctg | gaggatatca | aggcagctga | ttggtcagag | aatgtggccc | cattttggcc | 900 |
| cgctgtgata | aaatcagcac | taacatggaa | gggcctcacc | tctctactga | caagcggatg | 960 |

| | |
|---|---|
| gaagacgatc agaggggcga tggtgatgcc gctgatgatc caaggttaca agaaggggct | 1020 |
| catcaaattc accatcatca cctgtcgcaa gcctggagca gcgtaggtga ccaagggca | 1080 |
| gaagttactg tcaaagcacc tctgctaagt ccaataatgt agatccatgg ccccatcacc | 1140 |
| gtctattgta ctgtactgta ctgtaccaga atgaacagtc tcctgggaca tgttttccaa | 1200 |
| ttgccatgac atgtcaaatg atcttctacc | 1230 |

<210> SEQ ID NO 53
<211> LENGTH: 843
<212> TYPE: DNA
<213> ORGANISM: Arabidopsis thaliana

<400> SEQUENCE: 53

| | |
|---|---|
| atgagtgcaa cactttacca gcaaattcag caattttacg atgcttcatc tggtctgtgg | 60 |
| gaacagatat ggggcgaaca catgcaccac ggctattacg gcgctgatgg tacccagaaa | 120 |
| aaagaccgcc gtcaggctca aattgattta atcgaagaat tgcttaattg gcagggta | 180 |
| caagcagcag aagatatact agatgtgggt tgtggaattg gcggtagttc tttatacctg | 240 |
| gcgcaaaagt ttaatgctaa agctacaggg attacattga gtcctgtaca agctgcaaga | 300 |
| gcaacagaac gcgcattgga agctaatttg agtctgagaa cacagttcca agtcgctaat | 360 |
| gctcaagcaa tgccctttgc tgacgattct tttgacttgg tttggtcgct ggaaagtggc | 420 |
| gaacacatgc agataaaac caagtttctt caggagtgct atcgagtact gaagcctggt | 480 |
| ggcaagttaa ttatggtgac ttggtgtcat cgaccaactg atgaatctcc attaacggca | 540 |
| gatgaggaaa agcacttgca ggatatttat cgggtgtatt gtttgcctta tgtgatttct | 600 |
| ttgccagagt atgaagcgat cgcacatcaa ctaccattac ataatatccg cactgctgat | 660 |
| tggtcaactg ctgtcgcccc cttttggaat gtggtaattg attctgcatt cactccccaa | 720 |
| gcgctttggg gtttactaaa tgctggttgg actaccattc aagggcatt atcactggga | 780 |
| ttaatgcgtc gcggttatga acgtgggtta attcggtttg gcttactgtg cggcaataag | 840 |
| tag | 843 |

<210> SEQ ID NO 54
<211> LENGTH: 843
<212> TYPE: DNA
<213> ORGANISM: Arabidopsis thaliana

<400> SEQUENCE: 54

| | |
|---|---|
| atgagtgcaa cactttacca acaaattcag caattttacg atgcttcctc tgggctgtgg | 60 |
| gaagagattt ggggcgaaca tatgcaccac ggctattatg gtgcagacgg tactgaacaa | 120 |
| aaaaccgcc gtcaggcgca aattgattta attgaagaat tactcacttg gcaggagta | 180 |
| caaacagcag aaaatatact agatgtgggt tgtggtattg gtggtagttc tctgtatttg | 240 |
| gcaggaaagt tgaatgctaa agctacagga attaccctga gtccagtgca agccgctaga | 300 |
| gccacagaaa gagccaagga agctggttta agtggtagaa gtcagttttt agtggcaaat | 360 |
| gcccaagcaa tgccttttga tgataattct tttgacttgg tgtggtcgct agaaagtggc | 420 |
| gaacatatgc agataaaac caagtttttg caagagtgtt atcgagtctt gaaaccgggc | 480 |
| ggtaagttaa tcatggtgac atggtgtcat cgtcccactg ataaacacc actgacggct | 540 |
| gatgaaaaaa aacacctaga agatatttat cgggtgtatt gtttgcctta tgtaatttcg | 600 |
| ttgccggagt atgaagcgat cgcacgtcaa ctaccattaa ataatatccg caccgccgac | 660 |
| tggtcgcaat ccgtcgccca attttggaac atagtcatcg attccgcctt tacccccaa | 720 |

-continued

```
gcaatattcg gcttactccg cgcaggttgg actaccatcc aaggagcctt atcactaggc      780
ttaatgcgtc gcggctatga gcgcgggtta attcggtttg ggttgctttg tgggataag      840 tga                                                                    843

<210> SEQ ID NO 55
<211> LENGTH: 40
<212> TYPE: DNA
<213> ORGANISM: Arabidopsis thaliana

<400> SEQUENCE: 55
tgtaaaacga cggccagttg ctgaaagttg aaaagagcaa                             40

<210> SEQ ID NO 56
<211> LENGTH: 40
<212> TYPE: DNA
<213> ORGANISM: Arabidopsis thaliana

<400> SEQUENCE: 56
caggaaacag ctatgaccca atttgatcaa tgttccacga                             40

<210> SEQ ID NO 57
<211> LENGTH: 38
<212> TYPE: DNA
<213> ORGANISM: Arabidopsis thaliana

<400> SEQUENCE: 57
tgtaaaacga cggccagtag ctatgcggat tgatggtc                              38

<210> SEQ ID NO 58
<211> LENGTH: 38
<212> TYPE: DNA
<213> ORGANISM: Arabidopsis thaliana

<400> SEQUENCE: 58
caggaaacag ctatgacctc ctcctgggaa ctctagca                              38

<210> SEQ ID NO 59
<211> LENGTH: 38
<212> TYPE: DNA
<213> ORGANISM: Arabidopsis thaliana

<400> SEQUENCE: 59
tgtaaaacga cggccagttg ctgacttgcg agtttttg                              38

<210> SEQ ID NO 60
<211> LENGTH: 38
<212> TYPE: DNA
<213> ORGANISM: Arabidopsis thaliana

<400> SEQUENCE: 60
caggaaacag ctatgacccc tgtcaacaac cccttctc                              38

<210> SEQ ID NO 61
<211> LENGTH: 39
<212> TYPE: DNA
<213> ORGANISM: Arabidopsis thaliana

<400> SEQUENCE: 61
tgtaaaacga cggccagtcc acaagagggg tttacaatg                             39

<210> SEQ ID NO 62
```

```
<211> LENGTH: 38
<212> TYPE: DNA
<213> ORGANISM: Arabidopsis thaliana

<400> SEQUENCE: 62
caggaaacag ctatgaccac ccaaccttct ggctctct                              38

<210> SEQ ID NO 63
<211> LENGTH: 38
<212> TYPE: DNA
<213> ORGANISM: Arabidopsis thaliana

<400> SEQUENCE: 63
tgtaaaacga cggccagtgg tctttgggaa cgatctga                              38

<210> SEQ ID NO 64
<211> LENGTH: 38
<212> TYPE: DNA
<213> ORGANISM: Arabidopsis thaliana

<400> SEQUENCE: 64
caggaaacag ctatgaccag ggaagcgtac agggttct                              38

<210> SEQ ID NO 65
<211> LENGTH: 38
<212> TYPE: DNA
<213> ORGANISM: Arabidopsis thaliana

<400> SEQUENCE: 65
tgtaaaacga cggccagtcc tcttgagctg aacgtcct                              38

<210> SEQ ID NO 66
<211> LENGTH: 38
<212> TYPE: DNA
<213> ORGANISM: Arabidopsis thaliana

<400> SEQUENCE: 66
caggaaacag ctatgaccgg cggaactggt ttcactac                              38

<210> SEQ ID NO 67
<211> LENGTH: 38
<212> TYPE: DNA
<213> ORGANISM: Arabidopsis thaliana

<400> SEQUENCE: 67
tgtaaaacga cggccagttg tcagcataat cggttgga                              38

<210> SEQ ID NO 68
<211> LENGTH: 38
<212> TYPE: DNA
<213> ORGANISM: Arabidopsis thaliana

<400> SEQUENCE: 68
caggaaacag ctatgacctc cccaaaggtt taggttcc                              38

<210> SEQ ID NO 69
<211> LENGTH: 38
<212> TYPE: DNA
<213> ORGANISM: Arabidopsis thaliana

<400> SEQUENCE: 69
tgtaaaacga cggccagtaa gcctccttct tgtgctga                              38
```

```
<210> SEQ ID NO 70
<211> LENGTH: 38
<212> TYPE: DNA
<213> ORGANISM: Arabidopsis thaliana

<400> SEQUENCE: 70
caggaaacag ctatgacccg acttttccct tccatttg                              38

<210> SEQ ID NO 71
<211> LENGTH: 38
<212> TYPE: DNA
<213> ORGANISM: Arabidopsis thaliana

<400> SEQUENCE: 71
tgtaaaacga cggccagttg gaggttcggg taactgag                              38

<210> SEQ ID NO 72
<211> LENGTH: 38
<212> TYPE: DNA
<213> ORGANISM: Arabidopsis thaliana

<400> SEQUENCE: 72
caggaaacag ctatgaccca tcctctcgct agcaggtc                              38

<210> SEQ ID NO 73
<211> LENGTH: 38
<212> TYPE: DNA
<213> ORGANISM: Arabidopsis thaliana

<400> SEQUENCE: 73
tgtaaaacga cggccagtgg aaccagggga acctaaac                              38

<210> SEQ ID NO 74
<211> LENGTH: 38
<212> TYPE: DNA
<213> ORGANISM: Arabidopsis thaliana

<400> SEQUENCE: 74
caggaaacag ctatgaccgc cgtgagaaac agactcct                              38

<210> SEQ ID NO 75
<211> LENGTH: 38
<212> TYPE: DNA
<213> ORGANISM: Arabidopsis thaliana

<400> SEQUENCE: 75
tgtaaaacga cggccagtca aatggaaggg aaaagtcg                              38

<210> SEQ ID NO 76
<211> LENGTH: 38
<212> TYPE: DNA
<213> ORGANISM: Arabidopsis thaliana

<400> SEQUENCE: 76
caggaaacag ctatgaccga tccaaagaga acccagca                              38

<210> SEQ ID NO 77
<211> LENGTH: 74
<212> TYPE: DNA
<213> ORGANISM: Arabidopsis thaliana

<400> SEQUENCE: 77
gggacaagtt tgtacaaaaa agcaggctta gaaggagata gaaccatggc gacaagatgc      60
```

```
<210> SEQ ID NO 78
<211> LENGTH: 62
<212> TYPE: DNA
<213> ORGANISM: Arabidopsis thaliana

<400> SEQUENCE: 78
ggggaccact tgtacaaga aagctgggtc ctgcaggtca gatgggttgg tctttgggaa      60
cg                                                                   62

<210> SEQ ID NO 79
<211> LENGTH: 72
<212> TYPE: DNA
<213> ORGANISM: Arabidopsis thaliana

<400> SEQUENCE: 79
gggacaagtt tgtacaaaaa agcaggctta gaaggagata gaaccatgcg gctgaggtgc      60
gcggcgtcgt cg                                                        72

<210> SEQ ID NO 80
<211> LENGTH: 61
<212> TYPE: DNA
<213> ORGANISM: Arabidopsis thaliana

<400> SEQUENCE: 80
ggggaccact tgtacaaga aagctgggtc ctgcaggtta gatcggcatg cctttgggca      60
c                                                                    61

<210> SEQ ID NO 81
<211> LENGTH: 72
<212> TYPE: DNA
<213> ORGANISM: Arabidopsis thaliana

<400> SEQUENCE: 81
gggacaagtt tgtacaaaaa agcaggctta gaaggagata gaaccatgag gctgcgatgc      60
gcggcgtcgt cg                                                        72

<210> SEQ ID NO 82
<211> LENGTH: 62
<212> TYPE: DNA
<213> ORGANISM: Arabidopsis thaliana

<400> SEQUENCE: 82
ggggaccact tgtacaaga aagctgggtc ctgcaggtca gattggcatg cctttggca       60 cg                                                                   62

<210> SEQ ID NO 83
<211> LENGTH: 71
<212> TYPE: DNA
<213> ORGANISM: Arabidopsis thaliana

<400> SEQUENCE: 83
gggacaagtt tgtacaaaaa agcaggctta gaaggagata gaaccatggt acccaagtgt      60
agtgtctcgg c                                                         71

<210> SEQ ID NO 84
<211> LENGTH: 61
<212> TYPE: DNA
<213> ORGANISM: Arabidopsis thaliana
```

```
<400> SEQUENCE: 84
ggggaccact ttgtacaaga aagctgggtc ctgcaggtta gattggctga cctttgggaa    60
c                                                                    61

<210> SEQ ID NO 85
<211> LENGTH: 70
<212> TYPE: DNA
<213> ORGANISM: Arabidopsis thaliana

<400> SEQUENCE: 85
gggacaagtt tgtacaaaaa agcaggctta gaaggagata gaaccatgat ctttacatgc    60
agcgcgtcct                                                           70

<210> SEQ ID NO 86
<211> LENGTH: 61
<212> TYPE: DNA
<213> ORGANISM: Arabidopsis thaliana

<400> SEQUENCE: 86
ggggaccact ttgtacaaga aagctgggtc ctgcaggtca tatgggctgg cctttcggta    60
c                                                                    61

<210> SEQ ID NO 87
<211> LENGTH: 72
<212> TYPE: DNA
<213> ORGANISM: Arabidopsis thaliana

<400> SEQUENCE: 87
gggacaagtt tgtacaaaaa agcaggctta gaaggagata gaaccatggc cccgaggtgc    60
agcttatcag cg                                                        72

<210> SEQ ID NO 88
<211> LENGTH: 61
<212> TYPE: DNA
<213> ORGANISM: Arabidopsis thaliana

<400> SEQUENCE: 88
ggggaccact ttgtacaaga aagctgggtc ctgcaggtta gattggttga ccctctggta    60
c                                                                    61

<210> SEQ ID NO 89
<211> LENGTH: 65
<212> TYPE: DNA
<213> ORGANISM: Arabidopsis thaliana

<400> SEQUENCE: 89
ggggacaagt ttgtacaaaa aagcaggctg cggccgctga acaatggcct ctttgatgct    60
caacg                                                                65

<210> SEQ ID NO 90
<211> LENGTH: 62
<212> TYPE: DNA
<213> ORGANISM: Arabidopsis thaliana

<400> SEQUENCE: 90
ggggaccact ttgtacaaga aagctgggtc ctgcaggtca gatgggttgg tctttgggaa    60
cg                                                                   62
```

```
<210> SEQ ID NO 91
<211> LENGTH: 348
<212> TYPE: PRT
<213> ORGANISM: Arabidopsis thaliana

<400> SEQUENCE: 91

Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
                20                  25                  30

Pro Ser Ser Ser Ser Val Ser Met Thr Thr Thr Arg Gly Asn Val
            35                  40                  45

Ala Val Ala Ala Ala Thr Ser Thr Glu Ala Leu Arg Lys Gly Ile
50                  55                  60

Ala Glu Phe Tyr Asn Glu Thr Ser Gly Leu Trp Glu Glu Ile Trp Gly
65              70                  75                  80

Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ser His
                165                 170                 175

Lys Ala Ser Phe Gln Val Ala Asp Ala Leu Asp Gln Pro Phe Glu Asp
            180                 185                 190

Gly Lys Phe Asp Leu Val Trp Ser Met Glu Ser Gly Glu His Met Pro
        195                 200                 205

Asp Lys Ala Lys Phe Val Lys Glu Leu Val Arg Val Ala Ala Pro Gly
210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345

<210> SEQ ID NO 92
<211> LENGTH: 348
<212> TYPE: PRT
<213> ORGANISM: Arabidopsis thaliana
```

```
<400> SEQUENCE: 92

Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
            20                  25                  30

Pro Ser Ser Ser Ser Val Ser Met Thr Thr Thr Arg Gly Asn Val
        35                  40                  45

Ala Val Ala Ala Ala Thr Ser Thr Glu Ala Leu Arg Lys Gly Ile
50                  55                  60

Ala Glu Phe Tyr Asn Glu Thr Ser Gly Leu Trp Glu Glu Ile Trp Gly
65                  70                  75                  80

Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ala His
                165                 170                 175

Lys Ala Ser Phe Gln Val Ala Asp Ala Leu Asp Gln Pro Phe Glu Asp
            180                 185                 190

Gly Lys Phe Asp Leu Val Trp Ser Met Glu Ser Gly Glu His Met Pro
        195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345

<210> SEQ ID NO 93
<211> LENGTH: 364
<212> TYPE: PRT
<213> ORGANISM: Oryza sativa

<400> SEQUENCE: 93

Met Ala His Ala Ala Ala Ala Thr Gly Ala Leu Ala Pro Leu His Pro
1               5                   10                  15
```

```
Leu Leu Arg Cys Thr Ser Arg His Leu Cys Ala Ser Ala Ser Pro Arg
             20                  25                  30

Ala Gly Leu Cys Leu His His His Arg Arg Arg Arg Ser Ser Arg
         35                  40                  45

Arg Thr Lys Leu Ala Val Arg Ala Met Ala Pro Thr Leu Ser Ser Ser
     50                  55                  60

Ser Thr Ala Ala Ala Pro Pro Gly Leu Lys Glu Gly Ile Ala Gly
 65                  70                  75                  80

Leu Tyr Asp Glu Ser Ser Gly Val Trp Glu Ser Ile Trp Gly Glu His
                 85                  90                  95

Met His His Gly Phe Tyr Asp Ala Gly Glu Ala Ser Met Ser Asp
             100                 105                 110

His Arg Arg Ala Gln Ile Arg Met Ile Glu Ser Leu Ala Phe Ala
             115                 120                 125

Ala Val Pro Gly Ala Asp Asp Ala Glu Lys Lys Pro Lys Ser Val Val
 130                 135                 140

Asp Val Gly Cys Gly Ile Gly Gly Ser Ser Arg Tyr Leu Ala Asn Lys
 145                 150                 155                 160

Tyr Gly Ala Gln Cys Tyr Gly Ile Thr Leu Ser Pro Val Gln Ala Glu
                 165                 170                 175

Arg Gly Asn Ala Leu Ala Ala Glu Gln Gly Leu Ser Asp Lys Val Arg
             180                 185                 190

Ile Gln Val Gly Asp Ala Leu Glu Gln Pro Phe Pro Asp Gly Gln Phe
             195                 200                 205

Asp Leu Val Trp Ser Met Glu Ser Gly Glu His Met Pro Asp Lys Arg
 210                 215                 220

Gln Phe Val Ser Glu Leu Ala Arg Val Ala Ala Pro Gly Ala Arg Ile
 225                 230                 235                 240

Ile Ile Val Thr Trp Cys His Arg Asn Leu Glu Pro Ser Glu Glu Ser
             245                 250                 255

Leu Lys Pro Asp Glu Leu Asn Leu Leu Lys Arg Ile Cys Asp Ala Tyr
             260                 265                 270

Tyr Leu Pro Asp Trp Cys Ser Pro Ser Asp Tyr Val Lys Ile Ala Glu
             275                 280                 285

Ser Leu Ser Leu Glu Asp Ile Arg Thr Ala Asp Trp Ser Glu Asn Val
 290                 295                 300

Ala Pro Phe Trp Pro Ala Val Ile Lys Ser Ala Leu Thr Trp Lys Gly
 305                 310                 315                 320

Leu Thr Ser Leu Leu Arg Ser Gly Trp Lys Thr Ile Arg Gly Ala Met
             325                 330                 335

Val Met Pro Leu Met Ile Glu Gly Tyr Lys Lys Gly Leu Ile Lys Phe
             340                 345                 350

Thr Ile Ile Thr Cys Arg Lys Pro Glu Thr Thr Gln
             355                 360

<210> SEQ ID NO 94
<211> LENGTH: 352
<212> TYPE: PRT
<213> ORGANISM: Zea mays

<400> SEQUENCE: 94

Met Ala His Ala Ala Leu Leu His Cys Ser Gln Ser Ser Arg Ser Leu
 1               5                  10                  15

Ala Ala Cys Arg Arg Gly Ser His Tyr Arg Ala Pro Ser His Val Pro
```

-continued

```
                    20                  25                  30
Arg His Ser Arg Arg Leu Arg Arg Ala Val Val Ser Leu Arg Pro Met
            35                  40                  45
Ala Ser Ser Thr Ala Gln Ala Pro Ala Thr Ala Pro Pro Gly Leu Lys
        50                  55                  60
Glu Gly Ile Ala Gly Leu Tyr Asp Glu Ser Ser Gly Leu Trp Glu Asn
65                  70                  75                  80
Ile Trp Gly Asp His Met His His Gly Phe Tyr Asp Ser Ser Glu Ala
                85                  90                  95
Ala Ser Met Ala Asp His Arg Arg Ala Gln Ile Arg Met Ile Glu Glu
            100                 105                 110
Ala Leu Ala Phe Ala Gly Val Pro Ala Ser Asp Asp Pro Glu Lys Thr
        115                 120                 125
Pro Lys Thr Ile Val Asp Val Gly Cys Gly Ile Gly Gly Ser Ser Arg
130                 135                 140
Tyr Leu Ala Lys Lys Tyr Gly Ala Gln Cys Thr Gly Ile Thr Leu Ser
145                 150                 155                 160
Pro Val Gln Ala Glu Arg Gly Asn Ala Leu Ala Ala Ala Gln Gly Leu
                165                 170                 175
Ser Asp Gln Val Thr Leu Gln Val Ala Asp Ala Leu Glu Gln Pro Phe
            180                 185                 190
Pro Asp Gly Gln Phe Asp Leu Val Trp Ser Met Glu Ser Gly Glu His
        195                 200                 205
Met Pro Asp Lys Arg Lys Phe Val Ser Glu Leu Ala Arg Val Ala Ala
210                 215                 220
Pro Gly Gly Thr Ile Ile Ile Val Thr Trp Cys His Arg Asn Leu Asp
225                 230                 235                 240
Pro Ser Glu Thr Ser Leu Lys Pro Asp Glu Leu Ser Leu Leu Arg Arg
                245                 250                 255
Ile Cys Asp Ala Tyr Tyr Leu Pro Asp Trp Cys Ser Pro Ser Asp Tyr
            260                 265                 270
Val Asn Ile Ala Lys Ser Leu Ser Leu Glu Asp Ile Lys Thr Ala Asp
        275                 280                 285
Trp Ser Glu Asn Val Ala Pro Phe Trp Pro Ala Val Ile Lys Ser Ala
290                 295                 300
Leu Thr Trp Lys Gly Phe Thr Ser Leu Leu Thr Thr Gly Trp Lys Thr
305                 310                 315                 320
Ile Arg Gly Ala Met Val Met Pro Leu Met Ile Gln Gly Tyr Lys Lys
                325                 330                 335
Gly Leu Ile Lys Phe Thr Ile Ile Thr Cys Arg Lys Pro Gly Ala Ala
            340                 345                 350

<210> SEQ ID NO 95
<211> LENGTH: 345
<212> TYPE: PRT
<213> ORGANISM: Gossypium hirsutum

<400> SEQUENCE: 95

Met Ala Ala Ala Leu Gln Leu Gln Thr His Pro Cys Phe His Gly Thr
1               5                   10                  15
Cys Gln Leu Ser Pro Pro Pro Arg Pro Ser Val Ser Phe Pro Ser Ser
            20                  25                  30
Ser Arg Ser Phe Pro Ser Ser Arg Arg Ser Leu Ser Ala His Val Lys
        35                  40                  45
```

```
Ala Ala Ala Ser Ser Leu Ser Thr Thr Thr Leu Gln Glu Gly Ile Ala
            50                  55                  60

Glu Phe Tyr Asp Glu Ser Ser Gly Ile Trp Glu Asp Ile Trp Gly Asp
 65                  70                  75                  80

His Met His His Gly Tyr Tyr Glu Pro Gly Ser Asp Ile Ser Gly Ser
                85                  90                  95

Asp His Arg Ala Ala Gln Ile Arg Met Val Glu Glu Ser Leu Arg Phe
                100                 105                 110

Ala Gly Ile Ser Glu Asp Pro Ala Asn Arg Pro Lys Arg Ile Val Asp
            115                 120                 125

Val Gly Cys Gly Ile Gly Gly Ser Ser Arg Tyr Leu Ala Arg Lys Tyr
    130                 135                 140

Gly Ala Lys Cys Gln Gly Ile Thr Leu Ser Pro Val Gln Ala Gly Arg
145                 150                 155                 160

Ala Asn Ala Leu Ala Asn Ala Gln Gly Leu Ala Glu Gln Val Cys Phe
                165                 170                 175

Glu Val Ala Asp Ala Leu Asn Gln Pro Phe Pro Asp Asp Gln Phe Asp
                180                 185                 190

Leu Val Trp Ser Met Glu Ser Gly Glu His Met Pro Asp Lys Pro Lys
                195                 200                 205

Phe Val Lys Glu Leu Val Arg Val Ala Ala Pro Gly Gly Thr Ile Ile
    210                 215                 220

Val Val Thr Trp Cys His Arg Asp Leu Gly Pro Ser Glu Glu Ser Leu
225                 230                 235                 240

Gln Pro Trp Glu Gln Lys Leu Leu Asn Arg Ile Cys Asp Ala Tyr Tyr
                245                 250                 255

Leu Pro Glu Trp Cys Ser Thr Ser Asp Tyr Val Lys Leu Phe Gln Ser
                260                 265                 270

Leu Ser Leu Gln Asp Ile Lys Ala Gly Asp Trp Thr Glu Asn Val Ala
            275                 280                 285

Pro Phe Trp Pro Ala Val Ile Arg Ser Ala Leu Thr Trp Lys Gly Phe
    290                 295                 300

Thr Ser Leu Leu Arg Ser Gly Leu Lys Thr Ile Lys Gly Ala Leu Val
305                 310                 315                 320

Met Pro Leu Met Ile Glu Gly Phe Gln Lys Gly Val Ile Lys Phe Ala
                325                 330                 335

Ile Ile Ala Cys Arg Lys Pro Ala Glu
                340                 345

<210> SEQ ID NO 96
<211> LENGTH: 376
<212> TYPE: PRT
<213> ORGANISM: cuphea pulcherrima

<400> SEQUENCE: 96

Met Pro Ile Thr Ser Ile Ser Ala Asn Gln Arg Pro Phe Phe Pro Ser
1               5                   10                  15

Pro Tyr Arg Gly Ser Ser Lys Asn Met Ala Pro Pro Glu Leu Ala Gln
            20                  25                  30

Ser Gln Val Pro Met Gly Ser Asn Lys Ser Asn Lys Asn His Gly Leu
        35                  40                  45

Val Gly Ser Val Ser Gly Trp Arg Arg Met Phe Gly Thr Trp Ala Thr
    50                  55                  60

Ala Asp Lys Thr Gln Ser Thr Asp Thr Ser Asn Glu Gly Val Val Ser
65                  70                  75                  80
```

-continued

```
Tyr Asp Thr Gln Val Leu Gln Lys Gly Ile Ala Glu Phe Tyr Asp Glu
                85                  90                  95

Ser Ser Gly Ile Trp Glu Asp Ile Trp Gly Asp His Met His His Gly
            100                 105                 110

Tyr Tyr Asp Gly Ser Thr Pro Val Ser Leu Pro Asp His Arg Ser Ala
        115                 120                 125

Gln Ile Arg Met Ile Asp Glu Ala Leu Arg Phe Ala Ser Val Pro Ser
    130                 135                 140

Gly Glu Glu Asp Glu Ser Lys Ser Lys Ile Pro Lys Arg Ile Val Asp
145                 150                 155                 160

Val Gly Cys Gly Ile Gly Ser Ser Arg Tyr Leu Ala Arg Lys Tyr
                165                 170                 175

Gly Ala Glu Cys Arg Gly Ile Thr Leu Ser Pro Val Gln Ala Glu Arg
                180                 185                 190

Gly Asn Ser Leu Ala Arg Ser Gln Gly Leu Ser Asp Lys Val Ser Phe
            195                 200                 205

Gln Val Ala Asp Ala Leu Ala Gln Pro Phe Pro Asp Gly Gln Phe Asp
    210                 215                 220

Leu Val Trp Ser Met Glu Ser Gly Glu His Met Pro Asp Lys Ser Lys
225                 230                 235                 240

Phe Val Asn Glu Leu Val Arg Val Ala Ala Pro Gly Gly Thr Ile Ile
                245                 250                 255

Ile Val Thr Trp Cys His Arg Asp Leu Arg Glu Asp Glu Asp Ala Leu
                260                 265                 270

Gln Pro Arg Glu Lys Glu Ile Leu Asp Lys Ile Cys Asn Pro Phe Tyr
            275                 280                 285

Leu Pro Ala Trp Cys Ser Ala Ala Asp Tyr Val Lys Leu Leu Gln Ser
    290                 295                 300

Leu Asp Val Glu Asp Ile Lys Ser Ala Asp Trp Thr Pro Tyr Val Ala
305                 310                 315                 320

Pro Phe Trp Pro Ala Val Leu Lys Ser Ala Phe Thr Ile Lys Gly Phe
                325                 330                 335

Val Ser Leu Leu Arg Ser Gly Met Lys Thr Ile Lys Gly Ala Phe Ala
            340                 345                 350

Met Pro Leu Met Ile Glu Gly Tyr Lys Lys Gly Val Ile Lys Phe Ser
        355                 360                 365

Ile Ile Thr Cys Arg Lys Pro Glu
    370                 375

<210> SEQ ID NO 97
<211> LENGTH: 347
<212> TYPE: PRT
<213> ORGANISM: Brassica napus

<400> SEQUENCE: 97

Met Lys Ala Thr Leu Ala Pro Ser Ser Leu Ile Ser Leu Pro Arg His
1               5                   10                  15

Lys Val Ser Ser Leu Arg Ser Pro Ser Leu Leu Leu Gln Ser Gln Arg
            20                  25                  30

Pro Ser Ser Ala Leu Met Thr Thr Thr Ala Ser Arg Gly Ser Val
        35                  40                  45

Ala Val Thr Ala Ala Thr Ser Ser Val Glu Ala Leu Arg Glu Gly
    50                  55                  60

Ile Ala Glu Phe Tyr Asn Glu Thr Ser Gly Leu Trp Glu Glu Ile Trp
```

```
                65                  70                  75                  80
Gly Asp His Met His Gly Phe Tyr Asp Pro Asp Ser Ser Val Gln
                        85                  90                  95
Leu Ser Asp Ser Gly His Arg Glu Ala Gln Ile Arg Met Ile Glu Glu
            100                 105                 110
Ser Leu Arg Phe Ala Gly Val Thr Glu Glu Lys Ile Lys Arg
            115                 120                 125
Val Val Asp Val Gly Cys Gly Ile Gly Gly Ser Ser Arg Tyr Ile Ala
            130                 135                 140
Ser Lys Phe Gly Ala Glu Cys Ile Gly Ile Thr Leu Ser Pro Val Gln
145                 150                 155                 160
Ala Lys Arg Ala Asn Asp Leu Ala Ala Ala Gln Ser Leu Ser His Lys
                    165                 170                 175
Val Ser Phe Gln Val Ala Asp Ala Leu Glu Gln Pro Phe Glu Asp Gly
                180                 185                 190
Ile Phe Asp Leu Val Trp Ser Met Glu Ser Gly Glu His Met Pro Asp
                195                 200                 205
Lys Ala Lys Phe Val Lys Glu Leu Val Arg Val Ala Ala Pro Gly Gly
210                 215                 220
Arg Ile Ile Val Thr Trp Cys His Arg Asn Leu Ser Pro Gly Glu
225                 230                 235                 240
Glu Ala Leu Gln Pro Trp Glu Gln Asn Leu Leu Asp Arg Ile Cys Lys
                245                 250                 255
Thr Phe Tyr Leu Pro Ala Trp Cys Ser Thr Ser Asp Tyr Val Asp Leu
                260                 265                 270
Leu Gln Ser Leu Ser Leu Gln Asp Ile Lys Cys Ala Asp Trp Ser Glu
                275                 280                 285
Asn Val Ala Pro Phe Trp Pro Ala Val Ile Arg Thr Ala Leu Thr Trp
                290                 295                 300
Lys Gly Leu Val Ser Leu Leu Arg Ser Gly Met Lys Ser Ile Lys Gly
305                 310                 315                 320
Ala Leu Thr Met Pro Leu Met Ile Glu Gly Tyr Lys Lys Gly Val Ile
                325                 330                 335
Lys Phe Gly Ile Ile Thr Cys Gln Lys Pro Leu
                340                 345

<210> SEQ ID NO 98
<211> LENGTH: 347
<212> TYPE: PRT
<213> ORGANISM: Brassica napus

<400> SEQUENCE: 98

Met Lys Ala Thr Leu Ala Pro Pro Ser Ser Leu Ile Ser Leu Pro Arg
1               5                   10                  15
His Lys Val Ser Ser Leu Arg Ser Pro Ser Leu Leu Gln Ser Gln
                20                  25                  30
Arg Arg Ser Ser Ala Leu Met Thr Thr Thr Ala Ser Arg Gly Ser Val
            35                  40                  45
Ala Val Thr Ala Ala Ala Thr Ser Ser Ala Glu Ala Leu Arg Glu Gly
        50                  55                  60
Ile Ala Glu Phe Tyr Asn Glu Thr Ser Gly Leu Trp Glu Glu Ile Trp
65                  70                  75                  80
Gly Asp His Met His His Gly Phe Tyr Asp Pro Asp Ser Ser Val Gln
                        85                  90                  95
```

```
Leu Ser Asp Ser Gly His Arg Glu Ala Gln Ile Arg Met Ile Glu Glu
            100                 105                 110

Ser Leu Arg Phe Ala Gly Val Thr Glu Glu Lys Lys Ile Lys Arg
        115                 120                 125

Val Val Asp Val Gly Cys Gly Ile Gly Gly Ser Arg Tyr Ile Ala
    130                 135                 140

Ser Lys Phe Gly Ala Glu Cys Ile Gly Ile Thr Leu Ser Pro Val Gln
145                 150                 155                 160

Ala Lys Arg Ala Asn Asp Leu Ala Thr Ala Gln Ser Leu Ser His Lys
                165                 170                 175

Val Ser Phe Gln Val Ala Asp Ala Leu Asp Gln Pro Phe Glu Asp Gly
            180                 185                 190

Ile Ser Asp Leu Val Trp Ser Met Glu Ser Gly Glu His Met Pro Asp
        195                 200                 205

Lys Ala Lys Phe Val Lys Glu Leu Val Arg Val Thr Ala Pro Gly Gly
210                 215                 220

Arg Ile Ile Ile Val Thr Trp Cys His Arg Asn Leu Ser Gln Gly Glu
225                 230                 235                 240

Glu Ser Leu Gln Pro Trp Glu Gln Asn Leu Leu Asp Arg Ile Cys Lys
            245                 250                 255

Thr Phe Tyr Leu Pro Ala Trp Cys Ser Thr Thr Asp Tyr Val Glu Leu
        260                 265                 270

Leu Gln Ser Leu Ser Leu Gln Asp Ile Lys Tyr Ala Asp Trp Ser Glu
    275                 280                 285

Asn Val Ala Pro Phe Trp Pro Ala Val Ile Arg Thr Ala Leu Thr Trp
    290                 295                 300

Lys Gly Leu Val Ser Leu Leu Arg Ser Gly Met Lys Ser Ile Lys Gly
305                 310                 315                 320

Ala Leu Thr Met Pro Leu Met Ile Glu Gly Tyr Lys Lys Gly Val Ile
                325                 330                 335

Lys Phe Gly Ile Ile Thr Cys Gln Lys Pro Leu
            340                 345

<210> SEQ ID NO 99
<211> LENGTH: 310
<212> TYPE: PRT
<213> ORGANISM: Lycopersicon esculentum

<400> SEQUENCE: 99

Met Ala Ser Val Ala Ala Met Asn Ala Val Ser Ser Ser Ser Val Glu
1               5                   10                  15

Val Gly Ile Gln Asn Gln Gln Glu Leu Lys Lys Gly Ile Ala Asp Leu
            20                  25                  30

Tyr Asp Glu Ser Ser Gly Ile Trp Glu Asp Ile Trp Gly Asp His Met
        35                  40                  45

His His Gly Tyr Tyr Glu Pro Lys Ser Ser Val Glu Leu Ser Asp His
    50                  55                  60

Arg Ala Ala Gln Ile Arg Met Ile Glu Gln Ala Leu Ser Phe Ala Ala
65                  70                  75                  80

Ile Ser Glu Asp Pro Ala Lys Lys Pro Thr Ser Ile Val Asp Val Gly
                85                  90                  95

Cys Gly Ile Gly Gly Ser Ser Arg Tyr Leu Ala Lys Lys Tyr Gly Ala
            100                 105                 110

Thr Ala Lys Gly Ile Thr Leu Ser Pro Val Gln Ala Glu Arg Ala Gln
        115                 120                 125
```

```
Ala Leu Ala Asp Ala Gln Gly Leu Gly Asp Lys Val Ser Phe Gln Val
        130                 135                 140

Ala Asp Ala Leu Asn Gln Pro Phe Pro Asp Gly Gln Phe Asp Leu Val
145                 150                 155                 160

Trp Ser Met Glu Ser Gly Glu His Met Pro Asn Lys Glu Lys Phe Val
                165                 170                 175

Gly Glu Leu Ala Arg Val Ala Ala Pro Gly Thr Ile Ile Leu Val
            180                 185                 190

Thr Trp Cys His Arg Asp Leu Ser Pro Ser Glu Glu Ser Leu Thr Pro
                195                 200                 205

Glu Glu Lys Glu Leu Leu Asn Lys Ile Cys Lys Ala Phe Tyr Leu Pro
    210                 215                 220

Ala Trp Cys Ser Thr Ala Asp Tyr Val Lys Leu Gln Ser Asn Ser
225                 230                 235                 240

Leu Gln Asp Ile Lys Ala Glu Asp Trp Ser Glu Asn Val Ala Pro Phe
                245                 250                 255

Trp Pro Ala Val Ile Lys Ser Ala Leu Thr Trp Lys Gly Phe Thr Ser
            260                 265                 270

Val Leu Arg Ser Gly Trp Lys Thr Ile Lys Ala Ala Leu Ala Met Pro
        275                 280                 285

Leu Met Ile Glu Gly Tyr Lys Lys Gly Leu Ile Lys Phe Ala Ile Ile
    290                 295                 300

Thr Cys Arg Lys Pro Glu
305                 310

<210> SEQ ID NO 100
<211> LENGTH: 302
<212> TYPE: PRT
<213> ORGANISM: GLYCINE MAX

<400> SEQUENCE: 100

Met Ser Val Glu Gln Lys Ala Ala Gly Lys Glu Glu Gly Lys Leu
1               5                   10                  15

Gln Lys Gly Ile Ala Glu Phe Tyr Asp Glu Ser Ser Gly Ile Trp Glu
            20                  25                  30

Asn Ile Trp Gly Asp His Met His His Gly Phe Tyr Asp Pro Asp Ser
        35                  40                  45

Thr Val Ser Val Ser Asp His Arg Ala Ala Gln Ile Arg Met Ile Gln
    50                  55                  60

Glu Ser Leu Arg Phe Ala Ser Leu Leu Ser Glu Asn Pro Ser Lys Trp
65                  70                  75                  80

Pro Lys Ser Ile Val Asp Val Gly Cys Gly Ile Gly Gly Ser Ser Arg
                85                  90                  95

Tyr Leu Ala Lys Lys Phe Gly Ala Thr Ser Val Gly Ile Thr Leu Ser
            100                 105                 110

Pro Val Gln Ala Gln Arg Ala Asn Ala Leu Ala Ala Gln Gly Leu
        115                 120                 125

Ala Asp Lys Val Ser Phe Gln Val Ala Asp Ala Leu Gln Gln Pro Phe
130                 135                 140

Ser Asp Gly Gln Phe Asp Leu Val Trp Ser Met Glu Ser Gly Glu His
145                 150                 155                 160

Met Pro Asp Lys Ala Lys Phe Val Gly Glu Leu Ala Arg Val Ala Ala
                165                 170                 175

Pro Gly Ala Thr Ile Ile Ile Val Thr Trp Cys His Arg Asp Leu Gly
```

```
                    180                 185                 190
Pro Asp Glu Gln Ser Leu His Pro Trp Glu Gln Asp Leu Leu Lys Lys
                195                 200                 205

Ile Cys Asp Ala Tyr Tyr Leu Pro Ala Trp Cys Ser Thr Ser Asp Tyr
210                 215                 220

Val Lys Leu Leu Gln Ser Leu Ser Leu Gln Asp Ile Lys Ser Glu Asp
225                 230                 235                 240

Trp Ser Arg Phe Val Ala Pro Phe Trp Pro Ala Val Ile Arg Ser Ala
                245                 250                 255

Phe Thr Trp Lys Gly Leu Thr Ser Leu Leu Ser Ser Gly Gln Lys Thr
                260                 265                 270

Ile Lys Gly Ala Leu Ala Met Pro Leu Met Ile Glu Gly Tyr Lys Lys
                275                 280                 285

Asp Leu Ile Lys Phe Ala Ile Ile Thr Cys Arg Lys Pro Glu
                290                 295                 300

<210> SEQ ID NO 101
<211> LENGTH: 350
<212> TYPE: PRT
<213> ORGANISM: Glycine max

<400> SEQUENCE: 101

Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
                20                  25                  30

Pro Arg Ser Trp Ala Pro Ile Arg Ala Ser Ala Ala Ser Ser Glu Arg
            35                  40                  45

Gly Glu Ile Val Leu Glu Gln Lys Pro Lys Lys Glu Glu Gly Lys
        50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Pro Asp
                85                  90                  95

Ser Thr Val Ser Val Ser Asp His Arg Ala Ala Gln Ile Arg Met Ile
                100                 105                 110

Gln Glu Ser Leu Arg Phe Ala Ser Val Ser Glu Arg Ser Lys Trp
            115                 120                 125

Pro Lys Ser Ile Val Asp Val Gly Cys Gly Ile Gly Gly Ser Ser Arg
            130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
                165                 170                 175

Ala Asp Lys Val Ser Phe Gln Val Ala Asp Ala Leu Gln Gln Pro Phe
                180                 185                 190

Ser Asp Gly Gln Phe Asp Leu Val Trp Ser Met Glu Ser Gly Glu His
                195                 200                 205

Met Pro Asp Lys Ala Lys Phe Val Gly Glu Leu Ala Arg Val Ala Ala
        210                 215                 220

Pro Gly Ala Thr Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255
```

-continued

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

Trp Ser Arg Phe Val Ala Pro Phe Trp Pro Ala Val Ile Arg Ser Ala
    290                 295                 300

Phe Thr Trp Lys Gly Leu Thr Ser Leu Ser Ser Gly Leu Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350

<210> SEQ ID NO 102
<211> LENGTH: 350
<212> TYPE: PRT
<213> ORGANISM: Glycine max

<400> SEQUENCE: 102

Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Asp Lys Glu Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His Gly Phe Tyr Asp Pro Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
        165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Thr Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285

```
Trp Ser Arg Phe Gly Ala Pro Phe Trp Pro Ala Val Ile Arg Ser Ala
    290                 295                 300

Phe Thr Trp Lys Gly Leu Thr Ser Leu Leu Ser Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
            340                 345                 350

<210> SEQ ID NO 103
<211> LENGTH: 310
<212> TYPE: PRT
<213> ORGANISM: Tagetes erecta

<400> SEQUENCE: 103

Ala Leu Ser Val Val Ala Ala Glu Val Pro Thr Val Thr Pro Ala
1               5                   10                  15

Thr Thr Lys Ala Glu Asp Val Glu Leu Lys Lys Gly Ile Ala Glu Phe
                20                  25                  30

Tyr Asp Glu Ser Ser Glu Met Trp Glu Asn Ile Trp Gly Glu His Met
            35                  40                  45

His His Gly Tyr Tyr Asn Thr Asn Ala Val Val Glu Leu Ser Asp His
    50                  55                  60

Arg Ser Ala Gln Ile Arg Met Ile Glu Gln Ala Leu Leu Phe Ala Ser
65                  70                  75                  80

Val Ser Asp Asp Pro Val Lys Lys Pro Arg Ser Ile Val Asp Val Gly
                85                  90                  95

Cys Gly Ile Gly Gly Ser Ser Arg Tyr Leu Ala Lys Lys Tyr Glu Ala
                100                 105                 110

Glu Cys His Gly Ile Thr Leu Ser Pro Val Gln Ala Glu Arg Ala Gln
            115                 120                 125

Ala Leu Ala Ala Ala Gln Gly Leu Ala Asp Lys Ala Ser Phe Gln Val
    130                 135                 140

Ala Asp Ala Leu Asp Gln Pro Phe Pro Asp Gly Lys Phe Asp Leu Val
145                 150                 155                 160

Trp Ser Met Glu Ser Gly Glu His Met Pro Asp Lys Leu Lys Phe Val
                165                 170                 175

Ser Glu Leu Val Arg Val Ala Ala Pro Gly Ala Thr Ile Ile Ile Val
            180                 185                 190

Thr Trp Cys His Arg Asp Leu Ser Pro Gly Glu Lys Ser Leu Arg Pro
    195                 200                 205

Asp Glu Glu Lys Ile Leu Lys Lys Ile Cys Ser Ser Phe Tyr Leu Pro
210                 215                 220

Ala Trp Cys Ser Thr Ser Asp Tyr Val Lys Leu Leu Glu Ser Leu Ser
225                 230                 235                 240

Leu Gln Asp Ile Lys Ala Ala Asp Trp Ser Ala Asn Val Ala Pro Phe
                245                 250                 255

Trp Pro Ala Val Ile Lys Thr Ala Leu Ser Trp Lys Gly Ile Thr Ser
            260                 265                 270

Leu Leu Arg Ser Gly Trp Lys Ser Ile Arg Gly Ala Met Val Met Pro
    275                 280                 285

Leu Met Ile Glu Gly Phe Lys Lys Asp Ile Ile Lys Phe Ser Ile Ile
290                 295                 300

Thr Cys Lys Lys Pro Glu
```

```
305             310

<210> SEQ ID NO 104
<211> LENGTH: 354
<212> TYPE: PRT
<213> ORGANISM: Sorghum bicolor

<400> SEQUENCE: 104

Glu Arg Arg Ala Ala Gly Gly Arg Arg Glu Pro Leu Gly Gly Gly Ser
1               5                   10                  15

Val Pro Val Gly Ser His Tyr Tyr Arg Ala Pro Ser His Val Pro
            20                  25                  30

Arg Arg Ser Arg Pro Arg Gly Arg Gly Val Val Ser Leu Arg Pro
        35                  40                  45

Met Ala Ser Ser Thr Ala Ala Gln Pro Pro Ala Pro Ala Pro Pro Gly
    50                  55                  60

Leu Lys Glu Gly Ile Ala Gly Leu Tyr Asp Glu Ser Ser Gly Leu Trp
65                  70                  75                  80

Glu Asn Ile Trp Gly Asp His Met His His Gly Phe Tyr Asp Ser Gly
                85                  90                  95

Glu Ala Ala Ser Met Ala Asp His Arg Arg Ala Gln Ile Arg Met Ile
            100                 105                 110

Glu Glu Ala Leu Ala Phe Ala Ala Val Pro Ser Pro Asp Asp Pro Glu
        115                 120                 125

Lys Ala Pro Lys Thr Ile Val Asp Val Gly Cys Gly Ile Gly Gly Ser
    130                 135                 140

Ser Arg Tyr Leu Ala Lys Lys Tyr Gly Ala Gln Cys Lys Gly Ile Thr
145                 150                 155                 160

Leu Ser Pro Val Gln Ala Glu Arg Gly Asn Ala Leu Ala Thr Ala Gln
                165                 170                 175

Gly Leu Ser Asp Gln Val Thr Leu Gln Val Ala Asp Ala Leu Glu Gln
            180                 185                 190

Pro Phe Pro Asp Gly Gln Phe Asp Leu Val Trp Ser Met Glu Ser Gly
        195                 200                 205

Glu His Met Pro Asp Lys Arg Lys Phe Val Ser Glu Leu Ala Arg Val
    210                 215                 220

Ala Ala Pro Gly Gly Thr Ile Ile Ile Val Thr Trp Cys His Arg Asn
225                 230                 235                 240

Leu Glu Pro Ser Glu Thr Ser Leu Lys Pro Asp Glu Leu Ser Leu Leu
                245                 250                 255

Lys Arg Ile Cys Asp Ala Tyr Tyr Leu Pro Asp Trp Cys Ser Pro Ser
            260                 265                 270

Asp Tyr Val Asn Ile Ala Lys Ser Leu Ser Leu Glu Asp Ile Lys Ala
        275                 280                 285

Ala Asp Trp Ser Glu Asn Val Ala Pro Phe Trp Pro Ala Val Ile Lys
    290                 295                 300

Ser Ala Leu Thr Trp Lys Gly Leu Thr Ser Leu Leu Thr Ser Gly Trp
305                 310                 315                 320

Lys Thr Ile Arg Gly Ala Met Val Met Pro Leu Met Ile Gln Gly Tyr
                325                 330                 335

Lys Lys Gly Leu Ile Lys Phe Thr Ile Ile Thr Cys Arg Lys Pro Gly
            340                 345                 350

Ala Ala
```

<210> SEQ ID NO 105
<211> LENGTH: 128
<212> TYPE: PRT
<213> ORGANISM: Lilium asiaticum

<400> SEQUENCE: 105

```
Glu Ser Gly Glu His Met Pro Asp Lys Thr Lys Phe Val Gly Glu Leu
1               5                   10                  15

Ala Arg Val Ala Ala Pro Gly Ala Thr Ile Ile Ile Val Thr Trp Cys
            20                  25                  30

His Arg Asp Leu Leu Pro Ser Glu Asp Ser Leu Arg Pro Asp Glu Ile
        35                  40                  45

Ser Leu Leu Asn Lys Ile Cys Asp Ala Tyr Tyr Leu Pro Lys Trp Cys
    50                  55                  60

Ser Ala Val Asp Tyr Val Lys Ile Ala Glu Ser Tyr Ser Leu Glu Lys
65                  70                  75                  80

Ile Arg Thr Ala Asp Trp Ser Glu Asn Val Ala Pro Phe Trp Pro Ala
                85                  90                  95

Val Ile Arg Ser Ala Leu Thr Trp Lys Gly Phe Thr Ser Leu Leu Arg
            100                 105                 110

Ser Gly Trp Lys Thr Ile Arg Gly Ala Leu Val Met Pro Leu Met Ile
        115                 120                 125
```

<210> SEQ ID NO 106
<211> LENGTH: 280
<212> TYPE: PRT
<213> ORGANISM: Nostoc punctiforme

<400> SEQUENCE: 106

```
Met Ser Ala Thr Leu Tyr Gln Gln Ile Gln Gln Phe Tyr Asp Ala Ser
1               5                   10                  15

Ser Gly Leu Trp Glu Gln Ile Trp Gly Glu His Met His His Gly Tyr
            20                  25                  30

Tyr Gly Ala Asp Gly Thr Gln Lys Lys Asp Arg Arg Gln Ala Gln Ile
        35                  40                  45

Asp Leu Ile Glu Glu Leu Leu Asn Trp Ala Gly Val Gln Ala Ala Glu
    50                  55                  60

Asp Ile Leu Asp Val Gly Cys Gly Ile Gly Gly Ser Ser Leu Tyr Leu
65                  70                  75                  80

Ala Gln Lys Phe Asn Ala Lys Ala Thr Gly Ile Thr Leu Ser Pro Val
                85                  90                  95

Gln Ala Ala Arg Ala Thr Glu Arg Ala Leu Glu Ala Asn Leu Ser Leu
            100                 105                 110

Arg Thr Gln Phe Gln Val Ala Asn Ala Gln Ala Met Pro Phe Ala Asp
        115                 120                 125

Asp Ser Phe Asp Leu Val Trp Ser Leu Glu Ser Gly Glu His Met Pro
    130                 135                 140

Asp Lys Thr Lys Phe Leu Gln Glu Cys Tyr Arg Val Leu Lys Pro Gly
145                 150                 155                 160

Gly Lys Leu Ile Met Val Thr Trp Cys His Arg Pro Thr Asp Glu Ser
                165                 170                 175

Pro Leu Thr Ala Asp Glu Glu Lys His Leu Gln Asp Ile Tyr Arg Val
            180                 185                 190

Tyr Cys Leu Pro Tyr Val Ile Ser Leu Pro Glu Tyr Glu Ala Ile Ala
        195                 200                 205

His Gln Leu Pro Leu His Asn Ile Arg Thr Ala Asp Trp Ser Thr Ala
```

-continued

```
            210                 215                 220
Val Ala Pro Phe Trp Asn Val Val Ile Asp Ser Ala Phe Thr Pro Gln
225                 230                 235                 240

Ala Leu Trp Gly Leu Leu Asn Ala Gly Trp Thr Thr Ile Gln Gly Ala
                245                 250                 255

Leu Ser Leu Gly Leu Met Arg Arg Gly Tyr Glu Arg Gly Leu Ile Arg
                260                 265                 270

Phe Gly Leu Leu Cys Gly Asn Lys
                275                 280

<210> SEQ ID NO 107
<211> LENGTH: 280
<212> TYPE: PRT
<213> ORGANISM: Anabaena sp.

<400> SEQUENCE: 107

Met Ser Ala Thr Leu Tyr Gln Gln Ile Gln Gln Phe Tyr Asp Ala Ser
1               5                   10                  15

Ser Gly Leu Trp Glu Glu Ile Trp Gly Glu His Met His His Gly Tyr
                20                  25                  30

Tyr Gly Ala Asp Gly Thr Glu Gln Lys Asn Arg Arg Gln Ala Gln Ile
            35                  40                  45

Asp Leu Ile Glu Glu Leu Leu Thr Trp Ala Gly Val Gln Thr Ala Glu
50                  55                  60

Asn Ile Leu Asp Val Gly Cys Gly Ile Gly Gly Ser Ser Leu Tyr Leu
65                  70                  75                  80

Ala Gly Lys Leu Asn Ala Lys Ala Thr Gly Ile Thr Leu Ser Pro Val
                85                  90                  95

Gln Ala Ala Arg Ala Thr Glu Arg Ala Lys Glu Ala Gly Leu Ser Gly
                100                 105                 110

Arg Ser Gln Phe Leu Val Ala Asn Ala Gln Ala Met Pro Phe Asp Asp
                115                 120                 125

Asn Ser Phe Asp Leu Val Trp Ser Leu Glu Ser Gly Glu His Met Pro
130                 135                 140

Asp Lys Thr Lys Phe Leu Gln Glu Cys Tyr Arg Val Leu Lys Pro Gly
145                 150                 155                 160

Gly Lys Leu Ile Met Val Thr Trp Cys His Arg Pro Thr Asp Lys Thr
                165                 170                 175

Pro Leu Thr Ala Asp Glu Lys Lys His Leu Glu Asp Ile Tyr Arg Val
                180                 185                 190

Tyr Cys Leu Pro Tyr Val Ile Ser Leu Pro Glu Tyr Glu Ala Ile Ala
                195                 200                 205

Arg Gln Leu Pro Leu Asn Asn Ile Arg Thr Ala Asp Trp Ser Gln Ser
                210                 215                 220

Val Ala Gln Phe Trp Asn Ile Val Ile Asp Ser Ala Phe Thr Pro Gln
225                 230                 235                 240

Ala Ile Phe Gly Leu Leu Arg Ala Gly Trp Thr Thr Ile Gln Gly Ala
                245                 250                 255

Leu Ser Leu Gly Leu Met Arg Arg Gly Tyr Glu Arg Gly Leu Ile Arg
                260                 265                 270

Phe Gly Leu Leu Cys Gly Asp Lys
                275                 280

<210> SEQ ID NO 108
<211> LENGTH: 356
```

```
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(2)
<223> OTHER INFORMATION: Unknown residue.
<220> FEATURE:
<221> NAME/KEY: misc_feature
<222> LOCATION: (4)..(4)
<223> OTHER INFORMATION: Unknown residue.
<220> FEATURE:
<221> NAME/KEY: misc_feature
<222> LOCATION: (6)..(12)
<223> OTHER INFORMATION: Unknown residue.
<220> FEATURE:
<221> NAME/KEY: misc_feature
<222> LOCATION: (14)..(66)
<223> OTHER INFORMATION: Unknown residue.
<220> FEATURE:
<221> NAME/KEY: misc_feature
<222> LOCATION: (68)..(71)
<223> OTHER INFORMATION: Unknown residue.
<220> FEATURE:
<221> NAME/KEY: misc_feature
<222> LOCATION: (73)..(76)
<223> OTHER INFORMATION: Unknown residue.
<220> FEATURE:
<221> NAME/KEY: misc_feature
<222> LOCATION: (79)..(81)
<223> OTHER INFORMATION: Unknown residue.
<220> FEATURE:
<221> NAME/KEY: misc_feature
<222> LOCATION: (89)..(89)
<223> OTHER INFORMATION: Unknown residue.
<220> FEATURE:
<221> NAME/KEY: misc_feature
<222> LOCATION: (92)..(92)
<223> OTHER INFORMATION: Unknown residue.
<220> FEATURE:
<221> NAME/KEY: misc_feature
<222> LOCATION: (105)..(105)
<223> OTHER INFORMATION: Unknown residue.
<220> FEATURE:
<221> NAME/KEY: misc_feature
<222> LOCATION: (124)..(124)
<223> OTHER INFORMATION: Unknown residue.
<220> FEATURE:
<221> NAME/KEY: misc_feature
<222> LOCATION: (126)..(131)
<223> OTHER INFORMATION: Unknown residue.
<220> FEATURE:
<221> NAME/KEY: misc_feature
<222> LOCATION: (147)..(153)
<223> OTHER INFORMATION: Unknown residue.
<220> FEATURE:
<221> NAME/KEY: misc_feature
<222> LOCATION: (157)..(157)
<223> OTHER INFORMATION: Unknown residue.
<220> FEATURE:
<221> NAME/KEY: misc_feature
<222> LOCATION: (166)..(166)
<223> OTHER INFORMATION: Unknown residue.
<220> FEATURE:
<221> NAME/KEY: misc_feature
<222> LOCATION: (169)..(170)
<223> OTHER INFORMATION: Unknown residue.
<220> FEATURE:
<221> NAME/KEY: misc_feature
<222> LOCATION: (173)..(173)
<223> OTHER INFORMATION: Unknown residue.
<220> FEATURE:
<221> NAME/KEY: misc_feature
<222> LOCATION: (176)..(178)
<223> OTHER INFORMATION: Unknown residue.
<220> FEATURE:
<221> NAME/KEY: misc_feature
<222> LOCATION: (180)..(180)
```

```
<223> OTHER INFORMATION: Unknown residue.
<220> FEATURE:
<221> NAME/KEY: misc_feature
<222> LOCATION: (190)..(190)
<223> OTHER INFORMATION: Unknown residue.
<220> FEATURE:
<221> NAME/KEY: misc_feature
<222> LOCATION: (193)..(194)
<223> OTHER INFORMATION: Unknown residue.
<220> FEATURE:
<221> NAME/KEY: misc_feature
<222> LOCATION: (198)..(198)
<223> OTHER INFORMATION: Unknown residue.
<220> FEATURE:
<221> NAME/KEY: misc_feature
<222> LOCATION: (214)..(214)
<223> OTHER INFORMATION: Unknown residue.
<220> FEATURE:
<221> NAME/KEY: misc_feature
<222> LOCATION: (221)..(222)
<223> OTHER INFORMATION: Unknown residue.
<220> FEATURE:
<221> NAME/KEY: misc_feature
<222> LOCATION: (225)..(225)
<223> OTHER INFORMATION: Unknown residue.
<220> FEATURE:
<221> NAME/KEY: misc_feature
<222> LOCATION: (228)..(228)
<223> OTHER INFORMATION: Unknown residue.
<220> FEATURE:
<221> NAME/KEY: misc_feature
<222> LOCATION: (233)..(233)
<223> OTHER INFORMATION: Unknown residue.
<220> FEATURE:
<221> NAME/KEY: misc_feature
<222> LOCATION: (243)..(243)
<223> OTHER INFORMATION: Unknown residue.
<220> FEATURE:
<221> NAME/KEY: misc_feature
<222> LOCATION: (245)..(245)
<223> OTHER INFORMATION: Unknown residue.
<220> FEATURE:
<221> NAME/KEY: misc_feature
<222> LOCATION: (251)..(251)
<223> OTHER INFORMATION: Unknown residue.
<220> FEATURE:
<221> NAME/KEY: misc_feature
<222> LOCATION: (260)..(261)
<223> OTHER INFORMATION: Unknown residue.
<220> FEATURE:
<221> NAME/KEY: misc_feature
<222> LOCATION: (265)..(265)
<223> OTHER INFORMATION: Unknown residue.
<220> FEATURE:
<221> NAME/KEY: misc_feature
<222> LOCATION: (268)..(268)
<223> OTHER INFORMATION: Unknown residue.
<220> FEATURE:
<221> NAME/KEY: misc_feature
<222> LOCATION: (296)..(298)
<223> OTHER INFORMATION: Unknown residue.
<220> FEATURE:
<221> NAME/KEY: misc_feature
<222> LOCATION: (304)..(304)
<223> OTHER INFORMATION: Unknown residue.
<220> FEATURE:
<221> NAME/KEY: misc_feature
<222> LOCATION: (309)..(309)
<223> OTHER INFORMATION: Unknown residue.
<220> FEATURE:
<221> NAME/KEY: misc_feature
<222> LOCATION: (313)..(313)
<223> OTHER INFORMATION: Unknown residue.
<220> FEATURE:
<221> NAME/KEY: misc_feature
<222> LOCATION: (316)..(317)
<223> OTHER INFORMATION: Unknown residue.
<220> FEATURE:
<221> NAME/KEY: misc_feature
```

-continued

```
<222> LOCATION: (320)..(321)
<223> OTHER INFORMATION: Unknown residue.
<220> FEATURE:
<221> NAME/KEY: misc_feature
<222> LOCATION: (323)..(324)
<223> OTHER INFORMATION: Unknown residue.
<220> FEATURE:
<221> NAME/KEY: misc_feature
<222> LOCATION: (327)..(328)
<223> OTHER INFORMATION: Unknown residue.
<220> FEATURE:
<221> NAME/KEY: misc_feature
<222> LOCATION: (330)..(332)
<223> OTHER INFORMATION: Unknown residue.
<220> FEATURE:
<221> NAME/KEY: misc_feature
<222> LOCATION: (334)..(336)
<223> OTHER INFORMATION: Unknown residue.
<220> FEATURE:
<221> NAME/KEY: misc_feature
<222> LOCATION: (339)..(339)
<223> OTHER INFORMATION: Unknown residue.
<220> FEATURE:
<221> NAME/KEY: misc_feature
<222> LOCATION: (345)..(345)
<223> OTHER INFORMATION: Unknown residue.
<220> FEATURE:
<221> NAME/KEY: misc_feature
<222> LOCATION: (349)..(349)
<223> OTHER INFORMATION: Unknown residue.
<220> FEATURE:
<221> NAME/KEY: misc_feature
<222> LOCATION: (352)..(352)
<223> OTHER INFORMATION: Unknown residue.
<220> FEATURE:
<221> NAME/KEY: misc_feature
<222> LOCATION: (353)..(354)
<223> OTHER INFORMATION: Unknown residue.

<400> SEQUENCE: 108

Xaa Xaa Met Xaa Ser Xaa Xaa Xaa Xaa Xaa Xaa Gly Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Cys Xaa Xaa Xaa Xaa Ser Xaa Xaa Xaa Xaa Arg Pro Xaa Xaa
 65                  70                  75                  80

Xaa Pro Arg Phe Ile Gln His Lys Xaa Glu Ala Xaa Trp Phe Tyr Arg
                 85                  90                  95

Phe Leu Ser Ile Val Tyr Asp His Xaa Ile Asn Pro Gly His Trp Thr
            100                 105                 110

Glu Asp Met Arg Asp Asp Ala Leu Glu Pro Ala Xaa Leu Xaa Xaa Xaa
        115                 120                 125

Xaa Xaa Xaa Val Val Asp Val Gly Gly Gly Thr Gly Phe Thr Thr Leu
    130                 135                 140

Gly Ile Xaa Xaa Xaa Xaa Xaa Xaa Xaa Asn Val Thr Xaa Leu Asp Gln
145                 150                 155                 160

Ser Pro His Gln Leu Xaa Lys Ala Xaa Xaa Lys Glu Xaa Leu Lys Xaa
                165                 170                 175

Xaa Xaa Ile Xaa Glu Gly Asp Ala Glu Asp Leu Pro Phe Xaa Thr Asp
            180                 185                 190

Xaa Xaa Asp Arg Tyr Xaa Ser Ala Gly Ser Ile Glu Tyr Trp Pro Asp
        195                 200                 205
```

```
Pro Gln Arg Gly Ile Xaa Glu Ala Tyr Arg Val Leu Xaa Xaa Gly Gly
    210             215                 220

Xaa Ala Cys Xaa Ile Gly Pro Val Xaa Pro Thr Phe Trp Leu Ser Arg
225             230                 235                     240

Phe Phe Xaa Asp Xaa Trp Met Leu Phe Pro Xaa Glu Glu Glu Tyr Ile
            245                 250                 255

Glu Trp Phe Xaa Xaa Ala Gly Phe Xaa Asp Val Xaa Leu Lys Arg Ile
            260                 265             270

Gly Pro Lys Trp Tyr Arg Gly Val Arg Arg His Gly Leu Ile Met Gly
            275             280                 285

Cys Ser Val Thr Gly Val Lys Xaa Xaa Xaa Gly Asp Ser Pro Leu Xaa
    290             295                 300

Leu Gly Pro Lys Xaa Glu Asp Val Xaa Lys Pro Xaa Xaa Asn Pro Xaa
305             310                 315                     320

Xaa Phe Xaa Xaa Arg Phe Xaa Xaa Gly Xaa Xaa Xaa Ala Xaa Xaa Xaa
            325                 330                 335

Val Leu Xaa Pro Ile Tyr Met Trp Xaa Lys Asp Gln Xaa Val Pro Xaa
            340                 345                 350

Xaa Xaa Pro Ile
        355
```